US011168340B2

(12) United States Patent
Jeffries et al.

(10) Patent No.: US 11,168,340 B2
(45) Date of Patent: *Nov. 9, 2021

(54) COMPOSITIONS AND METHODS FOR PRODUCING LIPIDS AND OTHER BIOMATERIALS FROM GRAIN ETHANOL STILLAGE AND STILLAGE DERIVATIVES

(71) Applicant: Xylome Corporation, Madison, WI (US)

(72) Inventors: Thomas W. Jeffries, Madison, WI (US); David Z. Mokry, Madison, WI (US); Christopher H. Calvey, Madison, WI (US)

(73) Assignee: Xylome Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/854,468

(22) Filed: Apr. 21, 2020

(65) Prior Publication Data

US 2020/0270651 A1 Aug. 27, 2020

Related U.S. Application Data

(63) Continuation of application No. 15/679,825, filed on Aug. 17, 2017, now Pat. No. 10,662,448.

(Continued)

(51) Int. Cl.

*C12N 1/16* (2006.01)
*C12P 7/64* (2006.01)

(Continued)

(52) U.S. Cl.

CPC ................ *C12P 7/649* (2013.01); *C12N 1/16* (2013.01); *C12N 15/81* (2013.01); *C12P 7/6463* (2013.01);

(Continued)

(58) Field of Classification Search

None

See application file for complete search history.

(56) References Cited

U.S. PATENT DOCUMENTS 8,110,670 B2 2/2012 Hu et al.
9,322,038 B2 4/2016 Yu et al.

(Continued)

FOREIGN PATENT DOCUMENTS

DE 102004052115 A1 4/2006
WO WO 2007/136762 A2 11/2007

(Continued)

OTHER PUBLICATIONS

Tai et al., "Engineering the push and pull of lipid biosynthesis in oleaginous yeast Yarrowia lipolytica for biofuel production", Metabolic Engineering, vol. 15, pp. 1-9, 2013 (Year: 2013).*

(Continued)

*Primary Examiner* — Richard C Ekstrom
(74) *Attorney, Agent, or Firm* — Daniel A. Blasiole; DeWitt LLP

(57) ABSTRACT

Lipogenic yeasts bioengineered to overexpress genes for lipid production, and methods of use thereof. The yeasts are modified to express, constitutively express, or overexpress an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, an auxiliary activity family 9 enzyme, or combinations thereof. The yeasts in some cases are also modified to reduce or ablate activity of certain proteins. The methods include cultivating (Continued)

the yeast to convert low value soluble organic stillage byproducts into lipids suitable for biodiesel production and other higher value uses.

23 Claims, 23 Drawing Sheets

Specification includes a Sequence Listing.

Related U.S. Application Data

(60) Provisional application No. 62/409,126, filed on Oct. 17, 2016.

(51) Int. Cl.

| | |
|---|---|
| ***C12Q 1/48*** | (2006.01) |
| ***C12N 15/81*** | (2006.01) |
| ***C12Q 1/527*** | (2006.01) |
| ***C12P 21/00*** | (2006.01) |
| *C12N 15/10* | (2006.01) |
| *C12P 7/06* | (2006.01) |
| *C12Q 1/40* | (2006.01) |

(52) U.S. Cl.

CPC ................ *C12P 21/00* (2013.01); *C12Q 1/48* (2013.01); *C12Q 1/527* (2013.01); *C12N 15/1096* (2013.01); *C12P 7/06* (2013.01); *C12Q 1/40* (2013.01)

(56) References Cited

U.S. PATENT DOCUMENTS

| | | | | |
|---|---|---|---|---|
| 10,662,448 | B2 * | 5/2020 | Jeffries | C12P 7/649 |
| 2010/0305341 | A1 | 12/2010 | Bailey et al. | |
| 2012/0083023 | A1 | 4/2012 | Yu et al. | |
| 2012/0264983 | A1 | 10/2012 | Hu | |
| 2013/0137149 | A1 | 5/2013 | Phadnavis et al. | |
| 2013/0338385 | A1 * | 12/2013 | Franklin | C12P 7/64 554/223 |
| 2014/0234919 | A1 | 8/2014 | Yu et al. | |
| 2020/0270651 | A1 * | 8/2020 | Jeffries | C12P 21/00 |

FOREIGN PATENT DOCUMENTS

| | | | |
|---|---|---|---|
| WO | WO 2010/118409 | A1 | 10/2010 |
| WO | WO 2011/161317 | A3 | 12/2011 |

OTHER PUBLICATIONS

Courchesne et al., "Enhancement of lipid production using biochemical, genetic and transcription factor engineering approaches", Journal of Biotechnology, vol. 141, pp. 31-41, 2009 (Year: 2009).*

Oguro et al., "Multicopy integration and expression of heterologous genes in the oleaginous yeast, Lipomyces starkeyi", Bioscience, Biotechnology, and Biochemistry, vol. 79, No. 3, pp. 512-515, 2015 (Year: 2015).*

Gomma et al., "Improvement in oil production by increasing malonyl-CoA and glycerol-3-phosphate pools in Scenedesmus quadricauda", Indian Journal of Microbiology, vol. 55, No. 4, pp. 447-455, 2015 (Year: 2015).*

Geneseq Accession No. AXT55474, published Feb. 18, 2010 (Year: 2010).*

Geneseq Accession No. BCG84303, published Dec. 17, 2015 (Year: 2015).*

UniProt Accession No. E2CWD2_LIPST, published Nov. 30, 2010 (Year: 2010).*

UniProt Accession No. A0A0H3VB41_LIPST, published Oct. 14, 2015 (Year: 2015).*

Matsuzawa T, Maehara T, Kamisaka Y, Ara S, Takaku H, Yaoi K. Identification and characterization of Δ12 and Δ12/Δ15 bifunctional fatty acid desaturases in the oleaginous yeast Lipomyces starkeyi. Applied microbiology and biotechnology. Oct. 1, 2018;102(20):8817-26.

Athenstaedt, Karin. "YALI0E32769g (DGA1) and YALI0E16797g (LRO1) encode major triacylglycerol synthases of the oleaginous yeast Yarrowia lipolytica." Biochimica et Biophysica Acta (BBA)—Molecular and Cell Biology of Lipids 1811.10 (2011): 587-596.

Barcia-Vieitez, Ramiro, and Juan Ignacio Ramos-Martínez. "The regulation of the oxidative phase of the pentose phosphate pathway: new answers to old problems." IUBMB life 66.11 (2014): 775-779.

Becker, Judith, et al. "Metabolic flux engineering of 1-lysine production in Corynebacterium glutamicum—over expression and modification of G6P dehydrogenase." Journal of biotechnology 132.2 (2007): 99-109.

Beopoulos, Athanasios, et al. "Identification and characterization of DGA2, an acyltransferase of the DGAT1 acyl-CoA: diacylglycerol acyltransferase family in the oleaginous yeast Yarrowia lipolytica. New insights into the storage lipid metabolism of oleaginous yeasts." Applied microbiology and biotechnology 93.4 (2012): 1523-1537.

Bignell, Graham R., Ian J. Bruce, and Ivor H. Evans. "Amylolytic enzymes of Lipomyces starkeyi: purification and size-determination." Biotechnology letters 22.21 (2000): 1713-1718.

Bligh E. Graham, and W. Justin Dyer. "A rapid method of total lipid extraction and purification." Canadian journal of biochemistry and physiology 37.8 (1959): 911-917.

Boulton, Christopher A., and Colin Ratledge. "Use of transition studies in continuous cultures of Lipomyces starkeyi, an oleaginous yeast, to investigate the physiology of lipid accumulation." Microbiology 129.9 (1983): 2871-2876.

Calvey, Christopher H., Laura B. Willis, and Thomas W. Jeffries. "An optimized transformation protocol for Lipomyces starkeyi." Current genetics 60.3 (2014): 223-230.

Calvey, Christopher H., et al. "Nitrogen limitation, oxygen limitation, and lipid accumulation in Lipomyces starkeyi." Bioresource technology 200 (2016): 780-788.

Cannella, David, and Henning Jørgensen. "Do new cellulolytic enzyme preparations affect the industrial strategies for high solids lignocellulosic ethanol production?." Biotechnology and bioengineering 111.1 (2014): 59-68.

Cardenas, Javier, and Nancy A. Da Silva. "Engineering cofactor and transport mechanisms in *Saccharomyces cerevisiae* for enhanced acetyl-CoA and polyketide biosynthesis." Metabolic engineering 36 (2016): 80-89.

Chen, Lin, et al. "Expression, purification and characterization of a recombinant Lipomyces starkey dextranase in Pichia pastoris." Protein expression and purification 58.1 (2008): 87-93.

Choi, Jin Wook, and Nancy A. Da Silva. "Improving polyketide and fatty acid synthesis by engineering of the yeast acetyl-CoA carboxylase." Journal of biotechnology 187 (2014): 56-59.

Collett, James R., Pimphan A. Meyer, and Susanne B. Jones. Preliminary economics for hydrocarbon fuel production from cellulosic sugars. No. PNNL-23374. Pacific Northwest National Laboratory (PNNL), Richland, WA (US), Environmental Molecular Sciences Laboratory (EMSL), 2014.

Courchesne, Noémie Manuelle Dorval, et al. "Enhancement of lipid production using biochemical, genetic and transcription factor engineering approaches." Journal of biotechnology 141.1-2 (2009): 31-41.

Evans, Christopher Thomas, and Colin Ratledge. "Possible regulatory roles of ATP: citrate lyase, malic enzyme, and AMP deaminase in lipid accumulation by Rhodosporidium toruloides CBS 14." Canadian journal of microbiology 31.11 (1985): 1000-1005.

Flores, Carmen-Lisset, and Carlos Gancedo. "Yarrowia lipolytica mutants devoid of pyruvate carboxylase activity show an unusual growth phenotype." Eukaryotic cell 4.2 (2005): 356-364.

Gallagher, Anne M., Catherine T. Kelly, and William M. Fogarty. "A novel extracellular carbohydrase produced by Lipomyces tetrasporus." Applied microbiology and biotechnology 35.4 (1991): 455-460.

Garay, Luis A., et al. "Eighteen new oleaginous yeast species." Journal of industrial microbiology & biotechnology 43.7 (2016): 887-900.

(56) References Cited

OTHER PUBLICATIONS

Gibson, Daniel G., et al. "Enzymatic assembly of DNA molecules up to several hundred kilobases." Nature methods 6.5 (2009): 343.
Gietz, R. Daniel, and Robin A. Woods. "Transformation of yeast by lithium acetate/single-stranded carrier DNA/polyethylene glycol method." Methods in enzymology. vol. 350. Academic Press, 2002. 87-96.
Gomma, Ahmed E., et al. "Improvement in oil production by increasing Malonyl-CoA and Glycerol-3-Phosphate pools in Scenedesmus quadricauda." Indian journal of microbiology 55.4 (2015): 447-455.
Gong, Zhiwei, et al. "Co-fermentation of cellobiose and xylose by Lipomyces starkeyi for lipid production." Bioresource technology 117 (2012): 20-24.
Gorner, Christian, et al. "Genetic engineering and production of modified fatty acids by the non-conventional oleaginous yeast Trichosporon oleaginosus ATCC 20509." Green Chemistry 18.7 (2016): 2037-2046.
Hamid, Aidil Abdul, et al. "The role of ATP citrate lyase, malic enzyme and fatty acid synthase in the regulation of lipid accumulation in *Cunninghamella* sp. 2A1." Annals of Microbiology 61.3 (2011): 463-468.
Hammond, Earl G., et al. "Soybean oil." Bailey's industrial oil and fat products (2005).
Holdsworth, Jane E., and Colin Ratledge. "Lipid turnover in oleaginous yeasts." Microbiology 134.2 (1988): 339-346.
Holdsworth, Jane E., Marten Veenhuis, and Colin Ratledge. "Enzyme activities in oleaginous yeasts accumulating and utilizing exogenous or endogenous lipids." Microbiology 134.11 (1988): 2907-2915.
Kang, Hee-Kyoung, et al. "Cloning and characterization of a dextranase gene from Lipomyces starkeyi and its expression in *Saccharomyces cerevisiae*." Yeast 22.15 (2005): 1239-1248.
Kildegaard, Kanchana R., et al. "Engineering and systems-level analysis of *Saccharomyces cerevisiae* for production of 3-hydroxypropionic acid via malonyl-CoA reductase-dependent pathway." Microbial cell factories 15.1 (2016): 53.
Kim, Youngmi, et al. "Composition of corn dry-grind ethanol by-products: DDGS, wet cake, and thin stillage." Bioresource technology 99.12 (2008): 5165-5176.
Lee, So-Young, et al. "Demonstration of two independent dextranase and amylase active sites on a single enzyme elaborated by Lipomyces starkeyi KSM 22." Journal of microbiology and biotechnology 13.2 (2003): 313-316.
Li, Zhi, et al. "Overexpression of malic enzyme (ME) of Mucor circinelloides improved lipid accumulation in engineered Rhodotorula glutinis." Applied microbiology and biotechnology 97.11 (2012): 4927-4936.
Morgenstern, Ingo, Justin Powlowski, and Adrian Tsang. "Fungal cellulose degradation by oxidative enzymes: from dysfunctional GH61 family to powerful lytic polysaccharide monooxygenase family." Briefings in functional genomics 13.6 (2014): 471-481.
Moritz, Bernd, et al. "Kinetic properties of the glucose-6-phosphate and 6 phosphogluconate dehydrogenases from Corynebacterium glutamicum and their application for predicting pentose phosphate pathway flux in vivo." The FEBS Journal 267.12 (2000): 3442-3452.
Naganuma, T., et al. "Differences in enzyme activities of Lipomyces starkeyi between cells accumulating lipid and proliferating cells." Journal of basic microbiology 27.1 (1987): 35-42.
Oguro, Yoshifumi, et al. "Multicopy integration and expression of heterologous genes in the oleaginous yeast, Lipomyces starkeyi." Bioscience, biotechnology, and biochemistry 79.3 (2015): 512-515.
Ohnishi, Junko, et al. "A novel gnd mutation leading to increased L-lysine production in Corynebacterium glutamicum." FEMS microbiology letters 242.2 (2005): 265-274.
Pan, Li-Xia, et al. "Isolation of the oleaginous yeasts from the soil and studies of their lipid-producing capacities." Food technology and Biotechnology 47.2 (2009): 215-220.
Papanikolaou, Seraphim, et al. "Kinetic profile of the cellular lipid composition in an oleaginous Yarrowia lipolytica capable of producing a cocoa-butter substitute from industrial fats." Antonie van Leeuwenhoek 80.3-4 (2001): 215-224.
Punpeng, Boontiam, et al. "A novel raw-starch-digesting yeast a-amylase from Lipomyces starkeyi HN-606." Journal of fermentation and bioengineering 73.2 (1992): 108-111.
Rangasamy, Dhandapani, and Colin Ratledge. "Genetic enhancement of fatty acid synthesis by targeting rat liver ATP: citrate lyase into plastids of tobacco." Plant physiology 122.4 (2000): 1231-1238.
Ratledge, C. Lipid biotechnology—a wonderland for the microbial physiologist. Journal of the American Oil Chemists Society 64, 1647-1656 (1987).
Ratledge, Colin. "Regulation of lipid accumulation in oleaginous micro-organisms." (2002): 1047-1050.
Ratledge, Colin. "Fatty acid biosynthesis in microorganisms being used for single cell oil production." Biochimie 86.11 (2004): 807-815.
Ratledge, Colin. "The role of malic enzyme as the provider of NADPH in oleaginous microorganisms: a reappraisal and unsolved problems." Biotechnology letters 36.8 (2014): 1557-1568.
Riley Robert, et al. "Comparative genomics of biotechnologically important yeasts." Proceedings of the National Academy of Sciences 113.35 (2016): 9882-9887.
Rippa, Mario, et al. "6-Phosphogluconate dehydrogenase: the mechanism of action investigated by a comparison of the enzyme from different species1." Biochimica et Biophysica Acta (BBA)—Protein Structure and Molecular Enzymology 1429.1 (1998): 83-92.
Ruenwai, Rawisara, Supapon Cheevadhanarak, and Kobkul Laoteng. "Overexpression of acetyl-CoA carboxylase gene of Mucor rouxii enhanced fatty acid content in Hansenula polymorphs." Molecular biotechnology 42.3 (2009): 327-332.
Ryu, S.J. et al. "Purification and partial characterization of a novel glucanhydrolase from Lipomyces starkeyi KSM 22 and its use for inhibition of insoluble glucan formation." Bioscience, biotechnology, and biochemistry 64.2 (2000): 223-228.
Saenge, Chanika, et al. "Potential use of oleaginous red yeast Rhodotorula glutinis for the bioconversion of crude glycerol from biodiesel plant to lipids and carotenoids." Process Biochemistry 46.1 (2011): 210-218.
Shi, Shuobo, et al. "Improving production of malonyl coenzyme A-derived metabolites by abolishing Snf1-dependent regulation of Acc1." MBio 5.3 (2014): e01130-14.
Sitepu, I. R., et al. "An improved high-throughput Nile red fluorescence assay for estimating intracellular lipids in a variety of yeast species." Journal of microbiological methods 91.2 (2012): 321-328.
Steyn, Andries JC, Julius Marmur, and Isak S. Pretorius. "Cloning, sequence analysis and expression in yeasts of a cDNA containing a Lipomyces kononenkoae α-amylase-encoding gene." Gene 166.1 (1995): 65-71.
Tai, Mitchell, and Gregory Stephanopoulos. "Engineering the push and pull of lipid biosynthesis in oleaginous yeast Yarrowia lipolytica for biofuel production." Metabolic engineering 15 (2013): 1-9.
Tang, Wei, et al. "The isocitrate dehydrogenase gene of oleaginous yeast Lipomyces starkeyi is linked to lipid accumulation." Canadian journal of microbiology 55.9 (2009): 1062-1069.
Tang, Xiaoling, Huixing Feng, and Wei Ning Chen. "Metabolic engineering for enhanced fatty acids synthesis in *Saccharomyces cerevisiae*." Metabolic engineering 16 (2013): 95-102.
Tang, Xiaoling, and Wei Ning Chen. "Investigation of fatty acid accumulation in the engineered *Saccharomyces cerevisiae* under nitrogen limited culture condition." Bioresource technology 162 (2014): 200-206.
Van Rossum, Harmen M., et al. "Engineering cytosolic acetyl-coenzyme a supply in *Saccharomyces cerevisiae*: pathway stoichiometry, free-energy conservation and redox-cofactor balancing." Metabolic engineering 36 (2016): 99-115.
Velasco, Pilar, et al. "The modulation of the oxidative phase of the pentose phosphate pathway in mouse liver." The international journal of biochemistry & cell biology 27.10 (1995): 1015-1019.

(56) References Cited

OTHER PUBLICATIONS

Vicente, Gemma, et al. "Direct transformation of fungal biomass from submerged cultures into biodiesel." Energy & Fuels 24.5 (2010): 3173-3178.
Wang, Zhi-Peng, et al. "Disruption of the MIG1 gene enhances lipid biosynthesis in the oleaginous yeast Yarrowia lipolytica ACA-DC 50109." Biochimica et Biophysica Acta (BBA)—Molecular and Cell Biology of Lipids 1831.4 (2013): 675-682.
Wang, Jiancai, et al. "Overexpression of ACC gene from oleaginous yeast Lipomyces starkeyi enhanced the lipid accumulation in *Saccharomyces cerevisiae* with increased levels of glycerol 3-phosphate substrates." Bioscience, biotechnology, and biochemistry 80.6 (2016): 1214-1222.
Wilkie, Ann C., Kelly J. Riedesel, and John M. Owens. "Stillage characterization and anaerobic treatment of ethanol stillage from conventional and cellulosic feedstocks." Biomass and Bioenergy 19.2 (2000): 63-102.
Wynn, James P., Aidil bin Abdul Hamid, and Colin Ratledge. "The role of malic enzyme in the regulation of lipid accumulation in filamentous fungi." Microbiology 145.8 (1999): 1911-1917.
Xuan, Jian-Wu, Philippe Fournier, and Claude Gaillardin. "Cloning of the LYS5 gene encoding saccharopine dehydrogenase from the yeast Yarrowia lipolytica by target integration." Current Genetics 14.1 (1988): 15-21.
Yen, Hong-Wei, Ya-Chun Yang, and Yi-Huan Yu. "Using crude glycerol and thin stillage for the production of microbial lipids through the cultivation of Rhodotorula glutinis." Journal of bioscience and bioengineering 114.4 (2012): 453-456.
Zha, Jian, et al. "Enhanced expression of genes involved in initial xylose metabolism and the oxidative pentose phosphate pathway in the improved xylose-utilizing *Saccharomyces cerevisiae* through evolutionary engineering." Journal of industrial microbiology & biotechnology 41.1 (2014): 27-39.
Zhang, Ying, Ian P. Adams, and Colin Ratledge. "Malic enzyme: the controlling activity for lipid production? Overexpression of malic enzyme in Mucor circinelloides leads to a 2.5-fold increase in lipid accumulation." Microbiology 153.7 (2007): 2013-2025.
Zhang, Yong, et al. "New industrial brewing yeast strains with ILV2 disruption and LSD1 expression." International Journal of Food Microbiology 123 (2008): 18-24.
Zhang, Man, Luciano Galdieri, and Ales Vancura. "The yeast AMPK homolog SNF1 regulates acetyl coenzyme A homeostasis and histone acetylation." Molecular and cellular biology 33.23 (2013): 4701-4717.
Zhao, Xin, et al. "Medium optimization for lipid production through co-fermentation of glucose and xylose by the oleaginous yeast Lipomyces starkeyi." European Journal of Lipid Science and Technology 110.5 (2008): 405-412.
Zhou, Yongjin J., et al. "Production of fatty acid-derived oleochemicals and biofuels by synthetic yeast cell factories." Nature communications 7 (2016): ncomms11709.
Zhu, Z.W. et al. In Nature Communications, vol. 3 (2012).

* cited by examiner

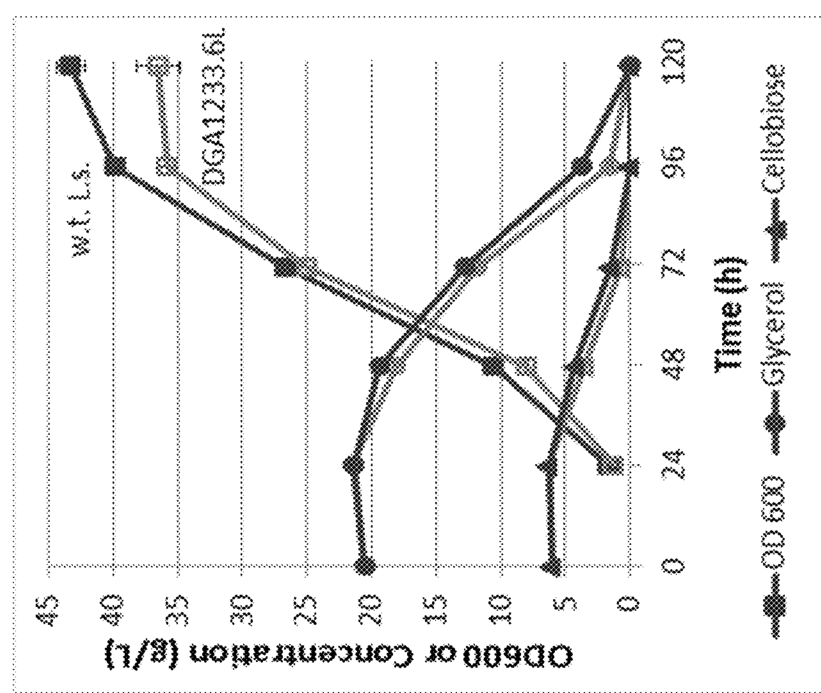
FIG. 11A
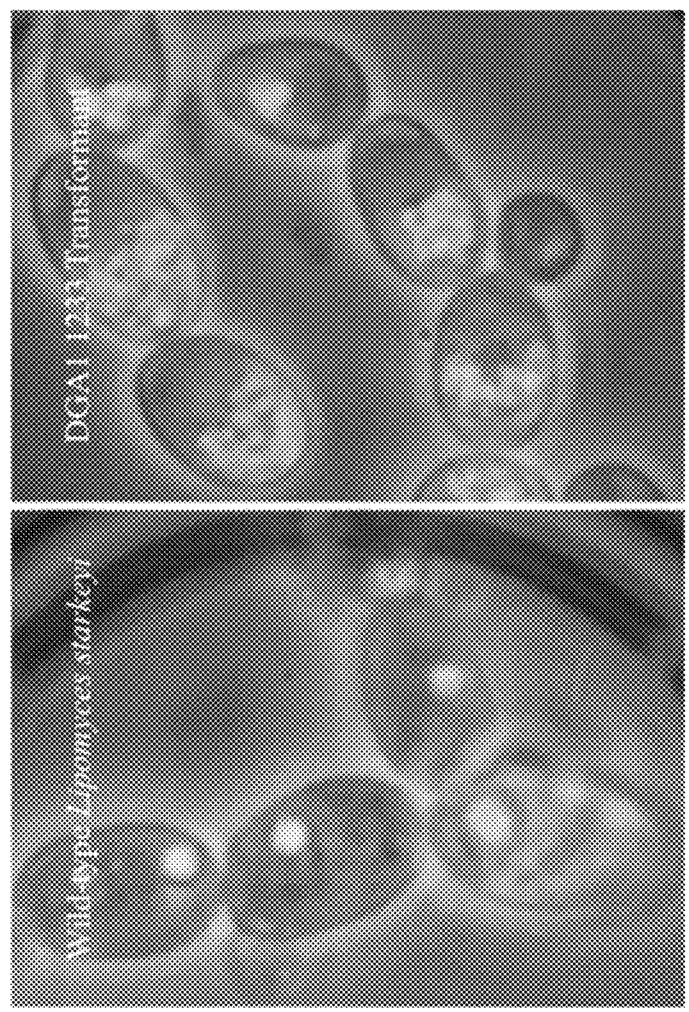
FIG. 11B
FIG. 11C

COMPOSITIONS AND METHODS FOR PRODUCING LIPIDS AND OTHER BIOMATERIALS FROM GRAIN ETHANOL STILLAGE AND STILLAGE DERIVATIVES

STATEMENT REGARDING FEDERALLY SPONSORED RESEARCH

This invention was made with Government support under IIP 1520485 and IIP 1632255 awarded by the National Science Foundation. The Government has certain rights in this invention.

FIELD OF THE INVENTION

The invention is directed to engineered yeasts and methods for converting stillage organics into lipids and other biomaterials.

SEQUENCE LISTING

The instant application contains a Sequence Listing which has been submitted in ASCII format via EFS-Web and is hereby incorporated by reference in its entirety. The ASCII copy, created on Aug. 11, 2017, is named USPTO—200421—SEQUENCE_LISTING_ST25.txt and is 401,461 bytes in size.

BACKGROUND

Renewable fuels are environmentally desirable, especially fuels with higher energy density such as biodiesel. U.S. biodiesel production capacity however, is underused. From January of 2014 to July 2016, annual production of biodiesel did not exceeded 60% of plant capacity. This was due in part to a lack of inexpensive feedstock supply, which the industry greatly needs as an alternative source of seed oils (Anon 2016).

Plant triglycerides from soybeans, canola, rapeseed and palm oil can be converted into methyl or ethyl esters for use as biodiesel. Biodiesel produced in the U.S. is mainly derived from waste cooking oils, the edible oils of soybean and rapeseed (canola) (Hammond et al. 2005), from the inedible corn oil recovered following fermentation and distillation of grain to ethanol, and with lesser amounts generated from animal fats.

If the U.S. were to use all of its domestic soybeans to make biodiesel, it would result in about 5.1 billion gallons of biofuel. This approach, however, is not realistic because these oilseeds are also key components of the food chain and are used for the production of many household and industrial products. Thus, increasing the production of biodiesel from foodstuffs would lead to higher prices of commodities derived from them, and economic hardship for the consumer.

Biodiesel can be made from the triglycerides generated by oleaginous (lipogenic) yeast or algae. In fact, 2 to 3 times more lipid/g dry weight is generated by these microbial sources than from seed oils. Certain algae can accumulate lipids when cultivated on sunlight and $CO_2$, but fixation of $CO_2$ by photosynthesis requires a great deal of metabolic energy, so cell growth and lipid accumulation is relatively slow. Some algae can grow heterotrophically on simple organic compounds dissolved in water, which greatly increases their rates of lipid accumulation. Algae, however, do not generally assimilate more complex organic materials such as starch, cellulosic or hemicellulosic oligomers. Ascomyceteous and basidiomyceteous lipogenic yeasts and filamentous fungi will, however, readily assimilate these compounds. Moreover, because these yeasts and fungi are heterotrophic, their growth rates on simple or complex dissolved organic materials are much faster than algae cultivated under heterotrophic conditions.

If it were possible to produce biodiesel from cellulosic residues or other waste organic materials in yields similar to what could be achieved with ethanol production, domestic biodiesel production could satisfy a significant fraction of the national transport energy demand without affecting the food supply. Furthermore, this increased domestic production would also decrease dependency on foreign oil.

Agricultural residue (e.g. corn stover) is a potential source of renewable biomass that could be converted into liquid transportation fuels such as biodiesel if recalcitrance of the biomass to hydrolysis, the presence of inhibitors mixed with the hydrolyzed sugars, and the difficulty in obtaining microbial catalysts that will convert the sugars to lipids in high yield can be overcome. The potential for biodiesel production from agricultural residues is significant. If the residues from U.S. soybean production alone were collected and converted by a microbial process with a mass yield of 35% based on the starting sugar, it would be possible to produce about 10 million metric tons of lipid annually or about 15% more oil than the total of what is presently recovered from the processing of soybeans itself.

Cellulosic biodiesel produced by a lipogenic yeast cultivated on agricultural hydrolysate would generate an animal feed byproduct similar to that obtained from processing oil from soybeans or palm oil. Based on comparisons with existing prices for wholesale yeast protein from brewing, biodiesel production by lipogenic yeast would yield residual yeast protein with the same or slightly higher market value as soy protein.

While several technologies exist to pretreat and enzymatically saccharify agricultural residues for hydrolysis to create fermentable sugars, new microbial biocatalysts are needed to convert the resulting mixed sugars into lipids and other higher value materials.

Grain ethanol plants are a potential source of unused, soluble and insoluble organic materials suitable for biodiesel production. In wet and dry-mill ethanol operations, cornstarch is enzymatically converted into sugar then fermented to ethanol. The process leaves behind significant amounts of corn fiber and generates soluble organics as byproducts of ethanol production.

Grain ethanol plants are becoming less economical to operate due to lack of demand for ethanol and to low profit margins when grain prices are high and petroleum prices are low. Ethanol derived from grain is also criticized for having poor compatibility with fuel distribution systems, reducing the food supply, contributing to soil erosion, and releasing net $CO_2$ emissions that are only marginally better than gasoline. Reduced operating costs, increased process efficiency, better fuel compatibility, and higher product value and diversity could significantly improve the economics and environmental acceptability of this process.

In a conventional dry mill process, whole grain is hammer milled, then steam treated in a jet cooker as it is sent to the fermentation tank for liquefaction with a thermostable alpha-amylase. Following cooling and saccharification, the mash is inoculated for fermentation. Variations on this basic process can involve separation of corn hulls (fiber), starch and germ gluten (protein) prior to saccharification, use of less steam for cooking, use of raw starch, recovery of edible corn oil from the germ and other changes. Following fermentation, ethanol is recovered by distillation, and the bulk of the fiber and protein, along with yeast cells and corn oil, are separated from the dissolved organics by centrifugation. This yields wet cake or distiller's wet grain (DWG) solids and thin stillage (TS) solubles. In a conventional process, the distiller's wet grain is dried to make distiller's dried grain (DDG) and the thin stillage containing the solubles (S) is evaporated to make a syrup, which is sprayed back onto the distiller's dried grain to make DDGS. Evaporation of the thin stillage separates a fraction of the inedible corn oil, which can be recovered for biodiesel production (FIG. 1).

Stillages (vinasse) following distillation of ethanol from industrial ethanol fermentations of grain include corn gluten and yeast protein, residual corn fiber, yeast cells, corn oil, and dissolved organics. Thin stillage contains significant quantities of glycerol (14 to 20 g/l), glucose disaccharides (e.g., cellobiose, trehalose, etc.) (6 to 10 g/l), xylose, lactic acid, corn oil and various oligosaccharides derived from residual undigested starch, dextrins, cellulose and hemicellulose. The total dissolved and suspended organic content of thin stillage is about 10% w/v. Table 1 presents a published summary of stillage components (Kim et al. 2008).

TABLE 1

Exemplary Stillage Composition

| Stillage Component | g/l |
|---|---|
| Glucose | 0.9 |
| Glucan (oligosaccharide) | 12.4 |
| Xylose | 0.7 |
| Xylan (oligosaccharide) | 3.7 |
| Arabinose | 0.4 |
| Arabinan (oligosaccharide) | 0.5 |
| Lactic acid | 16.8 |
| Glycerol | 14.4 |
| Acetic acid | 0.3 |
| Butanediol | 1.9 |
| Ethanol | 0.6 |

The glycerol and oligosaccharide contents of thin stillage retain water during evaporation and prevent drying. This makes thin stillage evaporation energy-inefficient.

Removing glycerol and oligosaccharides prior to evaporation is therefore desirable. Stillages from other ethanol distillation processes also present disposal problems. Stillage is difficult and non-economical to treat in a waste water system because of its high biological oxygen demand (BOD), its high organic content and low pH. Stillage can also have relatively high nitrogen and phosphorous contents, about 2 g/l and 130 mg/l respectively (Yen et al. 2012). The massive volumes of thin stillage resulting from fuel ethanol production are particularly difficult to handle. A significant fraction of the thin stillage is therefore recycled or "backset" into the liquefaction stage, which increases the level of dissolved organics in the fermentation and whole stillage.

Methods and tools for converting on-site low value soluble organic stillage byproducts from ethanol production into biodiesel are needed to increase fuel production without harvesting more grain. Such methods and tools would reduce the organic load in the backset while creating higher value products such as yeast oil, enzymes, and animal feed from underutilized organic byproducts.

SUMMARY OF THE INVENTION

The invention addresses the aforementioned needs by providing engineered yeasts and methods for converting stillage organics into lipids and other biomaterials.

An exemplary method of the invention for converting stillage organics into yeast oil, cell protein, and enzymes is shown in FIG. 2. This method is similar to standard dry mill operations up through the centrifugation of whole stillage to separate thin stillage (TS) and distiller's wet grain (DWG). Instead of sending thin stillage directly to evaporation, however, oil (e.g., corn oil) is first removed. Second stage thin film evaporators then remove 50 to 80% of the water, and residual protein is separated. The clarified, concentrated thin stillage (CTS) is used as a medium to cultivate native or bioengineered lipogenic yeasts that produce enzymes that will accelerate liquefaction of starch, rapidly consume glycerol, cellobiose, trehalose xylose, lactic acid and residual oligosaccharides while accumulating yeast lipids and biomass. An advantage of microbial bioconversion is that a glycerol byproduct generated during conversion of triglycerides to biodiesel can be fed back into the bioreactor to increase both the rate and yield of lipid production.

An amylolytic, lipogenic yeast specifically bioengineered for rapid lipid and enzyme production from dissolved organics in the clarified thin stillage and other stillage forms is preferred for use in this process. The yeasts are modified to express, constitutively express, or overexpress an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme, or any combination thereof. The yeasts are in some cases also modified to reduce or ablate activity of other enzymes. The bioengineered yeasts of the invention produce enzymes that accelerate liquefaction of starch, rapidly consume glycerol, cellobiose, trehalose, xylose, lactic acid and residual oligosaccharides while accumulating yeast lipids.

The technology described herein can increase profit margins for grain ethanol producers by making higher value and more diverse byproducts. The technology also has the added benefits of decreasing thin stillage viscosity, increasing protein production, reducing organic load from wastewaters, reducing natural gas-based processing expenses, and, in some cases, releasing a larger fraction of corn oil from the dried grain solids. Hence, the technologies would be of interest to several industries by providing a means to diversify products and increase the supply of high energy density renewable fuels while at the same time reducing environmental pressures.

The objects and advantages of the invention will appear more fully from the following detailed description of the preferred embodiment of the invention made in conjunction with the accompanying drawings.

citrate lyase; ACC, acetyl-CoA carboxylase; ICDH, isocitrate dehydrogenase; FAS, fatty acid synthase; DGA, diacylglycerol acyltransferase. a, b, c and d are transporters.

Figure 4:
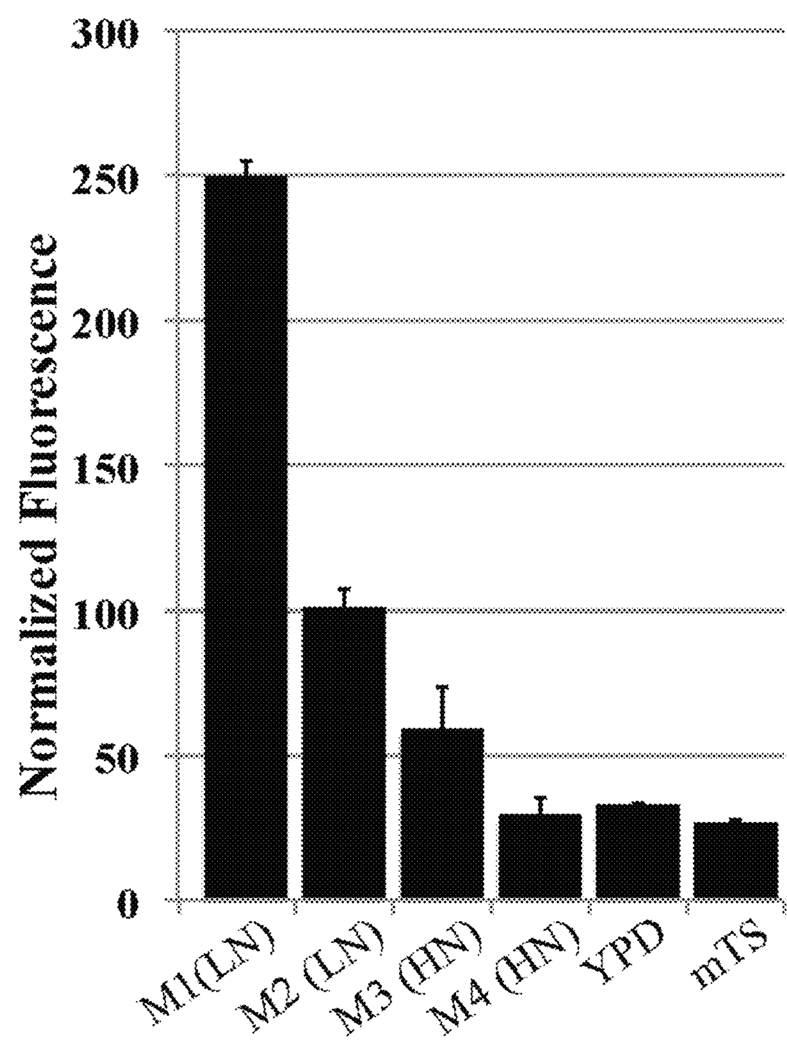

FIG. 4 shows a graph of the effects of different culture media on basal lipid content of *Lipomyces starkeyi* type strain NRRL Y-11557. The effects of six types of culture media on *L. starkeyi* basal lipid production were evaluated. YPD is yeast peptone dextrose media. M1 (LN) is a minimally defined, low nitrogen media containing yeast nitrogen base and supplemented with urea, M2 (LN) is a low nitrogen media having the same components as YPD but containing only 3.64% and 1.82% of the yeast extract and peptone contained in YPD. M3 (HN) and M4 (HN) are the high nitrogen containing versions of M1, with M4 HN containing peptone. mTS is modified thin stillage, prepared by clarifying and concentrating ethanol thin stillage. Results are shown as normalized fluorescence to OD630.

Figure 5:
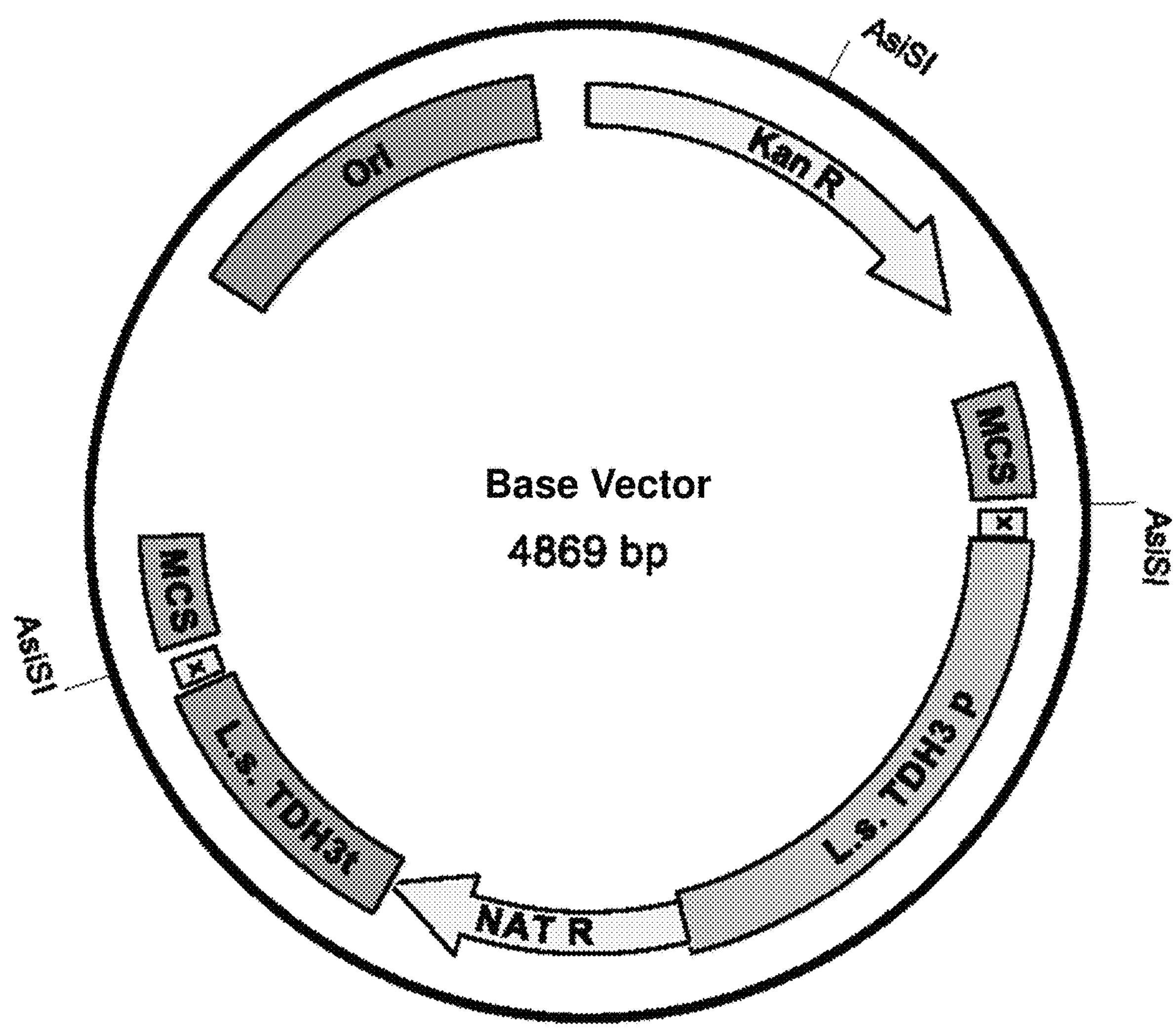

FIG. 5 is a diagram of a base vector used for creating genomic integrating cassettes. The origin of replication (Ori) and kanamycin resistance gene (Kan R) permit propagation and maintenance in *E. coli*. Two multiple cloning sites (MCSs) enable insertion of gene target cassettes adjacent to loxP sites (Xs), which flank an expression cassette for nourseothricin resistance (NAT R) driven by the constitutive TDH3 promoter (TDH3p) and terminator (TDH3t). Digestion of the vector with AsiS1 enables linearization and integration into the yeast genome. The sequence of the base vector is represented by SEQ ID NO:91.

Figure 6:
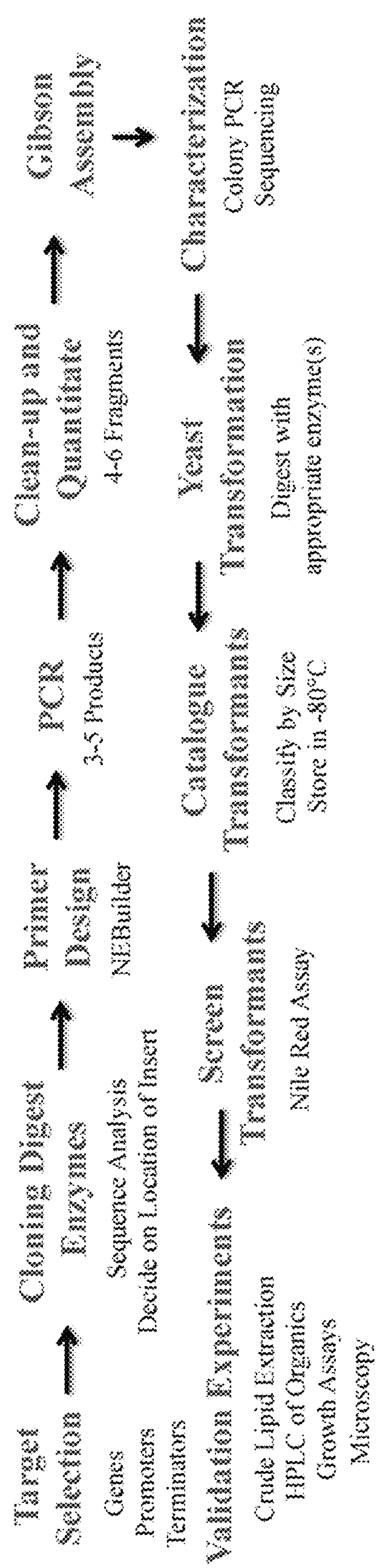

FIG. 6 shows a schema of a screening pipeline used for generating metabolically engineered yeast.

Figure 7:
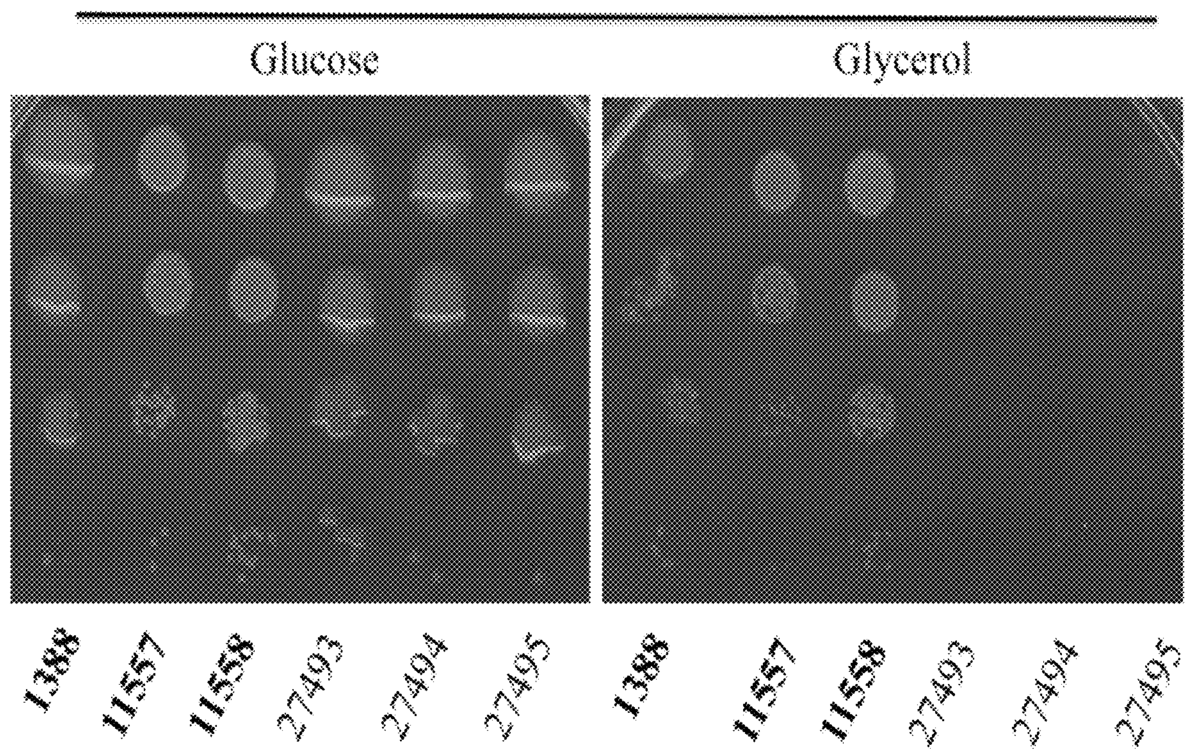

FIG. 7 shows growth of various strains of *L. starkeyi* on glucose as the sole carbon source (left panel) or glycerol as the sole carbon source (right panel).

Figure 8A:
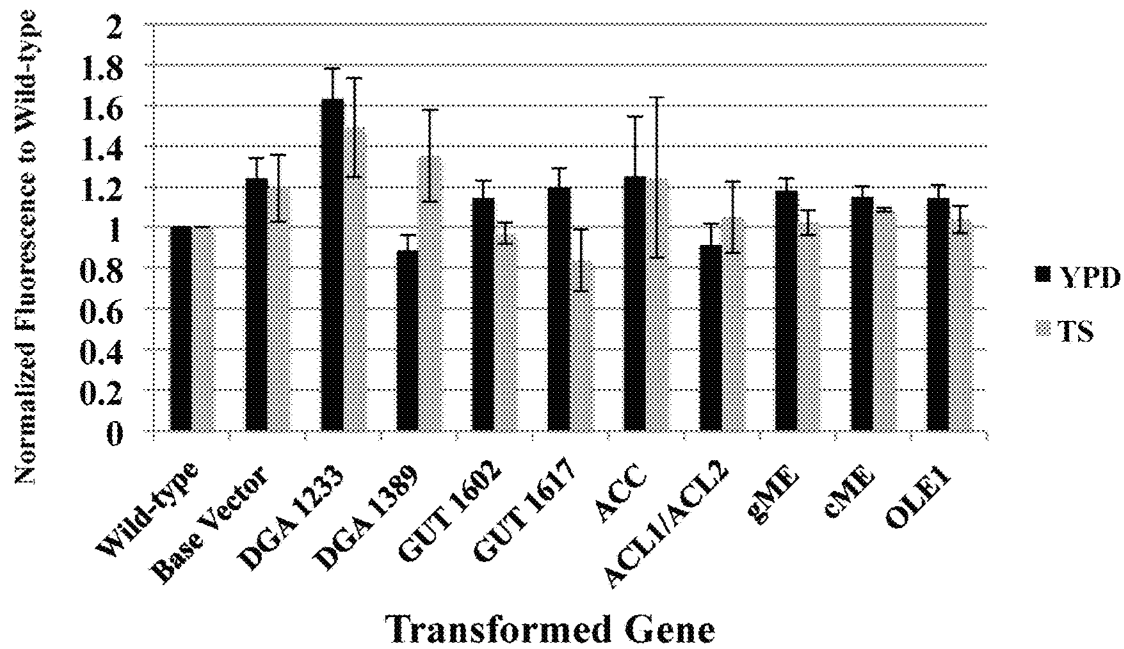
Figure 8B:
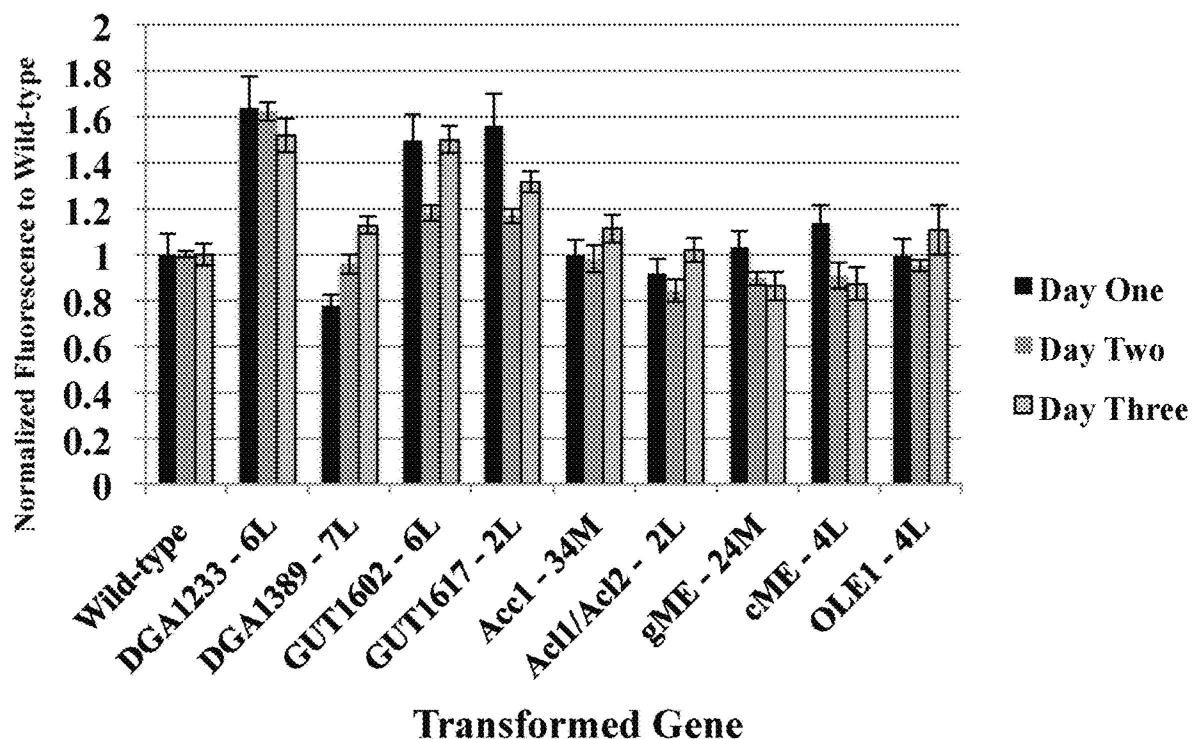

FIGS. 8A and B show Nile Red screening of yeast transformants in YPD or mTS. Results are shown normalized to the wild-type and OD600 after two (YPD) or three (mTS) days of growth. FIG. 8A shows averages of the top 50% of transformants with each gene in preliminary screening. Of 234 transformants cultivated, preliminary screening revealed three strains transformed with three genes (cDGA1-1233, cDGA1-1389, and cACC1) that showed large standard deviations or higher means than the base vector transformed strains. Data is shown for the end of the growth phase in each media (YPD=2 days, mTS=3 days). FIG. 8B shows results of a validation screen of the prime performers of each gene in mTS evaluated in triplicate, revealing that the transformants DGA1-1233 6L, GUT1-1602 6L, and GUT1-1617 2L show superior lipid accumulation over the WT as deemed by Nile Red fluorescence.

Figure 9:
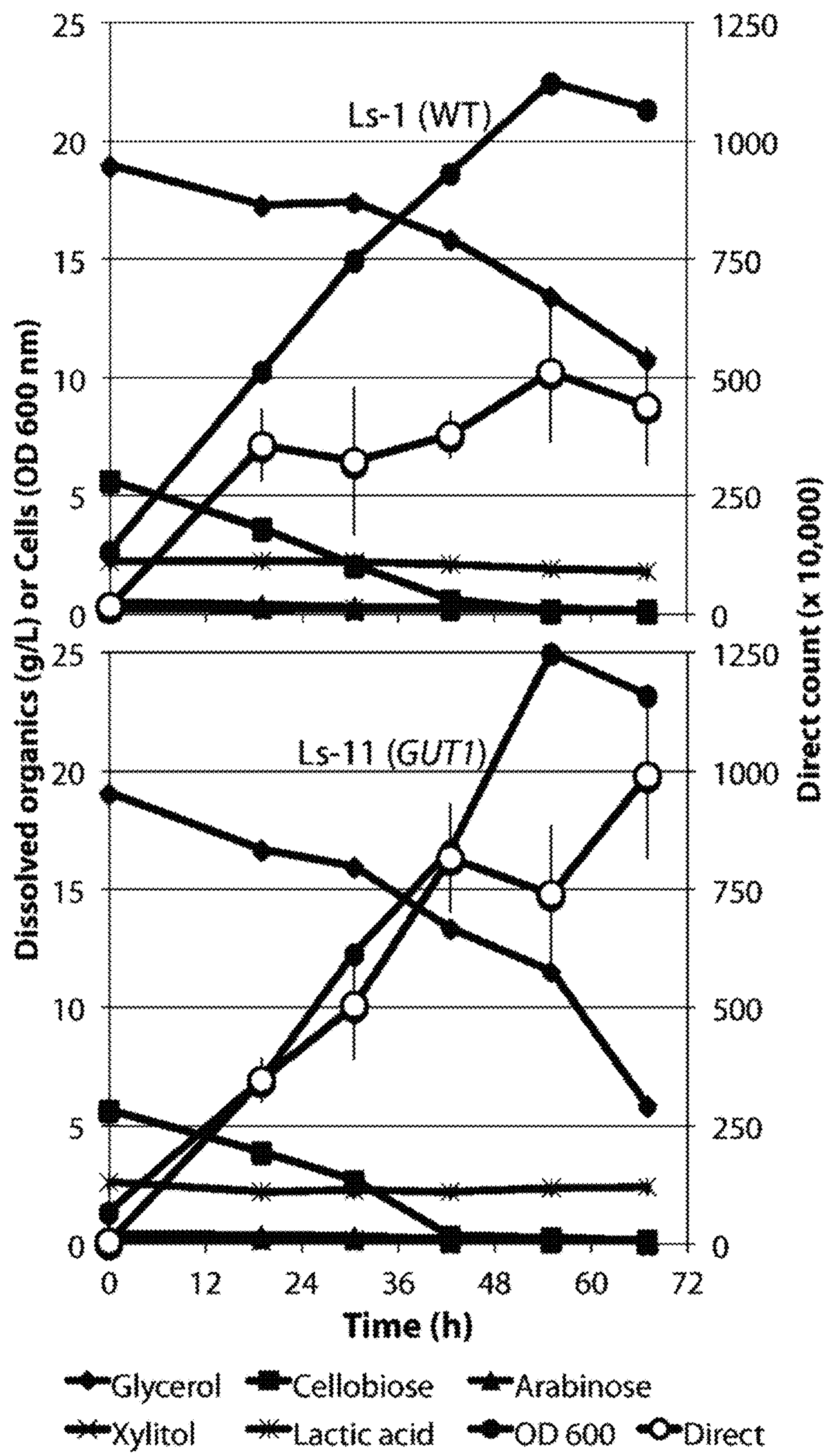

FIG. 9 shows consumption of organics and cell density of wild-type *L. starkeyi* (Ls-1) and a GUT1 engineered strain (Ls-11). The presence of glycerol, xylitol, cellobiose, lactic acid, and arabinose in 200 mL of mTS solution in shake flasks were monitored by HPLC analysis during cultivation of wild-type *L. starkeyi* (Ls-1) and a strain with an engineered version of the glycerol kinase gene (GUT1 Ls-11). Cell density (OD600) and direct cell counts were also determined. In this experiment, the Ls-11 engineered strain achieved higher cell density and consumed more glycerol than the wild-type strain.

Figure 10A:
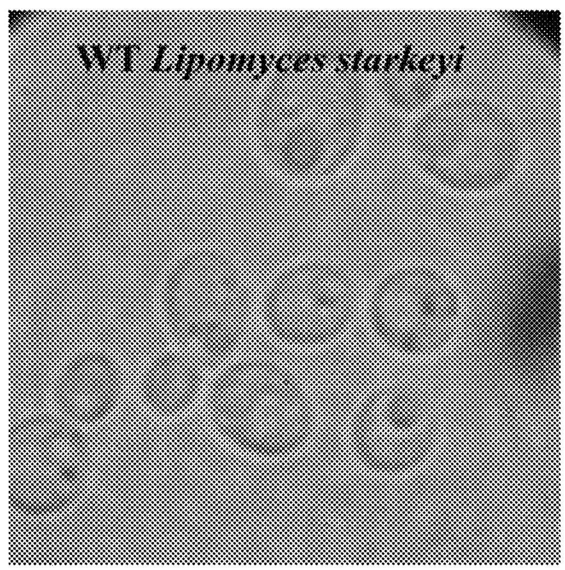
Figure 10B:
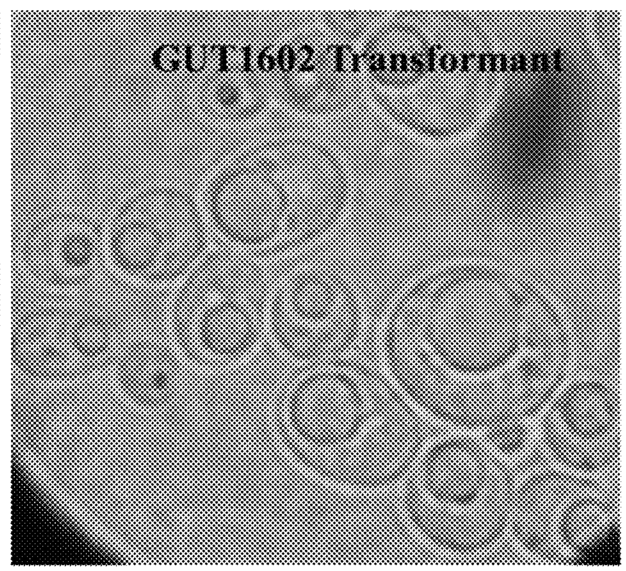

FIGS. 10A and 10B show a difference in the cellular morphologies of wild-type *L. starkeyi* (FIG. 10A) and a strain overexpressing GUT1 (FIG. 10B) when cultured on mTS. Besides generating larger liposomes in some cells, the strain overexpressing GUT1 also formed cellular assemblies similar to pseudomycelium. Photos were taken after two days of growth in mTS.

FIGS. 11A-11C show a comparison of wild-type *L. starkeyi* with engineered strain DGA1-1233 6L comprising the DGA1-1233 gene. FIG. 11A shows growth rates and carbon utilization of wild-type (solid shapes) and DGA1-1233 6L (open shapes) of glycerol and cellobiose. Cultures were grown in triplicate on mTS media, error bars denote the standard deviation. FIGS. 11B and 11C show cellular morphologies for wild-type (FIG. 11B) and DGA1-1233 6L (FIG. 11C), showing significantly more liposomes in DGA1-1233 6L.

Figure 12A:
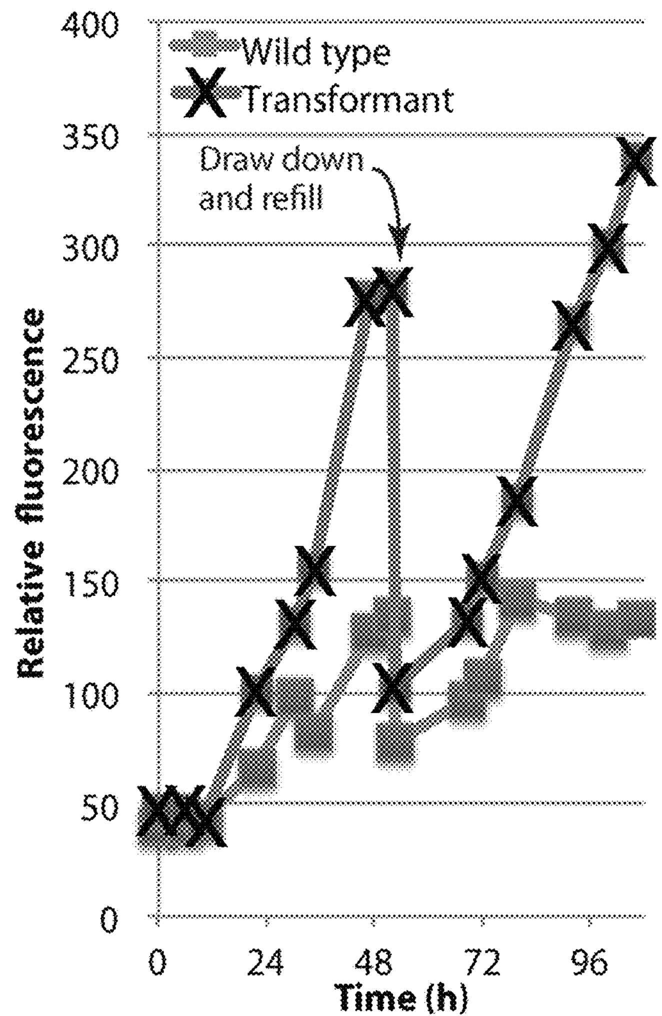
Figure 12B:
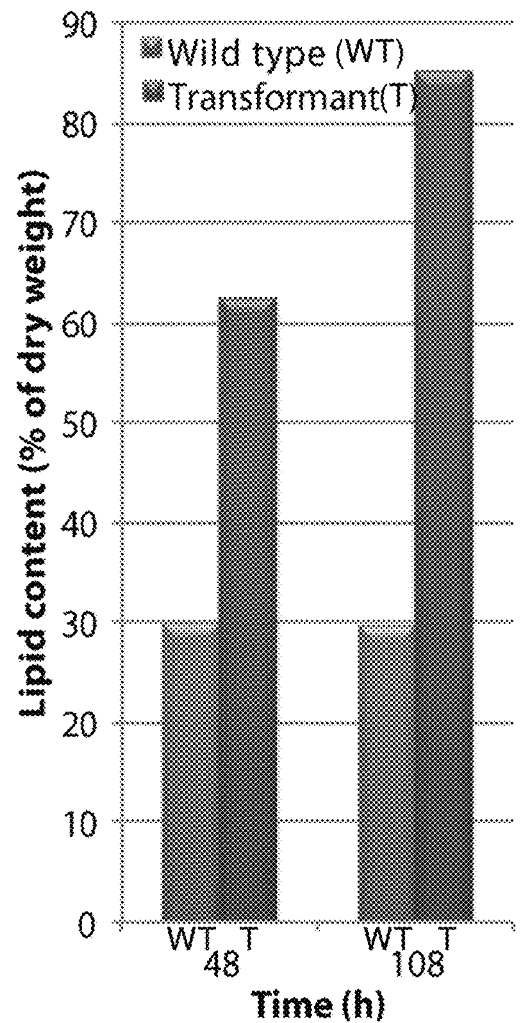

FIGS. 12A and 12B show Nile Red fluorescence and percent lipid analysis of wild-type *L. starkeyi* and the engineered strain designated DGA1-1233 6L cultured in mTS using bioreactors. FIG. 12A shows relative Nile Red fluorescence of the wild-type strain and the DGA1-1233 transformant measured at different time points. Spent media was drawn off and the bioreactors refilled with thin stillage after 48 hours of growth. FIG. 12B shows percent lipid content of cell dry weight of wild-type *L. starkeyi* and the DGA1-1233 transformant. The engineered DGA1-1233 6L strain had more than double the Nile Red fluorescence and percent lipid content.

Figure 13:
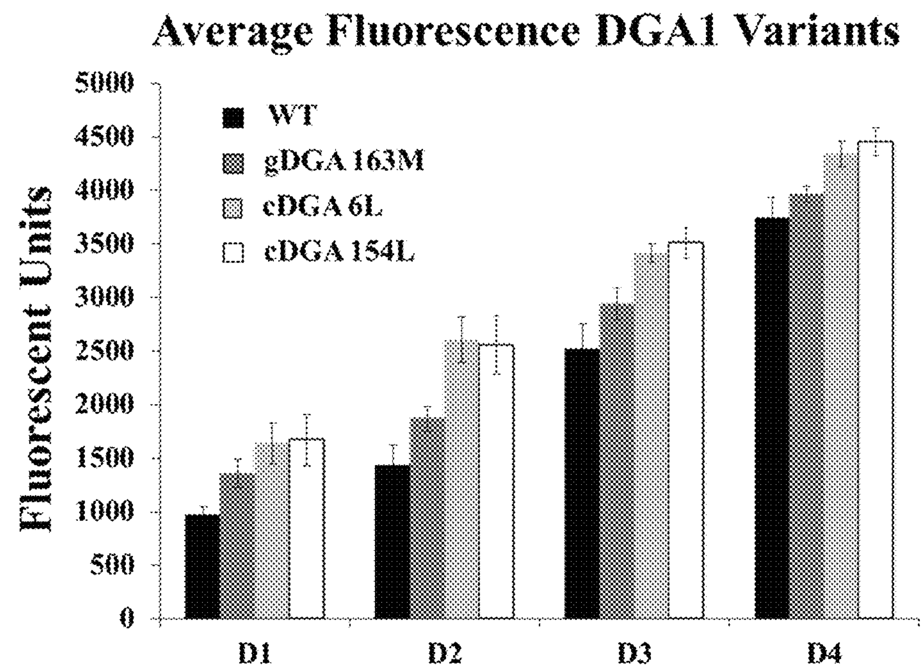

FIG. 13 shows a comparison of strains overexpressing DGA1 variants in synthetic thin stillage medium (sTS) by Bodipy fluorescence. A) Bodipy fluorescence of the wild-type Ls-1 (black), gDGA1 163M (dark gray), cDGA-1233 6L (light gray), and cDGA 154L (white) *L. starkeyi* transformants as monitored over the course of 4 days (denoted as D1, D2, D3, and D4). The cDGA 154L strain was chosen as the platform strain for further improvement due to its similar performance to cDGA 6L and Hygromycin B resistance marker.

Figure 14:
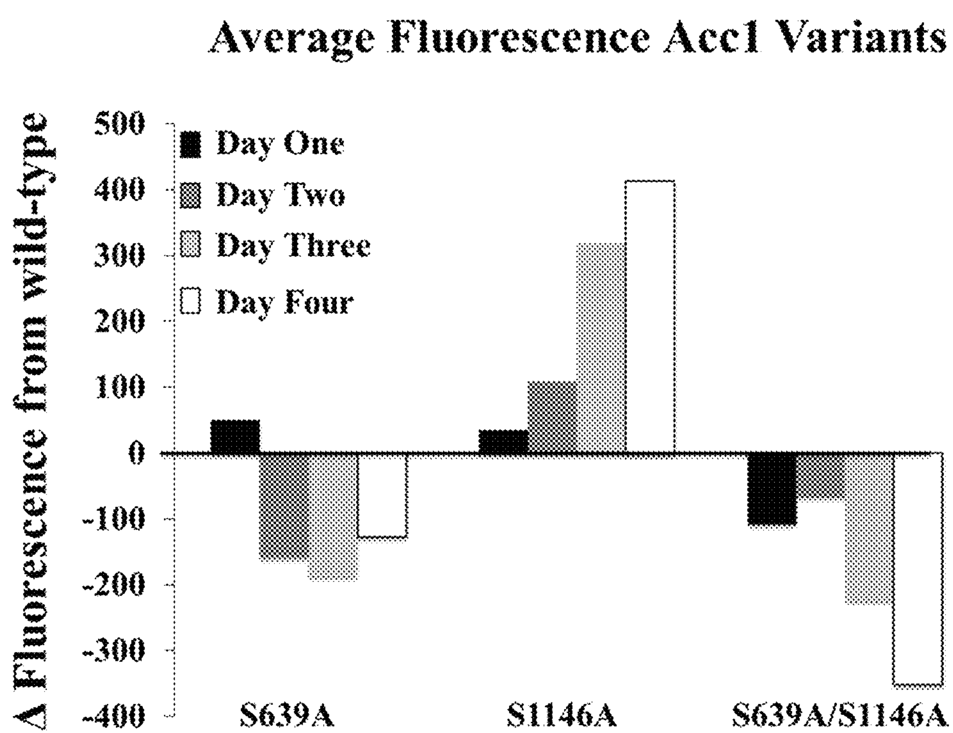

FIG. 14 shows dilution-corrected Bodipy fluorescence in mutant and wild-type Acc1-transformed *L. starkeyi*. The S1146 point mutation increases fluorescence values relative to the wild-type strain, whereas S639A and the double mutation leads to slightly inferior performance. Data is plotted as the average difference in fluorescence from the untransformed wild-type strain over the course of four days from 63-188 transformants in each pool.

Figure 15:
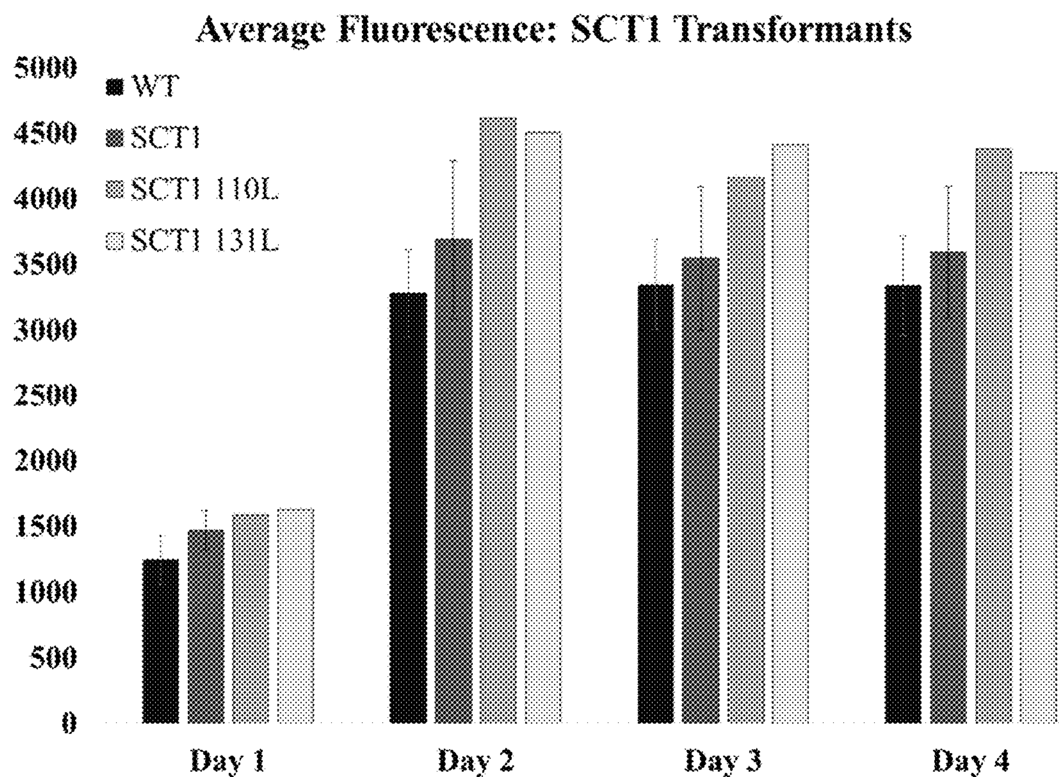

FIG. 15 shows dilution-corrected Bodipy fluorescence in wild-type and SCT1-transformed *L. starkeyi*. Average wild-type fluorescence, average transformant fluorescence, SCT1 110L transformant fluorescence, and transformant SCT1 131L fluorescence are shown. In FIG. 15, as well as in FIGS. 16, 24, 25, and 27, there are no error bars included with the data for the single transformants because each data point represents fluorescence from one culture of each transformant.

Figure 16:
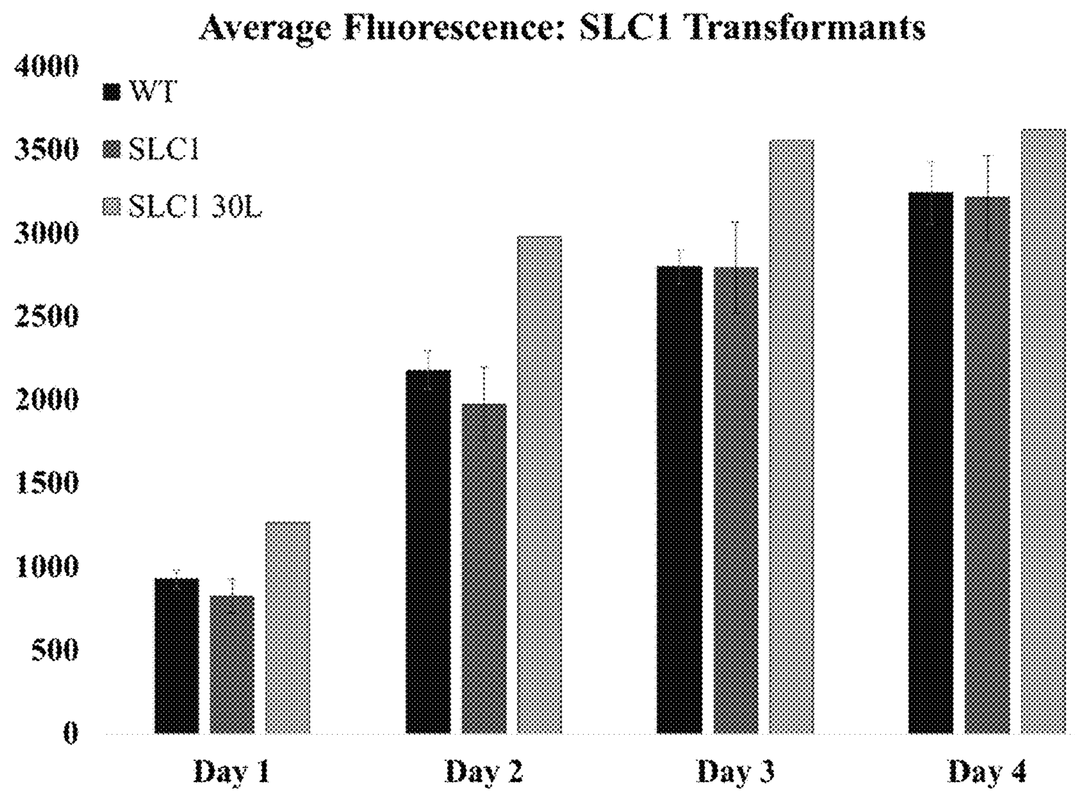

FIG. 16 shows dilution-corrected Bodipy fluorescence in wild-type and SLC1-transformed *L. starkeyi*. Average wild-type fluorescence, average transformant fluorescence, and SCT1 30L transformant fluorescence are shown.

Figure 17:
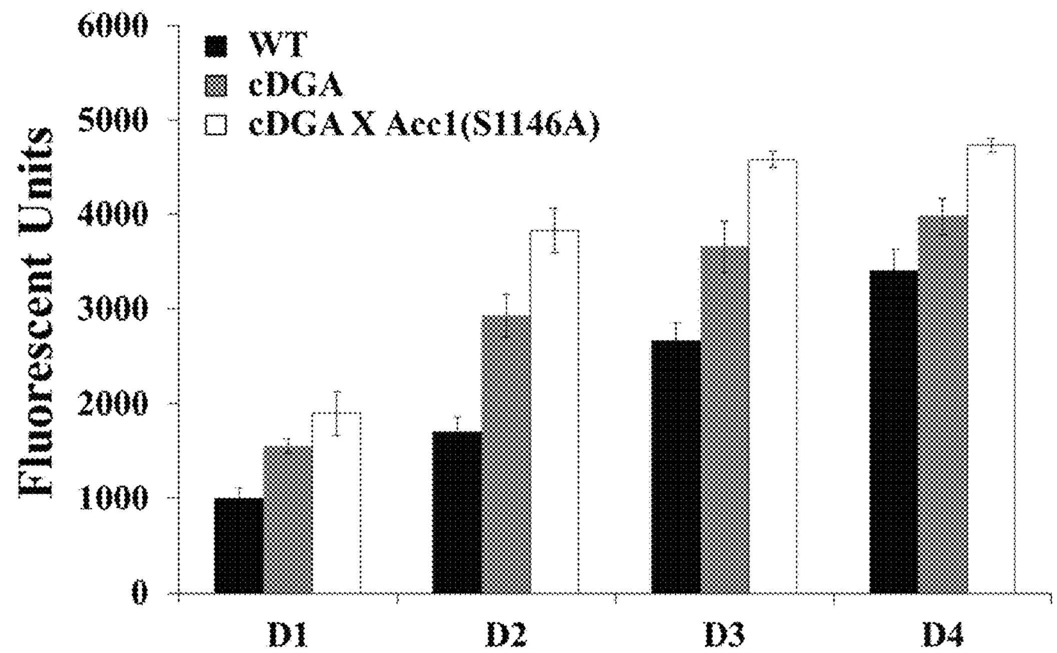

FIG. 17 shows dilution-corrected Bodipy fluorescence with dual overexpression of DGA1 and the gene for the deregulated protein Acc1(S1146A) in *L. starkeyi*. Dilution corrected Bodipy fluorescence of wild-type strain (black), the strain overexpressing cDGA1 (dark gray), and the strain in which overexpressed cDGA1 was crossed with Acc1 (S1146A) overexpressing strains was monitored over the course of 4 days (D1, D2, D3, and D4). The mated strain was obtained by crossing the top performers from each cDGA1 and Acc1(S1146A) transformant pool. Overexpression of both the DGA1 gene and the gene for the mutated protein Acc1(S1146A) synergistically enhanced lipid accumulation compared to overexpression of each gene alone.

Figure 18:
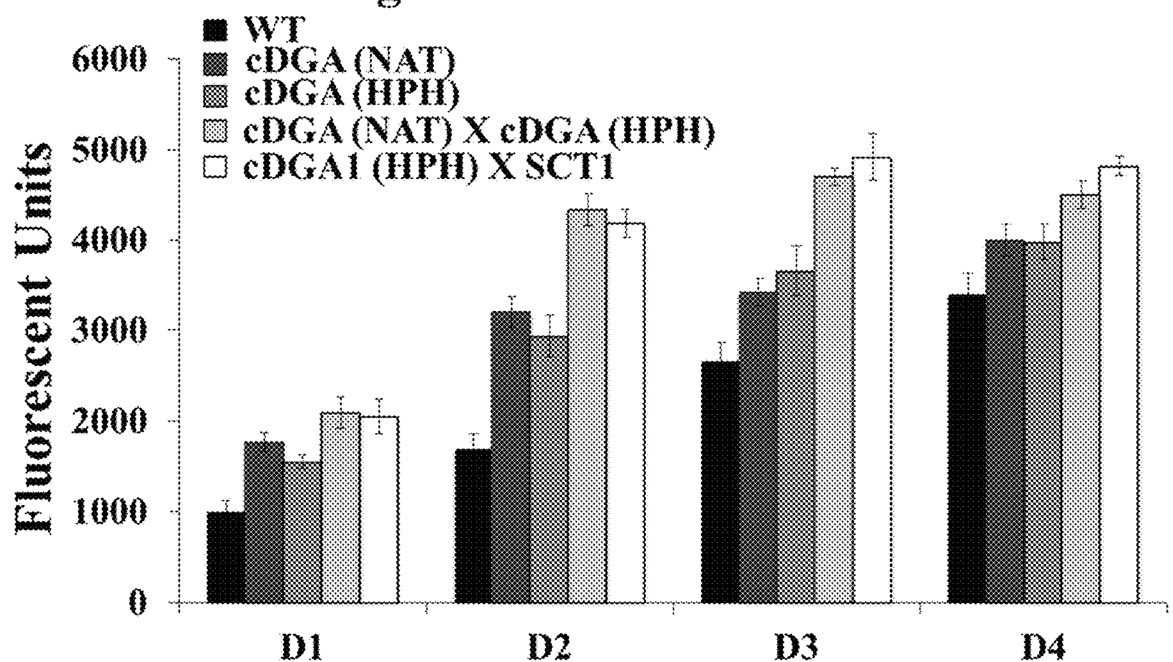

FIG. 18 shows dilution-corrected Bodipy fluorescence of *L. starkeyi* strains with combinatorial expression of lipogenic cassettes. The strains are shown in the following order (from left (black) to right (white): wild-type, cDGA-NAT (the top cDGA1-1233 strain), cDGA-HPH (a new platform strain), and cDGA-HPH crossed with either cDGA-NAT or a strain transformed with engineered SCT1. Fluorescence was monitored over the course of 4 days (D1, D2, D3, and D4). The top strains (lightest gray and white) exhibited improvement in lipid production through dual overexpression of lipogenic cassettes.

Figure 19:
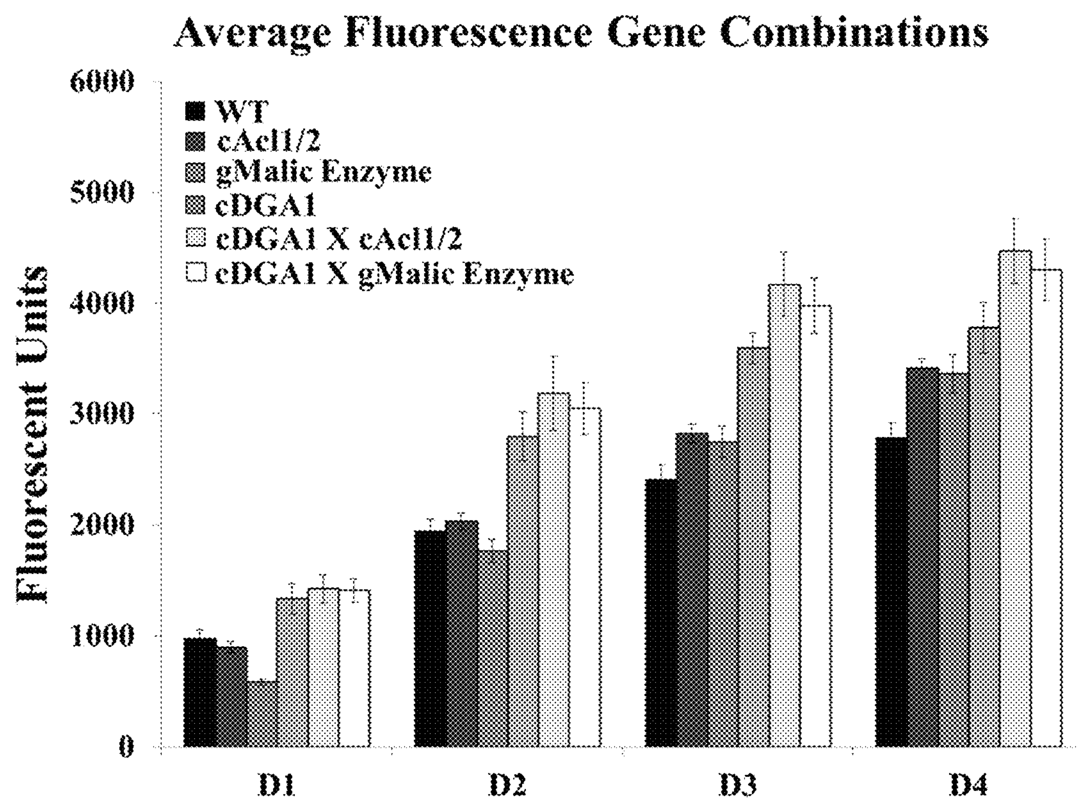

FIG. 19 shows dilution-corrected Bodipy fluorescence of *L. starkeyi* strains with combinatorial expression of lipogenic and auxiliary cassettes. The strains are shown in the following order (from left (black) to right (white): wild-type, ATP citrate lyase α and β subunit overexpressing strain (designated as cAcl1/2), malic enzyme cloned from gDNA overexpressing strain (designated as gMalic Enzyme), diacylglycerol transferase (designated as cDGA1-1233) cloned from cDNA overexpressing strain (cDGA1), combinatorial cDGA1-1233 and Acl1/2 overexpressing strain (cDGA1×cAcl1/2), and combinatorial cDGA1-1233 and genomic malic enzyme overexpressing strain (cDGA1×gMalic Enzyme). Combinatorial expression of lipogenic and auxiliary cassettes improved lipid production.

Figure 20:
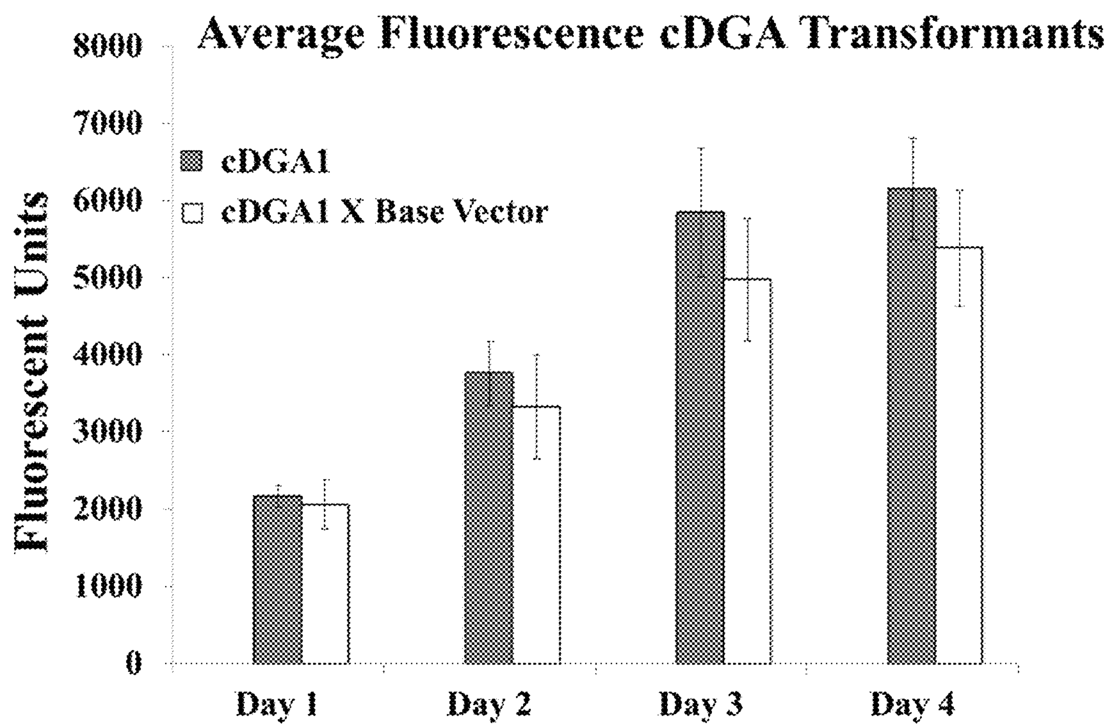

FIG. 20 shows Bodipy analysis in sTS of a lipogenic diacylglycerol transferase overexpressing strain (cDGA) and the same strain transformed with a second base vector. The introduction of expressing a second resistance marker does not increase lipid accumulation on its own, and may even decrease lipid levels.

Figure 21:
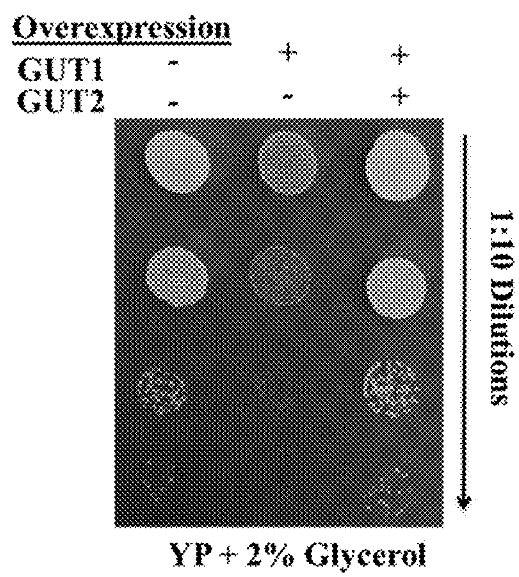

FIG. 21 shows wild-type *L. starkeyi* (first column), or transformed cells overexpressing the gene for glycerol kinase (GUT1, second column) or GUT1 and an FAD-dependent glycerol-3-phosphate dehydrogenase (GUT1/GUT2, third column) plated onto YP solid media containing 2% glycerol and incubated for 4-5 days at 30° C. The growth defect of the GUT1 single transformant was rescued by overexpression of GUT2.

Figure 22:
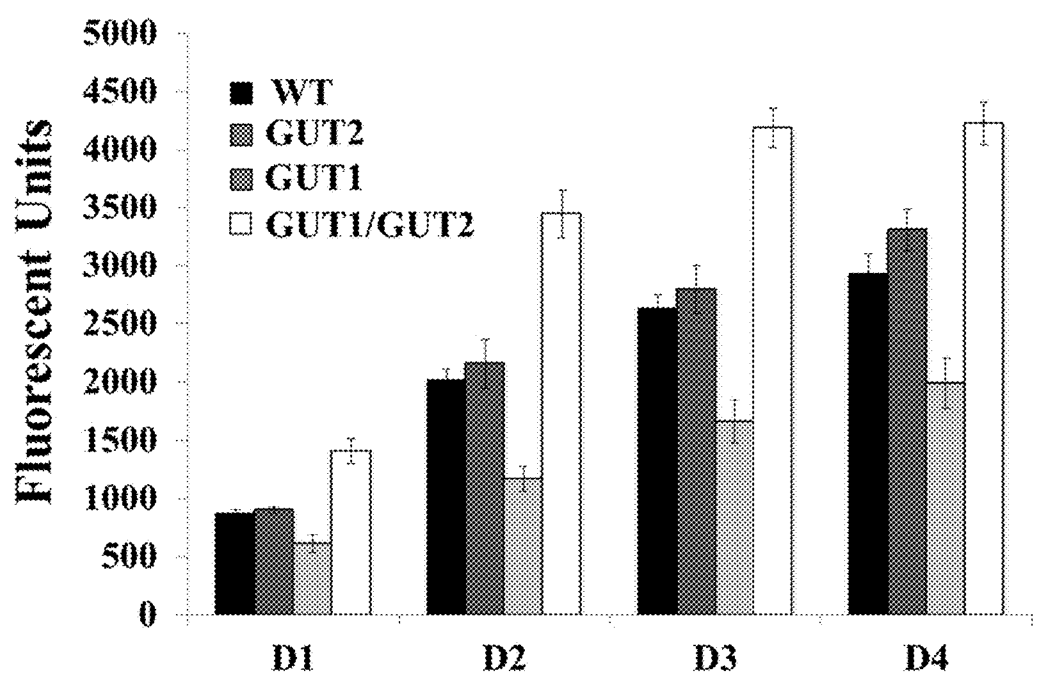

FIG. 22 shows average dilution-corrected Bodipy fluorescence in a parental wild-type *L. starkeyi* strain (black), a strain overexpressing GUT2 (dark gray), a strain overexpressing GUT1 (light gray), and a GUT1/GUT2 double transformant (white). The GUT1/GUT2 double transformant accumulates more lipid than parental wild-type or GUT1 overexpressing strains. Overexpression of GUT2 alone has little effect on lipid accumulation.

Figure 23A:
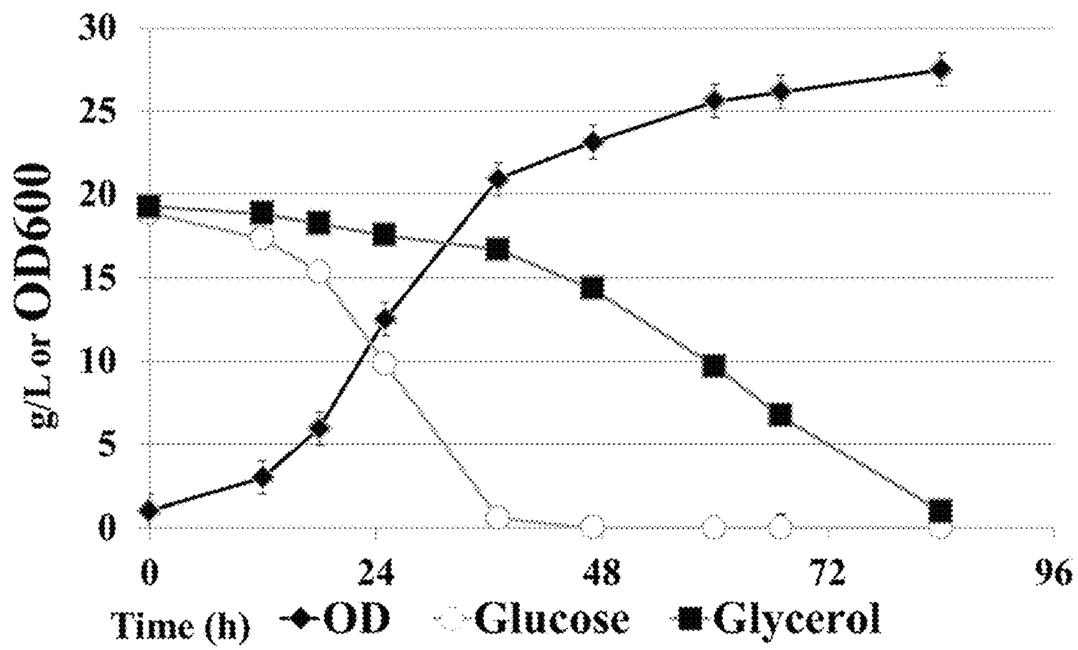
Figure 23B:
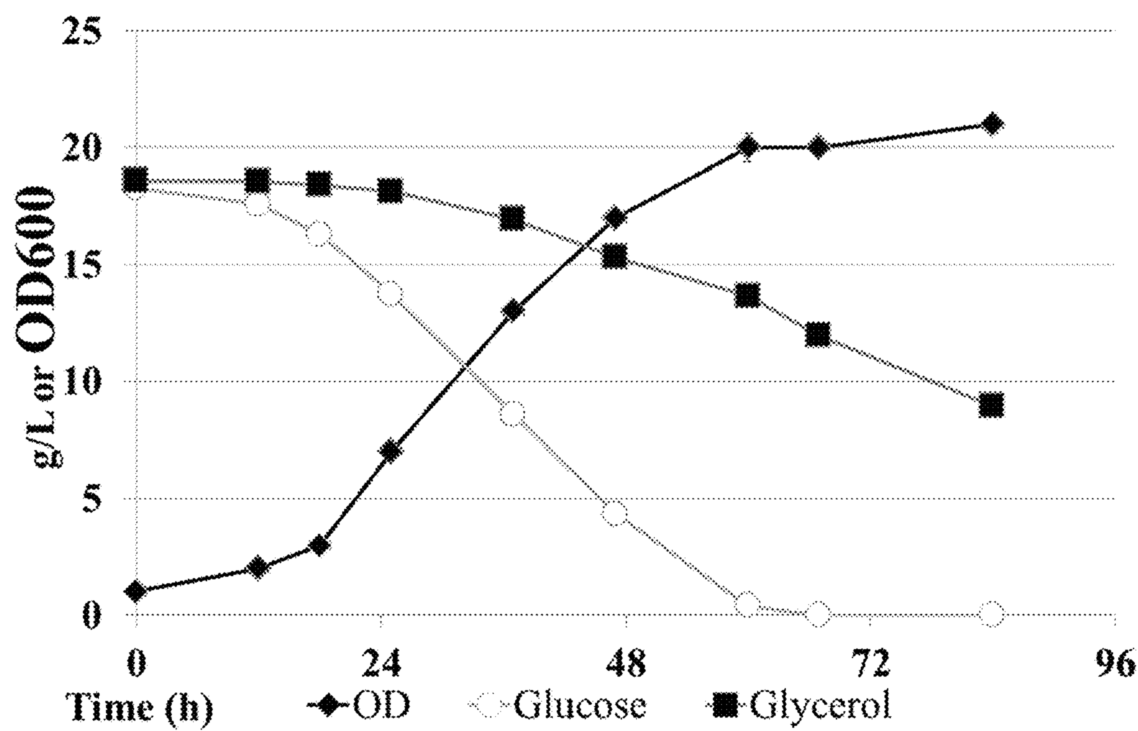
Figure 23C:
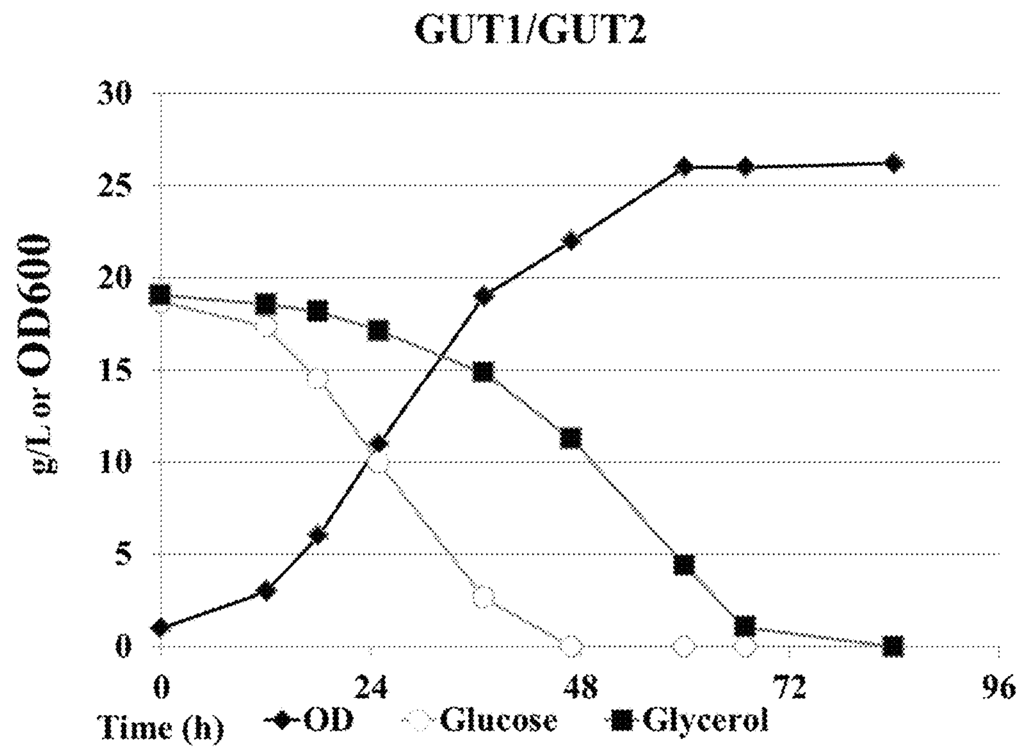
Figure 23D:
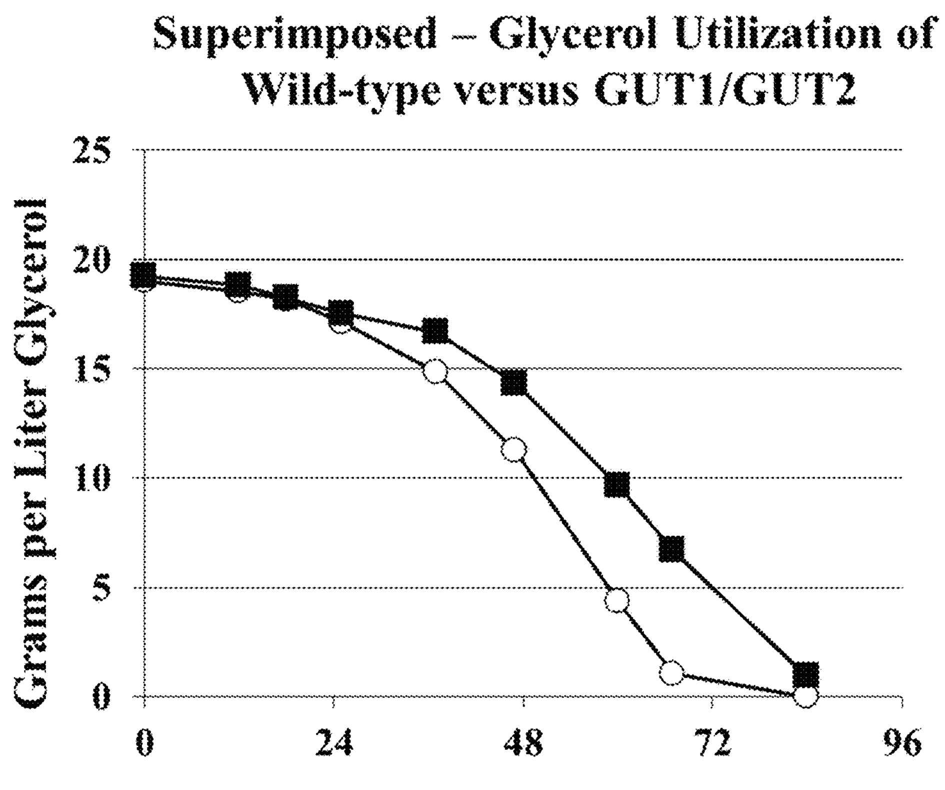

FIGS. 23A-23C show cell density (OD), glucose consumption, and glycerol consumption in a parental wild-type *L. starkeyi* strain (FIG. 23A), a GUT1 single transformant (FIG. 23B), and a GUT1/GUT2 double transformant (FIG. 23C). FIG. 23D shows superimposed curves of glycerol utilization in the wile-type strain and the GUT1/GUT2 double transformant. Glycerol was depleted in just 67 hours in the GUT1/GUT2 double transformant versus 84 hours in the wild-type strain.

Figure 24:
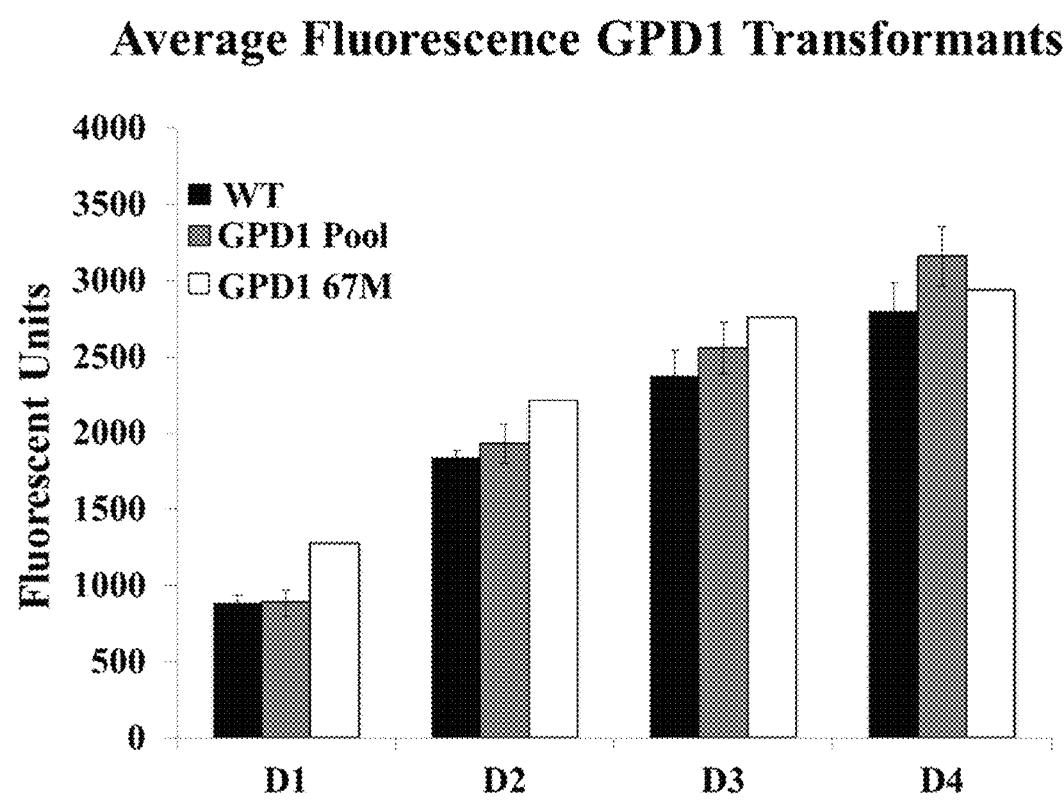

FIG. 24 shows dilution-corrected Bodipy fluorescence of wild-type *L. starkeyi* (black) and a pool of GPD1 transformants (gray). Bodipy fluorescence was monitored in synthetic thin stillage over the course of 4 days. Overall, the transformants exhibited moderately higher fluorescence over the wild-type, with almost 13% improvement on the fourth day. The top transformant GPD1 67M (white) is also shown. The data indicate that overexpression of glycerol-3-phosphate in *L. starkeyi* increases lipid production.

Figure 25:
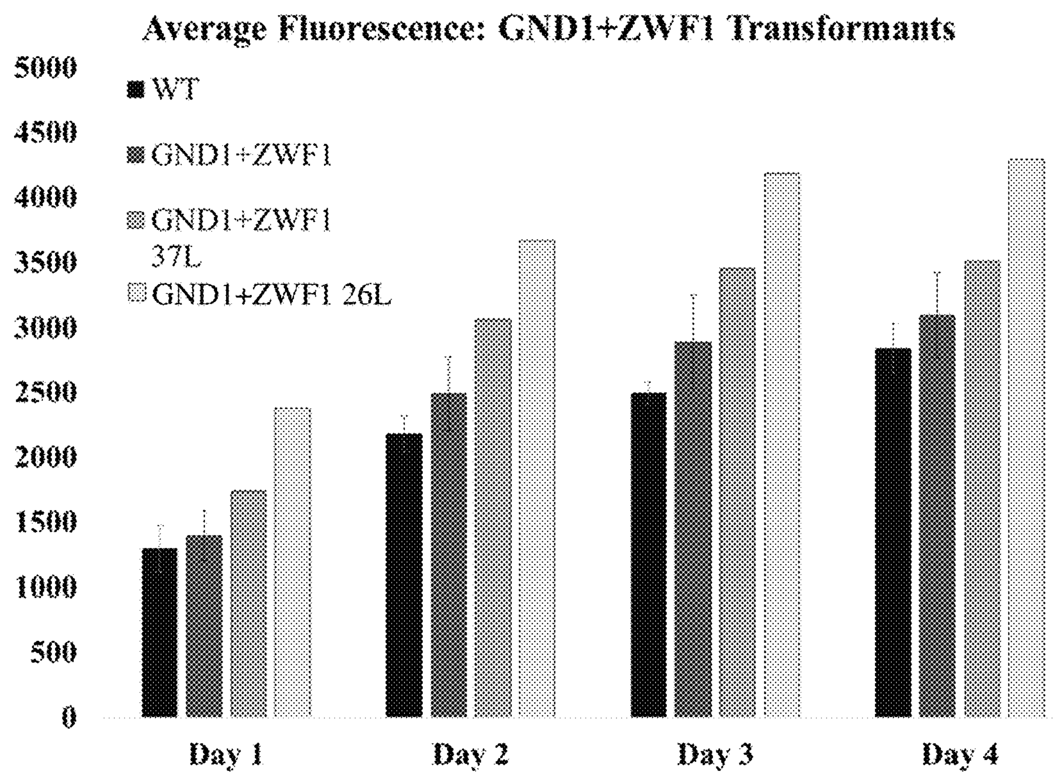

FIG. 25 shows dilution-corrected Bodipy fluorescence in wild-type *L. starkeyi* and GND1/ZWF1 transformants. Average wild-type fluorescence, average transformant fluorescence, transformant GND1+ZWF1 37L fluorescence, and transformant GND1+ZWF1 26L fluorescence are shown.

Figure 26:
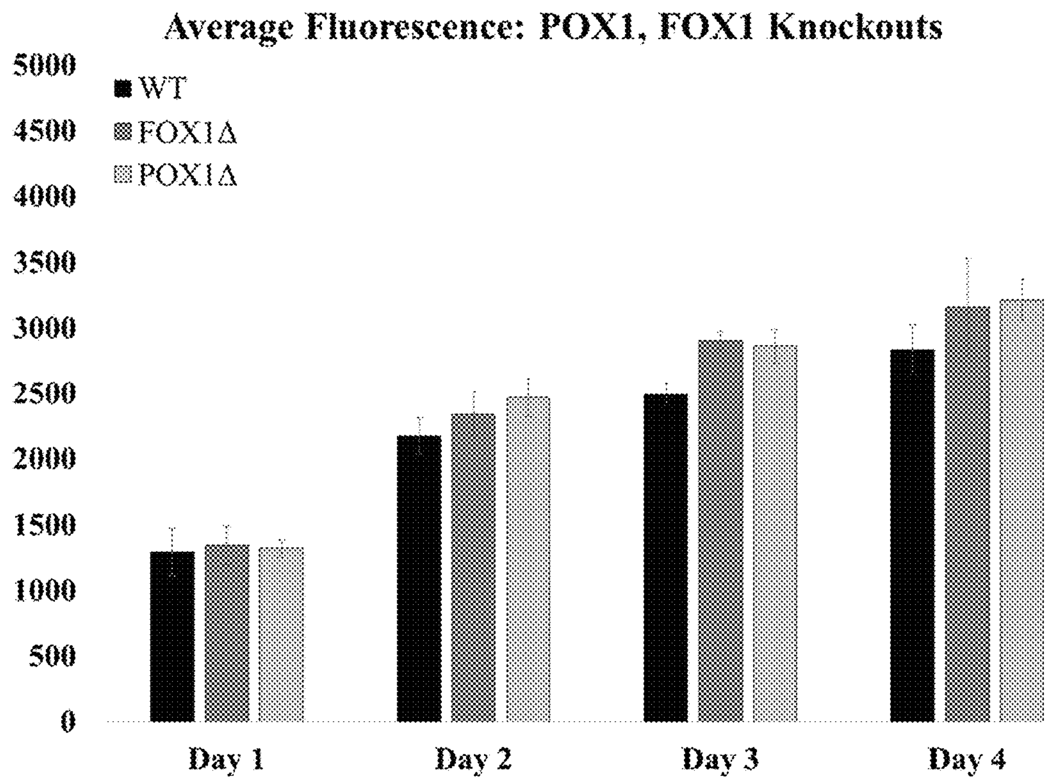

FIG. 26 shows dilution-corrected Bodipy fluorescence in wild-type *L. starkeyi* and FOX1 and PDX1 knockouts.

Figure 27:
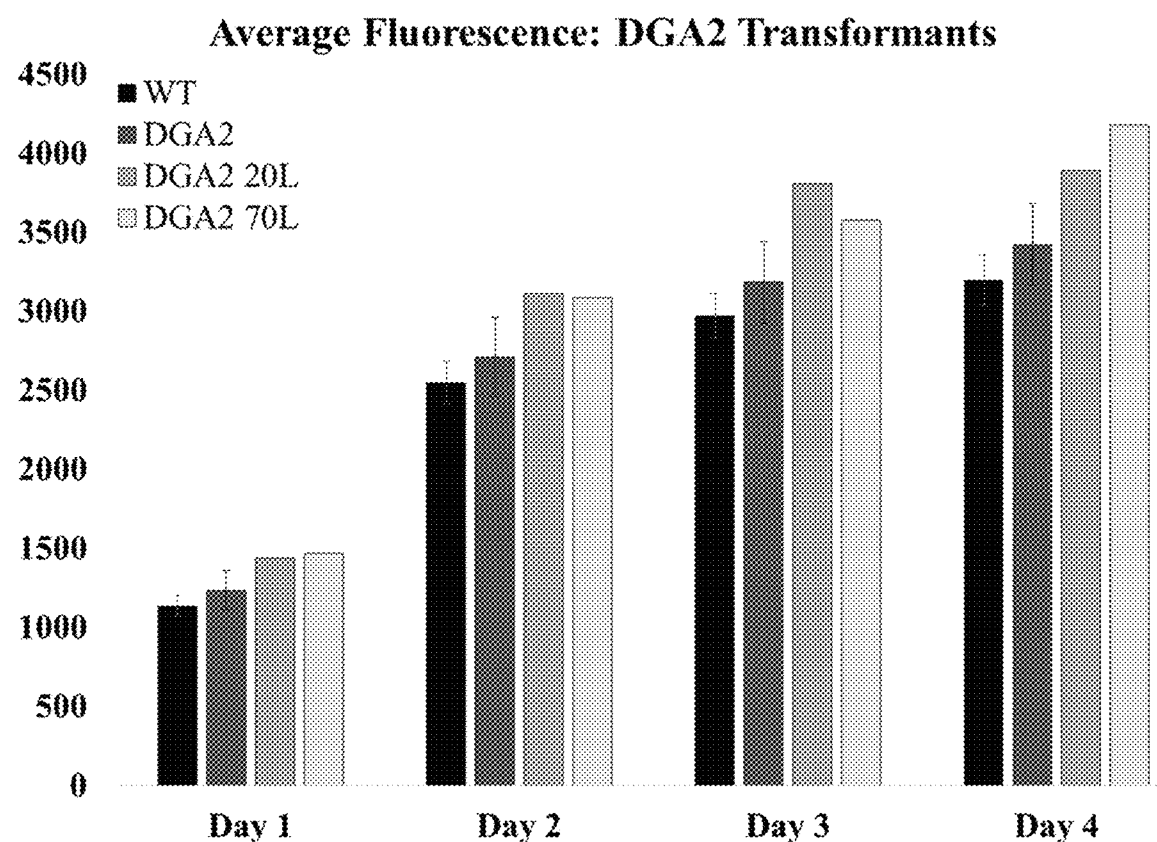

FIG. 27 shows dilution-corrected Bodipy fluorescence in wild-type *L. starkeyi* and DGA2 transformants. Average wild-type fluorescence, average transformant fluorescence, transformant DGA2 20L fluorescence, and transformant DGA2 70L fluorescence are shown.

Figure 28:
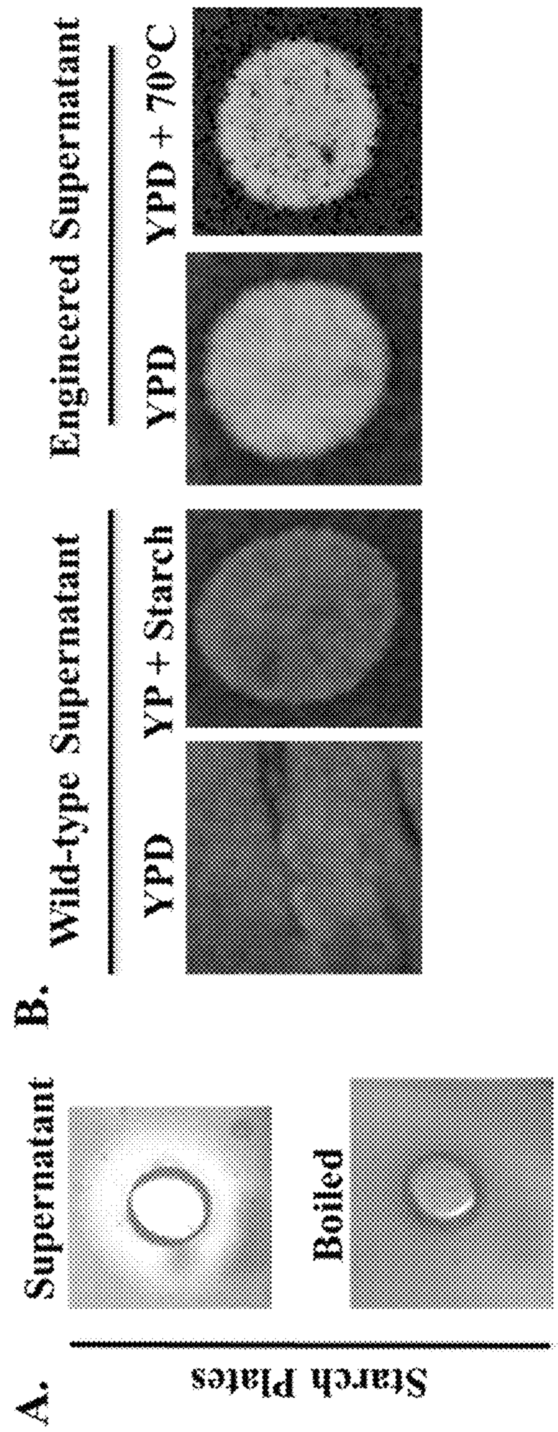

FIG. 28 shows an engineered yeast constitutively secreting a glucoamylase that retains activity following incubation for 1 hour at 70° C. A) Supernatant of a wild-type *L. starkeyi* culture conditioned to secrete enzyme incubated on 1% corn starch plates prior to (top) or after (bottom) boiling. The presence of a clearing zone indicates starch hydrolytic activity, which is lost after boiling. B) Supernatant of wild-type cells display glucoamylase activity when cultured in starch containing media, but not YPD (left two boxes). In this case, starch hydrolysis is indicated by a zone impervious to iodine staining on a 2% starch plate. The supernatant of the engineered strain exhibits activity when cultured on both YPD and starch containing media, and is retained following incubation for one hour at 70° C. (right two boxes).

DETAILED DESCRIPTION OF THE INVENTION

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

All protein identification (PID) numbers provided herein refer to proteins in the database of the Joint Genome Institute (JGI) of the United States Department of Energy. See, e.g., Jeffries 2013.

It is understood that the invention is not confined to the particular construction and arrangement of parts herein illustrated and described, but embraces such modified forms thereof as come within the scope of the claims.

Lipogenic (Oleaginous) Yeasts

An aspect of the invention encompasses bioengineered yeasts. The bioengineered yeasts are preferably derived from lipogenic yeasts. The methods of the invention are preferably performed with either native, non-bioengineered lipogenic yeasts or bioengineered lipogenic yeasts.

Lipogenic yeasts (also known as oleaginous yeasts) have been recognized for more than 50 years. They are defined as those that accumulate lipids in intracellular oil bodies to greater than 20% of their dry mass. In some yeasts, lipids have been reported to account for up to 71% of the cell's total biomass (Holdsworth et al. 1988). Out of the 1200 to 1500 known yeast species, only a fraction qualifies as lipogenic. *Lipomyces starkeyi* was among the earliest lipogenic yeasts studied (Lodder et al. 1952). Other known lipogenic yeasts include *Yarrowia lipolytica* (Papanikolaou et al. 2001), and species in the genera of *Rhodotorula, Cryptococcus* (Ratledge 2002), *Candida, Trichosporon* (Holdsworth et al. 1988), *Rhodosporidium, Sporidiobolus, Sporodobolomyces*, and various other ascomyceteous and basidiomycete genera amounting for a total of about 100 species (Garay et al. 2016).

Lipogenic yeasts belong to the larger taxonomic groups of filamentous ascomyceteous and basidiomycetous fungi. Exemplary lipogenic yeasts include yeasts from the genus Lipomyces, such as *L. starkeyi, L. anomalus, L. arxii, L. chichibuensis, L. doorenjongii, L. japonicus, L. kockii, L. kononenkoae, L. lipofer, L. mesembrius, L. oligophaga, L. orientalis, L. smithiae, L. spencermartinsiae, L. suomiensis, L. tetrasporus, L. yamadae, L. yarrowii*, and *L.* Sp.; yeasts from the genus *Yarrowia*, such as *Y. lipolytica, L. bubula, Y. deformans, Y. divulgata, Y. keelungensis, Y. porcina, Y. yakushimensis*, and *Y.* Sp.; yeasts from the genus *Candida*, such as *C.* Sp.; yeasts from the genus *Hansenula*, such as *H. polymorpha*; yeasts from the genus *Cunninghamella*, such as *S. bigelovii* sp nov CGMCC 8094, *S. echinulate, S. blakesleeana* JSK2, and *S.* Sp. *Salicorn* 5; yeasts from the genus *Mortierella*, such as *M. alpina, M. isabellina*, and *M.* Sp.; yeasts from the genus *Rhodosporidium*, such as *R. toruloides, R. babjevae, R. diobovatum, R. fluviale, R. kratochvilovae, R. paludigenum, R. sphaerocarpum, R. araucariae, R. colostri, R. dairenensis, R. graminis, R. lusitaniae*, and *R. mucilaginosa*; yeasts from the genus *Sporidiobolus*, such as *S. johnsonii, S. pararoseus, S. ruineniae, S. ruineniae*, and *S. salmonicolor*; yeasts from the genus *Sporobolomyces*, such as *S. bannaensis, S. beijingensis, S. carnicolor, S. metaroseus, S. odoratus, S. poonsookiae, S. singularis*, and *S. inositophilus*; yeasts from the genus *Occultifur*, such as *O. externus*; yeasts from the genus *Rhodotorula*, such as *R. bogoriensis, R. hylophila, R. glutinis*, and *R. rhodochrous*; yeasts from the genus *Trichosporon*, such as *T. fermentans, T. oleaginosus* ATCC 20509, and *T. cutaneum*; and yeasts from the genus *Cryptococcus*, such as *C. curvatus* and *C.* Sp.

Certain filamentous fungi and unicellular algae can also be lipogenic. These include filamentous fungi from the genus *Aspergillus*, such as *A. nidulans*, and from the genus *Mucor*, such as *M. circinelloides* and *M. rouxii*. Lipogenic algae include species from the genus *Scenedesmus*, such as *S. quadricauda.*

Nontraditional lipogenic yeasts have an innate ability to convert poorly metabolized wastes from ethanol fermentation into lipids, protein, and enzymes. Some lipogenic yeasts naturally make large amounts of lipids from a wide variety of carbon sources, and this prodigious capacity renders them amenable to many bioprocessing applications.

*Lipomyces starkeyi* is a particularly preferred lipogenic yeast in this regard. *L. starkeyi* can utilize many different substrates, including the oligosaccharides and sugars found in both agricultural waste products and the hydrolysates of lignocellulosic material (Calvey et al. 2014, Gong et al. 2012, Zhao et al. 2008).

Figure 1:
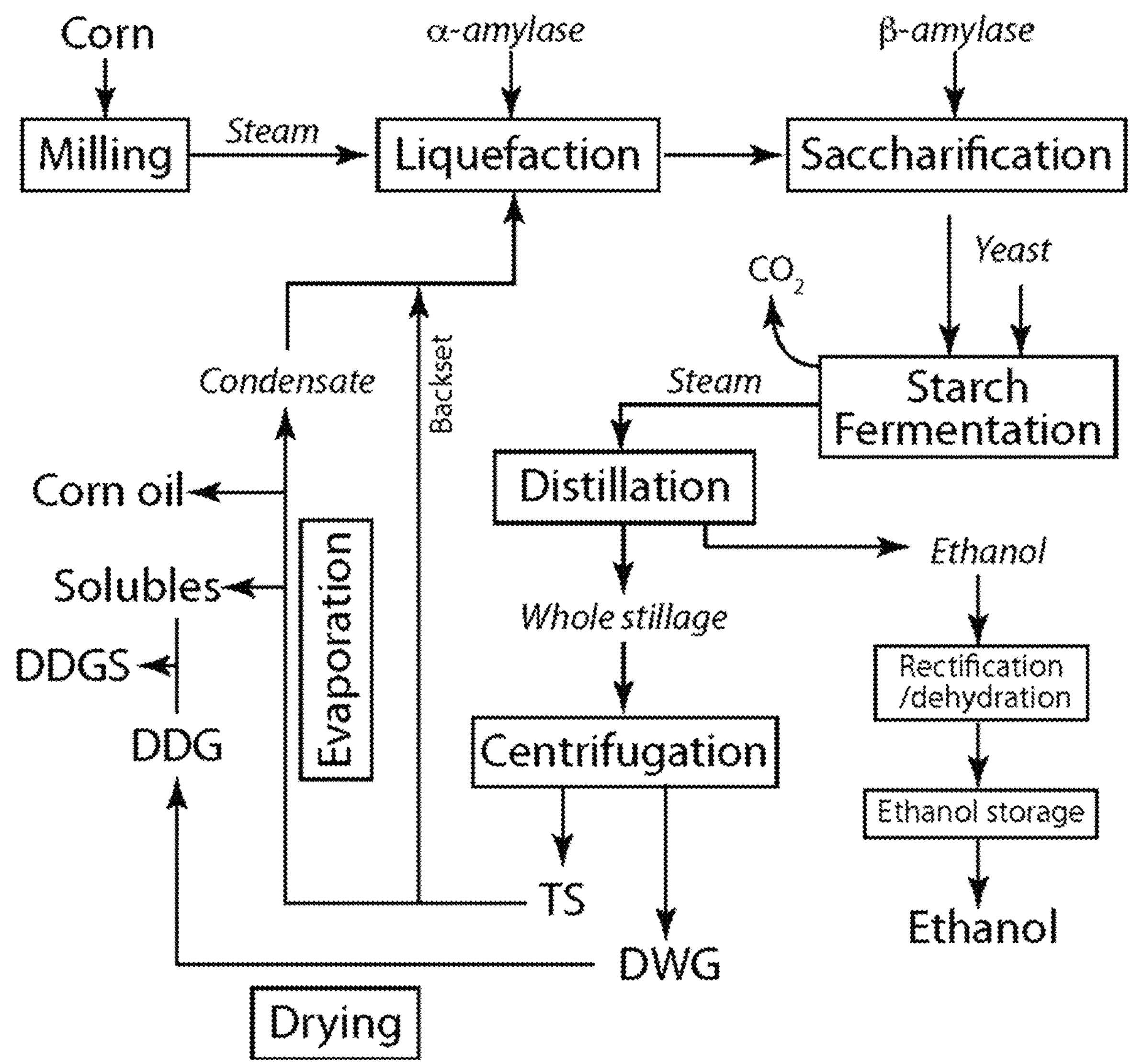
FIG. 1 shows a schema of a conventional dry mill ethanol process.
Figure 2:
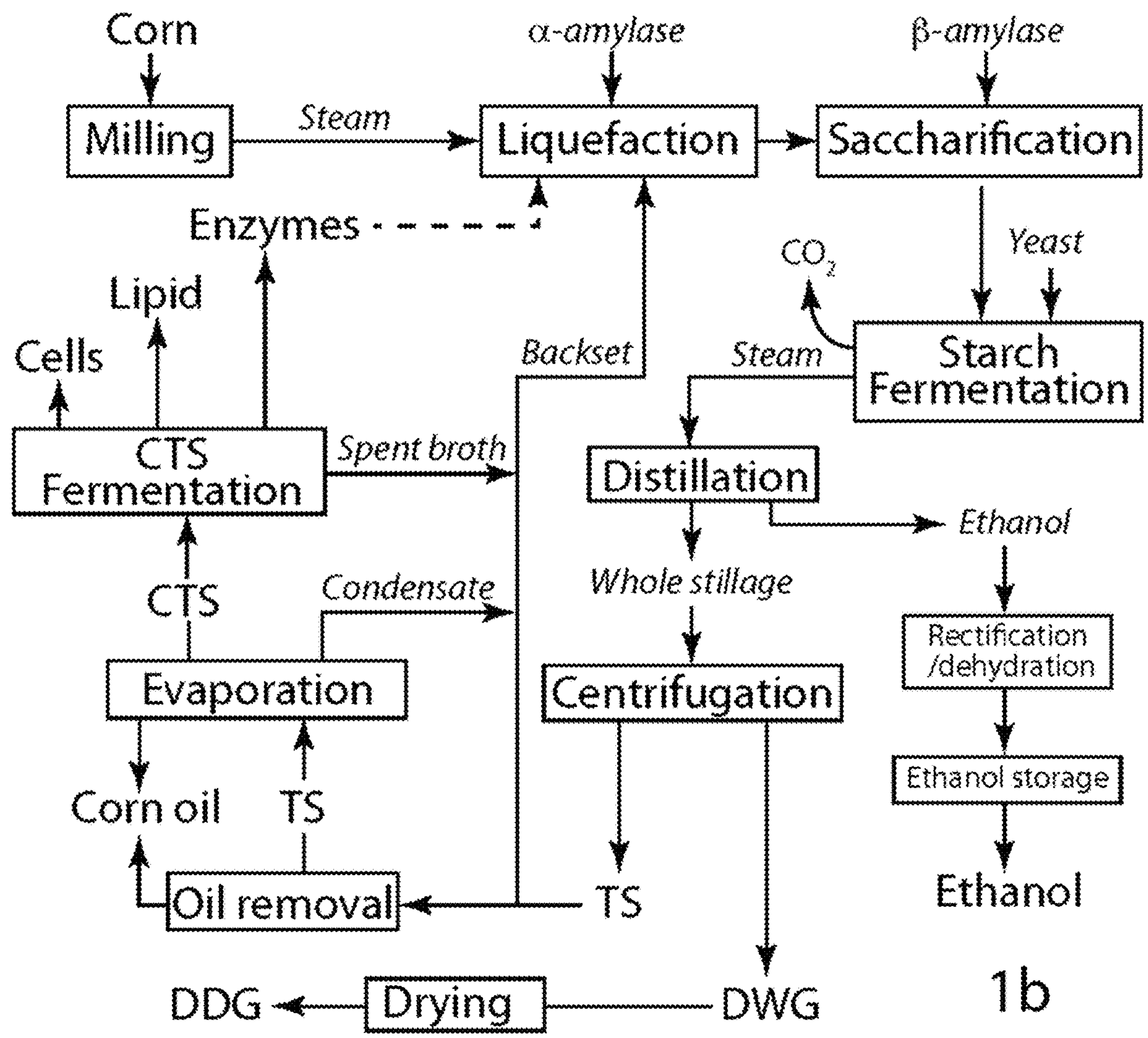
FIG. 2 shows a schema of a process of the present invention for converting stillage organics into yeast oil, protein, and enzymes.

*L. starkeyi* genes of notable importance include 24 glycoside hydrolases, three alpha-amylases, a highly versatile dextranase to metabolize the lateral starch side chains, and 15 copies of maltase that convert oligosaccharides into glucose (Riley et al. 2016, Kang et al. 2005). Overproduction and secretion of the thermostable alpha-amylase and dextranase found in *L. starkeyi* are particularly useful for starch saccharification in the integrated process described here (FIG. 2).

The *L. starkeyi* genome also encodes at least two secreted β-1,4-glucosidases and four non-secreted β-1,4-glucosidases, all of which have cellulosic carbohydrate binding domains, and at least two endo-1,4-β-D-glucanases (cellulases) (Chen et al. 2008). These enzymatic activities are useful for hydrolyzing corn fiber or other agricultural residues for additional ethanol or biodiesel production.

An ensemble of lipogenic genes are found in the genome of *L. starkeyi*, along with the metabolic machinery to supply the acetyl-CoA and NADPH needed to support high levels of lipid biosynthesis. For example, *L. starkeyi* has two complete genes for pyruvate carboxylase (LsPYC1, LsPYC2). This enzyme combines $CO_2$ with pyruvate to make oxaloacetate, which in turn citrate synthase (LsCIT1, LsCIT2, LsCIT3) combines with acetyl-CoA to make citrate. Genes coding for the alpha and beta subunits of ATP:citrate lyase (LsACL1, LsACL2) are found in a tandem bidirectional operon. Likewise, the genome of *L. starkeyi* codes for two complete fatty acid synthase complexes (LsFAS1.1, LsFAS1.2; LsFAS2.1, LsFAS2.2) with each organized into tandem bidirectional operons. Most yeasts and fungi have only a single FAS complex with the alpha and beta-subunits occurring in different parts of the genome. Mitochondrial NAD-dependent malate dehydrogenase (MDm, LsMDH2; PID_5229), and cytosolic NAD-dependent malate dehydrogenase (MDc, LSMDH1; PID_3988) exist as single copies in wild type *L. starkeyi*. Tandem bidirectional operons or clusters of metabolically associated genes indicate close interdependence and coordinated regulation of genes comprising a metabolic trait (Jeffries 2013).

*L. starkeyi* yeast maintains a basal lipid content that increases throughout fermentation, which already meets or exceeds that of any other native lipogenic yeast or alga. The lipid profile produced by *L. starkeyi* is remarkably similar to that of palm oil, one of the most common biodiesel feedstocks, which indicates that a biodiesel produced from this species naturally has desirable fuel properties (Calvey et al. 2016).

*L. starkeyi* is generally regarded as safe (GRAS) and is easily propagated, rendering residual cells and cell proteins useful for fortifying livestock or other animal feeds (Collett et al. 2014). Lastly, its genome has been sequenced, which enables the use of rational metabolic engineering methodologies to target specific genes for overexpression or deletion. By simply altering the expression or regulation of genes already present in the genome it is possible to improve lipid production and accumulation on poorly utilized substrates or under conditions when lipogenesis would not normally occur.

*Lipomyces starkeyi* is among the yeasts that can metabolize glucose, xylose and cellobiose, which are the main sugars released from the hydrolysis of lignocellulosic materials (Pan et al. 2009). With *L. starkeyi*, optimal lipid production is attained when growing on a 2:1 mixture of glucose and xylose, the same ratio found in enzymatic hydrolysates. Some strains of *L. starkeyi* also produce lipid from glycerol.

The lipid profile of Lipomyces is similar to that of palm oil (Calvey et al. 2016), which is important for both food and fuel production. By developing technology that uses Lipomyces to produce biofuels from the hydrolysates of agricultural cellulosic residues as an alternative to seed-based oils, the present invention provides for generating fuel from a renewable, environmentally benign resource that does not compete with food production. Furthermore, biodiesel derived from non-food sources such as lignocellulosic hydrolysate is advantageous because it meets the criteria delineated under Renewable Fuel Standard 2 (RFS2), which mandates the increased use of advanced cellulosic biofuels.

In addition to yeasts, a large number of eukaryotic algae also accumulate lipids, particularly when cultivated under heterotrophic conditions (U.S. Pat. No. 8,110,670). These eukaryotic algae can also be used in the methods of the present invention. One advantage to using lipogenic yeasts over algae, however, is that they can be grown readily in bioreactors and, unlike heterotrophically cultivated lipogenic algae, lipogenic yeasts can be cultivated on a wide range of organic substrates.

Lipid accumulation typically occurs when a readily assimilated carbon source is present in excess and nitrogen is limiting (Wei et al. 2009, Zhu et al. 2012). For example, when *L. starkeyi* transitions into a nitrogen-limited environment the biosynthetic pathways dependent on abundant nitrogen shut down and lipogenesis becomes the dominant metabolic feature of the cell. The cells continue to assimilate carbon, and in the absence of new cell growth, they store it as triacylglycerols. The most readily assimilated lipogenic carbon source is typically glucose (Ratledge 2002), and xylose has been reported to increase lipid accumulation even more (Gong et al. 2012, Zhao et al. 2008). Other substrates include cellobiose, glycerol, oligosaccharides, various industrial organic byproducts and hydrolysate from non-edible cellulosic feedstocks (Vicente et al. 2010). The yeasts engineered herein are capable of producing lipid when glucose is limited and carbon organics and nitrogen are in abundance.

Any or all of the genes described above can be driven by promoters that may be regulated or constitutive, strong, moderately strong or weak in *L. starkeyi* to modulate their activity therein. Alternately these genes may be deleted or inactivated. Likewise genes for metabolic pathways competing with the desired product of the genes described above may be modulated, deleted, or inactivated in order to improve the desired product or its formation rate.

Any or all of the genes described above in *L. starkeyi* can be incorporated in any other lipogenic yeast to confer similar benefits therein.

Biochemistry of Lipid Synthesis by Yeasts

Figure 3:
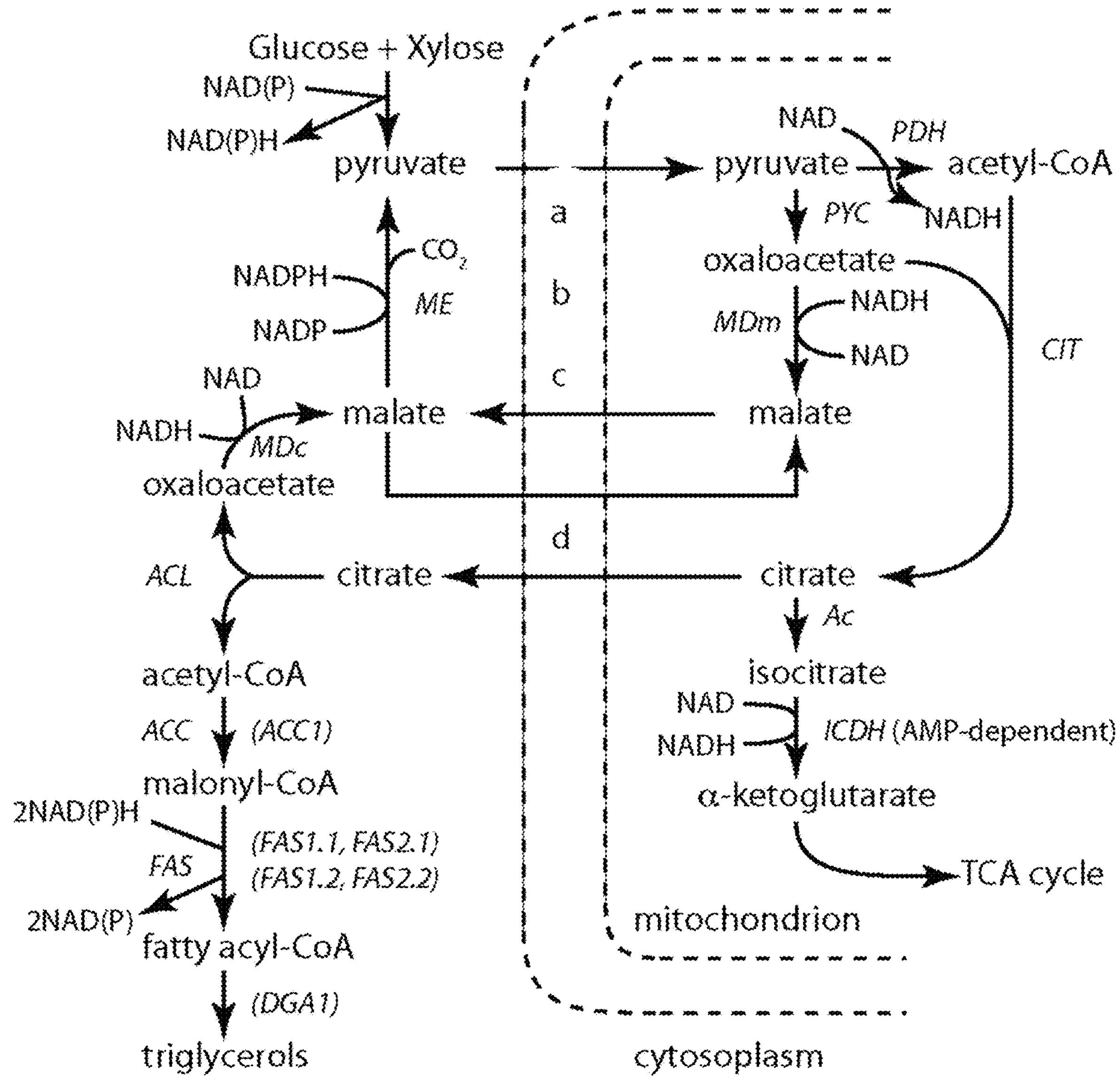
FIG. 3 shows a schema of intermediary metabolism linked to fatty acid biosynthesis in yeast. PDH, pyruvate dehydrogenase; PYC Pyruvate carboxylase; Ac, aconitase; ME malic enzyme; MDc malate decarboxylase, cytosolic; MDm malate dehydrogenase, mitochondrial; ACL ATP.

The biochemistry of lipid synthesis by yeasts is outlined in FIG. 3. Pyruvate is transported from the cytosol into the mitochondrion where pyruvate carboxylase (PYC) combines $CO_2$ with pyruvate to make oxaloacetate, and pyruvate dehydrogenase (PDH) oxidizes pyruvate to acetyl-CoA and NADH. Citrate synthase (CIT) combines with acetyl-CoA to make citrate while mitochondrial malate dehydrogenase (MDm) reduces oxaloacetate to malate.

The first step in response to nitrogen limitation is the activation of AMP deaminase, which cleaves adenosine monophosphate (AMP) into inosine monophosphate (IMP) and ammonia ($NH_4$). This activation lowers the intracellular concentrations of AMP, which inhibits the TCA cycle at the level of isocitrate dehydrogenase (ICDH), whose function is uniquely dependent on AMP in lipogenic yeasts (Ratledge 2004).

Significant evidence exists to support this mechanism. Intracellular AMP concentrations fall 11-fold within 24 hours after a transition to nitrogen limitation (Boulton et al. 1983). Also, assays of the Lipomyces ICDH1/2 enzyme show that its activity decreases about 5-fold when cells are transferred to a nitrogen-limiting medium (Tang et al. 2009). Activation of AMP deaminase and decreases in ICDH activity result in the accumulation of isocitrate and citrate (Boulton et al. 1983, Tang et al. 2009). Furthermore, lipid-accumulating Lipomyces cells display higher ACL enzymatic activity than proliferating cells (Naganuma et al. 1987).

When ICDH is no longer active, but the flux of glycolysis to pyruvate continues, isocitrate accumulates in the mitochondria and then equilibrates with citrate via isomerization. Citrate is exported into the cytosol via the citrate efflux system, which transports citrate out of the mitochondria in exchange for malate. The reduction in NADH formation by ICDH also results in less need for oxygen uptake and a lower rate of ATP synthesis.

Next, ATP:citrate lyase (ACL) catalyzes the cleavage of citrate into oxaloacetate and acetyl-CoA. This reaction is thought to be the primary source of the acetyl-CoA used for lipid synthesis and has been recognized as a key to efficient lipid production in lipogenic yeasts. ACL occurs in all lipogenic yeasts, but not in non-oleaginous species, which suggests a central role in lipid accumulation (Ratledge 2002, Evans et al. 1985). In the presence of CoA and ATP this enzyme cleaves citrate to acetyl-CoA and oxaloacetate, and supplies acetyl-CoA for lipid synthesis (Ratledge 1987). ACL is a dimeric protein with alpha and beta-subunits coded for by ACL1 and ACL2, which occur in a tandem bidirectional operon in the *Lipomyces starkeyi* genome (Jeffries 2013). The holoenzyme has a high affinity for citrate and ATP and is inhibited by ADP, glucose 6-phosphate, palmitoyl-CoA, and oleoyl-CoA. These allosteric inhibitors indicate that low ATP levels, high glycolytic flux, and the accumulation of fatty acid end products limit activity. The oxaloacetate formed by ACL can be converted to malate by a cytosolic malate dehydrogenase (MDc) and thus facilitate the export of more citrate from the mitochondrion.

Malate can also undergo conversion by malic enzyme (ME) into pyruvate and $CO_2$, while regenerating NADPH in the cytosol. The NADPH produced by the action of malic enzyme is thought to be the primary provider of reducing power for both fatty acid biosynthesis and desaturation reactions (Wynn et al. 1999). Lipid production may, however, draw on sources of NADPH in the cell such as the oxidative pentose phosphate pathway (Ratledge 2014). Specifically, two molecules of NADPH are required for each acetyl-CoA added to the growing fatty acyl chain during the standard fatty acid elongation cycle on the fatty acid synthase (FAS) complex (Ratledge 2004).

Malic enzyme (ME) has a high affinity for malate, and is only weakly inhibited by citrate, pyruvate, oxaloacetate, and ATP. ME is found in all lipogenic yeasts and its activity disappears following the period of active lipid accumulation. In contrast, acetyl-CoA carboxylase (ACC), fatty acid synthase (FAS), diacylglycerol acyltransferase (DGA), ATP:citrate lyase (ACL) and the NADPH-generating enzymes glucose-6-phosphate dehydrogenase, 6-phosphogluconate dehydrogenase and NADP(+):isocitrate dehydrogenase, do not demonstrate any changes in activities correlating with the accumulation of storage lipid (Wynn et al. 1999). ME therefore appears to be a source of NADPH for lipogenesis and a target for modification.

Metabolic pathways are often regulated at the first committing step. In this case, synthesis of malonyl-CoA, which is catalyzed by acetyl-CoA carboxylase (ACC), is a limiting step in attaining high titers of fatty acids and polyketides. Some versions of acetyl-CoA carboxylase are deactivated by a serine/threonine protein kinase, which is in turn activated by AMP. This relationship causes the acetyl-CoA carboxylase to be inactivated when glucose is depleted. To prevent this deactivation, a site-directed mutation is introduced in the serine residues of acetyl-CoA carboxylase that are phosphorylated by the AMP-activated protein kinase (AMPK). By converting these serines in Acct into an alanine or other non-serine and non-threonine residue, phosphorylation and inactivation is avoided. When the mutated gene is introduced into a host, acetyl-CoA carboxylase activity and total lipid accumulation increase.

Overexpression of the *L. starkeyi* ACC1 and GPD1 genes increase lipid production. Overexpression of ACC1, GUT2, and GUT1 also increases lipid production. In the case of GUT2 and GUT1 overexpression, higher levels of the coded proteins should increase the uptake of glycerol from thin stillage. In the case of ACC1 (acetyl-CoA carboxylase) overexpression and modification, altering the regulation should increase the formation of malonyl-CoA as a precursor for lipid synthesis and thereby increase the flux of malonyl-CoA into malonyl transferase which is an enzymatic activity of fatty acid synthase (FAS1).

Enzymes Involved in Substrate Assimilation

Lipomyces species and other lipogenic yeasts produce active amylases and other enzymes that degrade polysaccharides, and so are able to produce lipids from starch. *L. starkeyi* and other lipogenic yeasts also use a wide range of other polysaccharides (Gallagher et al. 1991, Punpeng et al. 1992, Steyn et al. 1995, Bignell et al. 2000, Ryu et al. 2000, Wilkie et al. 2000, Lee et al. 2003).

The genome of *Lipomyces starkeyi* contains numerous starch degrading alpha-amylase glycoside hydrolases (CAZY family GH13). Genes for several of these enzymes occur in clusters along with sugar transporters (e.g. *Lipomyces starkeyi* [PID_5034, PID_5035, PID_5036, PID_29016]; [PID_73677, PID_5097]; [PID_5097, PID_73677]; [PID_205534, PID_205437]; [PID_32360, PID_71673, PID_3625]). At least one of the alpha-amylases encoded in the *L. starkeyi* genome is thermostable (TAM1, PID_272826). Thermostable alpha-amylases are rarely found in yeasts. A gene for an amylo-alpha-1,6-glycosidase (dextranase) is also present (PID_5189) (Jeffries 2013). These features make *L. starkeyi* particularly suitable for lipid production when cultivated on starch (Gallagher et al. 1991, Punpeng et al. 1992).

Different strains of *Lipomyces starkeyi* show variable capacities for the assimilation of glycerol. The first step in glycerol metabolism is phosphorylation of glycerol by glycerol kinase (GUT1, PID_332345) to form glycerol-3-phosphate. This is followed by oxidation of glycerol-3-phosphate to dihydroxyacetone phosphate by an FAD-dependent glycerol-3-phosphate dehydrogenase (GUT2, PID_3942). Genes for both of these enzymes are present in *Lipomyces starkeyi* NRRL Y-11557 (Jeffries 2013).

Beta-1,4-endo-glucanase (BGL; GH5) depolymerizes glucan oligosaccharides. The genome of *L. starkeyi* encodes at least two GH5 cellulases, EGC1 and EGC2 (PID_72543 and PID_5513). The gene EGC1 is adjacent to a HXT2 sugar transporter (PID_4247) in the *Lipomyces starkeyi* genome. The HXT2 imports cellobiose (or cellulooligosaccharides). Beta-glucosidase (BGL; EC 3.2.1.21; GH3) is involved in the bioconversion of cellobiose to glucose. The genome of *Lipomyces starkeyi* encodes six putative enzymes in this family. At least one appears to be highly expressed (PID_69491) and at least two appear to be secreted (PID_147 and PID_5081). Several of the genes for GH3 proteins are proximally associated with genes coding for HXT2 sugar transporters (PID_3714, PID_334883, PID_7343).

Such proximal clustering of genes having associated physiological functions indicates that *L. starkeyi* has evolved for efficient use of beta- and alpha-linked glucans such as cellulose and starch.

The genome of *L. starkeyi* also contains a putative "glycoside hydrolase Family 61" auxiliary redox enzyme for cellulose hydrolysis (PID_61479) (Jeffries 2013). This protein includes a secretion signal and occurs rarely in ascomyceteous yeasts (Riley et al. 2016). This enzyme family is now known to not belong to the glycoside hydrolases, but rather is a "lytic polysaccharide mono-oxygenase" (LPMO). Enzymes belonging to this class are important components of commercial cellulase preparations (Cannella et al. 2014).

Glycerol kinase (GUT1) and glycerol-3-phosphate dehydrogenase (GUT2) are the first two genes involved in the assimilation of glycerol. Both of these genes are present in the genome of *L. starkeyi* NRRL-11557 (Jeffries 2013).

Any or all of the genes described above in *L. starkeyi* can be constitutively or overexpressed in *L. starkeyi* to enhance their activity therein.

Any or all of the genes described above in *L. starkeyi* can be incorporated in any other lipogenic yeast to confer similar benefits therein.

Genetic Targets for Metabolic Engineering

Various versions of the invention are directed to yeasts genetically modified to comprise one or more recombinant nucleic acids configured to express one or more proteins. The one or more recombinant nucleic acids are preferably configured to constitutively express or to overexpress the one or more proteins. The one or more recombinant nucleic acids preferably comprise one or more recombinant genes configured to constitutively express or to overexpress the one or more proteins. The expressed proteins include enzymes and other types of proteins such as transporters. If a cell endogenously expresses a particular protein, the nucleic acid expressing that protein may be modified to exchange or optimize promoters, exchange or optimize enhancers, or exchange or optimize any other genetic element that results in increased or constitutive expression of the proteins. Alternatively or additionally, one or more additional copies of a gene or coding sequence thereof may be introduced to the cell for enhanced expression of the proteins. If a cell does not endogenously express a particular protein, one or more copies of a recombinant nucleic acid configured to express that protein may be introduced to the cell for expression of the protein. The recombinant nucleic acid may be incorporated into the genome of the cell or may be contained on an extra-chromosomal plasmid. Techniques for genetic manipulation are described in further detail below. The genetically modified yeasts of the invention are also referred to herein as "recombinant," "engineered," or "bioengineered" yeasts, or other designations.

The recombinant yeasts of the invention may comprise one or more recombinant nucleic acids configured to express any one or more of the following proteins in any combination: an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme. The one or more recombinant nucleic acids preferably comprise one or more recombinant genes configured to express the above-referenced proteins.

For example, the recombinant yeasts of the invention may comprise one or more recombinant genes configured to express an acetyl-CoA carboxylase alone or with any one or more of an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express an alpha-amylase alone or with any one or more of an acetyl-CoA carboxylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express an ATP citrate lyase alone or with any one or more of an acetyl-CoA carboxylase, an alpha-amylase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a diacylglycerol acyltransferase alone or with any one or more of an acetyl-CoA carboxylase, an alpha-amylase, an ATP citrate lyase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a fatty acid synthase alone or with any one or more of an acetyl-CoA carboxylase, an alpha-amylase, an ATP citrate lyase, a diacylglycerol acyltransferase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol kinase alone or with any one or more of an acetyl-CoA carboxylase, an alpha-amylase, an ATP citrate lyase, a diacylglycerol acyltransferase, a fatty acid synthase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a 6-phosphogluconate dehydrogenase alone or with any one or more of an acetyl-CoA carboxylase, an alpha-amylase, an ATP citrate lyase, a diacylglycerol acyltransferase, a fatty acid synthase, a glycerol kinase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol-3-phosphate dehydrogenase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a malic enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a fatty acyl-CoA reductase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a delta-9 acyl-CoA desaturase, a glycerol-3-phosphate acyltransferase, a lysophosphatidate acyltransferase, a glucose- 6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a delta-9 acyl-CoA desaturase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glycerol-3-phosphate acyltransferase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a lysophosphatidate acyltransferase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a glucose-6-phosphate dehydrogenase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a glucose-6-phosphate dehydrogenase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a beta-glucosidase, a hexose transporter, a glycerol transporter, a glycoside hydrolase enzyme, and an auxiliary activity family 9 enzyme in any combination.

The recombinant yeasts of the invention may comprise one or more recombinant genes configured to express a beta-glucosidase alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a hexose transporter, a glycerol transporter, a glycoside hydrolase enzyme, and an auxiliary activity family 9 enzyme in any combination.

The recombinant yeasts of the invention may comprise one or more recombinant genes configured to express a hexose transporter alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a glycerol transporter, a glycoside hydrolase enzyme, and an auxiliary activity family 9 enzyme in any combination.

The recombinant yeasts of the invention may comprise one or more recombinant genes configured to express a glycerol transporter alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycoside hydrolase enzyme, and an auxiliary activity family 9 enzyme in any combination.

The recombinant yeasts of the invention may comprise one or more recombinant genes configured to express a glycoside hydrolase enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, and an auxiliary activity family 9 enzyme in any combination.

The recombinant yeasts of the invention may comprise one or more recombinant genes configured to express an auxiliary activity family 9 enzyme alone or with any one or more of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, and a glycoside hydrolase enzyme in any combination.

Acetyl-CoA carboxylases include enzymes falling under Enzyme Commission (EC) number 6.4.1.2. An exemplary acetyl-CoA carboxylase that may be expressed includes Acc1 (SEQ ID NO:2) encoded by Acc1 (SEQ ID NO:1) from *L. starkeyi* (PID_72701) Other exemplary acetyl-coA carboxylases include Acc1 mutants that comprise a residue other than serine at a position corresponding to position 1146 of SEQ ID NO:2. The residue at position 1146 is preferably a residue other than serine and threonine. The residue at position 1146 may be any amino acid other than serine or, more preferably any amino acid other than serine and threonine. The residue at position 1146 may be alanine.

Other exemplary acetyl-coA carboxylases include Acc1 mutants that comprise serine at a position corresponding to position 639 of SEQ ID NO:2 and a residue other than serine and threonine at a position corresponding to position 1146 of SEQ ID NO:2.

Alpha-amylases include enzymes falling under EC number 3.2.1.1. Exemplary alpha-amylases that may be expressed include the secreted alpha-amylase designated by PID_3772 (SEQ ID NO:4) encoded by the corresponding nucleic acid (SEQ ID NO:3) from *Lipomyces starkeyi*, the thermostable α-amylase designated by PID_272826 (SEQ ID NO:6) encoded by the corresponding nucleic acid (SEQ ID NO:5) from *L. starkeyi*, and a chimera of the secreted alpha-amylase and the thermostable α-amylase (SEQ ID NO:8) encoded by the corresponding nucleic acid (SEQ ID NO:7).

ATP citrate lyases include enzymes falling under EC number 2.3.3.8. An exemplary ATP citrate lyase that may be expressed includes the alpha subunit Acl1 (SEQ ID NO:10) encoded by Acl1 (SEQ ID NO:9) and the beta subunit Acl2 (SEQ ID NO:12) encoded by Acl2 (SEQ ID NO:11) from *L. starkeyi*. The alpha and beta subunits are preferably expressed as a pair.

Diacylglycerol acyltransferases (DGAs) include enzymes falling under EC number 2.3.1.20. Exemplary diacylglycerol acyltransferases that may be expressed include a 1233 variant of DGA1 (SEQ ID NO:14) encoded by DGA1-1233 (SEQ ID NO:13), a 1389 variant of DGA1 (SEQ ID NO:16) encoded by DGA1-1389 (SEQ ID NO:15), and DGA2 (SEQ ID NO:58) encoded by DGA2 (SEQ ID NO:57), all derived from *L. starkeyi*. The 1233 variant of DGA1 is identical to the 1389 variant except that it lacks the first 52 residues of the 1389 variant. The 1233 variant unexpectedly confers enhanced lipogenic properties compared to the 1389 variant. Accordingly, preferred diacylglycerol acyltransferases of the invention lack a sequence corresponding to positions 1-52 of SEQ ID NO:16.

Fatty acid synthases (FASs) include enzymes falling under EC number 2.3.1.85. Exemplary fatty acid synthases that may be expressed include any combination of alpha and beta fatty acid synthase subunits from *L. starkeyi*. Alpha fatty acid synthase subunits from *L. starkeyi* include FAS2.1 (SEQ ID NO:18) encoded by FAS2.1 (SEQ ID NO:17) and FAS2.2 (SEQ ID NO:22) encoded by FAS2.2 (SEQ ID NO:21). Beta fatty acid synthase subunits from *L. starkeyi* include FAS1.1 (SEQ ID NO:20) encoded by FAS1.1 (SEQ ID NO:19) and FAS1.2 (SEQ ID NO:24) encoded by FAS1.2 (SEQ ID NO:23). FAS2.1 is preferably expressed with FAS1.1, and FAS2.2 is preferably expressed with FAS1.2. However, FAS2.1 may be expressed with FAS1.2, and FAS2.2 may be expressed with FAS1.1.

Glycerol kinases include enzymes falling under EC number 2.7.1.30. Exemplary glycerol kinases that may be expressed include a 1602 variant of GUT1 (SEQ ID NO:26) encoded by GUT1-1602 (SEQ ID NO:25) and a 1617 variant of GUT1 (SEQ ID NO:28) encoded by GUT1-1617 (SEQ ID NO:27), both derived from *L. starkeyi*. The 1602 variant of DGA1 is identical to the 1617 variant except that it lacks the first 5 residues of the 1617 variant. Accordingly, some glycerol kinases of the invention lack a sequence corresponding to positions 1-5 of SEQ ID NO:28.

6-Phosphogluconate dehydrogenases include enzymes falling under EC number 1.1.1.44. An exemplary 6-phosphogluconate dehydrogenase that may be expressed includes GND1 (SEQ ID NO:30) encoded by GND1 (SEQ ID NO:29) from *L. starkeyi*.

Glycerol-3-phosphate dehydrogenases include enzymes falling under EC number 1.1.1.8. Exemplary glycerol-3-phosphate dehydrogenases that may be expressed include GPD1 (SEQ ID NO:32) encoded by GPD1 (SEQ ID NO:31) and the FAD-dependent glycerol-3-phosphate dehydrogenase GUT2 (SEQ ID NO:56) encoded by GUT2 (SEQ ID NO:55), both from *L. starkeyi*.

Malic enzymes include enzymes falling under EC numbers 1.1.1.38, 1.1.1.39, 1.1.1.40, and 83. An exemplary malic enzyme that may be expressed includes ME (SEQ ID NO:34) encoded by ME (SEQ ID NO:33) from *L. starkeyi*.

Fatty acyl-CoA reductases include enzymes falling under EC numbers 1.2.1, such as 1.2.1.84 and others. These enzymes include the preferred alcohol-forming fatty acyl-CoA reductases (EC 1.2.1.84). An exemplary fatty acyl-CoA reductase that may be expressed includes FALDR (SEQ ID NO:36) encoded by FALDR (SEQ ID NO:35) from *Marinobacter aquaeolei*.

Delta-9 acyl-CoA desaturases include enzymes falling under EC number 1.14.19.1. An exemplary delta-9 acyl-CoA desaturase that may be expressed includes OLE1 (SEQ ID NO:38) encoded by OLE1 (SEQ ID NO:37) from *L. starkeyi*. In addition to or instead of expressing a delta-9 acyl-CoA desaturase, other fatty acid desaturases may be expressed, such as acyl-CoA (8-3)-desaturases (delta-5 desaturases) (EC 1.14.19.44) and acyl-CoA 6-desaturases (delta-6 desaturases) (EC 1.14.19.3).

Glycerol-3-phosphate acyltransferases include enzymes falling under EC number 2.3.1.15. An exemplary glycerol-3-phosphate acyltransferase that may be expressed includes SCT1 (SEQ ID NO:40) encoded by SCT1 (SEQ ID NO:39) from *L. starkeyi*.

Lysophosphatidate acyltransferases include enzymes falling under EC number 2.3.1.51. An exemplary lysophosphatidate acyltransferase that may be expressed includes SLC1 (SEQ ID NO:42) encoded by SLC1 (SEQ ID NO:41) from *L. starkeyi*.

Glucose-6-phosphate dehydrogenases include enzymes falling under EC number 1.1.1.49. An exemplary glucose-6-phosphate dehydrogenase that may be expressed includes ZWF1 (SEQ ID NO:44) encoded by ZWF1 (SEQ ID NO:43) from *L. starkeyi*.

Beta-glucosidases include enzymes falling under EC number 3.2.1.21. An exemplary beta-glucosidase that may be expressed includes BGL1.1 (SEQ ID NO:46) encoded by BGL1.1 (SEQ ID NO:45) from *L. starkeyi*.

Hexose transporters include proteins falling under the Hxt family (e.g., Hxt1, Hxt2, Hxt3, Hxt4, Hxt5, Hxt6, Hxt7, Hxt8, Hxt9, Hxt11, etc.). An exemplary hexose transporter that may be expressed includes Hxt2.2 (SEQ ID NO:48) encoded by Hxt2.2 (SEQ ID NO:47) from *L. starkeyi*.

Glycerol transporters that may be expressed include the glycerol/H+symporters STL1 (SEQ ID NO:64) encoded by STL1 (SEQ ID NO:63) and STL2 (SEQ ID NO:66) encoded by STL2 (SEQ ID NO:65) from *L. starkeyi*. Glycerol transporters that may be expressed also include the glycerol facilitator FPS1 (SEQ ID NO:68) encoded by FPS1 (SEQ ID NO:67) from *L. starkeyi*.

Glycoside hydrolases include a number of families. Preferred glycoside hydrolases that may be expressed include glycoside hydrolase family 5 enzymes. Glycoside hydrolase family 5 enzymes include endoglucanases (EC 3.2.1.4), beta-mannanases (EC 3.2.1.78), exo-1,3-glucanases (EC 3.2.1.58), endo-1,6-glucanases (EC 3.2.1.75), xylanases (EC 3.2.1.8), endoglycoceramidases (EC 3.2.1.123), and trehalases (EC 3.2.1.28). Preferred glucosidase hydrolase family 5 enzymes that may be expressed include endoglucanases. Exemplary endoglucanases that may be expressed include EGC1 (SEQ ID NO:50) encoded by EGC1 (SEQ ID NO:49) from *L. starkeyi* and EGC2 (SEQ ID NO:52) encoded by EGC2 (SEQ ID NO:51) from *L. starkeyi*. Exemplary trehalases that may be expressed include the "neutral" trehalase NTH1 (SEQ ID NO:60) encoded by NTH1 (SEQ ID NO:59) and the "acidic" trehalase ATH1 (SEQ ID NO:62) encoded by ATH1 (SEQ ID NO:61), both from *L. starkeyi.*

Auxiliary activity family 9 enzymes are copper-dependent lytic polysaccharide monooxygenases (LPMOs). These enzymes are involved in the cleavage of cellulose chains with oxidation of various carbons (C-1, C-4 and C-6). Auxiliary activity family 9 enzymes were originally classified as glycoside hydrolases under glycoside hydrolase family 61 (GH61). An exemplary auxiliary activity family 9 enzyme that may be expressed includes AAC9 (SEQ ID NO:54) encoded by AAC9 (SEQ ID NO:53) from *L. starkeyi.*

Other suitable proteins that may be expressed include those comprising polypeptide sequences at least about 80%, at least about 85%, at least about 90%, at least about 95%, at least about 97%, or at least about 99% identical to the sequences listed above. Other suitable proteins that may be expressed include orthologs and paralogs of the proteins listed above. Other suitable proteins that may be expressed include those comprising polypeptide sequences at least about 80%, at least about 85%, at least about 90%, at least about 95%, at least about 97%, or at least about 99% identical to orthologs and paralogs of the proteins listed above. The orthologs are preferably from lipogenic yeasts, such as any of the lipogenic yeasts described herein. The recombinant gene encoding the proteins may include introns or be devoid of introns or any or all other non-coding regions in the native gene. Any nucleotide sequences capable of expressing the polypeptide sequences encompassed herein are acceptable. Tremendous variation from the exemplary nucleotide sequences described herein is possible due to the redundancy in the genetic code and codon optimization.

Coding sequences of the above-mentioned proteins are preferably operably linked to a promoter. The promoter may be a constitutive promoter or an inducible promoter. Exemplary promoters that may be operably linked to the coding sequences of the above-mentioned proteins include the *L. starkeyi* ATPase 3900 promoter (SEQ ID NO:75), the *L. starkeyi* citrate synthase (CIT1) promoter (SEQ ID NO:76), the *L. starkeyi* fructose bisphosphate aldolase (FBA1) promoter (SEQ ID NO:77), the *L. starkeyi* glutamine synthetase (GLN1) promoter (SEQ ID NO:78), the *L. starkeyi* glyceraldehyde 3-phosphate dehydrogenase (TDH3) promoter (SEQ ID NO:79), the *L. starkeyi* pyruvate kinase (PYK1) promoter (SEQ ID NO:80), the *L. starkeyi* translation elongation factor (TEF1) promoter (SEQ ID NO:81), the *L. starkeyi* triosephosphate isomerase (TPI) promoter (SEQ ID NO:82), the *L. starkeyi* enolase (ENO1) promoter (SEQ ID NO:83), the copper inducible (CUP1) promoter (SEQ ID NO:84), or sequence variants at least about at least about 80%, at least about 85%, at least about 90%, at least about 95%, at least about 97%, or at least about 99% identical thereto.

Coding sequences of the above-mentioned proteins are preferably operably linked to a terminator. Exemplary terminators that may be operably linked to the coding sequences of the above-mentioned proteins include the *L. starkeyi* ATPase 3900 terminator (SEQ ID NO:85), the *L. starkeyi* fructose bisphosphate aldolase (FBA1) terminator (SEQ ID NO:86), the *L. starkeyi* glutamine synthetase (GLN1) terminator (SEQ ID NO:87), the *L. starkeyi* glyceraldehyde 3-phosphate dehydrogenase (TDH3) terminator (SEQ ID NO:88), the *L. starkeyi* pyruvate kinase (PYK1) terminator (SEQ ID NO:89), the *L. starkeyi* triosephosphate isomerase (TPI) terminator (SEQ ID NO:90), or sequence variants at least about at least about 80%, at least about 85%, at least about 90%, at least about 95%, at least about 97%, or at least about 99% identical thereto.

In addition to expressing any one or more of the proteins listed above, the recombinant yeasts of the invention may be modified to reduce or ablate the activity of one or more native or non-native proteins. The recombinant yeasts, for example, may comprise a modification that reduces or ablates the activity of one or more of the following native proteins: a delta-9 acyl-CoA desaturase, a glycerol-3-phosphate dehydrogenase, an acyl-CoA oxidase, a 3-hydroxyacyl-CoA dehydrogenase, and an enoyl-CoA hydratase.

Delta-9 acyl-CoA desaturases include enzymes falling under EC number 1.14.19.1. An exemplary delta-9 acyl-CoA desaturase whose activity may be reduced or ablated includes OLE1 (SEQ ID NO:38) encoded by OLE1 (SEQ ID NO:37) from *L. starkeyi*. In addition to or instead of reducing or ablating the activity of a delta-9 acyl-CoA desaturase, the activity of other fatty acid desaturases may be reduced or ablated, such as acyl-CoA (8-3)-desaturases (delta-5 desaturases) (EC 1.14.19.44) and acyl-CoA 6-desaturases (delta-6 desaturases) (EC 1.14.19.3).

Glycerol-3-phosphate dehydrogenases include enzymes falling under EC number 1.1.1.8. An exemplary glycerol-3-phosphate dehydrogenase whose activity may be reduced or ablated includes the FAD-dependent glycerol-3-phosphate dehydrogenase GUT2 (SEQ ID NO:56) encoded by GUT2 (SEQ ID NO:55) from *L. starkeyi.*

Acyl-CoA oxidases include enzymes falling under EC number 1.3.3.6. An exemplary acyl-CoA oxidase whose activity may be reduced or ablated includes PDX1 (SEQ ID NO:70) encoded by PDX1 (SEQ ID NO:69) from *L. starkeyi*. Acyl-CoA oxidases catalyze the first step of beta oxidation.

Enoyl-CoA hydratases include enzymes falling under EC number 4.2.1.17. An exemplary enoyl-CoA hydratase whose activity may be reduced or ablated includes FOX1 (SEQ ID NO:72) encoded by FOX1 (SEQ ID NO:71) from *L. starkeyi*. Enoyl-CoA hydratases catalyze the third step of beta oxidation.

3-Hydroxyacyl-CoA dehydrogenases include enzymes falling under EC number 1.1.1.35. An exemplary 3-hydroxyacyl-CoA dehydrogenase whose activity may be reduced or ablated includes FOX1 (SEQ ID NO:72) encoded by FOX1 (SEQ ID NO:71) from *L. starkeyi.* 3-hydroxyacyl-CoA dehydrogenases catalyze the second step of beta oxidation.

Certain enzymes are multifunctional and have more than one enzymatic activity. Examples include the FOX1 (SEQ ID NO:72) encoded by FOX1 (SEQ ID NO:71) from *L. starkeyi*, which has both 3-hydroxyacyl-CoA dehydrogenase and enoyl-CoA hydratase activities, and is thereby considered to be both a 3-hydroxyacyl-CoA dehydrogenase and an enoyl-CoA hydratase.

Other suitable proteins whose activity may be reduced or ablated include those comprising amino acid sequences at least about 80%, at least about 85%, at least about 90%, at least about 95%, at least about 97%, or at least about 99% identical to the sequences listed above. Other suitable proteins whose activity may be reduced or ablated include orthologs and paralogs of the proteins listed above. Other suitable proteins whose activity may be reduced or ablated include those comprising amino acid sequences at least about 80%, at least about 85%, at least about 90%, at least about 95%, at least about 97%, or at least about 99% identical to orthologs and paralogs of the proteins listed above.

A modification that reduces or ablates the activity of a gene product such as a protein is referred to herein as a "functional deletion." "Functional deletion" or its grammatical equivalents refers to any modification to a microorganism that ablates, reduces, inhibits, or otherwise disrupts production of a gene product, renders a produced gene product non-functional, or otherwise reduces or ablates a produced gene product's activity. Accordingly, in some instances, a gene product that is functionally deleted means that the gene product is not produced by the microorganism at all. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. Various methods for introducing genetic modifications are well known in the art and include homologous recombination, among other mechanisms. See, e.g., Green et al., *Molecular Cloning: A laboratory manual,* 4$^{th}$ ed., Cold Spring Harbor Laboratory Press (2012) and Sambrook et al., *Molecular Cloning: A Laboratory Manual,* 3$^{rd}$ ed., Cold Spring Harbor Laboratory Press (2001). In some versions, functional deletion can be accomplished by expressing ribozymes or antisense sequences that target the mRNA of the gene of interest. Functional deletion can also be accomplished by inhibiting the activity of the gene product, for example, by chemically inhibiting a gene product with a small-molecule inhibitor, by expressing a protein that interferes with the activity of the gene product, or by other means. In some versions, the functional deletion may comprise an activity-reducing or activity-ablating mutation in the endogenous gene. The activity-reducing or activity-ablating mutation in the endogenous gene may comprise a nucleotide substitution in the endogenous gene, a nucleotide insertion in the endogenous gene, a partial deletion of the endogenous gene, and/or a complete deletion of the endogenous gene.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of the gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding microorganism. As used herein, "corresponding microorganism" refers to a microorganism of the same species having the same or substantially same genetic and proteomic composition as a microorganism of the invention, with the exception of genetic and proteomic differences resulting from the manipulations described herein for the microorganisms of the invention.

The yeasts of the invention with the modifications described herein preferably exhibit a property selected from the group consisting of increased lipid production, increased lipid secretion, increased lipid production under nitrogen-rich conditions, increased lipid yield, increased lipid secretion under nitrogen-rich conditions, increased enzyme production, increased enzyme secretion, increased carbohydrase production, increased carbohydrase secretion, increased growth rates, and/or increased organic consumption, such as increased glycerol consumption and/or and increased disaccharide (cellobiose and/or trehalose) consumption relative to a non-recombinant control. "Carbohydrase" refers to any enzyme capable of breaking down a carbohydrate, such as amylases, cellulases, glucosidases, etc.

Nitrogen-rich conditions exist when the form, the amount, or form and amount of nitrogen biologically available to the cell exceeds the amount of carbon source necessary for balanced cell growth. The form of nitrogen refers to the chemical form in which it is supplied to the cells. An easily assimilated nitrogen source includes amino acids or extracts of yeast cells. These nitrogen sources require less metabolic energy for assimilation and provide carbon at the same time. A less readily assimilated nitrogen source includes inorganic salts of ammonium or nitrate or nitrogen supplied as urea. Elemental nitrogen or nitrogen bound in insoluble minerals are not generally considered biologically available to fungi. Nitrogen-rich conditions can exist when either readily assimilated or less-readily assimilated nitrogen sources are provided to a cell in excess of the amount of carbon required for protein, nucleic acid and cell wall synthesis.

Nitrogen-poor conditions can exist when the amount of readily available or less readily available nitrogen supplied is substantially less than the amount of available carbon source that can be assimilated. A nitrogen-poor or nitrogen-limiting condition could also exist when an easily assimilated nitrogen source is supplied slowly or in a slow-release formulation.

As in the case of the nitrogen supply, the carbon source can be readily assimilated, less readily assimilated, poorly assimilated or not assimilated. The cell can use readily assimilated carbon source such as glucose to rapidly generate metabolic energy. A carbon source such as glycerol, cellobiose or other oligosaccharides might or might not be readily assimilated depending on the enzymes available for its metabolism and the conditions of growth such as the supply of oxygen.

A nitrogen-rich condition in a native organism can be identified as a concentration above a nitrogen-limited concentration, wherein the nitrogen-limited concentration includes all concentrations at or below the concentration of nitrogen in which any decreases thereof increase the amount of lipid produced and/or accumulated by the organism.

Acetyl-CoA carboxylase and diacylglycerol acyltransferase are both preferred targets for increasing lipid production. Overexpression of acetyl-CoA carboxylase results in increased rates of fatty acid biosynthesis and fatty acid content. The Acct acetyl-CoA carboxylase of *L. starkeyi* has serine residues at positions corresponding to 639 and 1146 of SEQ ID NO2. The inventors have determined that the serine at position 1146 is responsible for downregulating ACC1 activity upon post-translational modification. Certain versions of this invention modify the serine at position 1146 to an amino acid other than serine or threonine, such as alanine or any other amino acid, to prevent this downregulation.

Overexpression of diacylglycerol acyltransferase leads to an increase in lipid production. This lipid production is increased even further following overexpression of acetyl-CoA carboxylase. The present inventors surmise that a sink for triglyceride synthesis, such as through high expression of diacylglycerol acyltransferase, should be present in order for overexpression of acetyl-CoA carboxylase to be fully effective.

One of the prerequisites of oleaginous organisms is the ability to produce a continuous supply of acetyl-CoA precursors in the cytosol. ATP citrate lyase acts as the primary source of cytosolic acetyl-CoA in these species, and is believed to be one of the rate limiting steps of lipid biosynthesis. The activity of ATP citrate lyase correlates well with the specific rate of lipid biosynthesis in *L. starkeyi*. In Lipomyces both intracellular and extracellular citrate levels rise in response to nitrogen limitation (Holdsworth et al. 1988). Citrate accumulation may represent a bottleneck, which could be overcome by increasing ATP citrate lyase activity in the cytosol or citrate synthase (CS) in the mitochondria.

NADPH, which is required for lipid biosynthesis, is largely supplied by the oxidative pentose phosphate pathway (PPP). Native lipogenic yeasts possess a highly active oxidative pentose phosphate pathway along with an enzyme system that exports citric acid to the cytosol where it is converted into acetyl-CoA and NADPH that feed into lipid synthesis. Modification of lipogenic enzymes or alteration of gene expression that boosts these systems can further increase lipid synthesis in native lipogenic yeasts. Overexpression of 6-phosphogluconate dehydrogenase (GND1) and/or glucose-6-phosphate dehydrogenase (ZWF1), for example, are predicted to increase the supply of NADPH for lipid synthesis, but since ZWF1 and (particularly) GND1 are subject to strong allosteric regulation by physiological levels of NADPH (Barcia-Vieitez et al. 2014, Rippa et al. 1998, Velasco et al. 1995), modification of the regulatory controls are predicted to be more effective. For example, substitution of the tyrosine at position 99 (i.e., Y99) of the ZWF1 of *L. starkeyi* represented by SEQ ID NO:44 can alter binding of NADPH and thereby render this enzyme resistant to allosteric regulation by NADPH. The tyrosine in ZWF1 can be substituted by any amino acid. The tyrosine in ZWF1 is preferably substituted with serine, threonine, glutamine asparagine, cysteine, alanine, proline, leucine, isoleucine, phenylalanine, valine, histidine, lysine, asparagine, aspartic, glutamic acid, or glycine; more preferably substituted with serine or threonine; and most preferably substituted with serine. An analogous substitution in GND1 can also or alternatively be performed to render GND1 resistant to allosteric regulation by NADPH.

The NADPH supplied by malic enzyme has a strong influence on lipid accumulation in lipogenic yeasts. Increasing malic enzyme activity is predicted to provide lipogenic yeasts with more NADPH for lipid synthesis.

Another approach to increasing the production of lipid is to reduce activity of the β-oxidation pathway. The β-oxidation pathway is responsible for consuming lipid after lipogenic yeasts exhaust their carbohydrate sources Eliminating the breakdown of lipids is therefore another target for developing yeasts with enhanced lipid production. Exemplary modifications in this regard include functional deletion of an acyl-CoA oxidase, a 3-hydroxyacyl-CoA dehydrogenase, and/or an enoyl-CoA hydratase. Acyl-CoA oxidases catalyze the first step in beta oxidation. Enoyl-CoA hydratases catalyze the second step in beta oxidation. 3-Hydroxyacyl-CoA dehydrogenases catalyze the third step in beta oxidation. PDX1 is an exemplary acyl-CoA oxidase in *L. starkeyi*. FOX1 is a multifunctional enzyme in *L. starkeyi* that can be considered to be both a 3-hydroxyacyl-CoA dehydrogenase and an enoyl-CoA hydratase, as it has both 3-hydroxyacyl-CoA dehydrogenase and enoyl-CoA hydratase activities. Other modifications that inhibit lipid oxidation are acceptable.

Disruption of the gene for the regulatory protein CreA/Mig 1 in *Y lipolytica* increased the lipid content from 36% to 48.7% of its dry weight while increasing the $C_{18:1}$ content (Wang et al. 2013). A CreA homolog in the *L. starkeyi* genome is similar to the CreA transcriptional activator of *Y lipolytica*, and could be a good target to determine whether disruption of the CREA/MIG1 homolog in *L. starkeyi* results in an increase in lipid production.

For *Mucor circinelloides* (Zhang et al. 2008), *Rhodotorula glutinis* (Li et al. 2012), and *Yarrowia lipolytica* (Tai et al. 2013), the basal lipid production contents of the parental strains are all considerably lower than what has been observed in native (non-engineered) *L. starkeyi* under nitrogen limiting conditions (≈65%), indicating that there is substantial room for improvement in these strains with the modifications described herein.

Genetic Engineering

The cells of the invention may be genetically altered to functionally delete, express, or overexpress any of the specific genes or gene products explicitly described herein or homologs thereof. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known in the art using the gene name or accession number as a search term. Common sequence databases include GenBank (www.ncbi.nlm.nih-.gov), ExPASy (expasy.org), KEGG (www.genome.jp), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. Homologs include orthologs and paralogs. "Orthologs" are genes and products thereof in different species that evolved from a common ancestral gene by speciation. Normally, orthologs retain the same or similar function in the course of evolution. Paralogs are genes and products thereof related by duplication within a genome. As used herein, "orthologs" and "paralogs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to the genes or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-

410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule, genetic element (e.g., gene, promoter, etc.), or polypeptide in a particular cell, "endogenous" refers to a nucleic acid molecule, genetic element, or polypeptide that is in the cell and was not introduced into the cell or transferred within the genome of the cell using recombinant engineering techniques. For example, an endogenous genetic element is a genetic element that was present in a cell in its particular locus in the genome when the cell was originally isolated from nature. The term "native" is used herein interchangeably with "endogenous."

Exogenous: As used herein with reference to a nucleic acid molecule, genetic element (e.g., gene, promoter, etc.), or polypeptide in a particular cell, "exogenous" refers to any nucleic acid molecule, genetic element, or polypeptide that was introduced into the cell or transferred within the genome of the cell using recombinant engineering techniques. For example, an exogenous genetic element is a genetic element that was not present in its particular locus in the genome when the cell was originally isolated from nature. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using RT-PCR and protein levels can be assessed using SDS-PAGE gel analysis.

Recombinant: A recombinant nucleic acid molecule, genetic element (e.g., gene, promoter, etc.), or polypeptide is one that has a sequence that is not naturally occurring, is present in a different locus (e.g., genetic locus or on an extrachromosomal plasmid) within a particular cell than in a corresponding native cell, or both. A recombinant cell or microorganism is one that contains a recombinant nucleic acid molecule, genetic element, or polypeptide.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous nucleic acids can be introduced stably or transiently into a cell using techniques well known in the art, including electroporation, lithium acetate transformation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to nourseothricin, G418, hygromycin B, neomycin, tetracycline, chloramphenicol, or kanamycin, genes that complement auxotrophic deficiencies, and the like. (See below for more detail.)

Various embodiments of the invention use an expression vector that includes a recombinant nucleic acid encoding a protein involved in a metabolic or biosynthetic pathway. Suitable expression vectors include, but are not limited to viral vectors, phage vectors, bacteriophage vectors, plasmids, phagemids, cosmids, fosmids, bacterial artificial chromosomes, Pl-based artificial chromosomes, yeast plasmids, yeast artificial chromosomes, and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., nourseothricin, G418, hygromycin B, ampicillin, neomycin, methotrexate, or tetracycline, (b) complement auxotrophic deficiencies, or (c) supply critical nutrients not available from complex media. In alternative embodiments, the selectable marker gene is one that encodes orotidine 5'-phosphate decarboxylase, dihydrofolate reductase or confers neomycin resistance (for use in eukaryotic cell culture).

The coding sequence in the expression vector is operably linked to an appropriate expression control sequence (promoters, enhancers, and the like) to direct synthesis of the encoded gene product. Such promoters can be derived from endogenous or exogenous sources. Thus, the recombinant genes of the invention can comprise a coding sequence operably linked to a heterologous genetic element, such as a promoter, enhancer, ribosome binding site, etc. "Heterologous" in this context refers to a genetic element that is not operably linked to the coding sequence in nature. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology,* 153:516-544).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); and the yeast gal4 gene promoter (Johnston et al. (1982) *PNAS* (USA) 79:6971; Silver et al. (1984) PNAS (USA) 81:5951.

Coding sequences can be operably linked to an inducible promoter. Inducible promoters are those wherein addition of an effector induces expression. Suitable effectors include proteins, metabolites, chemicals, or culture conditions capable of inducing expression.

Alternatively, a coding sequence can be operably linked to a repressible promoter. Repressible promoters are those wherein addition of an effector represses expression.

In some versions, the cell is genetically modified with a recombinant nucleic acid encoding a biosynthetic pathway gene product that is operably linked to a constitutive promoter. Suitable constitutive promoters are known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with recombinant nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding proteins desired to be expressed in a cell may be codon-optimized for that particular type of cell. Codon optimization can be performed for any nucleic acid by "OPTIMUMGENE"-brand gene design system by GenScript (Piscataway, N.J.).

Methods for transforming yeast cells with recombinant DNA and producing polypeptides therefrom are disclosed by Clontech Laboratories, Inc., Palo Alto, Calif., USA (in the product protocol for the "YEASTMAKER"-brand yeast transformation system kit); Reeves et al. (1992) *FEMS Microbiology Letters* 99:193-198; Manivasakam and Schiestl (1993) *Nucleic Acids Research* 21(18):4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) Bio/Technology 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837,148; and 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300:706); and *Yarrowia lipolytica* (Davidow et al. (1985) *Curr. Genet.* 10:380-471 and Gaillardin et al. (1985) *Curr. Genet.* 10:49). Genetic transformation systems for metabolic engineering have been developed specifically for a number of lipogenic yeasts including *Mucor circinelloides* (Zhang et al. 2007), *Yarrowia lipolytica* (Xuan et al. 1988), *Rhodotorula glutinis* (Li et al. 2012), *Rhodosporidium toruloides* (Zhu et al. 2012), *Lipomyces starkeyi* (Calvey et al. 2014, Oguro et al. 2015), and *Trichosporon oleaginosus* (Gomer et al. 2016).

Organic Substrate Conversion

An aspect of the invention includes methods of processing organics. The methods can be performed with the native, non-genetically modified yeasts or genetically modified yeasts such as those described herein. If non-genetically modified, the yeasts are preferably native lipogenic (oleaginous) yeasts, such as *Lipomyces starkeyi.*

The methods involve consuming certain organics while producing other organics. As used herein, "organic" refers to any organic compound, molecule, or polymer capable of being consumed or produced by a microorganism. Exemplary organics include but are not limited to carbohydrates (simple sugars, oligosaccharides, polysaccharides), nucleotides, nucleosides, nucleic acids, polypeptides, organic acids (including amino acids), and organic compounds. Specific examples of organics include glucose, glucan, xylose, xylan, arabinose, arabinan, lactic acid, glycerol, acetic acid, butanediol, ethanol, fatty acids, acylglycerols, enzymes (amylases, glucosidases, etc.), among others. As used herein, "consume" refers to the reduction of a certain component from a medium and can encompass direct uptake of the component for internal metabolic processing thereof or external processing of the component optionally followed by uptake of resulting products for internal metabolic processing.

The engineered yeasts of the invention and certain lipogenic yeasts are particularly effective at consuming certain organics that other microorganisms either cannot consume or cannot do so effectively. These organics include glycerol, cellobiose, xylose, lactic acid, trehalose, and oligosaccharides. Accordingly, an aspect of the methods of the invention includes the consumption of these and other organics from the medium. In certain versions of the invention, contacting the medium with the yeast reduces an amount of any one or more of these or other organics to less than about 80%, less than about 70%, less than about 60%, less than about 50%, less than about 45%, less than about 40%, less than about 35%, less than about 30%, less than about 25%, less than about 20%, less than about 15%, less than about 10%, less than about 5%, less than about 2.5%, or less than about 1% of the initial amount.

In some aspects of the invention, the medium comprises one or more components selected from glucose, glucan, trehalose, xylose, xylan, arabinose, arabinan, lactic acid, glycerol, acetic acid, butanediol, and ethanol. The medium, for example, may comprise glucose in an amount of from about 0.01 to about 100 g/L, from about 0.1 g/L to about 10 g/L, or about 1 g/L; glucan in an amount of from about 0.1 g/L to about 1000 g/L, from about 1 g/L to about 100 g/L, or about 10 g/L; trehalose in an amount of from about 0.01 to about 100 g/L or from about 0.1 g/L to about 10 g/L; xylose in an amount of from about 0.01 g/L to about 100 g/L, from about 0.1 g/L to about 10 g/L, or about 1 g/L; xylan in an amount of from about 0.05 g/L to about 500 g/L, from 0.5 g/L to about 50 g/L, or about 5 g/L; arabinose in an amount of from about 0.005 g/L to about 50 g/L; from about 0.05 g/L to about 5 g/L, or about 0.5 g/L; arabinan in an amount of from about 0.005 g/L to about 50 g/L, from about 0.05 g/L to about 5 g/L, or about 0.5 g/L; lactic acid in an amount of from about 0.15 g/L to about 1500 g/L, about 1.5 g/L to about 150 g/L, or about 15 g/L; glycerol in an amount of from about 0.15 g/L to about 1500 g/L, from about 1.5 g/L to about 150 g/L, or about 15 g/L; acetic acid in an amount of from about 0.005 g/L to about 50 g/L; from about 0.05 g/L to about 5 g/L, or about 0.5 g/L; butanediol in an amount of from about 0.02 g/L to about 200 g/L, from about 0.2 g/L to about 20 g/L, or about 2 g/L; and/or ethanol in an amount of from about 0.005 g/L to about 50 g/L, from about 0.05 g/L to about 5 g/L, or about 0.5 g/L. Contacting the medium with a yeast may reduce an amount of any one or more of these or other organics to less than about 80%, less than about 70%, less than about 60%, less than about 50%, less than about 45%, less than about 40%, less than about 35%, less than about 30%, less than about 25%, less than about 20%, less than about 15%, less than about 10%, less than about 5%, less than about 2.5%, or less than about 1% of the initial amount.

In certain versions of the invention, the medium comprises a grain ethanol distillation stillage or a processed grain ethanol distillation stillage. The processed grain ethanol distillation stillage may be made by centrifuging distiller's wet grain therefrom, removing oil, concentrating, and filtering, or other thin-stillage processing steps described elsewhere herein or known in the art. The concentrating may comprise evaporating. In some versions, the processed grain ethanol distillation stillage comprises thin stillage. The thin stillage may be further processed by removing oil and concentrating to generate the medium.

The medium may comprise various amounts of the grain ethanol distillation stillage or processed grain ethanol distillation stillage. In some versions, the medium may comprise at least about 5%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 99%, or about 100% grain ethanol distillation stillage or processed grain ethanol distillation stillage. The grain ethanol distillation stillage or processed grain ethanol distillation stillage may be diluted with water or other solvents.

The engineered yeasts of the invention and certain lipogenic yeasts are particularly effective at producing certain organics that other microorganisms either cannot produce or cannot do so effectively. These organics include lipids (triacylglycerols, diacylglycerols, monoacylglycerols, fatty acids, etc.), enzymes (amylases, glucosidases, etc.), and other proteins. Particular enzymes include glycoside hydrolases, alpha-amylases (thermostable and secreted), dextranases (amylo-alpha-1,6-glycosidase), maltases, beta-1,4-glucosidases, endo-1,4-beta-D-glucanases (cellulases) or any other of the enzymes described elsewhere herein. Accordingly, an aspect of the methods of the invention includes the production of these and other organics.

The organic produced by the yeast may be separated or purified from any other component of the spent medium for downstream use in other applications. For example, enzymes produced by the yeast may be used in liquefaction of starch and/or saccharification of liquefaction-processed starch. Such enzymes may include any of the enzymes produced by the yeast as described above, such as carbohydrases. Lipid produced by the yeast may be used for producing biofuels therefrom or used as a replacement for palm or other oils in food applications or other applications. The yeast grown in the medium may themselves be harvested and processed to yield a source of protein as a replacement, for example, for soy protein or as a source of long-chain polyunsaturated fatty acids for fish grown in aquaculture.

The spent medium may also be mixed, either alone or with other liquids (such as thin stillage), with starch as a backset for liquefaction of the starch. The reduction in dissolved organics by virtue of the yeast consumption reduces the build-up of organics in grain ethanol production systems as a whole and in the liquefaction fermentation in particular.

EXAMPLES

Background and Overview

The existence of an annotated genome for *Lipomyces starkeyi* greatly facilitates cloning and homologous expression, but even with a complete or nearly-complete genome, various problems are encountered in cloning and expressing target genes.

One aspect of a suitable cloning strategy involves overexpressing endogenous genes involved in lipid production in *L. starkeyi* under constitutive promoters. Genomic DNA (gDNA) can be a preferable source for gene amplification, because all introns should be natively excised, and genomic DNA preparation is faster and cheaper than creating cDNA libraries. However, certain introns may have regulatory functions or their presence may impede or promote the post-transcriptional processing, subsequent protein translation, or stability of the transcript when overexpressed. Therefore, some gene targets are preferably cloned from cDNA and other targets are cloned from gDNA.

Another issue to consider in cloning involves possible alternate start codons present in the sequences of transcribed mRNA of certain gene targets. As an example, both GUT1 and DGA1 of *L. starkeyi* have two possible initiator methionine sites differing by a respective 15 and 156 base pairs upstream from the sequence annotated on the Joint Genome Institute site. Detailed sequence alignments with orthologs of these genes in yeast species with well-annotated sequences are inconclusive, owing to the large divergence of *L. starkeyi* from other yeast species and the high degree of variability at the N-terminus of these proteins. Hence, in such situations, both versions of these genes are cloned. As shown below, results sometimes demonstrate a large difference in lipid content, as in the case for the two DGA1 variants, whereas others, such as the two GUT1 variants, behave similarly.

It is not evident a priori whether genes from cDNA can be amplified under all conditions. For example, seven out of nine gene targets from cDNA could be amplified from cDNA derived from standard yeast cultures growing in liquid (yeast peptone dextrose) YPD media. However, one construct required gDNA as a cloning template. The exception was ACC1, which could not be amplified as a product from this cDNA library (as deemed by agarose gel electrophoresis) despite many PCR optimization efforts. Amplification of the gene was possible with the same primers when gDNA was used as the template. When *L. starkeyi* was cultivated under highly lipogenic conditions and a new cDNA library created from these cells, amplification of ACC1 was successful. Such evidence indicates that Acc1 is not constitutively expressed and that expression of ACC1 is inducible under lipogenic conditions. This finding emphasizes the importance of ACC1 as an important gene target for enhancing lipid biosynthesis.

Generation of vectors involves assembly of 4 to 6 fragments to create the desired gene cassettes using the well-established "Gibson" method for in vitro enzymatic assembly of DNA fragments (Gibson et al. 2009). Cloning attempts can be unsuccessful in producing any of the desired constructs. Gel purification methods to isolate amplified genes can introduce errors in DNA terminal regions. Therefore, gel extraction of DNA fragments and column PCR purification are preferred to improve the purity and concentration of the PCR products used in the assembly reaction.

Correct and complete constructs of the desired cassettes can be identified by colony PCR. This can be accomplished through colony PCR by amplifying either parts of the construct or the entire construct. During routine screening and sequencing, some of the construct candidates can contain partial cassettes (i.e. some will be missing part or all of one or more of the assembly components). To avoid selecting these partial constructs, it is preferable to use colony PCR for the entire cassette (instead of portions of the cassette). That way only candidates containing the appropriately sized insert are then sequenced.

*L. starkeyi* is cultivated under special conditions and genetic transformation is optimized in order to obtain transformants with genes integrated into the genome (Calvey et al. 2014). *L. starkeyi* can be transformed relatively easily with a base vector that contains only essential elements as well as a selectable marker. An exemplary base vector is represented by SEQ ID NO:91. Success depends upon having cells at an appropriate stage of development, at an appropriate cell density and with the correct ratio of cells to DNA. Transformation conditions are systematically evaluated for each method used to determine cell density, and for the activity and condition of critical reagents such as salmon sperm DNA.

In native strains of *L. starkeyi*, each DNA expression cassette integrates either randomly via non-homologous end joining (NHEJ) or in a targeted manner via homologous recombination to create a transformant. In native strains of *L. starkeyi*, NEHJ integration occurs much more frequently than homologous recombination. Even genes that normally increase lipid production when overexpressed from most integration sites can generate transformants with reduced lipid production relative to the wild-type when integrated randomly into various sites. Many strains are therefore screened under controlled conditions in order to obtain those with improved performance.

Nile Red fluorescence can be used as a rapid assay for cells or strains of cells showing greater relative lipid accumulation. However, the assay is highly variable, and it is important to conduct the trials under specific conditions. Selection of media that will enable identification of strains with the capacity for elevated lipid production on stillage is particularly critical. Some types of rich media used to cultivate *L. starkeyi*, such as YPD or those based on modified thin stillage (mTS), have intrinsic fluorescent properties that interfere with the proper quantification of the bona fide Nile Red fluorescent signal from the cells. Moreover, unmodified thin stillage contains significant amounts of corn oil and lipids from the hydrolysis of *Saccharomyces cerevisiae*. A partial solution to this problem is to perform a series of washes to remove the media from the cells, followed by suspension of the cells in $H_2O$. This treatment can eliminate interference due to media components that can be removed by washing. As described elsewhere herein, other methods can be used to reduce background fluorescence.

When examining cultures for increased lipid accumulation it is important to distinguish higher levels of lipid due to higher cell density from higher levels of lipid due to higher lipid content per cell. The fluorescence response is therefore normalized to the cell density.

Effects of Medium Components

The fluorescence assay is intended to identify transformants that overproduce lipid when cultivated on an industrial medium composed in part or in whole of thin stillage. Medium components can strongly affect the fluorescence assay for intracellular lipid by increasing or decreasing intracellular lipid production. When screening for a transformant with the capacity for increased lipid production, it is more difficult to identify improved mutants when the medium enables the cells to accumulate high levels of lipid than when native cells normally produce relatively little lipid under the growth conditions.

For example, wild-type, untransformed *L. starkeyi* cultivated in a defined minimal medium using an easily assimilated carbon source and a low amount of a poorly assimilated nitrogen source would produce a high level of lipid. The same organism cultivated with the same carbon source but an amount of readily assimilated nitrogen sufficient for cell growth would accumulate less lipid as illustrated by published studies (Calvey 2016).

It is easier to identify a transformant with increased capacity for lipid production when it is cultivated in a medium that allows lower lipid accumulation than in a medium that enables higher lipid accumulation.

As taught elsewhere in this disclosure, the relationship between the amount and the source of the carbon and the nitrogen provided to the cells can affect growth and lipid production in complex ways. Moreover, media used in certain commercial applications will include a complex mixture of glycerol, cellobiose, trehalose, xylose, xylitol, acetic acid residual corn oil and oligosaccharides derived from residual starch, hemicellulosic and cellulosic components from corn along with hydrolysis products from lysed yeast cells. In practice it is not reasonable to predict how strains or transformants will perform on a complex medium of such composition by screening their performance against simple or complex media composed of typical laboratory substrates such as glucose, yeast extract, peptone or other common medium constituents. For this reason, empirical testing is important to identify media that is representative of the industrial substrate and appropriate for strain screening. These considerations were addressed with various media as described below.

Six types of growth media were examined to determine how they influenced the native lipid accumulation of *L. starkeyi* over a 3-day fermentation period. The types of media included in the analysis were M1 (LN), M2 (LN), M3 (HN), M4 (HN), YPD, and mTS. M1 (LN) is a minimally defined low nitrogen media containing 1.72 g/L of yeast nitrogen base, 0.417 g/L ammonium sulfate 0.179 g/L urea, and 30 g/L of dextrose. The M1 (LN) formulation is nitrogen limiting and gives a C:N ratio of approximately 150:1. M2 (LN) is a low nitrogen media identical to YPD but containing only 3.64% of the amount of yeast extract that YPD contains and only 1.82% of the amount of peptone that YPD contains. Converted to grams/liter, M2 (LN) contains 0.364 g/L of yeast extract and 0.364 g/L of peptone. The amount of dextrose in M2 (LN) is the same as in traditional YPD (20 g/liter). The M2 (LN) formulation is nitrogen limiting and gives a C:N ratio of approximately 70:1. M3 (HN) and M4 (HN) are high nitrogen-containing versions of M1, with M4 HN containing peptone. More specifically, M3 (HN) contains 6.7 g/L yeast nitrogen base, 2.145 g/L urea, and 30 g/L dextrose. M4 HN media contains 6.7 g/L yeast nitrogen base, 2.145 g/L urea, 3.0 g/L peptone, and 30 g/L dextrose. YPD is yeast peptone dextrose media. mTS is modified thin stillage. The mTS was prepared by clarifying thin stillage to remove oil by skimming, boiling to concentrate the stillage, removing precipitates produced by the boiling, autoclaving, and removing precipitates generated during the autoclaving.

As shown in FIG. 4, the type of media greatly influences the basal lipid production of *L. starkeyi* NRRL Y-11557, even if nitrogen is not considered limiting. These wild-type cells appear to accumulate a moderate amount of lipids (≈30%) when cultivated in mTS during extended fermentation times, despite its nitrogen content. The mildly lipogenic property of mTS with *L. starkeyi* NRRL Y-11557 is likely due to the presence of glycerol and/or other compound(s).

The choice of a screening media should be done carefully. Choosing a media limiting in nitrogen could mask small lipogenic effects of certain genes, while media high in nitrogen or complexity may suppress those effects. Likewise, even media that is not nitrogen limiting can be slightly lipogenic, as seen in M3 (HN) media, because the lack of some nutrients can induce lipogenesis.

In light of these considerations, transformants of NRRL Y-11557 are screened using mTS medium to identify yeast strains that convert the soluble organics and sugars to other products. Evaluation on this medium also eliminates the possibility that some transformants perform well during screening on synthetic media but present significantly dampened or null effects when grown on a commercially relevant fermentation stream. Transformants are also screened using YPD to control for any possible variation in various sources of mTS.

Gene Cassette Selections and Primer Design

Gene cassette integration vectors are designed using a base vector as shown in FIG. 5 and having a sequence of SEQ ID NO:91. The base vector contains an origin of replication (Ori) and a kanamycin resistance cassette that permits maintenance and propagation in bacteria. In addition, it contains two multiple cloning sites (MCS) and two modified LoxP sites (RE and LE) that flank the strong constitutive LsTDH3 promoter coupled to a codon optimized nourseothricin (NAT) resistance gene and its respective transcription terminator region.

Measures are taken to ensure no antibiotic resistance gene is incorporated in the final yeast strain. The bacterial kanamycin resistance gene is not integrated into the yeast genome if it is interrupted by restriction digestion prior to transformation. The presence of the loxP sites enables excision of the NAT resistance gene after genome integration. The LoxP sites themselves are modified (i.e. dead) such that the product after one recombination event resists further recombination, thereby protecting the genomic integrity of the organism. The gene overexpression cassettes therefore include a constitutive promoter, the gene(s) of interest, and one or more transcription terminator regions inserted into one of the MCSs.

Genes are overexpressed to increase lipid production under nutrient-rich conditions. These include: acetyl-coenzyme-A carboxylase (LsACC1), delta-9 acyl-CoA desaturase (LsOLE1), ATP-citrate lyase alpha and beta subunits (LsACL1/LsACL2), two variants of glycerol kinase (LsGUT1-1602) and (LsGUT1-1617), two variants of diacylglycerol acyltransferase (LsDGA1-1233) and (LsDGA1-1389) having different start sites, and malic enzyme cloned from genomic DNA (LsgME) and cDNA (LscME), among other genes described herein. Precise promoter, gene, and terminator sequences are selected based on Illumina RNAseq data and knowledge of promoter strength and expression patterns in this organism. All contain a single promoter, gene, and terminator region, with exception to the LsAcl1/LsAcl2 construct, which involves a bidirectional promoter expressing the two genes with different transcription terminator regions. These sequences are then analyzed for the presence of specific restriction digest sites to determine into which one of two MCSs contained in the base vector they would be cloned. This step facilitates future subcloning into other vectors. For example, the diacylglycerol acyltransferase (LsDGA1) construct is capable of being inserted upstream of the loxP site using the Sbf1 restriction enzyme to linearize the vector. Other constructs are capable of being inserted downstream of the opposing loxP site, using RsrII and AvrII to linearize the vector. The desired sequence combinations and restriction enzyme sites are entered into the NEBuilder® assembly tool (nebuilder.neb.com/) with a minimum overlap setting of 20 base pairs to construct the primer sequences for performing the Gibson assembly reaction.

Schematic of the Pipeline for Creating and Characterizing Strains

An assembly line of sequential steps to create metabolically engineered yeast is shown in FIG. 6. These steps included target gene, promoter, and terminator selection, molecular biology techniques (PCR, Gibson assembly), yeast transformations, selection, cataloging and storage, Nile Red screening, and further validation assays.

gDNA Extraction and cDNA Library Creation:

A Masterpure™ Yeast DNA Purification Kit (Epicentre, Madison, Wis.) is used to extract *L. starkeyi* gDNA. Nitrogen rich (YPD) or nitrogen limited (YPD 70:1 (C:N)) cultures are used for RNA extraction. The YPD 70:1 media contain only 3.64% and 1.82% percent of the yeast extract and peptone as YPD, respectively. A freshly saturated 5 mL culture of *L. starkeyi* grown under constant agitation at 30° C. is pelleted by centrifugation, washed, suspended in 5 mL of sterile $H_2O$, then used to inoculate 50 mL of either YPD or YPD 70:1 media in a 125 mL shaker flask≈0.8 $OD_{600}$ and allowed to incubate overnight at 30° C. under 225 rpm. Cells are observed microscopically to determine lipid production in the YPD 70:1 media as compared to the YPD media, and the $OD_{600}$ is measured to calculate the quantity of cells to use in the RNA extraction protocol. RNA is extracted using an RNeasy Mini Kit (Qiagen), following enzymatic disruption. cDNA is synthesized from these RNA preparations using a QuantiTect® Reverse Transcription Kit (Qiagen), following the instructions of the manufacturer.

PCR of Fragments and Gibson Enzymatic Assembly:

The base vector (pXC301—FIG. 5—SEQ ID NO:91) linearized with the enzymes listed in Table 2 is used to clone *L. starkeyi* genes in conjunction with the "Gibson method" for in vitro enzymatic assembly of DNA fragments. All PCR amplifications are performed using Phusion High Fidelity Taq polymerase (NEB) and the manufacturer protocol in either 5× Phusion GC buffer (ACC1) or 5× Phusion buffer (all others) using the annealing temperatures in Table 2. Annealing steps are carried out using the lowest $T_m$ of the primer pair, or the experimentally optimized annealing temperature, where appropriate. The reaction products are analyzed by agarose gel electrophoresis containing ethidium bromide and subsequently visualized and photographed. Successful reactions of identical fragments are pooled and then all samples (including the digested base vector) are subjected to a PCR cleanup column (Qiagen), and then quantified on a Nanodrop 2000 instrument (Thermo Scientific). The vector and inserts are then added in equimolar quantities (0.1 pmoles/fragment) in a separate tube, and the final volume adjusted to 20 μL by the addition of 15 μL premade Gibson assembly reaction mix and water. All reactions are allowed to incubate at 50° C. for one hour, and then 5 μL of the assembly reaction is used to transform 20

µL of Endura™ DUO competent cells (Lucigen) using standard techniques. Transformants are selected on LB plates containing kanamycin, and positive candidates are identified by colony PCR and sent for sequencing confirmation.

TABLE 2

Summary of Gene Targets, Promoters, and Terminators with Cloning Information

| Target Gene | Full Name | Promoter and Teminator Pairings | PCR Annealing Temperature | Cloning Digest Enzymes | Enzymes for Yeast Transformation |
|---|---|---|---|---|---|
| ACC1 | Acetyl-coenzyme-A carboxylase | FBA1 Promoter | 55-64° C. | RsrII and AvrII | AsiSI |
| | | ACC1 | 67° C. | | |
| | | FBA1 Terminator | 55-64° C. | | |
| OLE1 | Delta-9 acyl-CoA desaturase | GLN1 Promoter | 60° C. | RsrII and AvrII | AsiSI |
| | | OLE1 | 63° C. | | |
| | | GLN1 Terminator | 60° C. | | |
| ACL1 and ACL2 | ATP-citrate lyase, alpha and beta subunits | ENO1 Promoter | 57° C. | RsrII and AvrII | AsiSI |
| | | ACL1 | 58° C. | | |
| | | ATPase Terminator | 64° C. | | |
| | | ACL2 | 58° C. | | |
| | | TPI Terminator | 65° C. | | |
| Glycerol Kinase 1602 | Glycerol Kinase 1602 Variant | ATPase (3900) Promoter | 55.3-61.2° C. | RsrII and AvrII | AsiSI |
| | | Glycerol Kinase | 63.9-67° C. | | |
| | | ATPase (3900) Terminator | 62.75-66.25° C. | | |
| Glycerol Kinase 1617 | Diacylglycerol acyltransferase 1617 Variant | ATPase (3900) Promoter | 58° C. | RsrII and AvrII | AsiSI |
| | | Glycerol Kinase 1617 | 65° C. | | |
| | | ATPase (3900) Terminator | 65° C. | | |
| DGA1 1233 | Diacylglycerol acyltransferase 1233 Variant | TEF1 Promoter | 60° C. | RsrII and AvrII | AsiSI |
| | | DGA1 | 72° C. | | |
| | | TDH3 Terminator | 70° C. | | |
| DGA1 1389 | Diacylglycerol acyltransferase 1389 Variant | TEF1 Promoter | 60° C. | SbfI | XmaI/AvrII |
| | | DGA1 | 72° C. | | |
| | | TDH3 Terminator | 70° C. | | |
| gMalic Enzyme | Malic Enzyme (gDNA) | TDH3 Promoter | 60° C. | SbfI | XmaI/AvrII |
| | | gMalic Enzyme | 60° C. | | |
| | | TDH3 Terminator | 60° C. | | |
| cMalic Enzyme | Malic Enzyme (cDNA) | TPI (196787) Promoter) | 62° C. | RsrII and AvrII | AsiSI |
| | | cMalic Enzyme | 58° C. | | |
| | | TPI (196787) Terminator | 66° C. | | |

Vectors are linearized so the entire target gene cassette, including the loxP flanked region, randomly integrates into the *L. starkeyi* genome as one fragment. Table 2 lists restriction enzymes for linearization. Linearized DNA is ethanol precipitated and suspended in TE to increase its concentration (>160 nM) and purity. To transform the cells, a procedure based on the lithium acetate method was used (Calvey et al. 2014, Gietz et al. 2002). A near stationary phase culture of *L. starkeyi* is inoculated into 50 ml YPD to between 0.6 and 0.8 $OD_{600}$ and grown overnight to reach between 3.0 and 4.0 $OD_{600}$. The culture is harvested and washed twice with 25 mL sterile water, and resuspended to 1.5 mL in sterile water or 0.1M LiAc. Aliquots of 150 µL are dispensed into 1.5 mL tubes and centrifuged. The remaining cell pellet is then suspended in 360 µL transformation mix containing 240 µL 50% w/v PEG 3350, 50 µL boiled ssDNA, 36 µL 1.0 M LiAc, and 36 µL of the desired plasmid DNA (added last). Samples are incubated at 30° C. for 3 hours, heat shocked at 40° C. for 5 minutes, and then centrifuged to remove the transformation suspension. Cells are allowed to recover in 3 mL YPD for 4 hours before being plated onto appropriate selective media. After 6 days of growth, transformants are selected, catalogued by size, and streaked onto appropriate antibiotic selection plates for creating glycerol stocks until characterization.

Yeast Lipid Screening Using Nile Red:

Both YPD and mTS are used to screen for lipid accumulation in *L. starkeyi*. Starter cultures are inoculated with the desired transformants in 5 mL tubes containing YPD-NAT or YPD liquid media at 30° C. under constant agitation. This lipid screening protocol is based on Nile Red fluorescence adapted from a previous study (Sitepu et al. 2012). Samples and appropriate dilutions are then prepared in a 96-well black clear-bottomed plate to contain 100 µL in each well. Nile Red is prepared as a 2 mg/mL stock solution and then diluted to a 2× working concentration (8 µg/mL). Fluorescent signals and $OD_{630}$ readings are read independently from two plate readers (BioTek™ FLx800 and BioWhittaker™ ELx808, respectively). Data is analyzed by normalizing the fluorescent signal to the $OD_{630}$ of the culture. To enable comparisons between different runs, normalized fluorescence is standardized relative to the WT culture of each group.

Lipid Extraction Analysis:

An extraction protocol is used for crude gravimetric assessments of total lipid content based on the classic Bligh and Dyer method (Bligh et al. 1959) (20). First, 2 mL of cell culture is centrifuged at 3,000 rpm for 5 minutes in 15 mL falcon tubes, and the cell pellets frozen at −20° C. until lipid extraction analysis. Thawed cell pellets are suspended in 1 mL $H_2O$ containing 200 µL of concentrated HCl, and the suspension was heated to 90° C. for 1 hour to lyse cells. Lipids are then extracted by addition of 6 mL of a 2:1 (v:v) methanol:chloroform solution and 3 mL of 1M NaCl, followed by vortexing for 5 minutes. Tubes are then centrifuged at 3,000 rpm for 10 minutes to induce phase separation. The lipid-containing lower chloroform layer (≈2 mL) is then carefully removed using a glass Pasteur pipette, and transferred into a clean, pre-weighed, 5 mL glass vial. Finally, the extracted chloroform layer is completely evaporated by incubation in a 40° C. heat block under a constant stream of air for 1 hour. Vials are then re-weighed to determine the mass of extracted total lipids.

HPLC Analysis of Organics:

Concentrations of sugars and mTS metabolites (including glucose, xylose, cellobiose, arabinose, xylitol, ethanol, glycerol, lactic acid, and acetic acid) are determined by high performance liquid chromatography (HPLC) using an Agilent 1100 Series auto sampler, pump, and refractive index detector, with a Bio-Rad Aminex HPX-87H ion exclusion column (300×7.8 mm) held at 65° C. The mobile phase is 0.01N $H_2SO_4$ at a flow rate of 0.6 mL/min. Samples are diluted 1:10 prior to injection.

Selection of a Yeast Platform

The constituents of thin stillage obtained from a supplier were characterized in order to better monitor the consumption of organics during fermentation of engineered yeast strains. It was discovered that mTS contains between 18.6 to 20.5 g/L glycerol, among other components. To establish a yeast platform for bioproces sing of mTS and metabolic engineering, the growth performance of several strains of *L. starkeyi* on different media was monitored. All of them grew well on starch but the Y-11558 strain grew slightly faster (Table 3).

When challenged with glycerol as a carbon source, none of the South African strains (Y-27493, 27494 and 27495) grew, and Y-11558 was much slower (μ=0.047; Td=21 h). See FIG. 7. However, mutagenesis and serial subculturing reduced the doubling time of Y-11557 to 9.9 h on glycerol. These findings established that *L. starkeyi* grows on glycerol, a major component of mTS, and that adaptation increases growth rates. Based on these results and given that the genome of *L. starkeyi* NRRL Y-11557 has been sequenced (Grigoriev et al. 2012 and DOEJGI 2011), this strain was selected as the exemplary platform yeast for metabolic engineering.

TABLE 3

Doubling Times of Different *Lipomyces starkeyi* Strains Grown on starch

| Strain | Doubling Time (Hrs) | μ |
|---|---|---|
| Y-1388 | 3.56 | 0.28 |
| Y-11557 | 3.60 | 0.28 |
| Y-11558 | 3.36 | 0.30 |
| Y-27493 | 3.52 | 0.28 |
| Y-27494 | 3.97 | 0.25 |
| Y-27495 | 4.28 | 0.23 |

Metabolic Engineering and Screening

The next objective was to modify the physiology of *L. starkeyi* so that it would generate lipids under high nitrogen conditions, such as those found in thin stillage (TS) and modified thin stillage (mTS). As described in Table 2, specific genes targets were selected with constitutive promoter and terminator pairings based on knowledge of the *L. starkeyi* genome, its lipid biochemistry, and gene expression profile under these conditions. These were all cloned into target vectors and transformed into *L. starkeyi*. Since the vector integrates at random within the genome, each transformant might display different lipid biosynthetic capabilities based simply upon the site of genomic integration, or on the number of copies introduced within the genome. It was hypothesized that although gene cassettes conferring genuine lipogenic effects could occasionally integrate into unfavorable regions that could mask their effect, the average normalized fluorescence of that particular transformant pool should be somewhat higher than the average of the WT and base vector transformed strains. In addition, there may also be more variation among the transformants of these genes than those with no effect, since each transformant could have different degrees of increased lipid biosynthesis, as opposed to genes with null effects. Following this logic, a total of 234 transformants were screened from the pool of metabolically engineered strains for Nile Red fluorescence when cultivated on YPD (234), mTS (11), or both (145). The screening was performed over the course of 2 (YPD) or 3 (mTS) days. The results of this preliminary screening are shown in FIG. 8A, which displays the top 50% performers of each gene. Three gene targets (DGA1-1233, DGA1-1389, and ACC1) had either large standard deviations, higher relative normalized fluorescence (1.5-2 times higher), or both when compared to the WT yeast transformed with the base vector. This behavior was independent of the screening medium for DGA1-1233 and ACC1. Additionally, DGA1-1389, GUT1-1617 and ACL1/ACL2 displayed moderate standard deviations when screened in mTS media. The complexity of mTS likely contributed to this phenomenon. In general, however, transformants that performed well in YPD media also performed well in mTS media. Considering the variability of thin stillage across ethanol plants, this is encouraging because it implies that the engineered strains have the flexibility to overproduce lipids in various types of media. In fact, a total of 12 transformants were identified that exhibited one full standard deviation higher normalized fluorescence compared to the empty vector transformed yeast at the end of the growth phase when cultivated on both YPD and mTS. Eight of these are DGA1-1233 transformants, while the other 4 are ACC1 transformed strains.

In order to obtain a more statistically significant analysis of these results, the top performers of each gene were rescreened in triplicate in mTS. The results of this analysis are shown in FIG. 8B, and clearly demonstrate increased normalized fluorescent signals relative to the WT in DGA1-1233 6L, GUT1-1602 6L, and GUT1-1617 2L. In these transformants, it was also confirmed that the entire cassette had integrated into the genome by PCR amplification from genomic DNA using primers specific to the cassette. All had the expected fragment (data not shown).

Effects of Overexpressing Glycerol Kinase in *L. Starkeyi*

The presence of sugars or oligosaccharides can repress glycerol utilization in some yeasts, so overexpressing the glycerol kinase gene (GUT1) in *L. starkeyi* could increase glycerol utilization if that were the rate limiting step. When this hypothesis was tested, *L. starkeyi* transformants showed increased lipid content by Nile Red fluorescence, but presented lower growth rates. In screening about twelve GUT1-1602 and GUT1-1617 transformants for growth on thin stillage plates, one GUT1-1617 transformant, Ls-11, appeared to grow relatively faster than the others. This strain was selected to use in shake flask and 3-L bioreactor trials to compare against the WT strain. Ls-11 showed higher cell growth and glycerol utilization rates as compared to WT cells in shake flasks (FIG. 9). The cells from the 200 ml shake flasks were then used to inoculate 200 ml of medium in 3-L bioreactors. In the bioreactor studies glycerol utilization by the Ls-11 transformant was initially faster. Besides these characteristics, the Ls-11 transformant accumulated larger liposomes when examined microscopically, and formed pseudomycelia structures (FIG. 10B).

It was hypothesized that in the GUT1 transformant, glycerol kinase shunts glycerol directly towards triglyceride production via glycerol-3-phosphate, and that this accounts for higher lipid accumulation with lower growth rates. To increase the growth rate on glycerol glycerol-3-phosphate dehydrogenase (GUT2) can also be overexpressed, as described in subsequent sections. Overexpression of GUT1 alone has complex and differing effects on the growth and morphology of *L. starkeyi*. Different transformants of GUT1 alone show various rates of growth and increased lipid accumulation, some of which are superior to the WT or Ls-11.

Remarkably, *L. starkeyi* is capable of using cellobiose, trehalose, amylodextrins, cellulo-oligosaccharides, xylose, xylan oligosaccharides and glycerol—the primary carbohydrate sources present in thin stillage. The fact that *L. starkeyi* effectively consumes all of the oligosaccharide components and all of the glycerol in thin stillage highlights the importance and bioprocessing capabilities of this organism.

Evaluation of Other Cellular Features of DGA1-Transformed Strain

To gain further insight into the physiology of the metabolically engineered strains, a deeper evaluation into the DGA1-transformed strain (DGA1-1233 6L) was performed by evaluating its whole crude lipid content, dry cell weight, growth rate, consumption of organics, and cellular morphology relative to the WT when cultivated in mTS in a bioreactor. The DGA1-1233 6L strain grew slightly slower than the WT, leading to marginally reduced glycerol and cellobiose utilization rates (FIG. 11). Nevertheless, both strains consumed all of the available oligosaccharides and carbon sources present in mTS within five days, except for trace amounts of lactic acid (data not shown). When the cells were examined under the microscope, significantly more liposomes were observed in the DGA1-1233 transformant than the WT (FIG. 11). Remarkably, it was found that overexpression of DGA1 increased the final lipid content from 8.25 g/L to 22.7 g/L, which is an increase of about 14.5 g/L or 275%. This also correlates to an increase in the lipid content (g lipid/g dry cell weight) from approximately 30% to 85% (FIG. 12). It is hypothesized that overexpression of DGA1 is seeding liposome formation, and this in turn is increasing the lipid carrying capacity of the cells. Taken together, the present examples have demonstrated the creation of a DGA1-1233 engineered strain of *L. starkeyi* capable of efficiently converting mTS into cell mass with nearly 85% lipid content and 22.7 g/L lipids. This was also accomplished without optimization of culturing conditions (aeration, pH, temperature, etc.), which will surely lead to further improvements in lipid production and productivity.

Improved Screening by Substituting Bodipy Dye for Nile Red

Nile Red dye is useful in identifying engineered yeast strains that produce more lipid when cultivated on modified thin stillage (mTS), but it has several limitations: First, thin stillages from different plants vary greatly, and this variance can affect the response of the Nile Red assay. Stillages are altered by the method and extent of corn oil extraction, the extent of stillage backset, and whether clarification, and/or concentration is employed. Each of these factors affect cell growth, lipid production and the response of the Nile Red assay. Second, the mTS medium used in the screens can interfere with the Nile Red fluorescent signal, which necessitates washing cells prior to dye addition. Third, Nile Red dye itself is unstable, and signal loss occurs within several minutes following addition. Finally the number of handling steps reduces throughput in sample processing. All of these factors are exacerbated because random integration of genes into the chromosome requires examining many transformants in order to identify the top performers. An effective screening assay must be rapid, offer similar responses on many different stillages and effective in-situ without cell harvest or washing. We therefore modified our screening process to accommodate higher sample throughput by using a different fluorescent dye, Bodipy, which is superior to Nile Red in many aspects, and by standardizing the medium for screening.

Bodipy (boron-dipyrromethene) fluorescent dyes are much more sensitive and stable than Nile Red. They have been used successfully for conducting in vivo lipid trafficking and accumulation studies. One Bodipy variant (4,4-Difluoro-1,3,5,7,8-Pentamethyl-4-Bora-3a,4a-Diaza-s-Indacene) is ideal for detecting neutral lipids, such as those that accumulate in the liposomes of *L. starkeyi*. We established a new screening methodology in which Bodipy dye (0.6 μg/mL) is added directly to a synthetic thin stillage (sTS) to mimic cultivation in mTS under more consistent conditions. Synthetic thin stillage is composed of 6.7 g/L yeast nitrogen base with ammonium sulfate and amino acids, 20 g/L glycerol, and 6 g/L cellobiose. This method enables a 6.5 fold higher throughput in screening. It also requires fewer steps, as samples from actively growing cultures can be immediately assessed for fluorescence without washing off stillage prior to dye addition.

We also developed an improved automated method for ranking transformants based on their raw fluorescence with Bodipy. In short, samples are normalized by dilution to a target OD630 and then measured for fluorescence once a day for four days. An algorithm is then applied to rank the transformants for easy identification of prime performers. The data can be presented as bar graphs of either entire transformant pools or replicates of the same transformants. These graphs account for the dilution factor of the cells/dye, which we refer to as fluorescence in the figures for simplicity, even though it is fluorescence following correction for dilution. This approach streamlines the data analysis process with minimal manipulation. As proof of principle, many of the same transformants that had been selected manually in Nile Red assays were also identified by this approach, along with other high performing strains that might have been overlooked based on the previous method.

Investigating DGA1 Cassette Variants on Lipid Accumulation

One of the most lipogenic cassettes discussed above overexpresses diacylglycerol acyltransferase (DGA1-1233), which was cloned from cDNA (cDGA1-1233). It employs a NAT marker for resistance to the antibiotic nourseothricin to enable selection of transformed strains. In order to facilitate overexpression of cDGA1-1233-NAT in combination with other genes—either by sequential transformations or by mating—we constructed a second DGA1-1233 overexpression cassette using an alternate resistance marker. We then determined the conditions under which *L. starkeyi* transformants could be recovered on plates containing an antibiotic other than nourseothricin.

We next questioned whether overexpression of cDNA or genomic DNA (gDNA) of DGA1 (gDGA1-1233) resulted in better transformants. The principal difference between the gDNA and cDNA clones of DGA1-1233 is the presence or absence of introns. Introns are known to enable alternative splicing of mRNA so a single gene can create multiple proteins, and while introns do not encode protein products, they can be integral to the regulation of gene expression.

Little is known about how or whether introns regulate gene expression in *L. starkeyi*. To address this, we created sibling cDGA1-1233 and gDGA1-1233 cassettes cloned from cDNA and gDNA into a vector that confers resistance to Hygromycin B. These were then transformed into *L. starkeyi* and the Bodipy fluorescence of the resulting transformant pools were monitored in sTS over the course of four days. Although both versions yielded more fluorescence over the wild-type strain, the gDNA version did not induce as many liposomes as the cDNA version, which indicated that the presence of introns modulated cDGA1-1233 expression. Subsequent screening tests revealed that the top cDNA transformant (cDGA1-1233 154L) outperformed the top gDNA transformant (gDGA 163M). Moreover, cDGA 154L behaved similarly to strain 6L, the top performer from the Nile Red screen. See FIG. 13. Therefore, we selected cDGA1-1233 154L as our platform strain for further development.

Deregulated Acc1 Mutants

ACC1 expression is induced under lipogenic conditions in *L. starkeyi*, and when overexpressed, we identified four transformants that exhibited one full standard deviation higher normalized fluorescence when compared to yeast transformed with the empty vector. However, these transformants were clearly less prodigious at producing lipids compared to our DGA1 transformants. This was surprising, since ACC catalyzes the carboxylation of acetyl-CoA into malonyl-CoA, which is a regulated commitment step in fatty acid biosynthesis.

Enzyme activity can be regulated by more factors than gene expression alone. In fact, ACC activity in *S. cerevisiae* and other organisms is regulated by an AMP-activated protein kinase (Snf1), which phosphorylates certain serine residues. Mutation of these residues can prevent inhibition of ACC, and increase lipid yields.

To determine if ACC could also be deregulated in *L. starkeyi*, we identified two possible serine phosphorylation sites in the *L. starkeyi* ACC1 ortholog based on the AMPK phosphorylation target motif, and created three mutated versions of the ACC1 gene (S639A, S1146A, and the double mutant S639A/S1146A). These were made because it was unknown which mutations and in what combination could deregulate Acct activity. Following transformation and fluorescence screening in yeast, we discovered that constitutive expression of the single S1146A mutant (but not S639A nor the double mutant cassette), increased average fluorescence levels, as shown in FIG. 14.

Overexpression of Acyltransferases

Given the dramatic improvement in lipid accumulation that occurs in DGA1-1233 engineered strains, we hypothesized that expression of additional genes involved in the biosynthesis of triacylglycerols might coax cellular metabolism towards additional lipid production. The DGA1 gene product carries out the third and final acylation step in triacylglycerol synthesis, so we focused our attention on the two acyltransferases that catalyze the previous reactions, namely SCT1 and SLC1. The former (SCT1) is a glycerol-3-phosphate acyltransferase that carries out the first acylation step, whereas the latter (SLC1) is a lysophosphatidate acyltransferase, which catalyzes the second acylation step. To test these genes, we constructed SCT1 and SLC1 overexpression cassettes from gDNA under the control of the CIT1 promoter/terminator pair (SCT1) or the FBA1 promoter/terminator pair (SLC1), and generated over 200 transformants from each cassette to assay for increased lipid production. These strains were evaluated on sTS medium using our Bodipy screening methodology.

Data gathered from an exemplary screen of SCT1 transformants is shown in FIG. 15. Overexpression of SCT1 caused a moderate increase in lipid accumulation under these conditions. SCT1 transformants, on average, yielded 5-10% increased lipid content as measured by Bodipy fluorescence. However, some of the top performing SCT1 strains produced fluorescent readings approximately 30% higher than the wildtype across all time points tested. Taken together, these results demonstrate that SCT1 plays a critical role in initiating triacylglycerol biosynthesis in *L. starkeyi*. Additionally, SCT1 is an attractive target because it utilizes glycerol-3-phosphate as a substrate, and could potentially improve the rate of glycerol utilization in feedstocks with high glycerol content, such as thin stillage. SCT1 was also introduced into other genetic backgrounds by both mating and secondary transformations, as described below, to generate strains with further improvements.

In contrast to SCT1, overexpression of SLC1 did not result in any statistically significant improvements in lipid accumulation. On average the SLC1 strains performed no better, or perhaps slightly worse, than the wild-type in terms of Bodipy fluorescence readings (FIG. 16). Growth rates of all strains were approximately similar. However, there were a few strains that performed better than any wild-type replicates (e.g. SLC1-30L, FIG. 16), which could occur if multicopy integration or specific integration sites are required for SLC1 to have a measurable impact on lipid production.

Given that overexpression of SLC1 alone does not typically increase lipid production, this suggests that the second acylation reaction catalyzed by SLC1 is not a rate-limiting or highly regulated step during the accumulation of lipids in Lipomyces. Since we have demonstrated that overexpression of SCT1 (1st acylation) and DGA1/2 (3rd acylation) have such significant effects on improving lipid accumulation, it follows that these are the more significant bottlenecks than the SLC1 reaction.

However, it remains to be seen if combinatorial expression of SLC1 with other genes may synergistically increase lipid production. It is possible that overexpression of SLC1 in a SCT1 engineered strain could further improve lipid production if the bottleneck resolved by acceleration of the first acylation step (SCT1) subsequently leads to the creation of a new rate-limiting step at the second acylation (SLC1). Alternatively, overexpression of SLC1 in a DGA1 engineered strain could also improve lipid production by introducing a metabolic "pull" towards triacylglycerol production.

Combinatorial Expression of Lipogenic Cassettes

In order to evaluate the effects of overexpressing more than one lipogenic cassette in the same organism, we pursued two strategies. First, top strains with different resistance markers were mated together and subjected to sporulation, and progeny harboring both integrated cassettes were selected on double antibiotic plates. Alternatively, top strains were also used as a platform for a second round of transformations with another cassette, as long as the resistance markers were different. The resulting double transformed strains were then evaluated in our Bodipy screen against the progenitor transformant strain for enhanced lipid production. In this way, we screened over 70 mated strains of top performers and 200 double transformed strains.

We first evaluated mated transformants overexpressing DGA1-1233 and ACC1, ACC1(S639A), and ACC1 (S1146A). In some cases, the mated strains performed better than the parental strains. The biggest improvement was seen in the DGA1-1233/ACC1(S1146A) cross (FIG. 17). The DGA1-1233/ACC1(S639A) cross performed no better than the DGA1-1233/ACC1 cross and also no better than the parental DGA1-1233 strain, again suggesting that S639 plays no role in regulating ACC1. Hence, the combination of overexpressing DGA1-1233 and ACC1 in *L. starkeyi* enhances lipid production compared to independent overexpression of these proteins, but is particularly pronounced when ACC1 is mutated at the S1146 phosphorylation site.

We also evaluated mated transformants constitutively expressing DGA1-1233 and SCT1, and a strain with two DGA1-1233 overexpression cassettes. In both cases, each strain performed better than the parental strains. These are shown in FIG. 18, along with the wild-type and our previously identified top performer (cDGA NAT) for comparison purposes.

Combinatorial Expression of Lipogenic and Auxiliary Cassettes

We previously determined that certain cassettes resulted in no significant increase in lipid accumulation relative to control strains as deemed by Nile Red analysis in *Lipomyces starkeyi*. See FIG. 8. These included the dual overexpression of ATP citrate lyase subunits 1 and 2 (Acl1/Acl2), and the cDNA and gDNA versions of the malic enzyme (gME and cME). We re-evaluated these transformants in our sTS screening methodology using Bodipy and obtained similar results. We hypothesized that overexpressing these genes has little effect on lipid accumulation since they are not directly involved in the regulatory mechanisms that govern lipogenesis. However, their activities may synergistically enhance lipid accumulation in strains that have been deregulated from one or more of these mechanisms.

To test this hypothesis, we selected our top DGA1 transformant (cDGA1) to cross with select transformants overexpressing the cDNA version of the ATP citrate lyase cassette (cAcl1/2), or the cDNA and gDNA versions of the malic enzyme cassettes (cMalic Enzyme, gMalic Enzyme). After mating, the progeny and parental strains were evaluated in sTS containing Bodipy for lipid accumulation. As observed previously, the Acl1/Acl2 and malic enzyme sole transformants performed marginally better than the wild-type strain due to the presence of resistance marker integration and overexpression (FIG. 19). Sole overexpression of a resistance marker cassette can be marginally lipogenic due to a number of possibilities, including slower transformant growth and the position in which the cassette integrated in the genome. However, when coupled with overexpression of DGA1, the crossed strains performed significantly better than either of the parental strains, particularly on the third and fourth days of culture growth (FIG. 19). As a control, we also evaluated the parental DGA1 strain transformed with the empty base vector overexpressing the same resistance marker as the lipogenic transformants. The overall performance of these control strains was slightly worse than the parental DGA1 strain (FIG. 20), implying that the lipid accumulation observed in the mated strains could be synergistic, as the total improvement is the same if not higher than the individual improvements combined.

Enhanced glycerol utilization is another feature that is particularly important, due to the large amount of glycerol present in thin stillage. Glycerol Kinase (GUT1) catalyzes the phosphorylation of glycerol to glycerol-3-phosphate, and is the first step in glycerol utilization. However, when GUT1 was overexpressed in *L. starkeyi*, the cells presented with significantly lower growth rates, presumably due to the introduction of a metabolic bottleneck. To overcome this, we transformed a strain overexpressing GUT1 with an FAD dependent glycerol-3-phosphate dehydrogenase (GUT2), which catalyzes the second reaction in glycerol utilization by conversion of glycerol-6-phosphate to dihydroxyacetone phosphate (DHAP), and screened the resulting double transformants for growth on glycerol and lipid accumulation. Dual overexpression of GUT1 and GUT2 rescued the growth rates in approximately half of the transformants evaluated (FIG. 21), with some exhibiting superior lipid accumulation relative to the parental strains (FIG. 22). Importantly, overexpression of GUT2 alone did not significantly affect lipid accumulation (FIG. 22). One of the highly lipogenic strains (GUT1/GUT2 1L) was chosen for scale-up in shake flask experiments to better evaluate its glycerol utilization rate in media containing both glucose and glycerol as a carbon source (FIGS. 23A-23D). The results of this experiment demonstrate that the GUT1/GUT2 double transformant consumed glycerol at a faster rate than the wild-type, once glucose catabolite repression was alleviated.

The highly lipogenic nature of some of the double GUT1/GUT2 transformants was not anticipated, since enhanced glycerol utilization might diminish glycerol pools needed for triacylglyceride synthesis. One explanation for this is that only one molecule of glycerol is needed for every triacylglyceride formed, and even though the wild-type strain uses glycerol as a substrate, expression of the assimilation pathway is not optimal. Biosynthesis of acyl carbon chains could be enhanced by increased metabolic carbon flux due to faster glycerol catabolism.

Overexpression of Glycerol-3-Phosphate Dehydrogenase (GPD1)

Intracellular production of glycerol involves the reduction of dihydroxyacetone phosphate (DHAP) into glycerol-3-phosphate by the NADH dependent enzyme glycerol-3-phosphate dehydrogenase (GPD1). Overexpression of GPD1 could alleviate a potential bottleneck in glycerol formation and introduce a metabolic "push" towards triacylglycerol production. Hence, we constructed a GPD1 overexpression cassette driven by a pyruvate kinase (PYK1) promoter and the cognate PYK1 terminator. This was transformed into *L. starkeyi* and several hundred transformants were obtained, of which a subset were selected for Bodipy analysis in sTS. The results of this are shown in FIG. 24. The transformant pool evaluated had moderately higher fluorescence over the wild-type, which became progressively more pronounced throughout the duration of the screen. In fact, by the last day the average fluorescence of the transformant pool was almost 13% higher than the wild-type. This is counterintuitive, since by this time the cells have consumed all of the cellobiose and most of the glycerol present in sTS. Lipogenic effects should be observed when the cells are consuming cellobiose and producing DHAP to convert into glycerol, not consuming glycerol. This could be explained if GPD1 favors conversion of glycerol-3-phosphate into DHAP during glycerol consumption. The DHAP could then enter the glycolytic pathway and be used to produce energy, which indirectly effects lipid levels and/or cell robustness. A similar Bodipy screen performed on media lacking glycerol but containing glucose could provide more insight into this phenomenon.

Engineering the Pentose Phosphate Pathway

To test our prediction that overexpression of 6-phospholuconate dehydrogenase (GND1) and/or glucose-6-phosphate dehydrogenase (ZWF1) could improve lipid production via increasing the cytoplasmic pool of NADPH, we constructed a plasmid to simultaneously express both genes. The plasmid was transformed into Lipomyces, and several hundred transformants were obtained. Of these, 60 colonies were selected for further screening using our sTS and Bodipy methodology. The results of this screen are shown in FIG. 25.

We found that dual overexpression of GND1 and ZWF1 leads to moderately improved lipid accumulation in Lipomyces (FIG. 25). The average fluorescence readings of all transformants outperformed the wild-type by about 10-15% at each time point. Two exceptional strains, "GND1+ZWF1 37L" and "GND1+ZWF1 26L" had fluorescent values approximately 30% and 60% higher than the wild-type, respectively. These results suggest that when engineered cells are grown on sTS, overexpression of GND1 and ZWF1 helps to "pull" glucose (derived from cellobiose or amylodextrins) towards the pentose phosphate pathway. Catabolism of glucose via this pathway generates more NADPH than via glycolysis, which increases the availability of reducing power required for lipid biosynthesis.

Generation and Use of an NHEJ-Deficient (lig4Δ) Strain for Further Metabolic Engineering In *Lipomyces starkeyi*, genetic transformation occurs primarily via random integration into the genome, likely by a non-homologous end joining (NHEJ) mechanism. Previous attempts to disrupt genes of interest using homologous recombination with knockout constructs were unsuccessful. However, it is well known that disruption of the NHEJ pathway in a wide range of yeast species greatly increases homologous recombination efficiencies, and facilitates targeted deletion or insertion of genes. Knockouts of Ku70, Ku80, and/or Lig4 have all been commonly used to ablate NHEJ. Therefore, we sought to disrupt the DNA ligase LIG4 (PID_2300, SEQ ID NO:73 (nucleotide) and SEQ ID NO:74 (protein)), to generate an NHEJ-deficient strain of Lipomyces. A strain with improved homologous recombination could be used to knock out members of the beta-oxidation pathway, for example, to eliminate the ability of *Lipomyces starkeyi* to consume accumulated lipids.

A LIG4 knockout construct was compiled, using a LoxP-flanked NAT resistance construct bordered by 3 kb of cloned genomic DNA homologous to the upstream (promoter) and downstream (terminator) regions neighboring the LIG4 gene. The transformation rate was very low when introduced into Lipomyces, due to the large size of the construct (≈8.4 kb). A total of 22 colonies were selected for further examination to determine if they were truly LIG4 knockouts (lig4Δ). Following genomic DNA extraction and PCR genotyping, we found that only 1/22 transformants (4.5%) harbored a band consistent with replacement of the LIG4 gene by the NAT resistance construct (lig4::NAT). Thus, random integration elsewhere into the genome was the dominant mode of genetic transformation and that homologous recombination occurs only about 5% of the time even when very long flanking regions are used. Subsequent amplification and sequencing of the LIG4 locus in the putative knockout strain confirmed that gene replacement by homologous recombination occurred exactly as intended.

To determine the utility of this strain as a genetic tool, we designed two additional knockout constructs, targeting the acyl-CoA oxidase PDX1 and multifunctional enzyme (3-hydroxyacyl-CoA dehydrogenase & enoyl-CoA hydratase) FOX1 in the lig4Δ strain. These constructs utilized a LoxP-flanked HPH resistance marker, bordered by only 1 kb of cloned genomic DNA homologous to the upstream/downstream regions neighboring each respective gene. Transformation of the lig4Δ strain with these constructs resulted in about 70 colonies each. From these, a total of 18 strains were selected for analysis by PCR genotyping. Of the PDX1 transformants, we found that 7 out of 9 (78%) were confirmed as true knockouts. As for the FOX1 transformants, only 2 out of 9 (22%) were confirmed to be true knockouts. Regardless, these significantly improved homology recombination rates demonstrate that gene deletions are much easier to achieve in the lig4Δ::NAT background, and can be accomplished with shorter regions of homology.

Disruption of the β-Oxidation Pathway in *L. Starkeyi*

As described above, we generated a NHEJ-deficient Lipomyces strain by gene replacement of the DNA ligase LIG4 with a NAT resistance construct (lig4Δ::NAT). Using this strain as a platform, two additional transformations were carried out in order to subsequently knock out either the acyl-CoA oxidase PDX1 or the multifunctional enzyme FOX1 by homologous recombination mediated gene replacement with a LoxP-flanked HPH construct. The resulting strains were knockouts for both LIG4 and either PDX1 or FOX1 (ligΔ::NAT, pox1Δ::HPH), (lig4Δ::NAT, fox1Δ::HPH).

To test our prediction that disruption of the β-oxidation pathway could improve lipid accumulation, we subjected several replicates of validated pox1Δ or fox1Δ knockouts to our standard Bodipy screening methodology in sTS medium (FIG. 26). We found that deletion of either PDX1 or FOX1 mildly enhances lipid accumulation when cells are incubated under aerobic conditions. Average fluorescent readings of these knockout strains ranged from about 5-15% higher values that the wildtype controls. These results suggest that, in addition to overexpressing lipogenic genes, eliminating lipid consumption by the β-oxidation pathway is another viable route for improving lipid accumulation in *Lipomyces starkeyi.*

Overexpression of DGA2—a Second Diacylglycerol Acyltransferase

Overexpression of diacylglycerol acyltransferases, alone or in combination with other lipogenic genes, is predicted to increase lipid accumulation. Unlike *Saccharomyces cerevisiae*, some oleaginous yeast species (e.g. *Yarrowia lipolytica*) possess two or more protein encoding genes with diacylglycerol acyltransferase activity. Upon searching the genome for additional putative DGA genes, we discovered that *Lipomyces starkeyi* contains a second, previously unknown, diacylglycerol acyltransferase gene (DGA2, PID_6231, SEQ ID NOS: 57 and 58). The sequences of DGA1 and DGA2 are quite divergent, as DGA2 is a member of the MBOAT family (Membrane Bound O-Acyl Transferase), and possesses several transmembrane domains. DGA1 is most likely localized to liposomes, while we predict DGA2 resides in the endoplasmic reticulum.

It is unknown whether DGA1 and DGA2 might have differing metabolic roles, activities, or regulation. We therefore tested whether overexpression of the DGA2 gene was capable of increasing lipid production. A plasmid was designed to overexpress DGA2 under the control of the native Lipomyces TPI1 promoter and PGK1 terminator. Hundreds of transformants were obtained and subjected to the Bodipy screening methodology described previously. In an exemplary screen, 87 individual DGA2 transformant strains were grown and assessed for lipid accumulation as compared to wild-type replicates. We found that overexpression of DGA2 leads to significantly improved lipid accumulation in Lipomyces (FIG. 27). The average of all DGA2 transformants, which includes poor performers, still outperformed the wild-type by 5-10% on each time point. Some of the most promising strains, such as "DGA2-20L" and "DGA2-70L," had fluorescent values 20-30% higher than the wildtype (FIG. 27). Therefore, we have identified a second diacylglycerol acyltransferase as an engineering target for increasing lipid accumulation in *Lipomyces starkeyi.*

Presence of Trehalose in Thin Stillage and its Utilization in *Lipomyces Starkeyi*

Thin stillage is a complex mixture containing a variety of short-chain oligosaccharides that are difficult to distinguish from each other using typical analytical methods (e.g. HPLC). For example, disaccharides of glucose include cellobiose, maltose, and trehalose, which differ only in the location of their glycosidic bonds. For simplicity, our synthetic thin stillage medium (sTS) includes cellobiose as the sole analog for all disaccharides which might be present. However, trehalose accumulates in *Saccharomyces cerevisiae* in response to many environmental stress conditions, particularly as an adaptation mechanism to ethanol tolerance. Consequently, in the yeast ethanol industry, trehalose is found among the residual sugars at the termination of fermentation. Trehalose makes up a significant portion of the remaining disaccharide fraction, referred to as the "DP2 peak" in reference to the degree of polymerization of the oligosaccharides eluted together during HPLC analysis.

Therefore, complete conversion of the organics present in thin stillage requires either addition of a trehalase enzyme or use of organisms capable of naturally utilizing trehalose as a carbon source. We have observed nearly complete disappearance of the "DP2 peak" when Lipomyces is cultured on thin stillage, which suggests that this species natively possesses the ability to consume the residual trehalose. We discovered two trehalases in *L. starkeyi*, which are categorized based on their predicted pH optimum: the "neutral" trehalase NTH1 (PID_4858, SEQ ID NOS: 59 and 60), and the "acidic" trehalase ATH1 (PID_4583, SEQ ID NOS: 61 and 62). Interestingly, the *L. starkeyi* ATH1 has a strong secretion signal, which indicates its usefulness in engineering strains for hyper-secretion of trehalase, or other glycoside hydrolases. If spent Lipomyces broth were recycled back into primary fermentation vessels, secreted trehalases would reduce the residual sugars present in the DP2 peak, resulting in increased ethanol yields and plant profitability.

Targeting Glycerol Transporters in Lipomyces Starkeyi for Enhanced Glycerol Utilization There are multiple potential routes for glycerol assimilation in yeast. The phosphorylative pathway, which involves the glycerol kinase GUT1 and the mitochondrial FAD-dependent glycerol 3-phosphate dehydrogenase GUT2, ultimately generates DHAP for glycolysis. Simultaneous overexpression of GUT1 and GUT2 improves the rate of glycerol utilization, as described elsewhere. Another strategy for improving glycerol utilization is the overexpression of transporters involved in the uptake of glycerol into the cell. Several glycerol transporters have been identified in yeast.

The primary route for glycerol uptake in *Saccharomyces* is through active transport via STL1, a glycerol/H+ symporter. STL1 is a member of the major facilitator superfamily, a broad group of transporters for many substrates, which can make identification of specific genes difficult. We have identified two a glycerol/H+ symporters in *Lipomyces starkeyi*, referred to as STL1 (PID_114515, SEQ ID NOS:63 and 64 and STL2 (PID_201837, SEQ ID NOS:65 and 66).

A secondary route for glycerol uptake in *Saccharomyces* is through passive transport by FPS1, a glycerol facilitator, which is mainly used for controlled export of glycerol during osmoregulation. However, FPS1 homologs in other species with superior glycerol utilization rates (such as *Pachysolen tannophilus*) have been shown to be the main route of glycerol import. We have identified a FPS1 homolog in *L. starkeyi* (PID_67294, SEQ ID NOS:67 and 68). Interestingly, the *L. starkeyi* FPS1 is more similar to the *Pachysolen* FPS1 than the *Saccharomyces* FPS1, so it may function as a passive glycerol transporter by facilitated diffusion.

We have observed that when Lipomyces is grown in the presence of both glucose and glycerol, glucose is preferentially utilized first due to the effects of carbon catabolite repression. One of the methods for controlling this response arises from transcriptional regulation of glycerol transporters, which are not highly expressed while glucose is present. Transporters unconstrained by transcriptional regulation could help to improve glycerol uptake and enable simultaneous utilization of glucose and glycerol. Therefore, the STL1, STL2, and FPS1 can be overexpressed with constitutive promoters to overcome carbon catabolite repression and improve glycerol utilization rates in *L. starkeyi.*

Engineering Constitutive Glucoamylase Secretion

Alpha-amylase and glucoamylases are major expenses in ethanol plants, required for the hydrolysis of starch polysaccharides into fermentable glucose monomers. Interestingly, *L. starkeyi* is known to synthesize both dextranases and amylases. We found evidence of inducible extracellular glucoamylase activity in the supernatant of cells cultured in media containing starch, but not dextrose. This activity was also eliminated by boiling, indicating that it is the result of one or more secreted enzymes, induced by the presence of complex carbohydrates (FIG. 28 (A)). If one or more of these secreted enzymes could be engineered for high levels of secretion in *L. starkeyi*, then it could serve as a valuable co-product during the production of lipid. To demonstrate the feasibility of this strategy, we identified a secreted α-amylase in *L. starkeyi* and engineered it for constitutive expression. The supernatant of the resulting transformants exhibited glucoamylase activity independent of the culture medium, and this activity was retained following incubation for 1 hour at 70° C. (FIG. 28, (B)). Thus, we have achieved constitutive secretion of a relatively thermostable α-amylase in *L. starkeyi*. Optimally, this will result in a spent culture broth rich in a collection of starch degrading enzymes with exceptional processivity and substrate diversity that could be used in ethanol plants to reduce operating costs, or other related industries.

Consolidation of Transformed Traits

Combinations of gene cassettes from the top lipid producing strains described above further enhance lipid accumulation, and can be done through yeast mating. Mating techniques for *Lipomyces starkeyi* and isolation of spores for screening progeny enables identification of crossed strains with more than one cassette integrated in the genome without needing to create cassettes with alternate resistance markers and repeat the screening process. Nonetheless, integration vectors that confer resistance to G418 and Hygromycin B that are functional in *L. starkeyi* can be used. Lastly, a *Lipomyces starkeyi* strain that constitutively secretes a native α-amylase and could be mated to the DGA1-1233 transformant to obtain a strain that converts mTS to lipids and α-amylase. Lipids and α-amylase are products of much higher value than the mTS substrate, which currently presents a disposal cost.

REFERENCES

Anon, Edn. Jul. 29, 2016 (U.S. Energy Information Administration, 2016).

Athenstaedt, K. YALI0E32769g (DGA1) and YALI0E16797g (LRO1) encode major triacylglycerol synthases of the oleaginous yeast Yarrowia lipolytica. *Biochimica Et Biophysica Acta-Molecular and Cell Biology of Lipids* 1811, 587-596 (2011).

Barcia-Vieitez, R. & Ramos-Martinez, J. I. The Regulation of the Oxidative Phase of the Pentose Phosphate Pathway: New Answers to Old Problems. *Iubmb Life* 66, 775-779 (2014).

Becker, J. et al. Metabolic flux engineering of L-lysine production in *Corynebacterium glutamicum*—over expression and modification of G6P dehydrogenase. *Journal of Biotechnology* 132, 99-109 (2007).

Beopoulos, A. et al. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. *Applied Microbiology and Biotechnology* 93, 1523-1537 (2012).

Bignell, G. R., Bruce, I. J. & Evans, I. H. Amylolytic enzymes of *Lipomyces starkeyi*: purification and size-determination. *Biotechnology Letters* 22, 1713-1718 (2000).

Bligh and Dyer. A rapid method of total lipid extraction and purification. *Canadian Journal of Biochemistry and Physiology* 37(8):911-7 (1959).

Boulton, C.A. & Ratledge, C. Use of transition studies in continuous cultures of *Lipomyces starkeyi*, an oleaginous yeast, to investigate the physiology of lipid accumulation. *Journal of general microbiology* 129, 2871-2876 (1983).

Calvey, C. H., Willis, L. B. & Jeffries, T. W. An optimized transformation protocol for *Lipomyces starkeyi. Current Genetics* 60, 223-230 (2014).

Calvey, C. H., Su, Y. K., Willis, L. B., McGee, M. & Jeffries, T. W. Nitrogen limitation, oxygen limitation, and lipid accumulation in *Lipomyces starkeyi. Bioresource Technology* 200, 780-788 (2016).

Cannella, D. & Jorgensen, H. Do New Cellulolytic Enzyme Preparations Affect the Industrial Strategies for High Solids Lignocellulosic Ethanol Production? *Biotechnology and Bioengineering* 111, 59-68 (2014).

Cardenas, J. & Da Silva, N. A. Engineering cofactor and transport mechanisms in *Saccharomyces cerevisiae* for enhanced acetyl-CoA and polyketide biosynthesis. *Metabolic Engineering* 36, 80-89 (2016).

Chen, L., Zhou, X. S., Fan, W. M. & Zhang, Y. X. Expression, purification and characterization of a recombinant *Lipomyces starkeyi* dextranase in *Pichia pastoris. Protein Expression and Purification* 58, 87-93 (2008).

Choi, J. W. & Da Silva, N. A. Improving polyketide and fatty acid synthesis by engineering of the yeast acetyl-CoA carboxylase. *Journal of Biotechnology* 187, 56-59 (2014).

Collett, J. R., Meyer, S. & Jones, S. Preliminary economics for hydrocarbon fuel production from cellulosic sugars. (2014).

Courchesne, N. M. D., Parisien, A., Wang, B. & Lan, C. Q. Enhancement of lipid production using biochemical, genetic and transcription factor engineering approaches. *J Biotechnol* 141, 31-41 (2009).

Evans, C. T. & Ratledge, C. Possible regulatory roles of ATP-citrate lyase, malic enzyme and AMP deaminate in lipid accumulation by *Rhodosporidium toruloides* CBS-14. *Canadian Journal of Microbiology* 31, 1000-1005 (1985).

Flores, C. L., and Gancedo, C. *Yarrowia lipolytica* mutants devoid of pyruvate carboxylase activity show an unusual growth phenotype, *Eukaryot. Cell* 4 (2005) 356-364.

Gallagher, A.M., Kelly, C. T. & Fogarty, W. M. A novel extracellular carbohydrase produced by *Lipomyces tetrasporus. Applied Microbiology and Biotechnology* 35, 455-460 (1991).

Garay, L. A. et al. Eighteen new oleaginous yeast species. *Journal of industrial microbiology & biotechnology* 43, 887-900 (2016).

Gibson, D. G. et al. Enzymatic assembly of DNA molecules up to several hundred kilobases. *Nature Methods* 6, 343-U341 (2009).

Gietz, R. D., and R. A. Woods, Transformation of yeast by lithium acetate/single stranded carrier DNA/polyethylene glycol method. *Methods in Enzymology* 350:87-96 (2002).

Gomma, A. E., Lee, S. K., Sun, S. M., Yang, S. H. & Chung, G. Improvement in Oil Production by Increasing Malonyl-CoA and Glycerol-3-Phosphate Pools in *Scenedesmus quadricauda. Indian Journal of Microbiology* 55, 447-455 (2015).

Gong, Z. W. et al. Co-fermentation of cellobiose and xylose by *Lipomyces starkeyi* for lipid production. *Bioresource Technology* 117, 20-24 (2012).

Gorner, C. et al. Genetic engineering and production of modified fatty acids by the non-conventional oleaginous yeast *Trichosporon oleaginosus* ATCC 20509. *Green Chemistry* 18, 2037-2046 (2016).

Hamid, A. A., Mokhtar, N. F., Taha, E. M., Omar, O. & Yusoff, W. M. W. The role of ATP citrate lyase, malic enzyme and fatty acid synthase in the regulation of lipid accumulation in *Cunninghamella* sp 2A1. *Annals of Microbiology* 61, 463-468 (2011).

Hammond, E. G., Johnson, L. A., Su, C., Wang, T. & White, P. J. Soybean oil. Bailey's Industrial Oil and Fat Products (2005).

Holdsworth, J. E. & Ratledge, C. Lipid turnover in oleaginous yeasts. *Journal of General Microbiology* 134, 339-346 (1988).

Holdsworth, J. E., Veenhuis, M. & Ratledge, C. Enzyme activities in oleaginous yeasts accumulating and utilizing exogenous or endogenous lipids. *Journal of General Microbiology* 134, 2907-2915 (1988).

Jeffries, T. W. *Lipomyces starkeyi* NRRL Y-11557 Genome Sequencing Project. *European Nucleotide Archive* (2013).

Kang, H. K. et al. Cloning and characterization of a dextranase gene from *Lipomyces starkeyi* and its expression in *Saccharomyces cerevisiae. Yeast* 22, 1239-1248 (2005).

Kildegaard, K. R. et al. Engineering and systems-level analysis of *Saccharomyces cerevisiae* for production of 3-hydroxypropionic acid via malonyl-CoA reductase-dependent pathway. *Microbial Cell Factories* 15 (2016).

Kim, Y. et al. Composition of corn dry-grind ethanol by-products: DDGS, wet cake, and thin stillage. *Bioresource Technology* 99, 5165-5176 (2008).

Lee, S. Y. et al. Demonstration of two independent dextranase and amylase active sites on a single enzyme elaborated by *Lipomyces starkeyi* KSM 22. *Journal of Microbiology and Biotechnology* 13, 313-316 (2003).

Li, Z. et al. Overexpression of malic enzyme (ME) of *Mucor circinelloides* improved lipid accumulation in engineered *Rhodotorula glutinis. Appl Microbiol Biotechnol* (2012).

Lodder, J., Acomina & Kreger-Van Rij, N. J. W. The yeasts-a taxonomic study. (1952).

Moritz, B., Striegel, K., De Graaf, A. A. & Sahm, H. Kinetic properties of the glucose-6-phosphate and 6-phosphogluconate dehydrogenases from *Corynebacterium glutamicum* and their application for predicting pentose phosphate pathway flux in vivo. *European journal of biochemistry/FEBS* 267, 3442-3452 (2000).

Naganuma, T., Uzuka, Y., Tanaka, K. & Iizuka, H. Differences in enzyme activities of *Lipomyces starkeyi* between cells accumulating lipid and proliferating cells. *Journal of basic microbiology* 27, 35-42 (1987).

Oguro, Y. et al. Multicopy integration and expression of heterologous genes in the oleaginous yeast, *Lipomyces starkeyi. Bioscience Biotechnology and Biochemistry* 79, 512-515 (2015).

Ohnishi, J., Katahira, R., Mitsuhashi, S., Kakita, S. & Ikeda, M. A novel gnd mutation leading to increased L-lysine production in *Corynebacterium glutamicum. FEMS Microbiology Letters* 242, 265-274 (2005).

Pan, L.-X. et al. Isolation of the oleaginous yeasts from the soil and studies of their lipid-producing capacities. *Food Technol. Biotechnol* 47, 215-220 (2009).

Papanikolaou, S., Chevalot, I., Komaitis, M., Aggelis, G. & Marc, I. Kinetic profile of the cellular lipid composition in an oleaginous *Yarrowia lipolytica* capable of producing a cocoa-butter substitute from industrial fats. *Antonie Van Leeuwenhoek International Journal of General and Molecular Microbiology* 80, 215-224 (2001).

Punpeng, B., Nakata, Y., Goto, M., Teramoto, Y. & Hayashida, S. A novel raw-starch digesting yeast alpha amylase from *Lipomyces starkeyi. Journal of Fermentation and Bioengineering* 73, 108-111 (1992).

Rangasamy, D. & Ratledge, C. Genetic Enhancement of Fatty Acid Synthesis by Targeting Rat Liver ATP:Citrate Lyase into Plastids of Tobacco. *Plant Physiology* 122, 1231-1238 (2000).

Ratledge, C. Lipid biotechnology—a wonderland for the microbial physiologist. *Journal of the American Oil Chemists Society* 64, 1647-1656 (1987).

Ratledge, C. Regulation of lipid accumulation in oleaginous micro-organisms. *Biochemical Society Transactions* 30, 1047-1050 (2002).

Ratledge, C. Fatty acid biosynthesis in microorganisms being used for Single Cell Oil production. *Biochimie* 86, 807-815 (2004).

Ratledge, C. The role of malic enzyme as the provider of NADPH in oleaginous microorganisms: a reappraisal and unsolved problems. *Biotechnol. Lett.* 36, 1557-1568 (2014).

Riley R, et al. (2016) Comparative genomics of biotechnologically important yeasts. *Proceedings of the National Academy of Sciences* 113(35):9882-9887.

Rippa, M., Giovannini, P. P., Barrett, M. P., Dallocchio, F. & Hanau, S. 6-phosphogluconate dehydrogenase: the mechanism of action investigated by a comparison of the enzyme from different species. *Biochimica Et Biophysica Acta-Protein Structure and Molecular Enzymology* 1429, 83-92 (1998).

Ruenwai, R., Cheevadhanarak, S. & Laoteng, K. Overexpression of acetyl-CoA carboxylase gene of *Mucor rouxii* enhanced fatty acid content in *Hansenula polymorpha*. Mol Biotechnol 42, 327-332 (2009).

Ryu, S. J. et al. Purification and partial characterization of a novel glucanhydrolase from *Lipomyces starkeyi* KSM 22 and its use for inhibition of insoluble glucan formation. *Bioscience Biotechnology and Biochemistry* 64, 223-228 (2000).

Saenge, C., Cheirsilp, B., Suksaroge, T. T. & Bourtoom, T. Potential use of oleaginous red yeast *Rhodotorula glutinis* for the bioconversion of crude glycerol from biodiesel plant to lipids and carotenoids. *Process Biochemistry* 46, 210-218 (2011).

Sitepu, et al. An improved high-throughput Nile red fluorescence assay for estimating intracellular lipids in a variety of yeast species. *Journal of Microbiological Methods* 91:321-328 (2012).

Shi, S. B., Chen, Y., Siewers, V. & Nielsen, J. Improving Production of Malonyl Coenzyme A-Derived Metabolites by Abolishing Snf1-Dependent Regulation of Acc1. *Mbio* 5 (2014).

Steyn, A. J. C., Marmur, J. & Pretorius, I. S. Cloning, sequence analysis and expression in yeasts of a cDNA-containing a *Lipomyces kononenkoae* alpha-amylase encoding gene. *Gene* 166, 65-71 (1995).

Tai, M. & Stephanopoulos, G. Engineering the push and pull of lipid biosynthesis in oleaginous yeast *Yarrowia lipolytica* for biofuel production. *Metabolic Engineering* 15, 1-9 (2013).

Tang, W., Zhang, S., Wang, Q., Tan, H. & Zhao, Z. K. The isocitrate dehydrogenase gene of oleaginous yeast *Lipomyces starkeyi* is linked to lipid accumulation. *Can J Microbiol* 55, 1062-1069 (2009).

Tang, X. L., Feng, H. X. & Chen, W. N. Metabolic engineering for enhanced fatty acids synthesis in *Saccharomyces cerevisiae. Metabolic Engineering* 16, 95-102 (2013).

Tang, X. L. & Chen, W. N. Investigation of fatty acid accumulation in the engineered *Saccharomyces cerevisiae* under nitrogen limited culture condition. *Bioresource Technology* 162, 200-206 (2014).

van Rossum, H. M., Kozak, B. U., Pronk, J. T. & van Maris, A. J. A. Engineering cytosolic acetyl-coenzyme A supply in *Saccharomyces cerevisiae*: Pathway stoichiometry, free-energy conservation and redox-cofactor balancing. *Metabolic Engineering* 36, 99-115 (2016).

Velasco, P., Sieiro, A. M., Ibarguren, I., Ramosmartinez, J. I. & Barcia, R. The Modulation of the Oxidative Phase of the Pentose-Phosphate Pathway in Mouse Liver. *International Journal of Biochemistry & Cell Biology* 27, 1015-1019 (1995).

Vicente, G. et al. Direct transformation of fungal biomass from submerged cultures into biodiesel. *Energy & Fuels* 24, 3173-3178 (2010).

Wang, Z. P., Xu, H. M., Wang, G. Y., Chi, Z. & Chi, Z. M. Disruption of the MIG1 gene enhances lipid biosynthesis in the oleaginous yeast *Yarrowia lipolytica* ACA-DC 50109. *Biochimica Et Biophysica Acta-Molecular and Cell Biology of Lipids* 1831, 675-682 (2013).

Wang, J. C., Xu, R. H., Wang, R. L., Hague, M. E. & Liu, A. Z. Overexpression of ACC gene from oleaginous yeast *Lipomyces starkeyi* enhanced the lipid accumulation in Saccharomyces cerevisiae with increased levels of glycerol 3-phosphate substrates. *Bioscience Biotechnology and Biochemistry* 80, 1214-1222 (2016).

Wei, T., Sufang, Z., Qian, W., Haidong, T. & Zongbao Kent, Z. The isocitrate dehydrogenase gene of oleaginous yeast *Lipomyces starkeyi* is linked to lipid accumulation. *Canadian Journal of Microbiology* 55, 1062-1069 (2009).

Wilkie, A. C., Riedesel, K. J. & Owens, J. M. Stillage characterization and anaerobic treatment of ethanol stillage from conventional and cellulosic feedstocks. *Biomass & Bioenergy* 19, 63-102 (2000).

Wynn, J. P., bin Abdul Hamid, A. & Ratledge, C. The role of malic enzyme in the regulation of lipid accumulation in filamentous fungi. *Microbiology* 145 (Pt 8), 1911-1917 (1999).

Wynn, J.P., Hamid, A. B. A. & Ratledge, C. The role of malic enzyme in the regulation of lipid accumulation in filamentous fungi. *Microbiology-Uk* 145, 1911-1917 (1999).

Xuan, J. W., Fournier, P. & Gaillardin, C. Cloning of the Lys5 gene endocing saccharopine dehydrogenase from the yeast *Yarrowia lipolytica. Current Genetics* 14, 15-21 (1988).

Yen, H.-W., Yang, Y.-C. & Yu, Y.-H. Using crude glycerol and thin stillage for the production of microbial lipids through the cultivation of *Rhodotorula glutinis. Journal of Bioscience and Bioengineering* 114, 453-456 (2012).

Zha, J., Shen, M. H., Hu, M. L., Song, H. & Yuan, Y. J. Enhanced expression of genes involved in initial xylose metabolism and the oxidative pentose phosphate pathway in the improved xylose-utilizing *Saccharomyces cerevisiae* through evolutionary engineering. *Journal of Industrial Microbiology & Biotechnology* 41, 27-39 (2014).

Zhang, Y., Adams, I. P. & Ratledge, C. Malic enzyme: the controlling activity for lipid production? Overexpression of malic enzyme in *Mucor circinelloides* leads to a 2.5-fold increase in lipid accumulation. *Microbiology-Sgm* 153, 2013-2025 (2007).

Zhang, Y., Wang, Z. Y., He, X. P., Liu, N. & Zhang, B. R. New industrial brewing yeast strains with ILV2 disruption and LSD1 expression. *International Journal of Food Microbiology* 123, 18-24 (2008).

Zhang, M., Galdieri, L. & Vancura, A. The Yeast AMPK Homolog SNF1 Regulates Acetyl Coenzyme A Homeostasis and Histone Acetylation. *Molecular and Cellular Biology* 33, 4701-4717 (2013).

Zhao, X., Kong, X. L., Hua, Y. Y., Feng, B. & Zhao, Z. B. Medium optimization for lipid production through co-fermentation of glucose and xylose by the oleaginous yeast *Lipomyces starkeyi. European Journal of Lipid Science and Technology* 110, 405-412 (2008).

Zhou, Y. J. J. et al. Production of fatty acid-derived oleochemicals and biofuels by synthetic yeast cell factories. *Nature Communications* 7 (2016).

Zhu, Z. W. et al. in *Nature Communications*, Vol. 3 (2012).

Exemplary Embodiments of the Invention

Exemplary embodiments of the invention are as follows:

Embodiment 1

A recombinant yeast comprising one or more recombinant nucleic acids configured to express one or more proteins selected from the group consisting of an acetyl-CoA carboxylase, an alpha-amylase, an ATP citrate lyase, a diacylglycerol acyltransferase, a fatty acid synthase, a glycerol kinase, a 6-phosphogluconate dehydrogenase, a glycerol-3-phosphate dehydrogenase, a malic enzyme, a fatty acyl-CoA reductase, a delta-9 acyl-CoA desaturase, a glycerol-3-phosphate acyltransferase, a lysophosphatidate acyltransferase, a glucose-6-phosphate dehydrogenase, a beta-glucosidase, a hexose transporter, a glycerol transporter, a glycoside hydrolase enzyme, and an auxiliary activity family 9 enzyme.

Embodiment 2

The recombinant yeast of embodiment 1, wherein the one or more recombinant nucleic acids comprises one or more recombinant genes configured to express the one or more proteins.

Embodiment 3

The recombinant yeast of any prior embodiment, wherein the one or more recombinant nucleic acids comprises one or more recombinant genes configured to express a glycerol kinase and a glycerol-3-phosphate dehydrogenase.

Embodiment 4

The recombinant yeast of any prior embodiment, wherein the one or more recombinant nucleic acids comprises one or more recombinant genes configured to express a diacylglycerol acyltransferase and at least one of an ATP citrate lyase and a malic enzyme.

Embodiment 5

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2.

Embodiment 6

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2, wherein the sequence comprises a residue other than serine and threonine at a position corresponding to position 1146 of SEQ ID NO:2.

Embodiment 7

The recombinant yeast of any prior embodiment, wherein the one or more recombinant nucleic acids comprises one or more recombinant genes configured to express an acetyl-CoA carboxylase comprising a sequence at least about 90% identical to SEQ ID NO:2, wherein the sequence comprises and a serine or threonine at a position corresponding to position 639 of SEQ ID NO:2 a residue other than serine and threonine at a position corresponding to position 1146 of SEQ ID NO:2.

Embodiment 8

The recombinant yeast of any prior embodiment, wherein the one or more recombinant nucleic acids comprises one or more recombinant genes configured to express one or more alpha-amylases comprising a sequence selected from the group consisting of a sequence at least about 90% identical to SEQ ID NO:4, a sequence at least about 90% identical to SEQ ID NO:6, and a sequence at least about 90% identical to SEQ ID NO:8.

Embodiment 9

The recombinant yeast of any prior embodiment, wherein the one or more recombinant nucleic acids comprises one or more recombinant genes configured to express an ATP citrate lyase comprising a sequence selected from the group consisting of a sequence at least about 90% identical to SEQ ID NO:10 and a sequence at least about 90% identical to SEQ ID NO:12.

Embodiment 10

The recombinant yeast of any prior embodiment, wherein the one or more recombinant nucleic acids comprises one or more recombinant genes configured to express a diacylglycerol acyltransferase comprising a sequence selected from the group consisting of a sequence at least about 90% identical to SEQ ID NO:14, a sequence at least about 90% identical to SEQ ID NO:16, and a sequence at least about 90% identical to SEQ ID NO:58.

Embodiment 11

The recombinant yeast of any prior embodiment, wherein the one or more recombinant nucleic acids comprises one or more recombinant genes configured to express a diacylglycerol acyltransferase comprising a sequence at least about 90% identical to SEQ ID NO:14 and devoid of a sequence corresponding to positions 1-52 of SEQ ID NO:16.

Embodiment 12

The recombinant yeast of any prior embodiment, wherein the one or more recombinant nucleic acids comprises one or more recombinant genes configured to express a fatty acid synthase comprising a sequence selected from the group consisting of a sequence at least about 90% identical to SEQ ID NO:18, a sequence at least about 90% identical to SEQ ID NO:20, a sequence at least about 90% identical to SEQ ID NO:22, and a sequence at least about 90% identical to SEQ ID NO:24.

Embodiment 13

The recombinant yeast of any prior embodiment, wherein the one or more recombinant nucleic acids comprises one or more recombinant genes configured to express a glycerol kinase comprising a sequence selected from the group consisting of a sequence at least about 90% identical to SEQ ID NO:26 and a sequence at least about 90% identical to SEQ ID NO:28.

Embodiment 14

The recombinant yeast of any prior embodiment, wherein the one or more recombinant nucleic acids comprises one or more recombinant genes configured to express a glycerol kinase comprising a sequence at least about 90% identical to SEQ ID NO:26 and devoid of a sequence corresponding to positions 1-5 of SEQ ID NO:28.

Embodiment 15

The recombinant yeast of any prior embodiment, wherein the one or more recombinant nucleic acids comprises one or more recombinant genes configured to express a 6-phosphogluconate dehydrogenase comprising a sequence at least about 90% identical to SEQ ID NO:30.

Embodiment 16

The recombinant yeast of any prior embodiment, wherein the one or more recombinant nucleic acids comprises one or more recombinant genes configured to express a glycerol-3-phosphate dehydrogenase comprising a sequence selected from the group consisting of a sequence at least about 90% identical to SEQ ID NO:32 and a sequence at least about 90% identical to SEQ ID NO:56.

Embodiment 17

The recombinant yeast of any prior embodiment, wherein the one or more recombinant nucleic acids comprises one or more recombinant genes configured to express a glycerol kinase comprising a sequence selected from the group consisting of a sequence at least about 90% identical to SEQ ID NO:26 and a sequence at least about 90% identical to SEQ ID NO:28 and a glycerol-3-phosphate dehydrogenase comprising a sequence at least about 90% identical to SEQ ID NO:56.

Embodiment 18

The recombinant yeast of any prior embodiment, wherein the one or more recombinant nucleic acids comprises one or more recombinant genes configured to express a malic enzyme comprising a sequence at least about 90% identical to SEQ ID NO:34.

Embodiment 19

The recombinant yeast of any prior embodiment, wherein the one or more recombinant nucleic acids comprises one or more recombinant genes configured to express a diacylglycerol acyltransferase comprising a sequence selected from the group consisting of a sequence at least about 90% identical to SEQ ID NO:14, a sequence at least about 90% identical to SEQ ID NO:16, and a sequence at least about 90% identical to SEQ ID NO:58, in combination with at least one of an ATP citrate lyase comprising a sequence selected from the group consisting of a sequence at least about 90% identical to SEQ ID NO:10 and a sequence at least about 90% identical to SEQ ID NO:12 and a malic enzyme comprising a sequence at least about 90% identical to SEQ ID NO:34.

Embodiment 20

The recombinant yeast of any prior embodiment, wherein the one or more recombinant nucleic acids comprises one or more recombinant genes configured to express a fatty acyl-CoA reductase comprising a sequence at least about 90% identical to SEQ ID NO:36.

Embodiment 21

The recombinant yeast of any prior embodiment, wherein the one or more recombinant nucleic acids comprises one or more recombinant genes configured to express a delta-9 acyl-CoA desaturase comprising a sequence at least about 90% identical to SEQ ID NO:38.

Embodiment 22

The recombinant yeast of any prior embodiment, wherein the one or more recombinant nucleic acids comprises one or more recombinant genes configured to express a glycerol-3-phosphate acyltransferase comprising a sequence at least about 90% identical to SEQ ID NO:40.

Embodiment 23

The recombinant yeast of any prior embodiment, wherein the one or more recombinant nucleic acids comprises one or more recombinant genes configured to express a lysophosphatidate acyltransferase comprising a sequence at least about 90% identical to SEQ ID NO:42.

Embodiment 24

The recombinant yeast of any prior embodiment, wherein the one or more recombinant nucleic acids comprises one or more recombinant genes configured to express a glucose-6-phosphate dehydrogenase comprising a sequence at least about 90% identical to SEQ ID NO:44.

Embodiment 25

The recombinant yeast of any prior embodiment, wherein the one or more recombinant nucleic acids comprises one or more recombinant genes configured to express a beta-glucosidase comprising a sequence at least about 90% identical to SEQ ID NO:46.

Embodiment 26

The recombinant yeast of any prior embodiment, wherein the one or more recombinant nucleic acids comprises one or more recombinant genes configured to express a hexose transporter comprising a sequence at least about 90% identical to SEQ ID NO:48.

Embodiment 27

The recombinant yeast of any prior embodiment, wherein the one or more recombinant nucleic acids comprises one or more recombinant genes configured to express a glycerol transporter comprising a sequence selected from the group consisting of a sequence at least about 90% identical to SEQ ID NO:66, a sequence at least about 90% identical to SEQ ID NO:66, and a sequence at least about 90% identical to SEQ ID NO:68.

Embodiment 28

The recombinant yeast of any prior embodiment, wherein the one or more recombinant nucleic acids comprises one or more recombinant genes configured to express one or more glycoside hydrolase family 5 enzymes comprising a sequence selected from the group consisting of a sequence at least about 90% identical to SEQ ID NO:50 and a sequence at least about 90% identical to SEQ ID NO:52.

Embodiment 29

The recombinant yeast of any prior embodiment, wherein the one or more recombinant nucleic acids comprises one or more recombinant genes configured to express a trehalase comprising a sequence selected from the group consisting of a sequence at least about 90% identical to SEQ ID NO:60 and a sequence at least about 90% identical to SEQ ID NO:62.

Embodiment 30

The recombinant yeast of any prior embodiment, wherein the one or more recombinant nucleic acids comprises one or more recombinant genes configured to express an auxiliary activity family 9 enzyme comprising a sequence at least about 90% identical to SEQ ID NO:54.

Embodiment 31

The recombinant yeast of any prior embodiment, wherein at least one of the one or more recombinant nucleic acids comprises a recombinant gene comprising a constitutive promoter or an inducible promoter.

Embodiment 32

The recombinant yeast of any prior embodiment, wherein at least one of the one or more recombinant nucleic acids comprise a recombinant gene comprising a promoter operably linked to a coding sequence of at least one of the one or more enzymes, wherein the promoter has a sequence selected from the group consisting of a sequence at least about 90% identical to any one of SEQ ID NOS:75-84.

Embodiment 33

The recombinant yeast of any prior embodiment, wherein at least one of the one or more recombinant nucleic acids comprise a recombinant gene comprising a terminator operably linked to a coding sequence of at least one of the one or more enzymes, wherein the terminator has a sequence selected from the group consisting of a sequence at least about 90% identical to any one of SEQ ID NOS:85-90.

Embodiment 34

The recombinant yeast of any prior embodiment, wherein the yeast exhibits increased expression of at least one of the one or more enzymes relative to a non-recombinant control.

Embodiment 35

The recombinant yeast of any prior embodiment, wherein the yeast comprises a modification that reduces or ablates the activity of one or more native enzymes in the yeast selected from the group consisting of a delta-9 acyl-CoA desaturase, a glycerol-3-phosphate dehydrogenase, an acyl-CoA oxidase, a 3-hydroxyacyl-CoA dehydrogenase, and an enoyl-CoA hydratase.

Embodiment 36

The recombinant yeast of any prior embodiment, wherein the yeast comprises a modification that reduces or ablates the activity of a native delta-9 acyl-CoA desaturase comprising a sequence at least about 90% identical to SEQ ID NO:38.

Embodiment 37

The recombinant yeast of any prior embodiment, wherein the yeast comprises a modification that reduces or ablates the activity of a native glycerol-3-phosphate dehydrogenase comprising a sequence at least about 90% identical to SEQ ID NO:56.

Embodiment 38

The recombinant yeast of any prior embodiment, wherein the yeast comprises a modification that reduces or ablates the activity of a native acyl-CoA oxidase comprising a sequence at least about 90% identical to SEQ ID NO:70.

Embodiment 39

The recombinant yeast of any prior embodiment, wherein the yeast comprises a modification that reduces or ablates the activity of a native 3-hydroxyacyl-CoA dehydrogenase comprising a sequence at least about 90% identical to SEQ ID NO:72.

Embodiment 40

The recombinant yeast of any prior embodiment, wherein the yeast comprises a modification that reduces or ablates the activity of a native enoyl-CoA hydratase comprising a sequence at least about 90% identical to SEQ ID NO:72.

Embodiment 41

The recombinant yeast of any prior embodiment, wherein the yeast exhibits a property selected from the group consisting of increased lipid production, increased lipid secretion, increased carbohydrase production, increased carbohydrase secretion, increased growth rate, increased glycerol consumption, increase trehalose consumption, and increased cellobiose consumption relative to a non-recombinant control.

Embodiment 42

The recombinant yeast of any prior embodiment, wherein the yeast is a recombinant lipogenic yeast.

Embodiment 43

The recombinant yeast of any prior embodiment, wherein the yeast is a recombinant *Lipomyces starkeyi.*

Embodiment 44

A method of processing comprising:

contacting a medium comprising a first organic with a yeast, wherein the yeast consumes the first organic and produces a second organic.

Embodiment 45

The method of embodiment 44, wherein the first organic is selected from the group consisting of glycerol, cellobiose, xylose, lactic acid, trehalose, and an oligosaccharide.

Embodiment 46

The method of any one of embodiments 44-45, wherein the contacting reduces an amount of the first organic to less than 25% of an initial amount in the medium.

Embodiment 47

The method of any one of embodiments 44-46, wherein the second organic is selected from the group consisting of a lipid and a protein.

Embodiment 48

The method of any one of embodiments 44-47, wherein the second organic is an enzyme.

Embodiment 49

The method of any one of embodiments 44-48, further comprising, after the contacting, separating at least a portion of a component selected from the group consisting of lipid produced by the yeast, enzymes produced by the yeast, and the yeast from at least a portion of one other component of spent medium resulting from the contacting.

Embodiment 50

The method of any one of embodiments 44-49, further comprising, after the contacting, conducting a process selected from the group consisting of liquefaction of starch and saccharification of liquified starch with enzymes produced by the yeast.

Embodiment 51

The method of any one of embodiments 44-50, further comprising, after the contacting, mixing spent medium resulting from the contacting with starch and conducting liquefaction of the starch in the presence of the spent medium.

Embodiment 52

The method of any one of embodiments 44-51, wherein the medium comprises a component selected from the group consisting of glucose, glucan, trehalose, xylose, xylan, arabinose, arabinan, lactic acid, glycerol, acetic acid, butanediol, and ethanol.

Embodiment 53

The method of any one of embodiments 44-52, wherein the medium comprises a component selected from the group consisting of glucose in an amount of from about 0.1 g/L to about 10 g/L, glucan in an amount of from about 1 g/L to about 100 g/L, xylose in an amount of from about 0.1 g/L to about 10 g/L, trehalose in an amount of from about 0.01 g/L to about 100 g/L, xylan in an amount of from 0.5 g/L to about 50 g/L, arabinose in an amount of from about 0.05 g/L to about 5 g/L, arabinan in an amount of from about 0.05 g/L to about 5 g/L, lactic acid in an amount of from about 1.5 g/L to about 150 g/L, glycerol in an amount of from about 1.5 g/L to about 150 g/L, acetic acid in an amount of from about 0.05 g/L to about 5 g/L, butanediol in an amount of from about 0.2 g/L to about 20 g/L, and ethanol in an amount of from about 0.05 g/L to about 5 g/L.

Embodiment 54

The method of any one of embodiments 44-53, wherein the medium comprises a grain ethanol distillation stillage or a processed grain ethanol distillation stillage.

Embodiment 55

The method of any one of embodiments 44-45, wherein the medium comprises a processed grain ethanol distillation stillage made by processing grain ethanol distillation stillage with a step selected from the group consisting of centrifuging, removing oil, and concentrating.

Embodiment 56

The method of any one of embodiments 44-54, wherein the yeast is a lipogenic yeast.

Embodiment 57

The method of any one of embodiments 44-55, wherein the yeast is a non-genetically modified lipogenic yeast.

Embodiment 58

The method of any one of embodiments 44-56, wherein the yeast is non-genetically modified *Lipomyces starkeyi.*

Embodiment 59

The method of any one of embodiments 44-57, wherein the yeast is a recombinant yeast as recited in any one of embodiments 1-43.

We claim:

1. A recombinant yeast comprising one or more recombinant genes, wherein the one or more recombinant genes are configured to express:

a diacylglycerol acyltransferase;

a malic enzyme; and a glycerol-3-phosphate acyltransferase, wherein the glycerol-3-phosphate acyltransferase comprises a sequence at least about 90% identical to SEQ ID NO:40.

2. The recombinant yeast of claim 1, wherein the yeast is a recombinant lipogenic yeast.

3. The recombinant yeast of claim 1, wherein the yeast is a recombinant *Lipomyces starkeyi*.

4. The recombinant yeast of claim 1, wherein the diacylglycerol acyltransferase comprises a sequence at least about 90% identical to SEQ ID NO:14.

5. The recombinant yeast of claim 4, wherein the one or more recombinant genes are further configured to express a second diacylglycerol acyltransferase, wherein the second diacylglycerol acyltransferase comprises a sequence at least about 90% identical to SEQ ID NO:58.

6. The recombinant yeast of claim 1, wherein the malic enzyme comprises a sequence at least about 90% identical to SEQ ID NO:34.

7. The recombinant yeast of claim 1, wherein:

the diacylglycerol acyltransferase comprises a sequence at least about 90% identical to SEQ ID NO:14;

the one or more recombinant genes are further configured to express a second diacylglycerol acyltransferase, wherein the second diacylglycerol acyltransferase comprises a sequence at least about 90% identical to SEQ ID NO:58; and the malic enzyme comprises a sequence at least about 90% identical to SEQ ID NO:34.

8. The recombinant yeast of claim 7, wherein the yeast is a recombinant lipogenic yeast.

9. The recombinant yeast of claim 7, wherein the yeast is a recombinant *Lipomyces starkeyi*.

10. The recombinant yeast of claim 1, wherein the recombinant genes are further configured to express a glycerol-3-phosphate dehydrogenase.

11. A recombinant yeast comprising one or more recombinant genes, wherein the one or more recombinant genes are configured to express:

a diacylglycerol acyltransferase;

a malic enzyme;

a glycerol-3-phosphate acyltransferase; and a glycerol-3-phosphate dehydrogenase, wherein the glycerol-3 -phosphate dehydrogenase comprises a sequence at least about 90% identical to SEQ ID NO:32.

12. The recombinant yeast of claim 11, wherein the one or more recombinant genes are further configured to express a second glycerol-3-phosphate dehydrogenase, wherein the second glycerol-3-phosphate dehydrogenase comprises a sequence at least about 90% identical to SEQ ID NO:56.

13. The recombinant yeast of claim 11, wherein the one or more recombinant genes are further configured to express a glycerol kinase.

14. A recombinant yeast comprising one or more recombinant genes, wherein the one or more recombinant genes are configured to express:

a diacylglycerol acyltransferase;

a malic enzyme;

a glycerol-3-phosphate acyltransferase;

a glycerol-3-phosphate dehydrogenase; and a glycerol kinase, wherein the glycerol kinase comprises a sequence at least about 90% identical to SEQ ID NO:26.

15. The recombinant yeast of claim 14, wherein:

the diacylglycerol acyltransferase comprises a sequence at least about 90% identical to SEQ ID NO:14;

the one or more recombinant genes are further configured to express a second diacylglycerol acyltransferase, wherein the second diacylglycerol acyltransferase comprises a sequence at least about 90% identical to SEQ ID NO:58;

the malic enzyme comprises a sequence at least about 90% identical to SEQ ID NO:34;

the glycerol-3-phosphate acyltransferase comprises a sequence at least about 90% identical to SEQ ID NO:40;

the glycerol-3-phosphate dehydrogenase comprises a sequence at least about 90% identical to SEQ ID NO:32; and the one or more recombinant genes are further configured to express a second glycerol-3- phosphate dehydrogenase, wherein the second glycerol-3-phosphate dehydrogenase comprises a sequence at least about 90% identical to SEQ ID NO:56.

16. The recombinant yeast of claim 15, wherein the yeast is a recombinant lipogenic yeast.

17. The recombinant yeast of claim 15, wherein the yeast is a recombinant *Lipomyces starkeyi.*

18. The recombinant yeast of claim 10, wherein the one or more recombinant genes are further configured to express an acetyl-CoA carboxylase.

19. The recombinant yeast of claim 18, wherein the acetyl-CoA carboxylase comprises a sequence at least about 90% identical to SEQ ID NO:2.

20. A recombinant yeast comprising one or more recombinant genes, wherein the one or more recombinant genes are configured to express:

a diacylglycerol acyltransferase;

a malic enzyme;

a glycerol-3-phosphate acyltransferase;

a glycerol-3-phosphate dehydrogenase;

an acetyl-CoA carboxylase, wherein the acetyl-CoA carboxylase comprises a sequence at least about 90% identical to SEQ ID NO:2 and the acetyl-CoA carboxylase comprises a residue other than serine and threonine at a position corresponding to position 1146 of SEQ ID NO:2.

21. The recombinant yeast of claim 18, wherein:

the diacylglycerol acyltransferase comprises a sequence at least about 90% identical to SEQ ID NO:14;

the one or more recombinant genes are further configured to express a second diacylglycerol acyltransferase, wherein the second diacylglycerol acyltransferase comprises a sequence at least about 90% identical to SEQ ID NO:58;

the malic enzyme comprises a sequence at least about 90% identical to SEQ ID NO:34;

the glycerol-3-phosphate dehydrogenase comprises a sequence at least about 90% identical to SEQ ID NO:32; and the acetyl-CoA carboxylase comprises a sequence at least about 90% identical to SEQ ID NO:2 and the acetyl-CoA carboxylase comprises a residue other than serine and threonine at a position corresponding to position 1146 of SEQ ID NO:2.

22. The recombinant yeast of claim 21, wherein the yeast is a recombinant lipogenic yeast.

23. The recombinant yeast of claim 21, wherein the yeast is a recombinant *Lipomyces starkeyi.*

* * * * *

SEQUENCE LISTING

<160> NUMBER OF SEQ ID NOS: 91

<210> SEQ ID NO 1
<211> LENGTH: 6932
<212> TYPE: DNA
<213> ORGANISM: Lipomyces starkeyi
<220> FEATURE:
<221> NAME/KEY: Intron
<222> LOCATION: (124)..(189)
<220> FEATURE:
<221> NAME/KEY: Intron
<222> LOCATION: (2833)..(2889)
<220> FEATURE:
<221> NAME/KEY: Intron
<222> LOCATION: (2972)..(3027)
<220> FEATURE:
<221> NAME/KEY: Intron
<222> LOCATION: (4522)..(4569)

<400> SEQUENCE: 1

```
atgtctgctg cggccagtag cctcccctcc cactttatcg gccttaacac cgtcgatgtg     60

gcggccaata gccccgttaa ggattttgtc cagaatcatg gtggtcacac cgtcatcact    120

tccgtacgtg accgatctgt ttcctctttg atctttgtcg catcatgact gacgatctaa    180

tccatttagg ttctcatagc gaacaacggt atcgccgctg tcaaggaaat ccgcagtgtc    240

cggaaatggg cctacgagac tttcggcgac gagcgcgcca tctccttcac cgtcatggcc    300

acgcctgagg atctcaaggc aaacgcggat tacatccgca tggcagatca gtacgtcgaa    360

gttcccggcg ggacaaacaa caacaatttc gccaacgtcg agctcatcgt cgatatcgcc    420

gagcgcatga acgtccacgc cgtctgggcc ggctggggac atgcctccga aaacccaaag    480

ctcccagagt ctctcgcgca gtcgccaaag aagatcgtct tcatcggccc gcccggatcc    540

gccatgcggt ctctcggtga caagatctcg tccaccatag ttgcccagca cgcaaaagtc    600

ccctgtattc cctggtctgg aaccggcgtg gacgaagtcc agattgattc tgttagcggt    660

ctcgtcaccg tgtccgatga gatatacgca aagggttgta cttccaccgc ggaagaggct    720

ctcgagaagg cccgcatcat cggcttcccc gtcatgatca aggcttccga aggtggcggt    780

ggcaaaggta ttcgaaaggt cgagagcgag gacaacttcc attctttgta cagccaggtt    840

gccaatgagg tccctggatc tcccatcttc gtcatgaagc ttgccggcaa cgcgcgacat    900

cttgaggtcc aattgcttgc cgatcaatac ggaaacaaca tctctctctt tggcagagat    960

tgctcagtcc agcgtcgtca ccagaagatt atcgaagagg cgcctgtcac tgttgccaac   1020

cccgcaacat tctcggcaat ggaacacgcc gctgttcgac ttggccagct tgtcggctat   1080

gtctccgccg gtacagtcga gtacctctac tctcacgacg acgacaaatt ctacttcttg   1140

gagctcaatc cccgtcttca ggtagagcat cctactaccg agatggtcac cggtgtcaac   1200

ttacccgccg ctcagctcca aatcgcgatg ggtgtgtctc tccaccgaat cagagatatc   1260

cggctcttct acggcgtcga tcctcacact tcgaccgaaa tcgactttga tttctccaag   1320

gagggctctc ttcaaactca gcgccgtcca gtgcccaagg gccacaccac ggcctgccga   1380

atcacgtccg aagatcctgg cgaaggtttc aaaccatcta gtggtgtcat gcacgaactg   1440

aactttagat cgagctccaa tgtctggggt tacttctccg tcggaaatca gggcggaatc   1500
```

```
cactcgttct ccgattccca gttcggtcat atctttgcat tcggcgaaaa cagaagcgcg   1560
agtcgcaagc acatggttgt cgcgttgaag gaattgtcta ttcgtggtga cttccgcact   1620
acggtcgaat atctcattaa gctgcttgag actcctgatt tcgagtctaa caagatcacc   1680
accggatggc tcgatgagct aatttccaag aagctcaccg ccgagcgccc tgatcctgtc   1740
gtcgctgttg tctgcggcgc tgtcacgaag gcacatcttg cttcagaggc ttgcttccag   1800
gagtacaaga attccctaga gaagggccag gtcccgtcga aggacatcct aaagactttg   1860
ttccctgtcg actttatcta cgagggcagc cgatacaagt tcactgtcac gcgatcgtcc   1920
atggatttgt atcagatttt catcaacggt tccaagtgcc tggtcggtgt caaatcactc   1980
agtgacggtg gtcttttggt tttgctcgga ggcaagtccc acaatgtgta ctggaaggac   2040
gaagttggaa ccaccagact cagtgtcgac tccaagactt gcttgttgga gcaggagaat   2100
gatcctaccc agctccgcac tccttccccc ggtaagctcg tcaagttctt ggtcgagaac   2160
ggtgagcacg tcaagactgg acagccgttt gctgaagttg aggtcatgaa gatgtacatg   2220
cccctgattg ctcaggagga cggtatcgtg caattgatca agcagcctgg agctactctc   2280
gaggctggcg atattctcgg cattttagct ctagatgatc catcccgcgt caaacacgcc   2340
aagcccttcg agggtcaact gcctgatttc ggttcgccat tggttctagg cagcaagcct   2400
tcgcagcgat tcaatctgtt gctaagcacc ctcaggaaca ttctggctgg ttttgacaac   2460
caggtcttgt tggcgtcgac tctcaaggat ctgagccaag tattaaagga cgacgcgctg   2520
ccctatagtg agtggaacgc tcagttctcc gcccttcaca gtcgtatccc gcagaagctc   2580
gacgcgactc tttccagtct tatcgagcgc tccaagtcca aggacgctga attcccggca   2640
aagttgctgt tgcgcgctat tgagcgattt gctgaagagt tcatccagcc gcaggatcta   2700
tttgtcttca agcaacaggt cgagcctctt gttaccattg ctacgagata ccaggctggt   2760
ttgaaagcac atgagtatgg tgtcattgct gaattgttgg agcagtattt ggctgtcgag   2820
aaattgtttt cggtgagccg cacacttttc tgttgctgtt atggacgggc cgcgtactaa   2880
catttgtagg gcgccaatat tcgggatgag gatgtttttc tcagacttag agatgaaaat   2940
aaggatgata ttttcaaggt tgtcatgact ggtatgttaa tttgttgtcg cgccggcttt   3000
cgagtaccag tatgttgatg tcactagtat tctctcacgg tcgcgttgga gctaagaaca   3060
acctcatcct cgcaatttta gccgcacttc gatccgacag atctgaggtt tccgaggtcg   3120
ctaaatactt gcggcctgct ctcaagacat taacggagct tgactcaggt gtcactgccc   3180
ctgtggctct caaggctcgt gaactattga tccagtgcgc acttccatct ctcgaggagc   3240
gaaccgccca gctcgaacat atattgcgct cgtctgttgt tgagtcgcga tacggtgagg   3300
tgggctttga gcacagtgct cccagaattg acgtcttgaa ggaggtcatt gactcgcaat   3360
acatcgtttt tgacgttctg ccaaagtttt tcgcgcactc ggatcgttat gtcaccttag   3420
ccgcactcga gctctacgtc cgtcgcgctt atcgcgcgta taacgtcatg agcatggagt   3480
accacaacga aggcgatctt gtgcccgtcg tcacgttcaa gtttttgctt gccgctattg   3540
gcaatcccgc ttacaacatc gtcggacagg gtgctccgtc aggcgattcg cgcattgatt   3600
tccagcgtgc tgcggcggtt tcggatctca catttatgat gagcaagtcc gacagcgagt   3660
ccttgcgatc cggtgtgatt gttcccgtgg ctgatattgc tgatattgac gaagttctcc   3720
ctcgtgcttt ggattacctc ccacagcgag ccggtgcggg atcgggaggc ttctccttct   3780
cggctaaatc tgatttggac tcgaagcgac gaccagcacc gccaaagcca gagtctttga   3840
gcaatatctg caacgttttg atccgcaaga cggcaaaaac cgacgacgct gcacttgtct   3900
```

```
cggatatcaa gttcatcgtc gatgagtaca aggaggagtt cttgcttcga tctattcgac   3960
gagttacatt cgtttgcggc cgcgaggacg gttcgtatcc tggttatttt acgttccgcg   4020
gtcctgacta cgtcgaggac gagagtatcc gacatattga gcctgcgttg gcgtaccagc   4080
ttgagttggg acgtttgtcg aactttaact ataagccgat tttcacggat aaccgcaaca   4140
ttcacgtcta ccaggccatc ggcaaggacg ttcctagcga caagcgtttc ttcgtgagag   4200
gtatcgtcag acccggccgt ctacgtgatg aaattccgac gtcggaatac cttatctctg   4260
aaaccgaccg actgatgtcg gacattttgg acgctctcga ggttatcggt cctaataaca   4320
cggatatgaa ccacattttc atcaactttt cgcccatttt ccatttggta ccggaagagg   4380
tcgaggcagc atttggacag ttcttggaga gatttggacg cagattgtgg agattgagag   4440
tgactggtgc ggagatccgg attatgtgca ccgacccgga gactaatgtg ccgtacccct   4500
tgcgtgcgat tatcacgaat ggtgagtatc tttcatactt ttttttcggc tgctgctaat   4560
tttcgttagt gtccggctat gtcgtccaga gtgagttgta cacggaggtc aagaatgata   4620
agggccaatg ggtgttcaag tcgttgggta agccaggtaa catgcacttg cgctcgatca   4680
cgactccata cgcgaccaag gaatggctac agccgaagag atacaaggca cacttgatgg   4740
gcacgacatt cgtgtacgat ttcccagagc ttttcaacca agctattcgt gctagttggc   4800
gtgcagcgca gcagcagtcg cccgagaatg tgcttacgta caaggagctt atcatggatg   4860
acagtggaga gttgtcggag gtttctcgag agccaggtgc gaatacttgc ggaatggttg   4920
cctggttgtt cacggcgctc actcccgaat atccaacggg ccgtcaattc atcgtggtcg   4980
ccaatgatat cacttacaag attggctcct tcggtcctca ggaggataag tacttccaca   5040
ctgtgaccca gctcgccgtc aaacttggca ttccccgaat ctatctctct gcaaactctg   5100
gtgcgcgaat tggcgttgcg gacgaatttg tgtcattgtt ctcggtcgcc tggaatgatt   5160
cttccaatcc tgaaaaggga ttcaagtact tgtacctcac gcctgcgatc tacaacggtc   5220
tttcggacgc ggccaagaag actgtgctta ccgaacgcat tgttgaggag ggcgaggagc   5280
gatatgttat caccaccatt atcggcgctg aagacggtct tggtgtcgag tgtcttcgtg   5340
gatcgggtct cattgccggc gctacttcga aggcttataa agacattttc acgattactt   5400
tggtcacttg ccgttcggtt ggtattggtg cttatctcgt ccgtctcgga cagcgtgcga   5460
tccagattga gggccagcct atcatactta ctggtgctcc tgcgatcaac aaactccttg   5520
gtcgggaagt ttacagttcg aatttgcagc tcggtggcac gcagatcatg tacaagaacg   5580
gtgtatcgca tcttaccgct aatgatgacc ttgctggtgt catgaagatt atcgagtgga   5640
tgtcatacgt accgtataag aaaggtggtc agctgccaat ttatccatca tcagatacct   5700
gggatcgtga tgtcacttat actcctccca aacaggtccc gtacgatgtc cgatggctga   5760
tcgctggtcg cgaggacgag gagggcggtt tcgagtacgg tttgttcgac aaagactcgt   5820
tccaggagac ccttagcggc tggggctcgaa ctgtcgttgt cggtcgtgcg cggttaggcg   5880
gcatccctgt cggcgtaatt ggcgttgaag tccgctcggt cgagaacatt ttccccgccg   5940
atcctgccaa tcccgattcg acagaaatgg tcgtccagga agccggccag gtttggtacc   6000
ccaactcggc atttaagact gctcaggcga ttaacgattt caaccacggt gaggagcttc   6060
cgctcgtaat cctcgccaac tggagaggtt tctctggcgg tcagcgtgat atgtacaacg   6120
aggtcttgaa gtacggttcg ttcatcgtgg atgcgctcgt tggttacaag cagcctattt   6180
tcgtctacat tccgccgcat gcagagctcc gtggtggttc atgggttgtt atcgatccca   6240
```

ccatcaactc tgatcagatg gagatgtacg cggatgacga ggcacgtgct ggtgtgttgg 6300
agcccgaggg tatggttggc atcaagtacc gtcgtgaccg tctcttggag accatgactc 6360
gtctcgaccc ggtctatgcc tcgctcaagc gccaggccga caagaaagat ctcgctccgg 6420
caatcgctca ggatctcaaa gtcaagttga gcgaacggga aagcacattg atgccaatct 6480
accgacagat cagcttacag ttcgccgact tgcatgaccg ggcaggacga atgaaggcga 6540
agggaactat ccgtgaagtc cttcactggc gtgaggctag acgtttcttc tactggcgtg 6600
ttagacgtcg tgttggcgag agctatattc ttcgtgatct ggaggctgct aacccgaaat 6660
cgacgagact agaacgcgtc gcgcgattga agtcttggta tgctgaggct ggtatcaacg 6720
aatcttccga cgcagacgtc gcaagctgga tcgagaagtc tggtgccgct atcaccagca 6780
aagtcaaaca ggttagaaag gatgcaaaga tccaggactt gttggctctt gtgcgcgcgg 6840
ataaggatgt cgctttgcag ggcctggttg agtccctcaa ggctttgtct actgaggaac 6900
gggatgcgat tttcaagcag gcttctaatt aa 6932

<210> SEQ ID NO 2
<211> LENGTH: 2234
<212> TYPE: PRT
<213> ORGANISM: Lipomyces starkeyi

<400> SEQUENCE: 2

Met Ser Ala Ala Ala Ser Ser Leu Pro Ser His Phe Ile Gly Leu Asn
1 5 10 15

Thr Val Asp Val Ala Ala Asn Ser Pro Val Lys Asp Phe Val Gln Asn
20 25 30

His Gly Gly His Thr Val Ile Thr Ser Val Leu Ile Ala Asn Asn Gly
35 40 45

Ile Ala Ala Val Lys Glu Ile Arg Ser Val Arg Lys Trp Ala Tyr Glu
50 55 60

Thr Phe Gly Asp Glu Arg Ala Ile Ser Phe Thr Val Met Ala Thr Pro
65 70 75 80

Glu Asp Leu Lys Ala Asn Ala Asp Tyr Ile Arg Met Ala Asp Gln Tyr
85 90 95

Val Glu Val Pro Gly Gly Thr Asn Asn Asn Asn Phe Ala Asn Val Glu
100 105 110

Leu Ile Val Asp Ile Ala Glu Arg Met Asn Val His Ala Val Trp Ala
115 120 125

Gly Trp Gly His Ala Ser Glu Asn Pro Lys Leu Pro Glu Ser Leu Ala
130 135 140

Gln Ser Pro Lys Lys Ile Val Phe Ile Gly Pro Pro Gly Ser Ala Met
145 150 155 160

Arg Ser Leu Gly Asp Lys Ile Ser Ser Thr Ile Val Ala Gln His Ala
165 170 175

Lys Val Pro Cys Ile Pro Trp Ser Gly Thr Gly Val Asp Glu Val Gln
180 185 190

Ile Asp Ser Val Ser Gly Leu Val Thr Val Ser Asp Glu Ile Tyr Ala
195 200 205

Lys Gly Cys Thr Ser Thr Ala Glu Glu Ala Leu Glu Lys Ala Arg Ile
210 215 220

Ile Gly Phe Pro Val Met Ile Lys Ala Ser Glu Gly Gly Gly Gly Lys
225 230 235 240

Gly Ile Arg Lys Val Glu Ser Glu Asp Asn Phe His Ser Leu Tyr Ser
245 250 255

```
Gln Val Ala Asn Glu Val Pro Gly Ser Pro Ile Phe Val Met Lys Leu
            260                 265                 270

Ala Gly Asn Ala Arg His Leu Glu Val Gln Leu Leu Ala Asp Gln Tyr
        275                 280                 285

Gly Asn Asn Ile Ser Leu Phe Gly Arg Asp Cys Ser Val Gln Arg Arg
    290                 295                 300

His Gln Lys Ile Ile Glu Glu Ala Pro Val Thr Val Ala Asn Pro Ala
305                 310                 315                 320

Thr Phe Ser Ala Met Glu His Ala Ala Val Arg Leu Gly Gln Leu Val
                325                 330                 335

Gly Tyr Val Ser Ala Gly Thr Val Glu Tyr Leu Tyr Ser His Asp Asp
            340                 345                 350

Asp Lys Phe Tyr Phe Leu Glu Leu Asn Pro Arg Leu Gln Val Glu His
        355                 360                 365

Pro Thr Thr Glu Met Val Thr Gly Val Asn Leu Pro Ala Ala Gln Leu
    370                 375                 380

Gln Ile Ala Met Gly Val Ser Leu His Arg Ile Arg Asp Ile Arg Leu
385                 390                 395                 400

Phe Tyr Gly Val Asp Pro His Thr Ser Thr Glu Ile Asp Phe Asp Phe
                405                 410                 415

Ser Lys Glu Gly Ser Leu Gln Thr Gln Arg Arg Pro Val Pro Lys Gly
            420                 425                 430

His Thr Thr Ala Cys Arg Ile Thr Ser Glu Asp Pro Gly Glu Gly Phe
        435                 440                 445

Lys Pro Ser Ser Gly Val Met His Glu Leu Asn Phe Arg Ser Ser Ser
    450                 455                 460

Asn Val Trp Gly Tyr Phe Ser Val Gly Asn Gln Gly Gly Ile His Ser
465                 470                 475                 480

Phe Ser Asp Ser Gln Phe Gly His Ile Phe Ala Phe Gly Glu Asn Arg
                485                 490                 495

Ser Ala Ser Arg Lys His Met Val Val Ala Leu Lys Glu Leu Ser Ile
            500                 505                 510

Arg Gly Asp Phe Arg Thr Thr Val Glu Tyr Leu Ile Lys Leu Leu Glu
        515                 520                 525

Thr Pro Asp Phe Glu Ser Asn Lys Ile Thr Thr Gly Trp Leu Asp Glu
    530                 535                 540

Leu Ile Ser Lys Lys Leu Thr Ala Glu Arg Pro Asp Pro Val Val Ala
545                 550                 555                 560

Val Val Cys Gly Ala Val Thr Lys Ala His Leu Ala Ser Glu Ala Cys
                565                 570                 575

Phe Gln Glu Tyr Lys Asn Ser Leu Glu Lys Gly Gln Val Pro Ser Lys
            580                 585                 590

Asp Ile Leu Lys Thr Leu Phe Pro Val Asp Phe Ile Tyr Glu Gly Ser
        595                 600                 605

Arg Tyr Lys Phe Thr Val Thr Arg Ser Ser Met Asp Leu Tyr Gln Ile
    610                 615                 620

Phe Ile Asn Gly Ser Lys Cys Leu Val Gly Val Lys Ser Leu Ser Asp
625                 630                 635                 640

Gly Gly Leu Leu Val Leu Leu Gly Gly Lys Ser His Asn Val Tyr Trp
                645                 650                 655

Lys Asp Glu Val Gly Thr Thr Arg Leu Ser Val Asp Ser Lys Thr Cys
            660                 665                 670
```

```
Leu Leu Glu Gln Glu Asn Asp Pro Thr Gln Leu Arg Thr Pro Ser Pro
        675                 680                 685

Gly Lys Leu Val Lys Phe Leu Val Glu Asn Gly Glu His Val Lys Thr
    690                 695                 700

Gly Gln Pro Phe Ala Glu Val Glu Val Met Lys Met Tyr Met Pro Leu
705                 710                 715                 720

Ile Ala Gln Glu Asp Gly Ile Val Gln Leu Ile Lys Gln Pro Gly Ala
                725                 730                 735

Thr Leu Glu Ala Gly Asp Ile Leu Gly Ile Leu Ala Leu Asp Asp Pro
            740                 745                 750

Ser Arg Val Lys His Ala Lys Pro Phe Glu Gly Gln Leu Pro Asp Phe
        755                 760                 765

Gly Ser Pro Leu Val Leu Gly Ser Lys Pro Ser Gln Arg Phe Asn Leu
    770                 775                 780

Leu Leu Ser Thr Leu Arg Asn Ile Leu Ala Gly Phe Asp Asn Gln Val
785                 790                 795                 800

Leu Leu Ala Ser Thr Leu Lys Asp Leu Ser Gln Val Leu Lys Asp Asp
                805                 810                 815

Ala Leu Pro Tyr Ser Glu Trp Asn Ala Gln Phe Ser Ala Leu His Ser
            820                 825                 830

Arg Ile Pro Gln Lys Leu Asp Ala Thr Leu Ser Ser Leu Ile Glu Arg
        835                 840                 845

Ser Lys Ser Lys Asp Ala Glu Phe Pro Ala Lys Leu Leu Leu Arg Ala
    850                 855                 860

Ile Glu Arg Phe Ala Glu Glu Phe Ile Gln Pro Gln Asp Leu Phe Val
865                 870                 875                 880

Phe Lys Gln Gln Val Glu Pro Leu Val Thr Ile Ala Thr Arg Tyr Gln
                885                 890                 895

Ala Gly Leu Lys Ala His Glu Tyr Gly Val Ile Ala Glu Leu Leu Glu
            900                 905                 910

Gln Tyr Leu Ala Val Glu Lys Leu Phe Ser Gly Ala Asn Ile Arg Asp
        915                 920                 925

Glu Asp Val Phe Leu Arg Leu Arg Asp Glu Asn Lys Asp Asp Ile Phe
    930                 935                 940

Lys Val Val Met Thr Val Phe Ser His Gly Arg Val Gly Ala Lys Asn
945                 950                 955                 960

Asn Leu Ile Leu Ala Ile Leu Ala Ala Leu Arg Ser Asp Arg Ser Glu
                965                 970                 975

Val Ser Glu Val Ala Lys Tyr Leu Arg Pro Ala Leu Lys Thr Leu Thr
            980                 985                 990

Glu Leu Asp Ser Gly Val Thr Ala  Pro Val Ala Leu Lys  Ala Arg Glu
        995                 1000                1005

Leu Leu  Ile Gln Cys Ala Leu  Pro Ser Leu Glu Glu  Arg Thr Ala
    1010                 1015                1020

Gln Leu  Glu His Ile Leu Arg  Ser Ser Val Val Glu  Ser Arg Tyr
    1025                 1030                1035

Gly Glu  Val Gly Phe Glu His  Ser Ala Pro Arg Ile  Asp Val Leu
    1040                 1045                1050

Lys Glu  Val Ile Asp Ser Gln  Tyr Ile Val Phe Asp  Val Leu Pro
    1055                 1060                1065

Lys Phe  Phe Ala His Ser Asp  Arg Tyr Val Thr Leu  Ala Ala Leu
    1070                 1075                1080

Glu Leu  Tyr Val Arg Arg Ala  Tyr Arg Ala Tyr Asn  Val Met Ser
```

```
    1085                1090                1095

Met Glu  Tyr His Asn Glu Gly  Asp Leu Val Pro Val  Val Thr Phe
    1100                1105                1110

Lys Phe  Leu Leu Ala Ala Ile  Gly Asn Pro Ala Tyr  Asn Ile Val
    1115                1120                1125

Gly Gln  Gly Ala Pro Ser Gly  Asp Ser Arg Ile Asp  Phe Gln Arg
    1130                1135                1140

Ala Ala  Ser Val Ser Asp Leu  Thr Phe Met Met Ser  Lys Ser Asp
    1145                1150                1155

Ser Glu  Ser Leu Arg Ser Gly  Val Ile Val Pro Val  Ala Asp Ile
    1160                1165                1170

Ala Asp  Ile Asp Glu Val Leu  Pro Arg Ala Leu Asp  Tyr Leu Pro
    1175                1180                1185

Gln Arg  Ala Gly Ala Gly Ser  Gly Gly Phe Ser Phe  Ser Ala Lys
    1190                1195                1200

Ser Asp  Leu Asp Ser Lys Arg  Arg Pro Ala Pro Pro  Lys Pro Glu
    1205                1210                1215

Ser Leu  Ser Asn Ile Cys Asn  Val Leu Ile Arg Lys  Thr Ala Lys
    1220                1225                1230

Thr Asp  Asp Ala Ala Leu Val  Ser Asp Ile Lys Phe  Ile Val Asp
    1235                1240                1245

Glu Tyr  Lys Glu Glu Phe Leu  Leu Arg Ser Ile Arg  Arg Val Thr
    1250                1255                1260

Phe Val  Cys Gly Arg Glu Asp  Gly Ser Tyr Pro Gly  Tyr Phe Thr
    1265                1270                1275

Phe Arg  Gly Pro Asp Tyr Val  Glu Asp Glu Ser Ile  Arg His Ile
    1280                1285                1290

Glu Pro  Ala Leu Ala Tyr Gln  Leu Glu Leu Gly Arg  Leu Ser Asn
    1295                1300                1305

Phe Asn  Tyr Lys Pro Ile Phe  Thr Asp Asn Arg Asn  Ile His Val
    1310                1315                1320

Tyr Gln  Ala Ile Gly Lys Asp  Val Pro Ser Asp Lys  Arg Phe Phe
    1325                1330                1335

Val Arg  Gly Ile Val Arg Pro  Gly Arg Leu Arg Asp  Glu Ile Pro
    1340                1345                1350

Thr Ser  Glu Tyr Leu Ile Ser  Glu Thr Asp Arg Leu  Met Ser Asp
    1355                1360                1365

Ile Leu  Asp Ala Leu Glu Val  Ile Gly Pro Asn Asn  Thr Asp Met
    1370                1375                1380

Asn His  Ile Phe Ile Asn Phe  Ser Pro Ile Phe His  Leu Val Pro
    1385                1390                1395

Glu Glu  Val Glu Ala Ala Phe  Gly Gln Phe Leu Glu  Arg Phe Gly
    1400                1405                1410

Arg Arg  Leu Trp Arg Leu Arg  Val Thr Gly Ala Glu  Ile Arg Ile
    1415                1420                1425

Met Cys  Thr Asp Pro Glu Thr  Asn Val Pro Tyr Pro  Leu Arg Ala
    1430                1435                1440

Ile Ile  Thr Asn Val Ser Gly  Tyr Val Val Gln Ser  Glu Leu Tyr
    1445                1450                1455

Thr Glu  Val Lys Asn Asp Lys  Gly Gln Trp Val Phe  Lys Ser Leu
    1460                1465                1470

Gly Lys  Pro Gly Asn Met His  Leu Arg Ser Ile Thr  Thr Pro Tyr
    1475                1480                1485
```

```
Ala Thr  Lys Glu Trp Leu Gln  Pro Lys Arg Tyr Lys  Ala His Leu
    1490                 1495                 1500

Met Gly  Thr Thr Phe Val Tyr  Asp Phe Pro Glu Leu  Phe Asn Gln
    1505                 1510                 1515

Ala Ile  Arg Ala Ser Trp Arg  Ala Ala Gln Gln Gln  Ser Pro Glu
    1520                 1525                 1530

Asn Val  Leu Thr Tyr Lys Glu  Leu Ile Met Asp Asp  Ser Gly Glu
    1535                 1540                 1545

Leu Ser  Glu Val Ser Arg Glu  Pro Gly Ala Asn Thr  Cys Gly Met
    1550                 1555                 1560

Val Ala  Trp Leu Phe Thr Ala  Leu Thr Pro Glu Tyr  Pro Thr Gly
    1565                 1570                 1575

Arg Gln  Phe Ile Val Val Ala  Asn Asp Ile Thr Tyr  Lys Ile Gly
    1580                 1585                 1590

Ser Phe  Gly Pro Gln Glu Asp  Lys Tyr Phe His Thr  Val Thr Gln
    1595                 1600                 1605

Leu Ala  Val Lys Leu Gly Ile  Pro Arg Ile Tyr Leu  Ser Ala Asn
    1610                 1615                 1620

Ser Gly  Ala Arg Ile Gly Val  Ala Asp Glu Phe Val  Ser Leu Phe
    1625                 1630                 1635

Ser Val  Ala Trp Asn Asp Ser  Ser Asn Pro Glu Lys  Gly Phe Lys
    1640                 1645                 1650

Tyr Leu  Tyr Leu Thr Pro Ala  Ile Tyr Asn Gly Leu  Ser Asp Ala
    1655                 1660                 1665

Ala Lys  Lys Thr Val Leu Thr  Glu Arg Ile Val Glu  Glu Gly Glu
    1670                 1675                 1680

Glu Arg  Tyr Val Ile Thr Thr  Ile Ile Gly Ala Glu  Asp Gly Leu
    1685                 1690                 1695

Gly Val  Glu Cys Leu Arg Gly  Ser Gly Leu Ile Ala  Gly Ala Thr
    1700                 1705                 1710

Ser Lys  Ala Tyr Lys Asp Ile  Phe Thr Ile Thr Leu  Val Thr Cys
    1715                 1720                 1725

Arg Ser  Val Gly Ile Gly Ala  Tyr Leu Val Arg Leu  Gly Gln Arg
    1730                 1735                 1740

Ala Ile  Gln Ile Glu Gly Gln  Pro Ile Ile Leu Thr  Gly Ala Pro
    1745                 1750                 1755

Ala Ile  Asn Lys Leu Leu Gly  Arg Glu Val Tyr Ser  Ser Asn Leu
    1760                 1765                 1770

Gln Leu  Gly Gly Thr Gln Ile  Met Tyr Lys Asn Gly  Val Ser His
    1775                 1780                 1785

Leu Thr  Ala Asn Asp Asp Leu  Ala Gly Val Met Lys  Ile Ile Glu
    1790                 1795                 1800

Trp Met  Ser Tyr Val Pro Tyr  Lys Lys Gly Gly Gln  Leu Pro Ile
    1805                 1810                 1815

Tyr Pro  Ser Ser Asp Thr Trp  Asp Arg Asp Val Thr  Tyr Thr Pro
    1820                 1825                 1830

Pro Lys  Gln Val Pro Tyr Asp  Val Arg Trp Leu Ile  Ala Gly Arg
    1835                 1840                 1845

Glu Asp  Glu Glu Gly Gly Phe  Glu Tyr Gly Leu Phe  Asp Lys Asp
    1850                 1855                 1860

Ser Phe  Gln Glu Thr Leu Ser  Gly Trp Ala Arg Thr  Val Val Val
    1865                 1870                 1875
```

```
Gly Arg  Ala Arg Leu Gly Gly  Ile Pro Val Gly Val  Ile Gly Val
    1880                 1885                 1890

Glu Val  Arg Ser Val Glu Asn  Ile Phe Pro Ala Asp  Pro Ala Asn
    1895                 1900                 1905

Pro Asp  Ser Thr Glu Met Val  Val Gln Glu Ala Gly  Gln Val Trp
    1910                 1915                 1920

Tyr Pro  Asn Ser Ala Phe Lys  Thr Ala Gln Ala Ile  Asn Asp Phe
    1925                 1930                 1935

Asn His  Gly Glu Glu Leu Pro  Leu Val Ile Leu Ala  Asn Trp Arg
    1940                 1945                 1950

Gly Phe  Ser Gly Gly Gln Arg  Asp Met Tyr Asn Glu  Val Leu Lys
    1955                 1960                 1965

Tyr Gly  Ser Phe Ile Val Asp  Ala Leu Val Gly Tyr  Lys Gln Pro
    1970                 1975                 1980

Ile Phe  Val Tyr Ile Pro Pro  His Ala Glu Leu Arg  Gly Gly Ser
    1985                 1990                 1995

Trp Val  Val Ile Asp Pro Thr  Ile Asn Ser Asp Gln  Met Glu Met
    2000                 2005                 2010

Tyr Ala  Asp Asp Glu Ala Arg  Ala Gly Val Leu Glu  Pro Glu Gly
    2015                 2020                 2025

Met Val  Gly Ile Lys Tyr Arg  Arg Asp Arg Leu Leu  Glu Thr Met
    2030                 2035                 2040

Thr Arg  Leu Asp Pro Val Tyr  Ala Ser Leu Lys Arg  Gln Ala Asp
    2045                 2050                 2055

Lys Lys  Asp Leu Ala Pro Ala  Ile Ala Gln Asp Leu  Lys Val Lys
    2060                 2065                 2070

Leu Ser  Glu Arg Glu Ser Thr  Leu Met Pro Ile Tyr  Arg Gln Ile
    2075                 2080                 2085

Ser Leu  Gln Phe Ala Asp Leu  His Asp Arg Ala Gly  Arg Met Lys
    2090                 2095                 2100

Ala Lys  Gly Thr Ile Arg Glu  Val Leu His Trp Arg  Glu Ala Arg
    2105                 2110                 2115

Arg Phe  Phe Tyr Trp Arg Val  Arg Arg Arg Val Gly  Glu Ser Tyr
    2120                 2125                 2130

Ile Leu  Arg Asp Leu Glu Ala  Ala Asn Pro Lys Ser  Thr Arg Leu
    2135                 2140                 2145

Glu Arg  Val Ala Arg Leu Lys  Ser Trp Tyr Ala Glu  Ala Gly Ile
    2150                 2155                 2160

Asn Glu  Ser Ser Asp Ala Asp  Val Ala Ser Trp Ile  Glu Lys Ser
    2165                 2170                 2175

Gly Ala  Ala Ile Thr Ser Lys  Val Lys Gln Val Arg  Lys Asp Ala
    2180                 2185                 2190

Lys Ile  Gln Asp Leu Leu Ala  Leu Val Arg Ala Asp  Lys Asp Val
    2195                 2200                 2205

Ala Leu  Gln Gly Leu Val Glu  Ser Leu Lys Ala Leu  Ser Thr Glu
    2210                 2215                 2220

Glu Arg  Asp Ala Ile Phe Lys  Gln Ala Ser Asn
    2225                 2230
```

<210> SEQ ID NO 3
<211> LENGTH: 2406
<212> TYPE: DNA
<213> ORGANISM: Lipomyces starkeyi
<220> FEATURE:
<221> NAME/KEY: Intron

<222> LOCATION: (1408)..(1461)

<400> SEQUENCE: 3

```
atgttgccga tcagctcgtt aatcgctctt ctgggagcga tatcattgtc tcctgctgtc      60
gttgctcgtc atattcttcg gcgagattgc agtacagtta ccgtgttgtc gtcgcctgag     120
actgtgacta gttcgaacca cgttcagcta gccagttatg agatgtgcga cggtaccttg     180
tcagcgtccc tttatatcta caatgatgat tacgataaga ttgtgacact ttattatctt     240
acatcgtcgg gcaatactgg gtctgcaaca gcctcttatt cttctggttt gagcaacaac     300
tgggaattat ggaccttatc cactaccgct acaggtgctg tcgaaattac tgaggctagc     360
tatattgata gtgatgcatc tgtgacatac acaacgtcgt tgaacgtgcc tctcacaacc     420
actacaacgt catcatcaat tactagtgca tattcaacgt ctagcattac tacatctagt     480
acgtcgacgt ctgcttgtgc cacagttact gtcttgtcgt cgcctgagac tgtgacgagt     540
tcgaaccatg ttcagctagc cagtcatgag atgtgcgaca gtaccttgtc agcgtccctt     600
tatatctaca atgatgatta tgataagatt gtgacacttt attatcttac atcgtcgggc     660
acaactgggt ccgtaacagc gtcttattct tctagtttga gtaacaactg ggaattgtgg     720
tctctctcgg ctccggctgc agatgctgtc gagatcactg gagctagtta tgtagacagc     780
gatgcatctg cgacatacgc cacgtctttt gatatacctc ttactaccac gacaacgtcg     840
tcgtcttctg ctagtgcgac ttcaacatct agtctaacca caacatctag tgtttccatt     900
tcggtgtccg tccctacagg aacagctgca aattggcgag gtagggctat ctatcagatc     960
gtgactgata gatttgcacg cactgacggc tccaccacat atttatgcga tgttaccgat    1020
agggtctatt gcggagggtc ttatcagggg attatcaata tgctggatta catccaaggc    1080
atgggcttta ctgctatttg gatttctcct atagtggaaa atattcccga tgacaccgga    1140
tacggttacg catatcatgg ttattggatg aaagatatct tcgccctgaa tacaaatttt    1200
ggtactgcag acgatttgat agcgttggct acggaattgc ataatcgcgg catgtacttg    1260
atggttgata ttgttgtcaa tcactttgct ttctcaggaa gtcatgccga cgtggactac    1320
tctgaatatt tcccgtattc gtcccaggat tattttcatt cattttgctg gattacagat    1380
tactcgaatc agacaaacgt tgaggtggta tgtatctaag catatttgta gcattctatc    1440
ttggaactga ccggccctca gtgctggctt ggcgacgata ctgttcctct cgtggacgtc    1500
aatacccaac ttgacaccgt gaaaagtgaa tatcaatcct gggttcaaga acttatagct    1560
aattactcta ttgacggcct aagaattgac accgtcaagc acgtgcagat ggatttttgg    1620
gcaccatttc aagaggctgc agggatttac gccgttggtg aagtattcga cggtgatcca    1680
tcctacacat gtccatatca ggaaaatctt gacggtgtct tgaattatcc tgtttattat    1740
cctgtcgtct ctgcgtttga gagtgttagt gggtcggtct cctcgttagt cgatatgatt    1800
gatacgctca agtctgaatg caccgacact actctcctag gctcctttct agagaatcaa    1860
gataatccgc gattccctag ctacacttct gatgagtctt taattaaaaa tgcgatcgct    1920
ttcactatgc tctcagacgg cattcccata atttattacg gtcaggagca aggcctcaat    1980
ggtggaaacg atccctataa tcgagaggcg ctttggctta cgggctactc cacaacgtcg    2040
acgttctaca aatacattgc gtcgttgaat cagattagaa atcaggctat atacaaagat    2100
gatacttatc tcacatatca gaactgggtt atttattcgg attccacgac aatagcaatg    2160
cggaaaggtt ttacagggaa ccaaataatt acggttctgt caaatcttgg gaccagtggc    2220
agttcgtaca ctttgacgct ttcgaatacg ggatataccg catctagcgt tgtatatgag    2280
```

atcttgacat gcacagctgt gactgtggat tcgtctggga atttggcagt gccgatgtcc 2340
agtggcctac caaaagtctt ttatcaggaa tcgcaactgg ttggctctgg aatctgctcc 2400
ttgtag 2406

<210> SEQ ID NO 4
<211> LENGTH: 783
<212> TYPE: PRT
<213> ORGANISM: Lipomyces starkeyi

<400> SEQUENCE: 4

Met Leu Pro Ile Ser Ser Leu Ile Ala Leu Leu Gly Ala Ile Ser Leu
1 5 10 15

Ser Pro Ala Val Val Ala Arg His Ile Leu Arg Arg Asp Cys Ser Thr
20 25 30

Val Thr Val Leu Ser Ser Pro Glu Thr Val Thr Ser Ser Asn His Val
35 40 45

Gln Leu Ala Ser Tyr Glu Met Cys Asp Gly Thr Leu Ser Ala Ser Leu
50 55 60

Tyr Ile Tyr Asn Asp Asp Tyr Asp Lys Ile Val Thr Leu Tyr Tyr Leu
65 70 75 80

Thr Ser Ser Gly Asn Thr Gly Ser Ala Thr Ala Ser Tyr Ser Ser Gly
85 90 95

Leu Ser Asn Asn Trp Glu Leu Trp Thr Leu Ser Thr Thr Ala Thr Gly
100 105 110

Ala Val Glu Ile Thr Glu Ala Ser Tyr Ile Asp Ser Asp Ala Ser Val
115 120 125

Thr Tyr Thr Thr Ser Leu Asn Val Pro Leu Thr Thr Thr Thr Thr Ser
130 135 140

Ser Ser Ile Thr Ser Ala Tyr Ser Thr Ser Ser Ile Thr Thr Ser Ser
145 150 155 160

Thr Ser Thr Ser Ala Cys Ala Thr Val Thr Val Leu Ser Ser Pro Glu
165 170 175

Thr Val Thr Ser Ser Asn His Val Gln Leu Ala Ser His Glu Met Cys
180 185 190

Asp Ser Thr Leu Ser Ala Ser Leu Tyr Ile Tyr Asn Asp Asp Tyr Asp
195 200 205

Lys Ile Val Thr Leu Tyr Tyr Leu Thr Ser Ser Gly Thr Thr Gly Ser
210 215 220

Val Thr Ala Ser Tyr Ser Ser Ser Leu Ser Asn Asn Trp Glu Leu Trp
225 230 235 240

Ser Leu Ser Ala Pro Ala Ala Asp Ala Val Glu Ile Thr Gly Ala Ser
245 250 255

Tyr Val Asp Ser Asp Ala Ser Ala Thr Tyr Ala Thr Ser Phe Asp Ile
260 265 270

Pro Leu Thr Thr Thr Thr Thr Ser Ser Ser Ser Ala Ser Ala Thr Ser
275 280 285

Thr Ser Ser Leu Thr Thr Thr Ser Ser Val Ser Ile Ser Val Ser Val
290 295 300

Pro Thr Gly Thr Ala Ala Asn Trp Arg Gly Arg Ala Ile Tyr Gln Ile
305 310 315 320

Val Thr Asp Arg Phe Ala Arg Thr Asp Gly Ser Thr Thr Tyr Leu Cys
325 330 335

Asp Val Thr Asp Arg Val Tyr Cys Gly Gly Ser Tyr Gln Gly Ile Ile

```
            340                 345                 350

Asn Met Leu Asp Tyr Ile Gln Gly Met Gly Phe Thr Ala Ile Trp Ile
        355                 360                 365

Ser Pro Ile Val Glu Asn Ile Pro Asp Asp Thr Gly Tyr Gly Tyr Ala
    370                 375                 380

Tyr His Gly Tyr Trp Met Lys Asp Ile Phe Ala Leu Asn Thr Asn Phe
385                 390                 395                 400

Gly Thr Ala Asp Asp Leu Ile Ala Leu Ala Thr Glu Leu His Asn Arg
                405                 410                 415

Gly Met Tyr Leu Met Val Asp Ile Val Val Asn His Phe Ala Phe Ser
            420                 425                 430

Gly Ser His Ala Asp Val Asp Tyr Ser Glu Tyr Phe Pro Tyr Ser Ser
        435                 440                 445

Gln Asp Tyr Phe His Ser Phe Cys Trp Ile Thr Asp Tyr Ser Asn Gln
    450                 455                 460

Thr Asn Val Glu Val Cys Trp Leu Gly Asp Asp Thr Val Pro Leu Val
465                 470                 475                 480

Asp Val Asn Thr Gln Leu Asp Thr Val Lys Ser Glu Tyr Gln Ser Trp
                485                 490                 495

Val Gln Glu Leu Ile Ala Asn Tyr Ser Ile Asp Gly Leu Arg Ile Asp
            500                 505                 510

Thr Val Lys His Val Gln Met Asp Phe Trp Ala Pro Phe Gln Glu Ala
        515                 520                 525

Ala Gly Ile Tyr Ala Val Gly Glu Val Phe Asp Gly Asp Pro Ser Tyr
    530                 535                 540

Thr Cys Pro Tyr Gln Glu Asn Leu Asp Gly Val Leu Asn Tyr Pro Val
545                 550                 555                 560

Tyr Tyr Pro Val Val Ser Ala Phe Glu Ser Val Ser Gly Ser Val Ser
                565                 570                 575

Ser Leu Val Asp Met Ile Asp Thr Leu Lys Ser Glu Cys Thr Asp Thr
            580                 585                 590

Thr Leu Leu Gly Ser Phe Leu Glu Asn Gln Asp Asn Pro Arg Phe Pro
        595                 600                 605

Ser Tyr Thr Ser Asp Glu Ser Leu Ile Lys Asn Ala Ile Ala Phe Thr
    610                 615                 620

Met Leu Ser Asp Gly Ile Pro Ile Ile Tyr Tyr Gly Gln Glu Gln Gly
625                 630                 635                 640

Leu Asn Gly Gly Asn Asp Pro Tyr Asn Arg Glu Ala Leu Trp Leu Thr
                645                 650                 655

Gly Tyr Ser Thr Thr Ser Thr Phe Tyr Lys Tyr Ile Ala Ser Leu Asn
            660                 665                 670

Gln Ile Arg Asn Gln Ala Ile Tyr Lys Asp Asp Thr Tyr Leu Thr Tyr
        675                 680                 685

Gln Asn Trp Val Ile Tyr Ser Asp Ser Thr Thr Ile Ala Met Arg Lys
    690                 695                 700

Gly Phe Thr Gly Asn Gln Ile Ile Thr Val Leu Ser Asn Leu Gly Thr
705                 710                 715                 720

Ser Gly Ser Ser Tyr Thr Leu Thr Leu Ser Asn Thr Gly Tyr Thr Ala
                725                 730                 735

Ser Ser Val Val Tyr Glu Ile Leu Thr Cys Thr Ala Val Thr Val Asp
            740                 745                 750

Ser Ser Gly Asn Leu Ala Val Pro Met Ser Ser Gly Leu Pro Lys Val
        755                 760                 765
```

```
Phe Tyr Gln Glu Ser Gln Leu Val Gly Ser Gly Ile Cys Ser Leu
    770                 775                 780


<210> SEQ ID NO 5
<211> LENGTH: 1845
<212> TYPE: DNA
<213> ORGANISM: Lipomyces starkeyi
<220> FEATURE:
<221> NAME/KEY: Intron
<222> LOCATION: (74)..(123)
<220> FEATURE:
<221> NAME/KEY: Intron
<222> LOCATION: (140)..(193)
<220> FEATURE:
<221> NAME/KEY: Intron
<222> LOCATION: (302)..(348)
<220> FEATURE:
<221> NAME/KEY: Intron
<222> LOCATION: (372)..(419)
<220> FEATURE:
<221> NAME/KEY: Intron
<222> LOCATION: (516)..(564)
<220> FEATURE:
<221> NAME/KEY: Intron
<222> LOCATION: (643)..(697)

<400> SEQUENCE: 5

atggccgaag agaacaagat tcctaccgag gaaaacgcga caatgctcca ggcatttgag     60

tggtacatcc ccggtacgtc cccatccata ttgccagttt tgctcagact aacgtgcgta    120

tagacgacca cacacattgg tattccgtga ctctttcgac attttacaga atgaataagc    180

tcacaaggta taggaaacga ctcgctcgtg atatcgagaa gtatcgcgac atcggcatca    240

ctgctttgtg gatcccgccc ccatgcaagg cttcgtcacc atctgggaat ggatatgata    300

tgtatgtcct attgtattcg ttataggtga tgcgtctaac gggaatagat acgatctgtg    360

ggatctcgga ggtacgatct tcgagttgtc gtcattgatg cctgtctgac catgcccaga    420

gttcgatcag aaaggttccg ttccgacaaa atggggcgat aaggacgatt tggtcaggct    480

agcccacaat gccgagaaag ccggtgtctt gctttgtaag atctcgctga tcagaatgct    540

ggatgcatgt tgctaaacac gcagacgccg acgccgtgct caaccacaaa gcagcagccg    600

acgaaactga gcgctgccga gtcgccgaag tcgacccaga gagtatgtct gtccgcatta    660

tctttttgta ttccctttgg gtcataacat ctggtagacc gcacgcggtt catctccgat    720

gagtacgaaa tcgacggctg gctaggcttc actttctctg gccgcggcga caagtattct    780

tccatgaaat ggcactggga gcatttctcc ggcacggatt acaacgccga gaataacaag    840

acggcgattt acaagattct tggagacttt aagtcttggg cgcagtcagt cgacaacgag    900

aaaggtaact ttgattactt gatgtttgcc gacattgatc attcgcatcc agacgtgaaa    960

aaggatatca acgattgggg aatctggatc gcggagctgc tgtcgttgag agggtttcga   1020

tttgatgccg tgaagcattt ctcggaggag tatttaaagg agtttatcac tcaattgaaa   1080

acgaacgtga acgaagattt tttctttgtg ggcgagtttt ggaaagattc gttgtcggac   1140

atgttgggat acctcgatcg tcttgatggc cacaagttca gcttgtttga cgcgccgctg   1200

gtgtacaatt tttcggaagc atcaaagacg gaatcctttg atctacgcgc gatctttgac   1260

ggcacgcttg tgcaagcgcg tcccatttcc gcagtgacgc tggtcatgaa ccatgacaca   1320

caaccgcacc aggcactcga ggcgccgatc gagggatttt tcaagccgat tgcgtacggt   1380

ttgatcctcc tccgtcagga ggggtatcca tgtgtgtttt ggggcgattt ggagggcatt   1440

tcaggggagt ataaagagga gccgagttgt gggggccagc tttcggatat tattctggca   1500
```

```
aggaagttgt atgcgtatgg cgagcaggac gattatttcg attaccctac gtgcttgggg   1560

tgggttcgtc gcggcgcgtg ggatagatta aacggatgcg cggtcattgt ttcgaacgcg   1620

ggtcccggtg agaagcgcat gtttgttggc gaagagcata agggggagat ctggaccgac   1680

gttcttgggt gggaacaggg cgaggtgcat attggcgagg acggaaatgc ggatttcaaa   1740

tgtcctgcta ctagtatggc gatctgggtt aacaaggacg cgccaggccg tgatcagttt   1800

ggaaagttca agcccggcaa ggggattttg caaggagtag tctag                   1845
```

<210> SEQ ID NO 6
<211> LENGTH: 513
<212> TYPE: PRT
<213> ORGANISM: Lipomyces starkeyi

<400> SEQUENCE: 6

```
Met Ala Glu Glu Asn Lys Ile Pro Thr Glu Glu Asn Ala Thr Met Leu
1               5                   10                  15

Gln Ala Phe Glu Trp Tyr Ile Pro Asp Asp His Thr His Trp Lys Arg
            20                  25                  30

Leu Ala Arg Asp Ile Glu Lys Tyr Arg Asp Ile Gly Ile Thr Ala Leu
        35                  40                  45

Trp Ile Pro Pro Pro Cys Lys Ala Ser Ser Pro Ser Gly Asn Gly Tyr
    50                  55                  60

Asp Ile Tyr Asp Leu Trp Asp Leu Gly Glu Phe Asp Gln Lys Gly Ser
65                  70                  75                  80

Val Pro Thr Lys Trp Gly Asp Lys Asp Asp Leu Val Arg Leu Ala His
                85                  90                  95

Asn Ala Glu Lys Ala Gly Val Leu Leu Tyr Ala Asp Ala Val Leu Asn
            100                 105                 110

His Lys Ala Ala Ala Asp Glu Thr Glu Arg Cys Arg Val Ala Glu Val
        115                 120                 125

Asp Pro Glu Asn Arg Thr Arg Phe Ile Ser Asp Glu Tyr Glu Ile Asp
    130                 135                 140

Gly Trp Leu Gly Phe Thr Phe Ser Gly Arg Gly Asp Lys Tyr Ser Ser
145                 150                 155                 160

Met Lys Trp His Trp Glu His Phe Ser Gly Thr Asp Tyr Asn Ala Glu
                165                 170                 175

Asn Asn Lys Thr Ala Ile Tyr Lys Ile Leu Gly Asp Phe Lys Ser Trp
            180                 185                 190

Ala Gln Ser Val Asp Asn Glu Lys Gly Asn Phe Asp Tyr Leu Met Phe
        195                 200                 205

Ala Asp Ile Asp His Ser His Pro Asp Val Lys Lys Asp Ile Asn Asp
    210                 215                 220

Trp Gly Ile Trp Ile Ala Glu Leu Leu Ser Leu Arg Gly Phe Arg Phe
225                 230                 235                 240

Asp Ala Val Lys His Phe Ser Glu Glu Tyr Leu Lys Glu Phe Ile Thr
                245                 250                 255

Gln Leu Lys Thr Asn Val Asn Glu Asp Phe Phe Phe Val Gly Glu Phe
            260                 265                 270

Trp Lys Asp Ser Leu Ser Asp Met Leu Gly Tyr Leu Asp Arg Leu Asp
        275                 280                 285

Gly His Lys Phe Ser Leu Phe Asp Ala Pro Leu Val Tyr Asn Phe Ser
    290                 295                 300

Glu Ala Ser Lys Thr Glu Ser Phe Asp Leu Arg Ala Ile Phe Asp Gly
```

```
305                 310                 315                 320

Thr Leu Val Gln Ala Arg Pro Ile Ser Ala Val Thr Leu Val Met Asn
                325                 330                 335

His Asp Thr Gln Pro His Gln Ala Leu Glu Ala Pro Ile Glu Gly Phe
            340                 345                 350

Phe Lys Pro Ile Ala Tyr Gly Leu Ile Leu Leu Arg Gln Glu Gly Tyr
        355                 360                 365

Pro Cys Val Phe Trp Gly Asp Leu Glu Gly Ile Ser Gly Glu Tyr Lys
    370                 375                 380

Glu Glu Pro Ser Cys Gly Gly Gln Leu Ser Asp Ile Ile Leu Ala Arg
385                 390                 395                 400

Lys Leu Tyr Ala Tyr Gly Glu Gln Asp Asp Tyr Phe Asp Tyr Pro Thr
                405                 410                 415

Cys Leu Gly Trp Val Arg Arg Gly Ala Trp Asp Arg Leu Asn Gly Cys
            420                 425                 430

Ala Val Ile Val Ser Asn Ala Gly Pro Gly Glu Lys Arg Met Phe Val
        435                 440                 445

Gly Glu Glu His Lys Gly Glu Ile Trp Thr Asp Val Leu Gly Trp Glu
    450                 455                 460

Gln Gly Glu Val His Ile Gly Glu Asp Gly Asn Ala Asp Phe Lys Cys
465                 470                 475                 480

Pro Ala Thr Ser Met Ala Ile Trp Val Asn Lys Asp Ala Pro Gly Arg
                485                 490                 495

Asp Gln Phe Gly Lys Phe Lys Pro Gly Lys Gly Ile Leu Gln Gly Val
            500                 505                 510

Val
```

<210> SEQ ID NO 7
<211> LENGTH: 1920
<212> TYPE: DNA
<213> ORGANISM: Artificial Sequence
<220> FEATURE:
<223> OTHER INFORMATION: Chimeric Thermostable Secreted Alpha-Amylase
<220> FEATURE:
<221> NAME/KEY: Intron
<222> LOCATION: (149)..(198)
<220> FEATURE:
<221> NAME/KEY: Intron
<222> LOCATION: (215)..(268)
<220> FEATURE:
<221> NAME/KEY: Intron
<222> LOCATION: (377)..(423)
<220> FEATURE:
<221> NAME/KEY: Intron
<222> LOCATION: (447)..(494)
<220> FEATURE:
<221> NAME/KEY: Intron
<222> LOCATION: (591)..(639)
<220> FEATURE:
<221> NAME/KEY: Intron
<222> LOCATION: (718)..(772)

<400> SEQUENCE: 7

```
atgttgccga tcagctcgtt aatcgctctt ctgggagcga tatcattgtc tcctgctgtc     60

gttgctcgtc atattcttgc cgaagagaac aagattccta ccgaggaaaa cgcgacaatg    120

ctccaggcat ttgagtggta catccccggt acgtccccat ccatattgcc agttttgctc    180

agactaacgt gcgtatagac gaccacacac attggtattc cgtgactctt tcgacatttt    240

acagaatgaa taagctcaca aggtatagga aacgactcgc tcgtgatatc gagaagtatc    300

gcgacatcgg catcactgct ttgtggatcc cgcccccatg caaggcttcg tcaccatctg    360
```

```
ggaatggata tgatatgtat gtcctattgt attcgttata ggtgatgcgt ctaacgggaa    420

tagatacgat ctgtgggatc tcggaggtac gatcttcgag ttgtcgtcat tgatgcctgt    480

ctgaccatgc ccagagttcg atcagaaagg ttccgttccg acaaaatggg gcgataagga    540

cgatttggtc aggctagccc acaatgccga gaaagccggt gtcttgcttt gtaagatctc    600

gctgatcaga atgctggatg catgttgcta aacacgcaga cgccgacgcc gtgctcaacc    660

acaaagcagc agccgacgaa actgagcgct gccgagtcgc cgaagtcgac ccagagagta    720

tgtctgtccg cattatcttt ttgtattccc tttgggtcat aacatctggt agaccgcacg    780

cggttcatct ccgatgagta cgaaatcgac ggctggctag gcttcacttt ctctggccgc    840

ggcgacaagt attcttccat gaaatggcac tgggagcatt tctccggcac ggattacaac    900

gccgagaata acaagacggc gatttacaag attcttggag actttaagtc ttgggcgcag    960

tcagtcgaca acgagaaagg taactttgat tacttgatgt ttgccgacat tgatcattcg   1020

catccagacg tgaaaaagga tatcaacgat tggggaatct ggatcgcgga gctgctgtcg   1080

ttgagagggt ttcgatttga tgccgtgaag catttctcgg aggagtattt aaaggagttt   1140

atcactcaat tgaaaacgaa cgtgaacgaa gattttttct ttgtgggcga gttttggaaa   1200

gattcgttgt cggacatgtt gggatacctc gatcgtcttg atggccacaa gttcagcttg   1260

tttgacgcgc cgctggtgta caatttttcg gaagcatcaa agacggaatc ctttgatcta   1320

cgcgcgatct ttgacggcac gcttgtgcaa gcgcgtccca tttccgcagt gacgctggtc   1380

atgaaccatg acacacaacc gcaccaggca ctcgaggcgc cgatcgaggg atttttcaag   1440

ccgattgcgt acggtttgat cctcctccgt caggaggggt atccatgtgt gttttggggc   1500

gatttggagg gcatttcagg ggagtataaa gaggagccga gttgtggggg ccagctttcg   1560

gatattattc tggcaaggaa gttgtatgcg tatggcgagc aggacgatta tttcgattac   1620

cctacgtgct tggggtgggt tcgtcgcggc gcgtgggata gattaaacgg atgcgcggtc   1680

attgtttcga acgcgggtcc cggtgagaag cgcatgtttg ttggcgaaga gcataagggg   1740

gagatctgga ccgacgttct tgggtgggaa cagggcgagg tgcatattgg cgaggacgga   1800

aatgcggatt tcaaatgtcc tgctactagt atggcgatct gggttaacaa ggacgcgcca   1860

ggccgtgatc agtttggaaa gttcaagccc ggcaagggga ttttgcaagg agtagtctag   1920
```

```
<210> SEQ ID NO 8
<211> LENGTH: 538
<212> TYPE: PRT
<213> ORGANISM: Artificial Sequence
<220> FEATURE:
<223> OTHER INFORMATION: Chimeric Thermostable Secreted Alpha-Amylase

<400> SEQUENCE: 8

Met Leu Pro Ile Ser Ser Leu Ile Ala Leu Leu Gly Ala Ile Ser Leu
1               5                   10                  15

Ser Pro Ala Val Val Ala Arg His Ile Leu Ala Glu Glu Asn Lys Ile
            20                  25                  30

Pro Thr Glu Glu Asn Ala Thr Met Leu Gln Ala Phe Glu Trp Tyr Ile
        35                  40                  45

Pro Asp Asp His Thr His Trp Lys Arg Leu Ala Arg Asp Ile Glu Lys
    50                  55                  60

Tyr Arg Asp Ile Gly Ile Thr Ala Leu Trp Ile Pro Pro Pro Cys Lys
65                  70                  75                  80

Ala Ser Ser Pro Ser Gly Asn Gly Tyr Asp Ile Tyr Asp Leu Trp Asp
```

```
                85                  90                  95

Leu Gly Glu Phe Asp Gln Lys Gly Ser Val Pro Thr Lys Trp Gly Asp
            100                 105                 110

Lys Asp Asp Leu Val Arg Leu Ala His Asn Ala Glu Lys Ala Gly Val
        115                 120                 125

Leu Leu Tyr Ala Asp Ala Val Leu Asn His Lys Ala Ala Ala Asp Glu
    130                 135                 140

Thr Glu Arg Cys Arg Val Ala Glu Val Asp Pro Glu Asn Arg Thr Arg
145                 150                 155                 160

Phe Ile Ser Asp Glu Tyr Glu Ile Asp Gly Trp Leu Gly Phe Thr Phe
                165                 170                 175

Ser Gly Arg Gly Asp Lys Tyr Ser Ser Met Lys Trp His Trp Glu His
            180                 185                 190

Phe Ser Gly Thr Asp Tyr Asn Ala Glu Asn Asn Lys Thr Ala Ile Tyr
        195                 200                 205

Lys Ile Leu Gly Asp Phe Lys Ser Trp Ala Gln Ser Val Asp Asn Glu
    210                 215                 220

Lys Gly Asn Phe Asp Tyr Leu Met Phe Ala Asp Ile Asp His Ser His
225                 230                 235                 240

Pro Asp Val Lys Lys Asp Ile Asn Asp Trp Gly Ile Trp Ile Ala Glu
                245                 250                 255

Leu Leu Ser Leu Arg Gly Phe Arg Phe Asp Ala Val Lys His Phe Ser
            260                 265                 270

Glu Glu Tyr Leu Lys Glu Phe Ile Thr Gln Leu Lys Thr Asn Val Asn
        275                 280                 285

Glu Asp Phe Phe Phe Val Gly Glu Phe Trp Lys Asp Ser Leu Ser Asp
    290                 295                 300

Met Leu Gly Tyr Leu Asp Arg Leu Asp Gly His Lys Phe Ser Leu Phe
305                 310                 315                 320

Asp Ala Pro Leu Val Tyr Asn Phe Ser Glu Ala Ser Lys Thr Glu Ser
                325                 330                 335

Phe Asp Leu Arg Ala Ile Phe Asp Gly Thr Leu Val Gln Ala Arg Pro
            340                 345                 350

Ile Ser Ala Val Thr Leu Val Met Asn His Asp Thr Gln Pro His Gln
        355                 360                 365

Ala Leu Glu Ala Pro Ile Glu Gly Phe Phe Lys Pro Ile Ala Tyr Gly
    370                 375                 380

Leu Ile Leu Leu Arg Gln Glu Gly Tyr Pro Cys Val Phe Trp Gly Asp
385                 390                 395                 400

Leu Glu Gly Ile Ser Gly Glu Tyr Lys Glu Glu Pro Ser Cys Gly Gly
                405                 410                 415

Gln Leu Ser Asp Ile Ile Leu Ala Arg Lys Leu Tyr Ala Tyr Gly Glu
            420                 425                 430

Gln Asp Asp Tyr Phe Asp Tyr Pro Thr Cys Leu Gly Trp Val Arg Arg
        435                 440                 445

Gly Ala Trp Asp Arg Leu Asn Gly Cys Ala Val Ile Val Ser Asn Ala
    450                 455                 460

Gly Pro Gly Glu Lys Arg Met Phe Val Gly Glu Glu His Lys Gly Glu
465                 470                 475                 480

Ile Trp Thr Asp Val Leu Gly Trp Glu Gln Gly Glu Val His Ile Gly
                485                 490                 495

Glu Asp Gly Asn Ala Asp Phe Lys Cys Pro Ala Thr Ser Met Ala Ile
            500                 505                 510
```

```
Trp Val Asn Lys Asp Ala Pro Gly Arg Asp Gln Phe Gly Lys Phe Lys
        515                 520                 525

Pro Gly Lys Gly Ile Leu Gln Gly Val Val
    530                 535


<210> SEQ ID NO 9
<211> LENGTH: 1996
<212> TYPE: DNA
<213> ORGANISM: Lipomyces starkeyi
<220> FEATURE:
<221> NAME/KEY: Intron
<222> LOCATION: (385)..(436)

<400> SEQUENCE: 9

atgtctcctc cttctgccga cgccaacatc acacgcttcg cgccgccaac cgcgccagcg     60

tcgccgctgc cggcgtacca gctcttccac aacaagacgc gtgcgttcgt ttatggcctg    120

cagccgcgtg cttgccaggg tatgctcgat ttcgacttca tctgcaagcg cacgaccccg    180

tcggtcgccg ctatcatcta tcctttcggc ggccagtttg tgtctaagat gtattggggc    240

acgaaggaga ccctcctccc tgtctaccag agcgccaaga aggccgcaga gaagcatccc    300

gaagtcgacg tcgtcgtcaa ctttgcctct tcccgatccg tctactcctc aacgatggag    360

cttctggaat taccccagat tagggtgtgt tttggtctaa gtttacttac tcaattgatg    420

ctaatatact gattagacaa ttgcgatcat tgcggaaggt gtgcctgagc gtcgcgctcg    480

cgagattctt ttcaaggcca aggaaaaggg cgtcgtcatc atcggccctg ctactgtcgg    540

cggtatcaaa cctggctgct ttaagatcgg caacaccggc ggtatgatgg acaacatcgt    600

tgcctccaaa ctctaccgac ctggatccgt cggctacgtc tccaagtccg gtggtatgtc    660

taacgaactc aataacatca tctctcagac caccgatggt gtctacgaag gtgtcgctat    720

tggcggtgac cgttatcccg gcaccacctt catcgaccac ctcctccgct acgaggccga    780

tcccgattgt aagatcctgg tgttgcttgg tgaggttggt ggtgttgagg aataccgcgt    840

catcgatgct gtcaagtctg gcacgatcac aaagccaatt gtcgcctggg ccatcggcac    900

ttgcgcatct atgttcacga ctgaggttca gtttggccac gctggttcgt tcgccaactc    960

ccagctcgag actgctaagg ccaagaatgc cgccatgaag gccgccggtt tttacgttcc   1020

tgacaccttc gaggatatgc cagatgtctt gggtgatctc tacaagagtc tcgtcaagaa   1080

gggtgtcatt gttccgaagc ccgagcccga gcctccaaag atcccgattg actacgcctg   1140

ggcccaggaa cttggcctca tccgtaagcc ggccgcgttc atctcgacca tttctgacga   1200

tcgtggccaa gagctgctct acgccggcat gcccattacc gacgtcttca aggagaatat   1260

tggcatcggt ggcgtcatgt cgcttctgtg gttccgtcgt cgtctgcccg actacgcttc   1320

caagttcctc gagatggtcc ttatgctcac tgcagaccac ggaccagctg tctcaggcgc   1380

catgaacacc atcatcacta ctcgtgctgg caaggacttg atctccgctc tcgtgtccgg   1440

tctgttgacc atcggtgagc gattcggtgg tgcgctcgac ggcgccgctc aggaattcac   1500

caatgcgttc gacaagggcc tttcgccccg ccagtttgtc gacaccatgc gcaagcagaa   1560

caagctcatc cccggtattg gccacaagat caagtcccgc aacaatccag atatgcgggt   1620

tgagttagtc aaggaatttg cccgcaacag cttcccatcc accaaacttc tcgactacgc   1680

gctcgccgtc gagactgtta ccacttccaa gaaggacaac ttgatcctca acgtcgacgg   1740

ctgtgtcgcc gtctgcttca tcgatttgat ccgccactgc ggtgctttca cccctgaaga   1800

agctgaagac tacctgaaga tgggagttct gaacggcctg ttcgttcttg gccgatccat   1860
```

```
tggtttgatc gcgcactatc tggatcagaa gcgcctgcgc actggcttgt acagacaccc   1920

ttgggatgat attacatatc tgctccccag tgttgactct ttgggcggca gcagtcgcgt   1980

tgaagtcacg gtctag                                                   1996


<210> SEQ ID NO 10
<211> LENGTH: 647
<212> TYPE: PRT
<213> ORGANISM: Lipomyces starkeyi

<400> SEQUENCE: 10

Met Ser Pro Pro Ser Ala Asp Ala Asn Ile Thr Arg Phe Ala Pro Pro
1               5                   10                  15

Thr Ala Pro Ala Ser Pro Leu Pro Ala Tyr Gln Leu Phe His Asn Lys
            20                  25                  30

Thr Arg Ala Phe Val Tyr Gly Leu Gln Pro Arg Ala Cys Gln Gly Met
        35                  40                  45

Leu Asp Phe Asp Phe Ile Cys Lys Arg Thr Thr Pro Ser Val Ala Ala
    50                  55                  60

Ile Ile Tyr Pro Phe Gly Gly Gln Phe Val Ser Lys Met Tyr Trp Gly
65                  70                  75                  80

Thr Lys Glu Thr Leu Leu Pro Val Tyr Gln Ser Ala Lys Lys Ala Ala
                85                  90                  95

Glu Lys His Pro Glu Val Asp Val Val Val Asn Phe Ala Ser Ser Arg
            100                 105                 110

Ser Val Tyr Ser Ser Thr Met Glu Leu Leu Glu Leu Pro Gln Ile Arg
        115                 120                 125

Thr Ile Ala Ile Ile Ala Glu Gly Val Pro Glu Arg Arg Ala Arg Glu
    130                 135                 140

Ile Leu Phe Lys Ala Lys Glu Lys Gly Val Val Ile Ile Gly Pro Ala
145                 150                 155                 160

Thr Val Gly Gly Ile Lys Pro Gly Cys Phe Lys Ile Gly Asn Thr Gly
                165                 170                 175

Gly Met Met Asp Asn Ile Val Ala Ser Lys Leu Tyr Arg Pro Gly Ser
            180                 185                 190

Val Gly Tyr Val Ser Lys Ser Gly Gly Met Ser Asn Glu Leu Asn Asn
        195                 200                 205

Ile Ile Ser Gln Thr Thr Asp Gly Val Tyr Glu Gly Val Ala Ile Gly
    210                 215                 220

Gly Asp Arg Tyr Pro Gly Thr Thr Phe Ile Asp His Leu Leu Arg Tyr
225                 230                 235                 240

Glu Ala Asp Pro Asp Cys Lys Ile Leu Val Leu Leu Gly Glu Val Gly
                245                 250                 255

Gly Val Glu Glu Tyr Arg Val Ile Asp Ala Val Lys Ser Gly Thr Ile
            260                 265                 270

Thr Lys Pro Ile Val Ala Trp Ala Ile Gly Thr Cys Ala Ser Met Phe
        275                 280                 285

Thr Thr Glu Val Gln Phe Gly His Ala Gly Ser Phe Ala Asn Ser Gln
    290                 295                 300

Leu Glu Thr Ala Lys Ala Lys Asn Ala Ala Met Lys Ala Ala Gly Phe
305                 310                 315                 320

Tyr Val Pro Asp Thr Phe Glu Asp Met Pro Asp Val Leu Gly Asp Leu
                325                 330                 335

Tyr Lys Ser Leu Val Lys Lys Gly Val Ile Val Pro Lys Pro Glu Pro
```

```
            340                 345                 350

Glu Pro Pro Lys Ile Pro Ile Asp Tyr Ala Trp Ala Gln Glu Leu Gly
        355                 360                 365

Leu Ile Arg Lys Pro Ala Ala Phe Ile Ser Thr Ile Ser Asp Asp Arg
    370                 375                 380

Gly Gln Glu Leu Leu Tyr Ala Gly Met Pro Ile Thr Asp Val Phe Lys
385                 390                 395                 400

Glu Asn Ile Gly Ile Gly Gly Val Met Ser Leu Leu Trp Phe Arg Arg
                405                 410                 415

Arg Leu Pro Asp Tyr Ala Ser Lys Phe Leu Glu Met Val Leu Met Leu
            420                 425                 430

Thr Ala Asp His Gly Pro Ala Val Ser Gly Ala Met Asn Thr Ile Ile
        435                 440                 445

Thr Thr Arg Ala Gly Lys Asp Leu Ile Ser Ala Leu Val Ser Gly Leu
    450                 455                 460

Leu Thr Ile Gly Glu Arg Phe Gly Gly Ala Leu Asp Gly Ala Ala Gln
465                 470                 475                 480

Glu Phe Thr Asn Ala Phe Asp Lys Gly Leu Ser Pro Arg Gln Phe Val
                485                 490                 495

Asp Thr Met Arg Lys Gln Asn Lys Leu Ile Pro Gly Ile Gly His Lys
            500                 505                 510

Ile Lys Ser Arg Asn Asn Pro Asp Met Arg Val Glu Leu Val Lys Glu
        515                 520                 525

Phe Ala Arg Asn Ser Phe Pro Ser Thr Lys Leu Leu Asp Tyr Ala Leu
    530                 535                 540

Ala Val Glu Thr Val Thr Thr Ser Lys Lys Asp Asn Leu Ile Leu Asn
545                 550                 555                 560

Val Asp Gly Cys Val Ala Val Cys Phe Ile Asp Leu Ile Arg His Cys
                565                 570                 575

Gly Ala Phe Thr Pro Glu Glu Ala Glu Asp Tyr Leu Lys Met Gly Val
            580                 585                 590

Leu Asn Gly Leu Phe Val Leu Gly Arg Ser Ile Gly Leu Ile Ala His
        595                 600                 605

Tyr Leu Asp Gln Lys Arg Leu Arg Thr Gly Leu Tyr Arg His Pro Trp
    610                 615                 620

Asp Asp Ile Thr Tyr Leu Leu Pro Ser Val Asp Ser Leu Gly Gly Ser
625                 630                 635                 640

Ser Arg Val Glu Val Thr Val
                645
```

<210> SEQ ID NO 11
<211> LENGTH: 1540
<212> TYPE: DNA
<213> ORGANISM: Lipomyces starkeyi
<220> FEATURE:
<221> NAME/KEY: Intron
<222> LOCATION: (445)..(496)

<400> SEQUENCE: 11

```
atgtccgcaa agtccatcca cgaggccgac ggaaaggcac tactctctta cttcctccca      60

cggtcaccgc tgctcacaaa ggaaggtact tcgaccgagt tcgtgcctgc tccaccgcgt     120

ctcgcgtcgc tcaccttccc tgacgactcc ccagcaaccg ttaaggccgt cctagatgct     180

gcagaatcga cctacgggtg gctgcttgcg ccgggtgcga agttcgtcgc caagcctgac     240

caattgatca agcgtcgtgg caagtccggt ctgctctcgc ttaacgtcac ctggcaacag     300
```

```
gctcgcgact ggatcacagt ccgcgctggt aagaagcttg ttgtcgaggg catccctggc    360

tacctgcgta ctttccttgt cgagcctttc gttccccatc cgcaagagac ggaatactac    420

atcaacatca actctgttcg tgaagtacgt attgtttgat cgcaactccg ggtgttatc     480

aatctaactt ttgtagggcg actggatttt gttttatcac gagggtggtg tcgatgtcgg    540

tgacgttgac tccaaggcct ctaagctgtt gatcccggtc gatctcgaca aggagtaccc    600

gacgaatgct actataatct ccactctcct ctccaaagtg ccagaggcac agcacgctac    660

gcttgtcgac ttcatcaacc gcctgtacgc cgtctatgtc gacctgcaat tcacgtacct    720

cgagattaac ccactcgtcg tcatcccgac cgcgtctggc gtcgaggtcc actatcttga    780

tctcgcggcc aagctcgacc aaacagcgga gttcgagtgc ggcgccaagt gggcaggtgc    840

ccgcgctcct actgcgctcg gaatcactcc ggccaagaac ggcgcctcga tcaacatcga    900

tgccggtccc ccaatggttt tccctgcgcc gtttggtcgt gagctttcgg acgaggaggc    960

ctacatcgcc gagcttgatg ccaaaaccgg tgcgtcgctc aagcttactg tgctcaatcc   1020

actaggccgc gtgtggacac tcgtcgcggg cggcggtgcg tccgtcgtgt acgccgatgc   1080

catcgcgtct gccggctacg ctaacgacat tgccaactac ggtgaatact ctggtgcacc   1140

taccgagacg caaacttacg agtacgcgaa gactgtgctg gatctgatga cccgcggtac   1200

tcccgtcgaa ggtggtaagg tcctgttcat tggcggtggt atcgcgaact tcacacaggt   1260

cggctcgaca ttcaagggca taattcgcgc gttcaaggac taccagtccc aactccacct   1320

ccatggcgtg aagatgtacg tccgccgcgg tgggcctaac tggcaggaag gtctccgtct   1380

gatcaaatcc tgcggcgagg agctctctat ccctatggag gtctacggac cagacatgca   1440

cgtatctggt attgtccctc tcgcactgct caaaaagcga cctgctggca tctatccgtt   1500

tggctcttct gccagcagca gtgccgtcag tgtgctgtaa                         1540
```

```
<210> SEQ ID NO 12
<211> LENGTH: 495
<212> TYPE: PRT
<213> ORGANISM: Lipomyces starkeyi

<400> SEQUENCE: 12

Met Ser Ala Lys Ser Ile His Glu Ala Asp Gly Lys Ala Leu Leu Ser
1               5                   10                  15

Tyr Phe Leu Pro Arg Ser Pro Leu Leu Thr Lys Glu Gly Thr Ser Thr
            20                  25                  30

Glu Phe Val Pro Ala Pro Pro Arg Leu Ala Ser Leu Thr Phe Pro Asp
        35                  40                  45

Asp Ser Pro Ala Thr Val Lys Ala Val Leu Asp Ala Ala Glu Ser Thr
    50                  55                  60

Tyr Gly Trp Leu Leu Ala Pro Gly Ala Lys Phe Val Ala Lys Pro Asp
65                  70                  75                  80

Gln Leu Ile Lys Arg Arg Gly Lys Ser Gly Leu Leu Ser Leu Asn Val
                85                  90                  95

Thr Trp Gln Gln Ala Arg Asp Trp Ile Thr Val Arg Ala Gly Lys Lys
            100                 105                 110

Leu Val Val Glu Gly Ile Pro Gly Tyr Leu Arg Thr Phe Leu Val Glu
        115                 120                 125

Pro Phe Val Pro His Pro Gln Glu Thr Glu Tyr Tyr Ile Asn Ile Asn
    130                 135                 140

Ser Val Arg Glu Gly Asp Trp Ile Leu Phe Tyr His Glu Gly Gly Val
```

-continued

```
145                 150                 155                 160

Asp Val Gly Asp Val Asp Ser Lys Ala Ser Lys Leu Leu Ile Pro Val
                165                 170                 175

Asp Leu Asp Lys Glu Tyr Pro Thr Asn Ala Thr Ile Ile Ser Thr Leu
            180                 185                 190

Leu Ser Lys Val Pro Glu Ala Gln His Ala Thr Leu Val Asp Phe Ile
        195                 200                 205

Asn Arg Leu Tyr Ala Val Tyr Val Asp Leu Gln Phe Thr Tyr Leu Glu
    210                 215                 220

Ile Asn Pro Leu Val Val Ile Pro Thr Ala Ser Gly Val Glu Val His
225                 230                 235                 240

Tyr Leu Asp Leu Ala Ala Lys Leu Asp Gln Thr Ala Glu Phe Glu Cys
                245                 250                 255

Gly Ala Lys Trp Ala Gly Ala Arg Ala Pro Thr Ala Leu Gly Ile Thr
            260                 265                 270

Pro Ala Lys Asn Gly Ala Ser Ile Asn Ile Asp Ala Gly Pro Pro Met
        275                 280                 285

Val Phe Pro Ala Pro Phe Gly Arg Glu Leu Ser Asp Glu Glu Ala Tyr
    290                 295                 300

Ile Ala Glu Leu Asp Ala Lys Thr Gly Ala Ser Leu Lys Leu Thr Val
305                 310                 315                 320

Leu Asn Pro Leu Gly Arg Val Trp Thr Leu Val Ala Gly Gly Gly Ala
                325                 330                 335

Ser Val Val Tyr Ala Asp Ala Ile Ala Ser Ala Gly Tyr Ala Asn Asp
            340                 345                 350

Ile Ala Asn Tyr Gly Glu Tyr Ser Gly Ala Pro Thr Glu Thr Gln Thr
        355                 360                 365

Tyr Glu Tyr Ala Lys Thr Val Leu Asp Leu Met Thr Arg Gly Thr Pro
    370                 375                 380

Val Glu Gly Gly Lys Val Leu Phe Ile Gly Gly Gly Ile Ala Asn Phe
385                 390                 395                 400

Thr Gln Val Gly Ser Thr Phe Lys Gly Ile Ile Arg Ala Phe Lys Asp
                405                 410                 415

Tyr Gln Ser Gln Leu His Leu His Gly Val Lys Met Tyr Val Arg Arg
            420                 425                 430

Gly Gly Pro Asn Trp Gln Glu Gly Leu Arg Leu Ile Lys Ser Cys Gly
        435                 440                 445

Glu Glu Leu Ser Ile Pro Met Glu Val Tyr Gly Pro Asp Met His Val
    450                 455                 460

Ser Gly Ile Val Pro Leu Ala Leu Leu Lys Lys Arg Pro Ala Gly Ile
465                 470                 475                 480

Tyr Pro Phe Gly Ser Ser Ala Ser Ser Ser Ala Val Ser Val Leu
                485                 490                 495
```

<210> SEQ ID NO 13
<211> LENGTH: 1387
<212> TYPE: DNA
<213> ORGANISM: Lipomyces starkeyi
<220> FEATURE:
<221> NAME/KEY: Intron
<222> LOCATION: (42)..(89)
<220> FEATURE:
<221> NAME/KEY: Intron
<222> LOCATION: (168)..(220)
<220> FEATURE:
<221> NAME/KEY: Intron
<222> LOCATION: (747)..(799)

<400> SEQUENCE: 13

```
atgagtgaga aggcagagat cgaggttccg ccgcaaaaat cgtgagtacg tcggatgctt     60
gcttaggaca gatgctgatt gctatttagg acattccctc gcagtgtgca cttcgctcca    120
cttcatattc cactggagag acgcctacag actttggcag tcttattgta agtctcgtct    180
accttacggt gacatggagt cgctaatgat atgagggtag ccacactgtc gcgctaccat    240
actgcatcgg tctgttcttt ctcatgctcg cgttccctcc tttttggcca ttattggtaa    300
tgtatgtcat atacgcatac gggttcgacc actcgagctc gaacggagag atctcccgcc    360
ggcgatcgcc gctgtttcga agactcccgt tgttcaggct gtattgtgat tacttcccca    420
tccacattca ccgggaggtt ccgctcgagc cgacgtttcc tggtcgcctt cgcgaaccga    480
gtggccttgt cgagcggtgg attgcgaaga tgttcggcgt gcaggacgct gttgtcgagg    540
gaaatgaatc tgacgttaag gccacggcca acggcaatgg gacgacgaaa gaaatcggac    600
cgacgtatgt tttcggctat catccgcatg gaattgttag cttgggtgcg tttggtgcta    660
ttggtacgga aggcgctgga tgggagaagc tctttcctgg gatcccggtg tcactgctga    720
ctctcgaaac aaatttcagc cttccagtag gttgatgttt gggtttgtct gccatgggat    780
agtactaata acagattagt tttacagaga gtatttgctg tcacttggga ttgcttcagt    840
atctcgacgg tcttgtacca atctcctcaa acacgaccaa tccatctgca tcgttatcgg    900
cggcgcccaa gagtcgctct tagcggaacc aggcactcta gatctgatcc tcgttaaacg    960
tcgcggtttt gtcaaacttg caatgtcaac ggcgcgggta tctgaccaac cgatttgtct   1020
tgttccgatc ctcagtttcg gcgagaacga cgtgtacgac caagtccgcg ggaccgatc   1080
gtcgaagttg tataagatcc agacttttat caagaaagcg gccgggttta cgctaccatt   1140
gatgtatgcg cgcggtatat ttaattacga ctttgggctg atgccgtacc gcaggcaaat   1200
gacgctcgtg gtcggcaagc cgattgcagt gccgtacgtg gcccagccta cggaggctga   1260
aatcgaagtg tatcacaagc agtacatgga tgaattgagg aggttatggg acacgtataa   1320
ggacgactat tttgtagacc acaagggcaa gggggtcaag aattccgaga tgcgttttgt   1380
ggagtaa                                                             1387
```

<210> SEQ ID NO 14
<211> LENGTH: 410
<212> TYPE: PRT
<213> ORGANISM: Lipomyces starkeyi

<400> SEQUENCE: 14

```
Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110
```

```
Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410
```

<210> SEQ ID NO 15
<211> LENGTH: 1543
<212> TYPE: DNA
<213> ORGANISM: Lipomyces starkeyi
<220> FEATURE:
<221> NAME/KEY: Intron
<222> LOCATION: (198)..(245)
<220> FEATURE:
<221> NAME/KEY: Intron
<222> LOCATION: (324)..(376)
<220> FEATURE:
<221> NAME/KEY: Intron
<222> LOCATION: (903)..(955)

<400> SEQUENCE: 15

```
atgcatggcg tcgcagtgcc ccaccttcct ccccctctcg ctcccgattt ccgcttcgtc      60

cggctgcccg tcgactgcct cttcgctgtg ctggccttta catatttaga acaaacggat     120
```

```
catcggacaa gcggcatttt ctgtatcatt ttagcaatga gtgagaaggc agagatcgag     180

gttccgccgc aaaaatcgtg agtacgtcgg atgcttgctt aggacagatg ctgattgcta     240

tttaggacat tccctcgcag tgtgcacttc gctccacttc atattccact ggagagacgc     300

ctacagactt tggcagtctt attgtaagtc tcgtctacct tacggtgaca tggagtcgct     360

aatgatatga gggtagccac actgtcgcgc taccatactg catcggtctg ttctttctca     420

tgctcgcgtt ccctcctttt tggccattat tggtaatgta tgtcatatac gcatacgggt     480

tcgaccactc gagctcgaac ggagagatct cccgccggcg atcgccgctg tttcgaagac     540

tcccgttgtt caggctgtat tgtgattact tccccatcca cattcaccgg gaggttccgc     600

tcgagccgac gtttcctggt cgccttcgcg aaccgagtgg ccttgtcgag cggtggattg     660

cgaagatgtt cggcgtgcag gacgctgttg tcgagggaaa tgaatctgac gttaaggcca     720

cggccaacgg caatgggacg acgaaagaaa tcggaccgac gtatgttttc ggctatcatc     780

cgcatggaat tgttagcttg ggtgcgtttg gtgctattgg tacggaaggc gctggatggg     840

agaagctctt tcctgggatc ccggtgtcac tgctgactct cgaaacaaat ttcagccttc     900

cagtaggttg atgtttgggt ttgtctgcca tgggatagta ctaataacag attagtttta     960

cagagagtat ttgctgtcac ttgggattgc ttcagtatct cgacggtctt gtaccaatct    1020

cctcaaacac gaccaatcca tctgcatcgt tatcggcggc gcccaagagt cgctcttagc    1080

ggaaccaggc actctagatc tgatcctcgt taaacgtcgc ggttttgtca aacttgcaat    1140

gtcaacggcg cgggtatctg accaaccgat ttgtcttgtt ccgatcctca gtttcggcga    1200

gaacgacgtg tacgaccaag tccgcgggga ccgatcgtcg aagttgtata agatccagac    1260

ttttatcaag aaagcggccg ggtttacgct accattgatg tatgcgcgcg gtatatttaa    1320

ttacgacttt gggctgatgc cgtaccgcag gcaaatgacg ctcgtggtcg gcaagccgat    1380

tgcagtgccg tacgtggccc agcctacgga ggctgaaatc gaagtgtatc acaagcagta    1440

catggatgaa ttgaggaggt tatgggacac gtataaggac gactattttg tagaccacaa    1500

gggcaagggg gtcaagaatt ccgagatgcg ttttgtggag taa                      1543
```

```
<210> SEQ ID NO 16
<211> LENGTH: 462
<212> TYPE: PRT
<213> ORGANISM: Lipomyces starkeyi

<400> SEQUENCE: 16

Met His Gly Val Ala Val Pro His Leu Pro Pro Pro Leu Ala Pro Asp
1               5                   10                  15

Phe Arg Phe Val Arg Leu Pro Val Asp Cys Leu Phe Ala Val Leu Ala
            20                  25                  30

Phe Thr Tyr Leu Glu Gln Thr Asp His Arg Thr Ser Gly Ile Phe Cys
        35                  40                  45

Ile Ile Leu Ala Met Ser Glu Lys Ala Glu Ile Glu Val Pro Pro Gln
    50                  55                  60

Lys Ser Thr Phe Pro Arg Ser Val His Phe Ala Pro Leu His Ile Pro
65                  70                  75                  80

Leu Glu Arg Arg Leu Gln Thr Leu Ala Val Leu Phe His Thr Val Ala
                85                  90                  95

Leu Pro Tyr Cys Ile Gly Leu Phe Phe Leu Met Leu Ala Phe Pro Pro
            100                 105                 110

Phe Trp Pro Leu Leu Val Met Tyr Val Ile Tyr Ala Tyr Gly Phe Asp
        115                 120                 125
```

```
His Ser Ser Ser Asn Gly Glu Ile Ser Arg Arg Arg Ser Pro Leu Phe
    130                 135                 140

Arg Arg Leu Pro Leu Phe Arg Leu Tyr Cys Asp Tyr Phe Pro Ile His
145                 150                 155                 160

Ile His Arg Glu Val Pro Leu Glu Pro Thr Phe Pro Gly Arg Leu Arg
                165                 170                 175

Glu Pro Ser Gly Leu Val Glu Arg Trp Ile Ala Lys Met Phe Gly Val
            180                 185                 190

Gln Asp Ala Val Val Glu Gly Asn Glu Ser Asp Val Lys Ala Thr Ala
        195                 200                 205

Asn Gly Asn Gly Thr Thr Lys Glu Ile Gly Pro Thr Tyr Val Phe Gly
    210                 215                 220

Tyr His Pro His Gly Ile Val Ser Leu Gly Ala Phe Gly Ala Ile Gly
225                 230                 235                 240

Thr Glu Gly Ala Gly Trp Glu Lys Leu Phe Pro Gly Ile Pro Val Ser
                245                 250                 255

Leu Leu Thr Leu Glu Thr Asn Phe Ser Leu Pro Phe Tyr Arg Glu Tyr
            260                 265                 270

Leu Leu Ser Leu Gly Ile Ala Ser Val Ser Arg Arg Ser Cys Thr Asn
        275                 280                 285

Leu Leu Lys His Asp Gln Ser Ile Cys Ile Val Ile Gly Gly Ala Gln
    290                 295                 300

Glu Ser Leu Leu Ala Glu Pro Gly Thr Leu Asp Leu Ile Leu Val Lys
305                 310                 315                 320

Arg Arg Gly Phe Val Lys Leu Ala Met Ser Thr Ala Arg Val Ser Asp
                325                 330                 335

Gln Pro Ile Cys Leu Val Pro Ile Leu Ser Phe Gly Glu Asn Asp Val
            340                 345                 350

Tyr Asp Gln Val Arg Gly Asp Arg Ser Ser Lys Leu Tyr Lys Ile Gln
        355                 360                 365

Thr Phe Ile Lys Lys Ala Ala Gly Phe Thr Leu Pro Leu Met Tyr Ala
    370                 375                 380

Arg Gly Ile Phe Asn Tyr Asp Phe Gly Leu Met Pro Tyr Arg Arg Gln
385                 390                 395                 400

Met Thr Leu Val Val Gly Lys Pro Ile Ala Val Pro Tyr Val Ala Gln
                405                 410                 415

Pro Thr Glu Ala Glu Ile Glu Val Tyr His Lys Gln Tyr Met Asp Glu
            420                 425                 430

Leu Arg Arg Leu Trp Asp Thr Tyr Lys Asp Asp Tyr Phe Val Asp His
        435                 440                 445

Lys Gly Lys Gly Val Lys Asn Ser Glu Met Arg Phe Val Glu
    450                 455                 460
```

<210> SEQ ID NO 17
<211> LENGTH: 5724
<212> TYPE: DNA
<213> ORGANISM: Lipomyces starkeyi
<220> FEATURE:
<221> NAME/KEY: Intron
<222> LOCATION: (1927)..(1977)
<220> FEATURE:
<221> NAME/KEY: Intron
<222> LOCATION: (2192)..(2245)
<220> FEATURE:
<221> NAME/KEY: Intron
<222> LOCATION: (4798)..(4848)

<400> SEQUENCE: 17

```
atgcgtcccg agactgagca agagctcgcc catatcctac tcgtcgagct actcgcctac      60
cagttcgcgt cccccgtccg ctggatcgaa actcaggatg tcatcttcca ggagttcaac     120
tccgagcgtc tcgtcgaaat cggtccgtcc ccgacccttg cgggaatggc acagcgcact     180
ctaaaggcaa aatacgagtc atacgatgct gcactctcac ttcagcgcca ggttctctgc     240
tactctaagg acgccaagga gatctactac accccagatc ccgtcgtcgt cgaagccgct     300
ccagagcctg ctgcggctac tgctggcgct cctgctactg ctgctcctgc tgcagctgca     360
gcagccgttg cagctgctcc atccggacca gttgccgctg tttctgatga gcctgtcaag     420
gctgtcgaaa tcttgcgctc gctcgtcgct cagaaactca agaagcctta cgaccaggtg     480
ccacttgcaa aggccattaa agatcttgtc ggcggcaagt ccactctcca gaacgaaatt     540
ctgggtgatc tgggcaagga gttcggctcg gctcctgaga aggcagagga gactcctcta     600
gaagagctag gcgccgctat ccagggttcc ggcttcaatg gccagctcgg caaacagtca     660
ctctcgctca tcggtcgact agtcgcttct aagatgcctg gtggcttcaa cctcacctcc     720
actcgcaagt atctccagga cagatggggt cttggacctg gtcgccagga cggtgttttg     780
ctcctcgcca tcacgatcga gccacctgcg cgtctcgcgg ccgaagccga tgcaaagaaa     840
tatctcgacg aagtcgctgc caagtacgct tccttcgccg gcatctcgct ctcgtccggc     900
agtggtgacg ccggtgccgg tggtgccgga ggcggcgcta ttgccatcga ctctgccgcg     960
ttcgaggagc tcaccaagga ccaaacccat ctcgttcgcc agcaaatgga attgtttgcc    1020
aagtacctca aggtcgacct ccgggccggc gataagcttt tcgtcgacga gcaggacgcg    1080
tcctccgaac tccgcaagga acttgacctc tggattgccg aacatggcga cttttacgcg    1140
accggcatca ttccctcctt ctcgccgctc aaggcccgcg tgtacgactc gtcttggaat    1200
tgggctcgcc aggatgcgct taccatgtac tacgacatca tctttggccg tctctctgtt    1260
gtcgataggg agattgtgtc ccactgcatt ctcctcatga accgctcgaa ccctacttta    1320
ctcgaattca tgcagtatca tatcgaccat tgcccggaga agcgtgggga cacataccag    1380
ctcgcgaagc agcttggcca gcagctcatc gacaactgcc gagatgcact cggcgtggag    1440
ccagtctata aggacgtcat gtacccaaca gctccccaga ccgccattga tgttaaagga    1500
aatatcaagt acgacgaagt ccctcgtgtc gcagtccgca agctcgagca atacgtcaag    1560
gaaatggccg ccggtggcaa gatcacggag aatcgcagcc gcacgaagtt gcacgccggc    1620
cttgcccgca tctacaaaat aatccgccag caacaaaagc ttagcaagag ttccaagctt    1680
cagatcaaga ccttgtacga ggacgtcatc caatctctct cgcttgaatc cggtcttgcc    1740
aacggcagtc cctcacccga tggcacaggc cgcccaactt cgcctaagcg caggaagggc    1800
ggcaagggaa agaaatacac cgaaacgatt ccgttcttgc acttgaagaa gaaggatatg    1860
cacggttggg actacagcaa gcctctgact ggcatctatc tcgagtgcct cgagcaggcc    1920
gcaaaagtaa gttttctcca catttgtata ctgcgagcat catacttact tatctagtcc    1980
ggtgtctcat ttaaagacaa gtacgctttg atgaccggtg ctggcgctgg ctctattggt    2040
gccgctgtct tgcagggact tttgtccggt ggtgcgaagg ttgttgtcac tacgtcgcga    2100
tattcgaagg aagtgaccga gtactatcaa tctatctacg cgaagtacgg cgccagcaac    2160
agtacattga ttgtcgttcc tttcaatcag ggtatgttta ttgaagagtt catttatcga    2220
aatttgttgc tgacaggttt gtcaggctct aagcaggacg ttgacgctct cgttgactac    2280
gtttacgaca ccaagaaggg tctcggctgg gatcttgatt atgtcattcc gtttgccgcc    2340
```

```
attccagaga acggccgtga gatcgacggc attgactcca agtccgagct tgctcaccga   2400
atgatgctta ctaacttact ccgcattctc ggcaatgtta agactcagaa gctcgctcac   2460
ggctacgcga ctcgtccggc tcaggtcatc ctaccgatgt cccccaacca cggtactttc   2520
gggtccgacg gcttgtattc ggagtctaag cttgcactcg agacattgtt caacagatgg   2580
tactccgagt cctggggtcc gtacctcacg atctgcggtg ccgtcattgg ctggactcgt   2640
ggcaccggtc ttatgaacca gaacaacttg atcgctgaac gtattgagag tcttggtgtc   2700
cgcaccttct ctcagcagga gatggctttc aacatcctcg gtcttatgtc ccccgcgatc   2760
gtcaaccttt gccagatgga gcctgttttc gcggacttga atggtggcat gcagtatatt   2820
cccaatctca aggaggcctc agcccagatt cgtcaggagc tcctccagac gtccgagatt   2880
cgccgggcag tttcagcaga gagtgcgatc gagtacaagc ttgtcaatgg cgcagaagct   2940
gagcgtctgc aaaagtctgt cgtcatccag ccgcgtgcca atattaaatt cgagttcccg   3000
aggctcaagg agtactcaga aatcgctcac cttgccgaaa acctcaaggg catggtcgac   3060
ctcgagaaag tcgtcgtcgt cactggtttc gccgaagtcg gtccttgggg caacgctcgc   3120
acgcggtggg agatggaagc ctatggccag ttctctcttg aaggttgcat cgaaatggct   3180
tggattatgg gtctcattaa gcaccacaat ggtcaattga agggcaagat gtactctggc   3240
tgggtcgata ccaagagcaa cgagcctgtc gacgactttg acgtcaagtc gaagtacgag   3300
aaacatattc ttgagcactc cggcatccgg ttgattgagg ctgagttgtt tgacggctat   3360
gaccccaaga agaagaagat gcttcaggaa gttgttatcg agcatgatct cgagcctttc   3420
gagacctcga aggagaccgc gtacgagttt aagcgcgagc acggcgacaa ggtcgagatt   3480
ttcgagattg ctgagacagg gcagtggact gtccgactgc tcaagggcgc cagtctgcta   3540
attcccaagg cgctccagtt cgatcgtttg gttgctggtc agatcccgac cggctgggac   3600
gctcgacgat acggtatcgg ggaggacatc atttcgcagg tcgatccgat cactctctat   3660
gttcttgtct ccactgtcga ggcactgctt tctgccggtg ttaccgaccc gtacgagttc   3720
tacaagtacg tccatgtttc tgaggtcggt aactgcaccg gttccggtgt cggtggcatg   3780
agcgctcttc gcggcatgta caaggaccga tttatggaca agccggtcca gaaagatatt   3840
cttcaggaat ctttcatcaa cactatgtct gcatgggtta acatgttgct cctctcctcg   3900
tccggtccaa tcaagactcc tgtcggtgcc tgcgctactt ccattgagtc tgtcgatatt   3960
ggctacgaga ccatcatttc cggcaaggcc aagatatgtc tggtcggcgg ctacgacgat   4020
ttccaggaag aaggttcatt cgagttcggc aacatgggtg ccacatccaa ctccgagacc   4080
gagattgccc atgggcgtac cccagctgag atgtcccgtc cgacgacgac tacgcgtgcc   4140
ggtttcatgg agtcccatgg tgctggtatc cagttgatta tgacggccaa gctcgctctc   4200
gcaatgggtg tcccggtcta cggtatcatt ggtatgaccg ccaccgcgac cgacaagatc   4260
ggccgatccg tgccggcgcc tggtaagggt atcctcacca cagcgcgtga gaacagggag   4320
tccaagttcc cgtcgccact gcttgacatc aagtaccgac gccgccagct tgagaagcgt   4380
cagtcccaga tccgcgagtg gaccgagtcc gagatcttgt atttgcagca ggaagtcaat   4440
tccatgcgcg accaatatga gaatttcgat gagagggagt atttgaccga gcgccttgcc   4500
catgttgagc gtgaggctgc gcgacaggag aaggacgcct tggcgcagtg gggtaatgat   4560
ttctacaagc aagatgcaag aatcgcgcct ctgcgtggtg cgcttgctgt ttggaatctt   4620
acggttgatg atcttggtgt tgcgtcgttc catggcacgt ccactgttgc aaatgataag   4680
```

```
aacgagagca tgacaattgc caacatgatg actcatctcg gacgatcaaa gggtaatgcc   4740

atcctcggca ttttccagaa gtatttgacc ggtcacccta agggtgccgc aggtgctgta   4800

agtttcaagc atttttatta catttcagga gtgggctaac aatgacagtg gatgttgaac   4860

ggtgcgctcc aggtcctcaa cactggtctg gtgcccggta accgcaatgc cgacaatgtt   4920

gacaaggttc tcgaacagtt cgactcgatt ttgtatccgt cacgcagtat ccaaacggac   4980

ggtatcaagg ccgcgtccgt gacgtcgttc ggtttcggcc agaagggtgc ccaggcaatc   5040

atcattaact ctgattacct tttcgccact ctcgatgagg acgcatacaa cgcctacacc   5100

gcgaaggtcg tggcgcgtca caagagggcg tacagataca tccatcatgc catggccact   5160

aacaccatgt tcgtcgccaa gaacgatccg ccatatgcca aggacctcga gagcactgtc   5220

tatctcgacc cgcttgtgcg cgttgagccg gataagaagg ctggcacgta cgcgtacccg   5280

gcaaagaagc ccgctcagcc atccaataag gagactgagg atgtgttgct gaagttaacc   5340

cagtccaccg cgtcaactgg caccaacgtc ggagtcgacg tagaggcttt gtcggccatc   5400

ccgattgaca acgagacctt tatcgagcgt aactacactc ccgccgaaat cagttactgc   5460

tcttcttctg ctgatccccg ggcaagcttt gctggcactt ggtgcgcgaa ggaagctgtc   5520

ttcaagagct tgggcgttaa atccgacggc gcgggtgcgg cgttgaaaga aatcgagatc   5580

gttcggaaat cgggcaagcc cgaggtcgtg ttctcaggcg ttgcgaagca acgggcggaa   5640

gaaaagggcg tcaaggacgt cagtgttagt atcagtcata acgaattcca ggcggtcgcg   5700

gttgctgttg cagagttggt ttaa                                          5724
```

<210> SEQ ID NO 18
<211> LENGTH: 1855
<212> TYPE: PRT
<213> ORGANISM: Lipomyces starkeyi

<400> SEQUENCE: 18

```
Met Arg Pro Glu Thr Glu Gln Glu Leu Ala His Ile Leu Leu Val Glu
1               5                   10                  15

Leu Leu Ala Tyr Gln Phe Ala Ser Pro Val Arg Trp Ile Glu Thr Gln
            20                  25                  30

Asp Val Ile Phe Gln Glu Phe Asn Ser Glu Arg Leu Val Glu Ile Gly
        35                  40                  45

Pro Ser Pro Thr Leu Ala Gly Met Ala Gln Arg Thr Leu Lys Ala Lys
    50                  55                  60

Tyr Glu Ser Tyr Asp Ala Ala Leu Ser Leu Gln Arg Gln Val Leu Cys
65                  70                  75                  80

Tyr Ser Lys Asp Ala Lys Glu Ile Tyr Tyr Thr Pro Asp Pro Val Val
                85                  90                  95

Val Glu Ala Ala Pro Glu Pro Ala Ala Ala Thr Ala Gly Ala Pro Ala
            100                 105                 110

Thr Ala Ala Pro Ala Ala Ala Ala Ala Ala Val Ala Ala Ala Pro Ser
        115                 120                 125

Gly Pro Val Ala Ala Val Ser Asp Glu Pro Val Lys Ala Val Glu Ile
    130                 135                 140

Leu Arg Ser Leu Val Ala Gln Lys Leu Lys Lys Pro Tyr Asp Gln Val
145                 150                 155                 160

Pro Leu Ala Lys Ala Ile Lys Asp Leu Val Gly Gly Lys Ser Thr Leu
                165                 170                 175

Gln Asn Glu Ile Leu Gly Asp Leu Gly Lys Glu Phe Gly Ser Ala Pro
            180                 185                 190
```

```
Glu Lys Ala Glu Glu Thr Pro Leu Glu Glu Leu Gly Ala Ala Ile Gln
        195                 200                 205

Gly Ser Gly Phe Asn Gly Gln Leu Gly Lys Gln Ser Leu Ser Leu Ile
    210                 215                 220

Gly Arg Leu Val Ala Ser Lys Met Pro Gly Gly Phe Asn Leu Thr Ser
225                 230                 235                 240

Thr Arg Lys Tyr Leu Gln Asp Arg Trp Gly Leu Gly Pro Gly Arg Gln
                245                 250                 255

Asp Gly Val Leu Leu Leu Ala Ile Thr Ile Glu Pro Pro Ala Arg Leu
            260                 265                 270

Ala Ala Glu Ala Asp Ala Lys Lys Tyr Leu Asp Glu Val Ala Ala Lys
        275                 280                 285

Tyr Ala Ser Phe Ala Gly Ile Ser Leu Ser Ser Gly Ser Gly Asp Ala
    290                 295                 300

Gly Ala Gly Gly Ala Gly Gly Gly Ala Ile Ala Ile Asp Ser Ala Ala
305                 310                 315                 320

Phe Glu Glu Leu Thr Lys Asp Gln Thr His Leu Val Arg Gln Gln Met
                325                 330                 335

Glu Leu Phe Ala Lys Tyr Leu Lys Val Asp Leu Arg Ala Gly Asp Lys
            340                 345                 350

Leu Phe Val Asp Glu Gln Asp Ala Ser Ser Glu Leu Arg Lys Glu Leu
        355                 360                 365

Asp Leu Trp Ile Ala Glu His Gly Asp Phe Tyr Ala Thr Gly Ile Ile
    370                 375                 380

Pro Ser Phe Ser Pro Leu Lys Ala Arg Val Tyr Asp Ser Ser Trp Asn
385                 390                 395                 400

Trp Ala Arg Gln Asp Ala Leu Thr Met Tyr Tyr Asp Ile Ile Phe Gly
                405                 410                 415

Arg Leu Ser Val Val Asp Arg Glu Ile Val Ser His Cys Ile Leu Leu
            420                 425                 430

Met Asn Arg Ser Asn Pro Thr Leu Leu Glu Phe Met Gln Tyr His Ile
        435                 440                 445

Asp His Cys Pro Glu Lys Arg Gly Asp Thr Tyr Gln Leu Ala Lys Gln
    450                 455                 460

Leu Gly Gln Gln Leu Ile Asp Asn Cys Arg Asp Ala Leu Gly Val Glu
465                 470                 475                 480

Pro Val Tyr Lys Asp Val Met Tyr Pro Thr Ala Pro Gln Thr Ala Ile
                485                 490                 495

Asp Val Lys Gly Asn Ile Lys Tyr Asp Glu Val Pro Arg Val Ala Val
            500                 505                 510

Arg Lys Leu Glu Gln Tyr Val Lys Glu Met Ala Ala Gly Gly Lys Ile
        515                 520                 525

Thr Glu Asn Arg Ser Arg Thr Lys Leu His Ala Gly Leu Ala Arg Ile
    530                 535                 540

Tyr Lys Ile Ile Arg Gln Gln Gln Lys Leu Ser Lys Ser Ser Lys Leu
545                 550                 555                 560

Gln Ile Lys Thr Leu Tyr Glu Asp Val Ile Gln Ser Leu Ser Leu Glu
                565                 570                 575

Ser Gly Leu Ala Asn Gly Ser Pro Ser Pro Asp Gly Thr Gly Arg Pro
            580                 585                 590

Thr Ser Pro Lys Arg Arg Lys Gly Gly Lys Gly Lys Lys Tyr Thr Glu
        595                 600                 605
```

```
Thr Ile Pro Phe Leu His Leu Lys Lys Lys Asp Met His Gly Trp Asp
    610                 615                 620

Tyr Ser Lys Pro Leu Thr Gly Ile Tyr Leu Glu Cys Leu Glu Gln Ala
625                 630                 635                 640

Ala Lys Ser Gly Val Ser Phe Lys Asp Lys Tyr Ala Leu Met Thr Gly
                645                 650                 655

Ala Gly Ala Gly Ser Ile Gly Ala Ala Val Leu Gln Gly Leu Leu Ser
            660                 665                 670

Gly Gly Ala Lys Val Val Val Thr Thr Ser Arg Tyr Ser Lys Glu Val
        675                 680                 685

Thr Glu Tyr Tyr Gln Ser Ile Tyr Ala Lys Tyr Gly Ala Ser Asn Ser
    690                 695                 700

Thr Leu Ile Val Val Pro Phe Asn Gln Gly Ser Lys Gln Asp Val Asp
705                 710                 715                 720

Ala Leu Val Asp Tyr Val Tyr Asp Thr Lys Lys Gly Leu Gly Trp Asp
                725                 730                 735

Leu Asp Tyr Val Ile Pro Phe Ala Ala Ile Pro Glu Asn Gly Arg Glu
            740                 745                 750

Ile Asp Gly Ile Asp Ser Lys Ser Glu Leu Ala His Arg Met Met Leu
        755                 760                 765

Thr Asn Leu Leu Arg Ile Leu Gly Asn Val Lys Thr Gln Lys Leu Ala
    770                 775                 780

His Gly Tyr Ala Thr Arg Pro Ala Gln Val Ile Leu Pro Met Ser Pro
785                 790                 795                 800

Asn His Gly Thr Phe Gly Ser Asp Gly Leu Tyr Ser Glu Ser Lys Leu
                805                 810                 815

Ala Leu Glu Thr Leu Phe Asn Arg Trp Tyr Ser Glu Ser Trp Gly Pro
            820                 825                 830

Tyr Leu Thr Ile Cys Gly Ala Val Ile Gly Trp Thr Arg Gly Thr Gly
        835                 840                 845

Leu Met Asn Gln Asn Asn Leu Ile Ala Glu Arg Ile Glu Ser Leu Gly
    850                 855                 860

Val Arg Thr Phe Ser Gln Gln Glu Met Ala Phe Asn Ile Leu Gly Leu
865                 870                 875                 880

Met Ser Pro Ala Ile Val Asn Leu Cys Gln Met Glu Pro Val Phe Ala
                885                 890                 895

Asp Leu Asn Gly Gly Met Gln Tyr Ile Pro Asn Leu Lys Glu Ala Ser
            900                 905                 910

Ala Gln Ile Arg Gln Glu Leu Leu Gln Thr Ser Glu Ile Arg Arg Ala
        915                 920                 925

Val Ser Ala Glu Ser Ala Ile Glu Tyr Lys Leu Val Asn Gly Ala Glu
    930                 935                 940

Ala Glu Arg Leu Gln Lys Ser Val Val Ile Gln Pro Arg Ala Asn Ile
945                 950                 955                 960

Lys Phe Glu Phe Pro Arg Leu Lys Glu Tyr Ser Glu Ile Ala His Leu
                965                 970                 975

Ala Glu Asn Leu Lys Gly Met Val Asp Leu Glu Lys Val Val Val Val
            980                 985                 990

Thr Gly Phe Ala Glu Val Gly Pro  Trp Gly Asn Ala Arg  Thr Arg Trp
        995                 1000                 1005

Glu Met  Glu Ala Tyr Gly Gln  Phe Ser Leu Glu Gly  Cys Ile Glu
    1010                 1015                 1020

Met Ala  Trp Ile Met Gly Leu  Ile Lys His His Asn  Gly Gln Leu
```

```
    1025                1030                1035

Lys Gly  Lys Met Tyr Ser Gly  Trp Val Asp Thr Lys  Ser Asn Glu
    1040                1045                1050

Pro Val  Asp Asp Phe Asp Val  Lys Ser Lys Tyr Glu  Lys His Ile
    1055                1060                1065

Leu Glu  His Ser Gly Ile Arg  Leu Ile Glu Ala Glu  Leu Phe Asp
    1070                1075                1080

Gly Tyr  Asp Pro Lys Lys Lys  Lys Met Leu Gln Glu  Val Val Ile
    1085                1090                1095

Glu His  Asp Leu Glu Pro Phe  Glu Thr Ser Lys Glu  Thr Ala Tyr
    1100                1105                1110

Glu Phe  Lys Arg Glu His Gly  Asp Lys Val Glu Ile  Phe Glu Ile
    1115                1120                1125

Ala Glu  Thr Gly Gln Trp Thr  Val Arg Leu Leu Lys  Gly Ala Ser
    1130                1135                1140

Leu Leu  Ile Pro Lys Ala Leu  Gln Phe Asp Arg Leu  Val Ala Gly
    1145                1150                1155

Gln Ile  Pro Thr Gly Trp Asp  Ala Arg Arg Tyr Gly  Ile Gly Glu
    1160                1165                1170

Asp Ile  Ile Ser Gln Val Asp  Pro Ile Thr Leu Tyr  Val Leu Val
    1175                1180                1185

Ser Thr  Val Glu Ala Leu Leu  Ser Ala Gly Val Thr  Asp Pro Tyr
    1190                1195                1200

Glu Phe  Tyr Lys Tyr Val His  Val Ser Glu Val Gly  Asn Cys Thr
    1205                1210                1215

Gly Ser  Gly Val Gly Gly Met  Ser Ala Leu Arg Gly  Met Tyr Lys
    1220                1225                1230

Asp Arg  Phe Met Asp Lys Pro  Val Gln Lys Asp Ile  Leu Gln Glu
    1235                1240                1245

Ser Phe  Ile Asn Thr Met Ser  Ala Trp Val Asn Met  Leu Leu Leu
    1250                1255                1260

Ser Ser  Ser Gly Pro Ile Lys  Thr Pro Val Gly Ala  Cys Ala Thr
    1265                1270                1275

Ser Ile  Glu Ser Val Asp Ile  Gly Tyr Glu Thr Ile  Ile Ser Gly
    1280                1285                1290

Lys Ala  Lys Ile Cys Leu Val  Gly Gly Tyr Asp Asp  Phe Gln Glu
    1295                1300                1305

Glu Gly  Ser Phe Glu Phe Gly  Asn Met Gly Ala Thr  Ser Asn Ser
    1310                1315                1320

Glu Thr  Glu Ile Ala His Gly  Arg Thr Pro Ala Glu  Met Ser Arg
    1325                1330                1335

Pro Thr  Thr Thr Thr Arg Ala  Gly Phe Met Glu Ser  His Gly Ala
    1340                1345                1350

Gly Ile  Gln Leu Ile Met Thr  Ala Lys Leu Ala Leu  Ala Met Gly
    1355                1360                1365

Val Pro  Val Tyr Gly Ile Ile  Gly Met Thr Ala Thr  Ala Thr Asp
    1370                1375                1380

Lys Ile  Gly Arg Ser Val Pro  Ala Pro Gly Lys Gly  Ile Leu Thr
    1385                1390                1395

Thr Ala  Arg Glu Asn Arg Glu  Ser Lys Phe Pro Ser  Pro Leu Leu
    1400                1405                1410

Asp Ile  Lys Tyr Arg Arg Arg  Gln Leu Glu Lys Arg  Gln Ser Gln
    1415                1420                1425
```

```
Ile Arg  Glu Trp Thr Glu Ser  Glu Ile Leu Tyr Leu  Gln Gln Glu
    1430                 1435                 1440

Val Asn  Ser Met Arg Asp Gln  Tyr Glu Asn Phe Asp  Glu Arg Glu
    1445                 1450                 1455

Tyr Leu  Thr Glu Arg Leu Ala  His Val Glu Arg Glu  Ala Ala Arg
    1460                 1465                 1470

Gln Glu  Lys Asp Ala Leu Ala  Gln Trp Gly Asn Asp  Phe Tyr Lys
    1475                 1480                 1485

Gln Asp  Ala Arg Ile Ala Pro  Leu Arg Gly Ala Leu  Ala Val Trp
    1490                 1495                 1500

Asn Leu  Thr Val Asp Asp Leu  Gly Val Ala Ser Phe  His Gly Thr
    1505                 1510                 1515

Ser Thr  Val Ala Asn Asp Lys  Asn Glu Ser Met Thr  Ile Ala Asn
    1520                 1525                 1530

Met Met  Thr His Leu Gly Arg  Ser Lys Gly Asn Ala  Ile Leu Gly
    1535                 1540                 1545

Ile Phe  Gln Lys Tyr Leu Thr  Gly His Pro Lys Gly  Ala Ala Gly
    1550                 1555                 1560

Ala Trp  Met Leu Asn Gly Ala  Leu Gln Val Leu Asn  Thr Gly Leu
    1565                 1570                 1575

Val Pro  Gly Asn Arg Asn Ala  Asp Asn Val Asp Lys  Val Leu Glu
    1580                 1585                 1590

Gln Phe  Asp Ser Ile Leu Tyr  Pro Ser Arg Ser Ile  Gln Thr Asp
    1595                 1600                 1605

Gly Ile  Lys Ala Ala Ser Val  Thr Ser Phe Gly Phe  Gly Gln Lys
    1610                 1615                 1620

Gly Ala  Gln Ala Ile Ile Ile  Asn Ser Asp Tyr Leu  Phe Ala Thr
    1625                 1630                 1635

Leu Asp  Glu Asp Ala Tyr Asn  Ala Tyr Thr Ala Lys  Val Val Ala
    1640                 1645                 1650

Arg His  Lys Arg Ala Tyr Arg  Tyr Ile His His Ala  Met Ala Thr
    1655                 1660                 1665

Asn Thr  Met Phe Val Ala Lys  Asn Asp Pro Pro Tyr  Ala Lys Asp
    1670                 1675                 1680

Leu Glu  Ser Thr Val Tyr Leu  Asp Pro Leu Val Arg  Val Glu Pro
    1685                 1690                 1695

Asp Lys  Lys Ala Gly Thr Tyr  Ala Tyr Pro Ala Lys  Lys Pro Ala
    1700                 1705                 1710

Gln Pro  Ser Asn Lys Glu Thr  Glu Asp Val Leu Leu  Lys Leu Thr
    1715                 1720                 1725

Gln Ser  Thr Ala Ser Thr Gly  Thr Asn Val Gly Val  Asp Val Glu
    1730                 1735                 1740

Ala Leu  Ser Ala Ile Pro Ile  Asp Asn Glu Thr Phe  Ile Glu Arg
    1745                 1750                 1755

Asn Tyr  Thr Pro Ala Glu Ile  Ser Tyr Cys Ser Ser  Ser Ala Asp
    1760                 1765                 1770

Pro Arg  Ala Ser Phe Ala Gly  Thr Trp Cys Ala Lys  Glu Ala Val
    1775                 1780                 1785

Phe Lys  Ser Leu Gly Val Lys  Ser Asp Gly Ala Gly  Ala Ala Leu
    1790                 1795                 1800

Lys Glu  Ile Glu Ile Val Arg  Lys Ser Gly Lys Pro  Glu Val Val
    1805                 1810                 1815
```

```
Phe Ser  Gly Val Ala Lys Gln  Arg Ala Glu Glu Lys  Gly Val Lys
    1820                 1825                 1830

Asp Val  Ser Val Ser Ile Ser  His Asn Glu Phe Gln  Ala Val Ala
    1835                 1840                 1845

Val Ala  Val Ala Glu Leu Val
    1850                 1855


<210> SEQ ID NO 19
<211> LENGTH: 6456
<212> TYPE: DNA
<213> ORGANISM: Lipomyces starkeyi
<220> FEATURE:
<221> NAME/KEY: Intron
<222> LOCATION: (821)..(866)
<220> FEATURE:
<221> NAME/KEY: Intron
<222> LOCATION: (2665)..(2722)
<220> FEATURE:
<221> NAME/KEY: Intron
<222> LOCATION: (5302)..(5355)
<220> FEATURE:
<221> NAME/KEY: Intron
<222> LOCATION: (5425)..(5473)

<400> SEQUENCE: 19

atgtacgctg gcgctgagac tggcgtcgca acgcctcaca ctcaggcctc tctgcgtccg     60

ctctcgctcc agcatggctc gctggagcac accgtgtttg taccaaccgc gctctatctc    120

tcaatcctcc atctacggga cgaattcgcc gccactcttc ctactccaac tgaagacttc    180

gccggagacg aagagcctgc atccaactgc gagcttgttg cccgattcct cgccttttta    240

gtcgctcagg tcgaggaaga gccagaccag tatgatgacg ttctcgcgct cgtccttgcc    300

gactttgaat ctcgcttcct ccgtgcaaat gaagtccatg ccgtcgcagc tgcgcttcct    360

ggggatctgg ccaagcgtga ggtcgtcatc agcgcctact acgcagccag gctcgctgcc    420

aatcgtccaa tcaaaggcca cgattcagcg ctgcttcgtg cctccgctga cggtcgtgct    480

tccattttcg caattttcgg cggccaggga aatatcgagg aatattttga tgagctccgc    540

aatgtctact ccctctatca tggtcttatt gacgactttg ttcagcactg cgctcgcgac    600

ttgctcaagc ttgcttccga cgatcgcacc atgaaagtct actcgaatgg cctcgacatc    660

atgcgatggc tccgcgagcc cgagtcgact cctgacctcg attatcttgt ttcggcacct    720

gtctcacttc ctttgatcgg tgtcactcag ctcactcatt acgctgccac ttgcaagatc    780

ctcggcaagg agccaggtga atttagatca cacttgtccg gtatgtattg attagtctga    840

caagtgacat ttgctaacgt cgacaggaac aaccggtcac tctcaaggtg tcgtcacggc    900

cgctgccatt tcggcctcga ctacatggga gtccttcttc gacgtcgcgt ccaagactct    960

ccagatcctg ttctggatcg gttgccgcgc tcagcagacc tatcctcgca cctctctcgc   1020

gccttccgtc ctccaggact cggtcaacga aggcgaaggc aaaccatcgc ctatgctttc   1080

ggtgcgcgac cttgtcaagt cccaggtcca gaagcacgtt gatttgacaa attcccatct   1140

tccaccagag aagcacgtct cgatctcgct cgagaacggt gcccgtaact ttgtcgtcac   1200

cggtccgcct cagtcgctct acggtctcag cttgtcgctc cgcaagtccc gtgcgccgcc   1260

cggactcgag cagaacagag tcccatattc ccagcgcaag ctcaagttct ccaatagatt   1320

cttacccatc actgctcctt tccactcgcc gtacgttcat gaggcatacg aaactatcgt   1380

cgatgatctc aaatctgcca atgtttcgtt tgcgccggag gagctcggca tcccagtcta   1440

cgatacatac gatggacatg acttacgcaa gcttacggac gaggacggct ccgttgtcga   1500
```

```
gcgtctcgtc aagatggtta ccagcctgcc tgtcaactgg gagcaagcca cagccttcgg   1560
caaggtcacg cacattctcg actttgggcc tggcggtgtg tctggcctag gtgtcttgac   1620
acatcgcaat aaggagggaa ctggtgtccg tgtcatcttg gccggcactt tggagggtac   1680
tctatcggag cttggttaca agtccgaatt gtttgatcgc gaggacgacg ctgtcaaatt   1740
tgccgctgac tggggtcttg agttcgcacc caaacttgtc aagactgcgc aagggcagac   1800
ctatgttgac acgaagtttt cgcgtttact tggacagccg cccatcatgg ttgctggtat   1860
gactccgtca accgttccgc ctgatttcgt tgctgccact atgaacgccg gataccacat   1920
cgaacttggc ggtggtggct actttaacgc cagtggtctc acccaagcgt tctacaagat   1980
cgaaaaatct actttccctg gcgccggtat tacagtcaat ttgatctatg tcaacccccg   2040
ggccatggga tgggcaatcc ctctcattca gaagctccgc gctgaaggcg ttccgatcga   2100
aggtctcacc atcggcgcag gtgttccatc gaccgaagtc gcgaacgagt acatcgaaac   2160
tctcggcatc aagcacctgg gtctcaaacc tgggtctata gacgcgatcc agcaggtcat   2220
taccatcgcg caggccaacc caacattccc gatcgtcttg cagtggacag gtggtcgtgg   2280
tggcggtcat cattcgttcg aggacttcca cagcccgatc ttgcagatgt acccgcgcat   2340
ccgtcggtgc agcaacatca tcctcctcgc gggctcaggt ttcggtggtg ccgaagacac   2400
gtacccgtac ttgactggtc agtgggcgac caggttcgcg tacccgccaa tgccatttga   2460
cggtgtctta tttggcagca gaatcatgac tgcgaaggaa gcgcacacgt cactaggggc   2520
aaagcaagct attgttgatg cgcctggtgt ggatgagttg cagtgggaga aaacgtataa   2580
tggtgctgct ggtggcgtca ttacagtctt gtccgagatg ggcgagccca ttcacaagtt   2640
ggctacgcga ggtgttgtgt tttggtaagt tccacagttt atatacctcc ctgggaaaaa   2700
tagctctgac gtacttgtgc aggaaggaga tggataccac gattttcagt ctgcccaaga   2760
acaagcgcgt cgatgccctc aaggccaaga aggactacat catcaagaag ctcaatgccg   2820
acttccaaaa ggtttggttc ggtaagaact ctgccggtga ggtagtcgaa ctcgaggaca   2880
tgacctacgg tgagattctc aagcgccttg ttgaactcat gtttgttgcc cacgagaagc   2940
gctggatcga cctttcgctg cgcaacatga ccggtgacta tatccgccgt attgaggagc   3000
gcttcacgca tgagacaggt cgcccatcgc tcctgcagtc gtacaccgag ctggatgagc   3060
cgacgccgac ggttgacaga atcctggcgg cgtatcccga ggccactgag cagattatca   3120
acgtgcaaga caaggagttt ttccttatgc tgaccctccg acctggtcag aagccggttc   3180
cgtttgttcc ggcgttggat gataattttg agttgtactt caagaaggac tcgctctggc   3240
agtctgagga ccttgctgcc gtcgtcggtc aggatgtgca gcgcacatgt gttctgcaag   3300
gtcctgtcgc tgtcaagtac gccaagatcg tcaacgaacc cgtgaaggac attttggatg   3360
gcattcacga caaacatatc gagttcttga ccaaggacat ttatggaggc gaggagtcga   3420
agattccggt tatcgaatac tttggaggca aagatattgt tccatctgtc tttgagaccg   3480
cattgaaggt agacagtttg actgttaccg aggccgacga ctccatcacc tatgtgctcg   3540
atgccggtgt cagcggcaac gctactcttc ccgacgttga gtcgtggttg agtttgcttg   3600
gtggtgaatg ttatggctgg cgccacgcat tcttcaccac cgatgttttt gttcagggca   3660
cgaagtatga gacgagcccg cttaagcggt tgttcaagcc ggcttttggg gtcaaggtca   3720
ccattcagca tccggaagat ttggaaaaga ctcgcattat cgtttccgag aaaatcaacg   3780
gcaaggatgt cgtcgttatt gacaccttca agcgtccgga ttctaatacc atcgaaatga   3840
cgatttatga tgatcgtact gcagagggca agtctgttgg catgctgctg ttgttcacat   3900
```

```
atcaccctga agtcggattt gcgccaatcc gcgaggtcat ggccggccgc aacgacagaa   3960
tcaaggagtt ttactggaag ctgtggttcg gttctgagga gtacccggcc aacttatccg   4020
tcaccgacgc attcgaaggt ggctcgacca ccgtcactgg caaggcaatt gctgactttg   4080
tatatgctgt cgggaacaac ggtgaggcat ttgtcgaccg gcctggtaag actacattcg   4140
cacctatgga ttttgctatt gtagtagggt ggaaggctat tactaaggcg ctcttcccca   4200
aggccatcga cggtgacttg ttgaagctgg tccatctttc gaactcgttc aaaatgtacc   4260
ctggtgcaga gccgctcaag aaggacgacg tcgttaccac cactgccaag atcaatgctg   4320
tgttgaacca ggattccggt aagatggttg aagtcagcgg cgttatctcc cgtgattaca   4380
tgccagtcat ggaggtcacc tcccagttct tttacagagg cgcgtacacc gactacgaga   4440
acacgttcca gcgcaagtcg gagttgccga tggaggtcac gctcaagtct cccaaggatg   4500
ttgcggtttt gcgatcgaag gactggttcg agctcaatga cgatcctcac gttgacctac   4560
tcaaccagac tctcacattc cggctcgaaa ccttcgtcag atacaaaaac aagactgtct   4620
tttcgtctgt ccgcaccact ggtcaggttt tgcttgaatt gcctacgcgt gagattatcc   4680
agatcggcac cgttgagtac gaggccagtg aatcccatgg aaacccggtc atcgactatc   4740
ttgagcgcca cggcagcacg attgaacagc cgattatgtt cgaaaactcg atcccattga   4800
acgcctcgac ggagcttgtc taccgcgcgc ctgcttccaa cgaaggctac gctcgtgtgt   4860
ctggtgacta caacccgatc catgtgtccc gtgtgttcgc agagtatgcc aacctccgag   4920
gcaacatcac tcacggcatg tactcctccg ctgccgtccg gtcgctcgtc gagacctggg   4980
cagcggagaa ccacgtcgca cgcgtgcgtg ggtttaattg ctctttcgtc ggtatggtcc   5040
tgcctaacga gaatatcgag acgaaattgc accatgtcgg tatgattgcg ggccggaaga   5100
ttatcaaggt tgagaccacg aacaaggact caggtgatgt cgtcttgatc ggccaggcag   5160
aggtcgagca gcccgtgtcg acgtatatct tcactggcca gggttcgcag gagcagggta   5220
tgggaatgga tctatacgag tctagcgctg tagcgcgtga ggtttgggac cgcgctgata   5280
gacatttcct caataactat ggtatgtttt aatccgaagt agctcgaagg tgaattgaac   5340
taatgtcgtg aacaggcttt tcaattatca atattgttaa gaacaatcct aaagagttta   5400
ctgttcactt tggtggtcca cgaggtgcgt attctctcct ttgataaaat taatgatatc   5460
tgacatttcg caggcaaggc aattaggcac aactacacat cgatgatgtt cgagtctgtt   5520
gatgcggacg gtcagctcaa gtccgagaag atcttcaagg acatcacgga gaacacatct   5580
tcttacacct tccgttcgcc tactggcttg ttgtcagcca ctcagttcac gcagccggct   5640
ttgacgctta tggagaaggc ttcgttcgag gacatgaacg ccaagggtct tgtcccggct   5700
gactgctcgt acgcaggcca ctcgttgggc gaatactctg cgctcgcggc actcggcgac   5760
gtcatgccga tcgagtctct tgtcgatgtc gtgttctacc gtggtatgac catgcaagtc   5820
gcagtcccgc gtgacgcgct aggacgatcg aattatggta tgtgtgctgt caacccgtct   5880
cgtatctcgc cgaccttcaa cgatgccgca ctccgctatg tcgtcgaaca catatcctct   5940
cagaccaagt ggctcttgga gattgtcaat tacaatgttg agaacacgca atacgtcacc   6000
gccggagatc tccgtggact tgactgtctt accaacgtgc tcaatttcat gaaggtacag   6060
aagatcgacc tcgacaagct catgaagacc atgtcgatgg aagacgttaa ggagcagctc   6120
accgacattg tcgaagaaat agcgaagaag agcatcgcaa agccgcagcc gatcgagctc   6180
gaccgtggtt tcgccactat ccctctcaaa ggtatttcgg tgccgttcca ctccagttat   6240
```

```
ctgcgcagcg gtgtcaagcc gtttaaccgg ttcttgatca agaagttgcc acagcaggcg   6300

ctcaagccgg ccaatttaat tggaaagtat attcccaatt tgactgccaa gccattctcg   6360

atctcgaagg agtatttcca ggaagtgtat gacttgaccg gtagcgccaa gatcaggagc   6420

attttggaca actgggagaa gtatgagact gcttag                             6456


<210> SEQ ID NO 20
<211> LENGTH: 2082
<212> TYPE: PRT
<213> ORGANISM: Lipomyces starkeyi

<400> SEQUENCE: 20

Met Tyr Ala Gly Ala Glu Thr Gly Val Ala Thr Pro His Thr Gln Ala
1               5                   10                  15

Ser Leu Arg Pro Leu Ser Leu Gln His Gly Ser Leu Glu His Thr Val
            20                  25                  30

Phe Val Pro Thr Ala Leu Tyr Leu Ser Ile Leu His Leu Arg Asp Glu
        35                  40                  45

Phe Ala Ala Thr Leu Pro Thr Pro Thr Glu Asp Phe Ala Gly Asp Glu
    50                  55                  60

Glu Pro Ala Ser Asn Cys Glu Leu Val Ala Arg Phe Leu Ala Phe Leu
65                  70                  75                  80

Val Ala Gln Val Glu Glu Glu Pro Asp Gln Tyr Asp Asp Val Leu Ala
                85                  90                  95

Leu Val Leu Ala Asp Phe Glu Ser Arg Phe Leu Arg Ala Asn Glu Val
            100                 105                 110

His Ala Val Ala Ala Ala Leu Pro Gly Asp Leu Ala Lys Arg Glu Val
        115                 120                 125

Val Ile Ser Ala Tyr Tyr Ala Ala Arg Leu Ala Ala Asn Arg Pro Ile
    130                 135                 140

Lys Gly His Asp Ser Ala Leu Leu Arg Ala Ser Ala Asp Gly Arg Ala
145                 150                 155                 160

Ser Ile Phe Ala Ile Phe Gly Gly Gln Gly Asn Ile Glu Glu Tyr Phe
                165                 170                 175

Asp Glu Leu Arg Asn Val Tyr Ser Leu Tyr His Gly Leu Ile Asp Asp
            180                 185                 190

Phe Val Gln His Cys Ala Arg Asp Leu Leu Lys Leu Ala Ser Asp Asp
        195                 200                 205

Arg Thr Met Lys Val Tyr Ser Asn Gly Leu Asp Ile Met Arg Trp Leu
    210                 215                 220

Arg Glu Pro Glu Ser Thr Pro Asp Leu Asp Tyr Leu Val Ser Ala Pro
225                 230                 235                 240

Val Ser Leu Pro Leu Ile Gly Val Thr Gln Leu Thr His Tyr Ala Ala
                245                 250                 255

Thr Cys Lys Ile Leu Gly Lys Glu Pro Gly Glu Phe Arg Ser His Leu
            260                 265                 270

Ser Gly Thr Thr Gly His Ser Gln Gly Val Val Thr Ala Ala Ala Ile
        275                 280                 285

Ser Ala Ser Thr Thr Trp Glu Ser Phe Phe Asp Val Ala Ser Lys Thr
    290                 295                 300

Leu Gln Ile Leu Phe Trp Ile Gly Cys Arg Ala Gln Gln Thr Tyr Pro
305                 310                 315                 320

Arg Thr Ser Leu Ala Pro Ser Val Leu Gln Asp Ser Val Asn Glu Gly
                325                 330                 335
```

```
Glu Gly Lys Pro Ser Pro Met Leu Ser Val Arg Asp Leu Val Lys Ser
            340                 345                 350

Gln Val Gln Lys His Val Asp Leu Thr Asn Ser His Leu Pro Pro Glu
        355                 360                 365

Lys His Val Ser Ile Ser Leu Glu Asn Gly Ala Arg Asn Phe Val Val
    370                 375                 380

Thr Gly Pro Pro Gln Ser Leu Tyr Gly Leu Ser Leu Ser Leu Arg Lys
385                 390                 395                 400

Ser Arg Ala Pro Pro Gly Leu Glu Gln Asn Arg Val Pro Tyr Ser Gln
                405                 410                 415

Arg Lys Leu Lys Phe Ser Asn Arg Phe Leu Pro Ile Thr Ala Pro Phe
            420                 425                 430

His Ser Pro Tyr Val His Glu Ala Tyr Glu Thr Ile Val Asp Asp Leu
        435                 440                 445

Lys Ser Ala Asn Val Ser Phe Ala Pro Glu Glu Leu Gly Ile Pro Val
    450                 455                 460

Tyr Asp Thr Tyr Asp Gly His Asp Leu Arg Lys Leu Thr Asp Glu Asp
465                 470                 475                 480

Gly Ser Val Val Glu Arg Leu Val Lys Met Val Thr Ser Leu Pro Val
                485                 490                 495

Asn Trp Glu Gln Ala Thr Ala Phe Gly Lys Val Thr His Ile Leu Asp
            500                 505                 510

Phe Gly Pro Gly Gly Val Ser Gly Leu Gly Val Leu Thr His Arg Asn
        515                 520                 525

Lys Glu Gly Thr Gly Val Arg Val Ile Leu Ala Gly Thr Leu Glu Gly
    530                 535                 540

Thr Leu Ser Glu Leu Gly Tyr Lys Ser Glu Leu Phe Asp Arg Glu Asp
545                 550                 555                 560

Asp Ala Val Lys Phe Ala Ala Asp Trp Gly Leu Glu Phe Ala Pro Lys
                565                 570                 575

Leu Val Lys Thr Ala Gln Gly Gln Thr Tyr Val Asp Thr Lys Phe Ser
            580                 585                 590

Arg Leu Leu Gly Gln Pro Pro Ile Met Val Ala Gly Met Thr Pro Ser
        595                 600                 605

Thr Val Pro Pro Asp Phe Val Ala Ala Thr Met Asn Ala Gly Tyr His
    610                 615                 620

Ile Glu Leu Gly Gly Gly Gly Tyr Phe Asn Ala Ser Gly Leu Thr Gln
625                 630                 635                 640

Ala Phe Tyr Lys Ile Glu Lys Ser Thr Phe Pro Gly Ala Gly Ile Thr
                645                 650                 655

Val Asn Leu Ile Tyr Val Asn Pro Arg Ala Met Gly Trp Ala Ile Pro
            660                 665                 670

Leu Ile Gln Lys Leu Arg Ala Glu Gly Val Pro Ile Glu Gly Leu Thr
        675                 680                 685

Ile Gly Ala Gly Val Pro Ser Thr Glu Val Ala Asn Glu Tyr Ile Glu
    690                 695                 700

Thr Leu Gly Ile Lys His Leu Gly Leu Lys Pro Gly Ser Ile Asp Ala
705                 710                 715                 720

Ile Gln Gln Val Ile Thr Ile Ala Gln Ala Asn Pro Thr Phe Pro Ile
                725                 730                 735

Val Leu Gln Trp Thr Gly Gly Arg Gly Gly Gly His His Ser Phe Glu
            740                 745                 750

Asp Phe His Ser Pro Ile Leu Gln Met Tyr Pro Arg Ile Arg Arg Cys
```

-continued

```
        755                 760                 765

Ser Asn Ile Ile Leu Leu Ala Gly Ser Gly Phe Gly Gly Ala Glu Asp
    770                 775                 780

Thr Tyr Pro Tyr Leu Thr Gly Gln Trp Ala Thr Arg Phe Ala Tyr Pro
785                 790                 795                 800

Pro Met Pro Phe Asp Gly Val Leu Phe Gly Ser Arg Ile Met Thr Ala
                805                 810                 815

Lys Glu Ala His Thr Ser Leu Gly Ala Lys Gln Ala Ile Val Asp Ala
            820                 825                 830

Pro Gly Val Asp Glu Leu Gln Trp Glu Lys Thr Tyr Asn Gly Ala Ala
        835                 840                 845

Gly Gly Val Ile Thr Val Leu Ser Glu Met Gly Glu Pro Ile His Lys
    850                 855                 860

Leu Ala Thr Arg Gly Val Val Phe Trp Lys Glu Met Asp Thr Thr Ile
865                 870                 875                 880

Phe Ser Leu Pro Lys Asn Lys Arg Val Asp Ala Leu Lys Ala Lys Lys
                885                 890                 895

Asp Tyr Ile Ile Lys Lys Leu Asn Ala Asp Phe Gln Lys Val Trp Phe
            900                 905                 910

Gly Lys Asn Ser Ala Gly Glu Val Val Glu Leu Glu Asp Met Thr Tyr
        915                 920                 925

Gly Glu Ile Leu Lys Arg Leu Val Glu Leu Met Phe Val Ala His Glu
    930                 935                 940

Lys Arg Trp Ile Asp Leu Ser Leu Arg Asn Met Thr Gly Asp Tyr Ile
945                 950                 955                 960

Arg Arg Ile Glu Glu Arg Phe Thr His Glu Thr Gly Arg Pro Ser Leu
                965                 970                 975

Leu Gln Ser Tyr Thr Glu Leu Asp Glu Pro Thr Pro Thr Val Asp Arg
            980                 985                 990

Ile Leu Ala Ala Tyr Pro Glu Ala  Thr Glu Gln Ile Ile  Asn Val Gln
        995                 1000                1005

Asp Lys  Glu Phe Phe Leu Met  Leu Thr Leu Arg Pro  Gly Gln Lys
    1010                1015                1020

Pro Val  Pro Phe Val Pro Ala  Leu Asp Asp Asn Phe  Glu Leu Tyr
    1025                1030                1035

Phe Lys  Lys Asp Ser Leu Trp  Gln Ser Glu Asp Leu  Ala Ala Val
    1040                1045                1050

Val Gly  Gln Asp Val Gln Arg  Thr Cys Val Leu Gln  Gly Pro Val
    1055                1060                1065

Ala Val  Lys Tyr Ala Lys Ile  Val Asn Glu Pro Val  Lys Asp Ile
    1070                1075                1080

Leu Asp  Gly Ile His Asp Lys  His Ile Glu Phe Leu  Thr Lys Asp
    1085                1090                1095

Ile Tyr  Gly Gly Glu Glu Ser  Lys Ile Pro Val Ile  Glu Tyr Phe
    1100                1105                1110

Gly Gly  Lys Asp Ile Val Pro  Ser Val Phe Glu Thr  Ala Leu Lys
    1115                1120                1125

Val Asp  Ser Leu Thr Val Thr  Glu Ala Asp Asp Ser  Ile Thr Tyr
    1130                1135                1140

Val Leu  Asp Ala Gly Val Ser  Gly Asn Ala Thr Leu  Pro Asp Val
    1145                1150                1155

Glu Ser  Trp Leu Ser Leu Leu  Gly Gly Glu Cys Tyr  Gly Trp Arg
    1160                1165                1170
```

```
His Ala  Phe Phe Thr Thr Asp  Val Phe Val Gln Gly  Thr Lys Tyr
    1175                 1180                 1185

Glu Thr  Ser Pro Leu Lys Arg  Leu Phe Lys Pro Ala  Phe Gly Val
    1190                 1195                 1200

Lys Val  Thr Ile Gln His Pro  Glu Asp Leu Glu Lys  Thr Arg Ile
    1205                 1210                 1215

Ile Val  Ser Glu Lys Ile Asn  Gly Lys Asp Val Val  Val Ile Asp
    1220                 1225                 1230

Thr Phe  Lys Arg Pro Asp Ser  Asn Thr Ile Glu Met  Thr Ile Tyr
    1235                 1240                 1245

Asp Asp  Arg Thr Ala Glu Gly  Lys Ser Val Gly Met  Leu Leu Leu
    1250                 1255                 1260

Phe Thr  Tyr His Pro Glu Val  Gly Phe Ala Pro Ile  Arg Glu Val
    1265                 1270                 1275

Met Ala  Gly Arg Asn Asp Arg  Ile Lys Glu Phe Tyr  Trp Lys Leu
    1280                 1285                 1290

Trp Phe  Gly Ser Glu Glu Tyr  Pro Ala Asn Leu Ser  Val Thr Asp
    1295                 1300                 1305

Ala Phe  Glu Gly Gly Ser Thr  Thr Val Thr Gly Lys  Ala Ile Ala
    1310                 1315                 1320

Asp Phe  Val Tyr Ala Val Gly  Asn Asn Gly Glu Ala  Phe Val Asp
    1325                 1330                 1335

Arg Pro  Gly Lys Thr Thr Phe  Ala Pro Met Asp Phe  Ala Ile Val
    1340                 1345                 1350

Val Gly  Trp Lys Ala Ile Thr  Lys Ala Leu Phe Pro  Lys Ala Ile
    1355                 1360                 1365

Asp Gly  Asp Leu Leu Lys Leu  Val His Leu Ser Asn  Ser Phe Lys
    1370                 1375                 1380

Met Tyr  Pro Gly Ala Glu Pro  Leu Lys Lys Asp Asp  Val Val Thr
    1385                 1390                 1395

Thr Thr  Ala Lys Ile Asn Ala  Val Leu Asn Gln Asp  Ser Gly Lys
    1400                 1405                 1410

Met Val  Glu Val Ser Gly Val  Ile Ser Arg Asp Tyr  Met Pro Val
    1415                 1420                 1425

Met Glu  Val Thr Ser Gln Phe  Phe Tyr Arg Gly Ala  Tyr Thr Asp
    1430                 1435                 1440

Tyr Glu  Asn Thr Phe Gln Arg  Lys Ser Glu Leu Pro  Met Glu Val
    1445                 1450                 1455

Thr Leu  Lys Ser Pro Lys Asp  Val Ala Val Leu Arg  Ser Lys Asp
    1460                 1465                 1470

Trp Phe  Glu Leu Asn Asp Asp  Pro His Val Asp Leu  Leu Asn Gln
    1475                 1480                 1485

Thr Leu  Thr Phe Arg Leu Glu  Thr Phe Val Arg Tyr  Lys Asn Lys
    1490                 1495                 1500

Thr Val  Phe Ser Ser Val Arg  Thr Thr Gly Gln Val  Leu Leu Glu
    1505                 1510                 1515

Leu Pro  Thr Arg Glu Ile Ile  Gln Ile Gly Thr Val  Glu Tyr Glu
    1520                 1525                 1530

Ala Ser  Glu Ser His Gly Asn  Pro Val Ile Asp Tyr  Leu Glu Arg
    1535                 1540                 1545

His Gly  Ser Thr Ile Glu Gln  Pro Ile Met Phe Glu  Asn Ser Ile
    1550                 1555                 1560
```

```
Pro Leu Asn Ala Ser Thr Glu Leu Val Tyr Arg Ala Pro Ala Ser
    1565                1570                1575

Asn Glu Gly Tyr Ala Arg Val Ser Gly Asp Tyr Asn Pro Ile His
    1580                1585                1590

Val Ser Arg Val Phe Ala Glu Tyr Ala Asn Leu Arg Gly Asn Ile
    1595                1600                1605

Thr His Gly Met Tyr Ser Ser Ala Ala Val Arg Ser Leu Val Glu
    1610                1615                1620

Thr Trp Ala Ala Glu Asn His Val Ala Arg Val Arg Gly Phe Asn
    1625                1630                1635

Cys Ser Phe Val Gly Met Val Leu Pro Asn Glu Asn Ile Glu Thr
    1640                1645                1650

Lys Leu His His Val Gly Met Ile Ala Gly Arg Lys Ile Ile Lys
    1655                1660                1665

Val Glu Thr Thr Asn Lys Asp Ser Gly Asp Val Val Leu Ile Gly
    1670                1675                1680

Gln Ala Glu Val Glu Gln Pro Val Ser Thr Tyr Ile Phe Thr Gly
    1685                1690                1695

Gln Gly Ser Gln Glu Gln Gly Met Gly Met Asp Leu Tyr Glu Ser
    1700                1705                1710

Ser Ala Val Ala Arg Glu Val Trp Asp Arg Ala Asp Arg His Phe
    1715                1720                1725

Leu Asn Asn Tyr Gly Phe Ser Ile Ile Asn Ile Val Lys Asn Asn
    1730                1735                1740

Pro Lys Glu Phe Thr Val His Phe Gly Gly Pro Arg Gly Lys Ala
    1745                1750                1755

Ile Arg His Asn Tyr Thr Ser Met Met Phe Glu Ser Val Asp Ala
    1760                1765                1770

Asp Gly Gln Leu Lys Ser Glu Lys Ile Phe Lys Asp Ile Thr Glu
    1775                1780                1785

Asn Thr Ser Ser Tyr Thr Phe Arg Ser Pro Thr Gly Leu Leu Ser
    1790                1795                1800

Ala Thr Gln Phe Thr Gln Pro Ala Leu Thr Leu Met Glu Lys Ala
    1805                1810                1815

Ser Phe Glu Asp Met Asn Ala Lys Gly Leu Val Pro Ala Asp Cys
    1820                1825                1830

Ser Tyr Ala Gly His Ser Leu Gly Glu Tyr Ser Ala Leu Ala Ala
    1835                1840                1845

Leu Gly Asp Val Met Pro Ile Glu Ser Leu Val Asp Val Val Phe
    1850                1855                1860

Tyr Arg Gly Met Thr Met Gln Val Ala Val Pro Arg Asp Ala Leu
    1865                1870                1875

Gly Arg Ser Asn Tyr Gly Met Cys Ala Val Asn Pro Ser Arg Ile
    1880                1885                1890

Ser Pro Thr Phe Asn Asp Ala Ala Leu Arg Tyr Val Val Glu His
    1895                1900                1905

Ile Ser Ser Gln Thr Lys Trp Leu Leu Glu Ile Val Asn Tyr Asn
    1910                1915                1920

Val Glu Asn Thr Gln Tyr Val Thr Ala Gly Asp Leu Arg Gly Leu
    1925                1930                1935

Asp Cys Leu Thr Asn Val Leu Asn Phe Met Lys Val Gln Lys Ile
    1940                1945                1950

Asp Leu Asp Lys Leu Met Lys Thr Met Ser Met Glu Asp Val Lys
```

```
    1955                1960                1965

Glu Gln  Leu Thr Asp Ile Val  Glu Glu Ile Ala Lys  Lys Ser Ile
    1970                1975                1980

Ala Lys  Pro Gln Pro Ile Glu  Leu Asp Arg Gly Phe  Ala Thr Ile
    1985                1990                1995

Pro Leu  Lys Gly Ile Ser Val  Pro Phe His Ser Ser  Tyr Leu Arg
    2000                2005                2010

Ser Gly  Val Lys Pro Phe Asn  Arg Phe Leu Ile Lys  Lys Leu Pro
    2015                2020                2025

Gln Gln  Ala Leu Lys Pro Ala  Asn Leu Ile Gly Lys  Tyr Ile Pro
    2030                2035                2040

Asn Leu  Thr Ala Lys Pro Phe  Ser Ile Ser Lys Glu  Tyr Phe Gln
    2045                2050                2055

Glu Val  Tyr Asp Leu Thr Gly  Ser Ala Lys Ile Arg  Ser Ile Leu
    2060                2065                2070

Asp Asn  Trp Glu Lys Tyr Glu  Thr Ala
    2075                2080


<210> SEQ ID NO 21
<211> LENGTH: 5159
<212> TYPE: DNA
<213> ORGANISM: Lipomyces starkeyi
<220> FEATURE:
<221> NAME/KEY: Intron
<222> LOCATION: (63)..(216)
<220> FEATURE:
<221> NAME/KEY: Intron
<222> LOCATION: (244)..(365)
<220> FEATURE:
<221> NAME/KEY: Intron
<222> LOCATION: (827)..(882)

<400> SEQUENCE: 21

atgacttcgg tttcagacga agagagagcg cgcactcaca cattggtatt ggagctcttg     60

gcgtaagtct tctacccttg gtccaagttt tcccaatttg gcagttagcc ctaaatgctg    120

ggctgggcga tctcgacacg agaagctgta atatcgacta cagcaaggat agaaaacata    180

taggagcaag agctaatagt tattctttcc tgacagtcat cagttcgcat atcctgtaca    240

atggtaagct tcccattctt tcccaccact tcaaagacgc tgtcatgtca tgtgctcgat    300

catgttgacc tcgtacattg attttgttca cccaaaggca atatgctgac aggtggatgg    360

tgaaggattg atacacaaga tgccctcttg ggggaagaaa agatcgagcg attcgtcgag    420

attgggccat cgaacacact cactggactg gctaaacaaa ctatccaaac gaaatatcaa    480

gaccatgaca ctgccctgtc aatccaaagg cagcttttaa gcatcaaaca gactgagagt    540

gacatctact atgcaactgg agaggccgtg gaggtgccaa aacaagcacc tgctaaaacc    600

gacgcaaaac ctactgctcc agctccgtcg ccagagcctg ctgcaaccgc gcccgcgcca    660

tctgctccct cgcccgcacc gagtggagct ggtgccagat cgattgcaac agctgaggat    720

gtcccagtga agtcagaaga tatagttctt actattattg ctcaaaagtt gaagaagtcc    780

accaaggata tttcgctcag cagtaatatc aaagcgctcg ttggaggtat gaaatccatc    840

gaatgaaact tcagtgacat aaaactgatt tgaatatttt aggtcgctca actttggaga    900

atgagattgt cggagacctc cttagtgaat tcggcaacct acctgaaaga tccgaggaac    960

tcagtttgac cgagctggga gaaaccctta acagcgcaaa tgctcaaaga cgactcggca   1020

agcagacaaa taccctagta caacgtctta ttgctgcgtc aatgccggga gattttagca   1080
```

```
tgacaagggt cagaaaatat cttgaggatc gttggggctt tcaagctggc cgccaagatt   1140
ccgtgcttct atctgcaatt ccctcgcctc ctaaaaaccg acttggggat ccaaaggaag   1200
tcaatgctta tctggattca ttggttaagg agtatgcgca agccgctgga ttggcactgg   1260
aagaagcacc acagcagcag cagcagtctg ccgtccaagt caatccggaa gccataaatg   1320
ctgttgttcg gagacaagag caactggcag aacagcagct caaagtctac gctcaatttc   1380
tggatgttga tctccatgct gatggcaagt ctgcagagca atcggaaagc gccatgtcgg   1440
ctcttcagaa acagttagat ttgtgggtag ctgaacatgg tgaggcgtat gctagtggta   1500
tcactccagt ctttgatgcc aagaagcttc gagagtactc ctcttactgg acttgggcct   1560
tgcaagacct cacagctact ttctacgata tcagtcgcgg aacattaaaa gtcgaccctg   1620
aggtgattga tgatatttct taccggctgg ccaacaaatc aagcccaccg ttagtggact   1680
caatcagata cctgttgacg caatgtcatg atgaaaaatc aaaggccttc taccaactcc   1740
ttctcaatac tgttgcgcag tcaattggat ctattcccgt tttcaagacc tccacgaatt   1800
tccttggccc tcgaacaact atcgacgagc tgggcaatat cacatactct gaacacccga   1860
ggtctgaaga cggatcaaag gagcatttgg gtgaaccgac tcgtcttcca catattaaac   1920
gcaagaatga caaagaatgg acattcgatt cggcaacgac cgcattgtac aacaaagcta   1980
tcgatcaaat ctcaagcaca ggtctctcac tcgccaataa aacgattctc ctaactggag   2040
ccggaacgaa ctccatcggt gaagagcttc tgaaaggcct tctcgctggt ggtgcacaag   2100
tcattgttac gaccaatagc ttttcatcca agacagctct caagtatcag aagatctacc   2160
agggtcacgg ctctaaaggg tccaaactgg ttttggttcc atttaaccaa ggtagccagc   2220
aggatgtcga atctctggtt gattatatct acaaccagaa acaaggcctc ggttgggatc   2280
ttgatgttgt catcccattc gccgcaattt ctgttacagg gcgacaaata gacgagattg   2340
actccaagag tgagatagca cagcgtatca tgctgacaaa tactattcga cttctcggag   2400
ctatcaagag acataaggag gctgcaggct accgaacccg gcccacccat gctatacttc   2460
ccctgtcacc caaccatggt gtctttggtg gtgatggtct atactctgag tcgaagatgg   2520
cactcgaaag tctgttcgca aaatggcatt ctgaaggttg gagcgattat ctctccatct   2580
gtggtacttc aatcggttgg actcgcggca ccggtctgat gcatcagaac gatacagtgg   2640
ccgagggcgt cgaaaaactt ggcgtgagaa cattctcccg accagaaatg gctctctgca   2700
ttctcgcctt attgagtcgt cctttggtcg agttttctca agaagaaccc ctgtacgccg   2760
acttcagcgg tggtatggat aaagtaccag atttcccgag tgagttgaac gcgatccagg   2820
ataacatcaa aagcctgagc gagatccgaa gagctgttgc agcggaatta gcgcttgaca   2880
acggatctga tcttaaagcg acaaagtcag ccaaaaatga acaggatgcc ataaaaaaac   2940
gtgcgaagat cgagcttgga tttccgacct tgccaaacta tgaaacagag attcagccgc   3000
tccgctccca attggattcc atggtctcgc ttgaacacac tgttgtgatt gtaggctttt   3060
cggagctagg accttgcgga aattctcgta ctcgctggga aatggaagcc tatgatgaac   3120
tctcgctcga aggatgcacc gaaatggctt ggatcatggg cctcataaaa tattccaagg   3180
cctctggtaa taaaccagcc ggatggatcg atgtcaagac aaaagagccc gttgaggaat   3240
ttgacgtgaa aaagcgttac gagtcatata ttcgcgagca tacgggcatt cgactaattg   3300
agccgactct tttcgacaag tacaatcctg aaaagaagca aatgactcaa gagattgtcg   3360
tccaagaaga tcttgcacca ttcgaaacat ctaaggatgc tgcactcagc tttaagagag   3420
aacacggaga caaggtggaa atattcccag gcgtggagtc tgactcttac agtgtcgtca   3480
```

```
tgaaaaaggg ggcagtgata catgttccca aggccgtgaa gttcagacaa actgtcgcgg   3540

cacagattcc tacaggatgg gatccacgga cgtatggcat ttcagacgat attatcaacc   3600

aggtcgatcc ggtcacctta tatacacttg taacaactgt cgaaggcctt ctttcagcgg   3660

gtatcacgga tccttacgag atctacaagt acatccatgt ctccgaactt ggcaattgct   3720

ttggaagcgg tttgggtggt acaaactcct cagaaaagat gtaccgggat cggttggcag   3780

acaagcctgt gcagaatgat atcttgcaag agacattttt gaacacagtt ggagcttggg   3840

tgaacatgct cttgctctca tcaagtggac caaacaagac atccgttgga gcctgcgcaa   3900

cttctgtgga atcacttgac acagcctacg atctcattct tgctggcaag gcaaagatgt   3960

gtttcgttgg tagcgttgac gagttctcag aatacacgtc tttggagttt tcgaacatga   4020

aagcaactat caatgccgag acggagcgtg aggctggtcg ggacccgaag gagatgtcac   4080

gtcctgcagc ctcttcaagg aaaggtttca tggaatccca cggcgctggt ctccatatag   4140

cttgcacggc aaagcttgcc attgagatgg gactgcctat atatggtgtc atcgccttca   4200

caggcatctc cagtgacaag gtcggccgct ctgttcccgc tccgggcaag ggagtcctgt   4260

caaatgcaag agaatcgaca gctgggttcc catcgccact tcttgatatc gaatatcgtc   4320

gacgacagat tgatatacga cgacagcaaa tcaccaactt cagagaggtg gagctcagta   4380

accttgagga cacgattctg catcttatgg ccaataataa tcatttcaat gcatctgaat   4440

atcgagcata tatggtcaag cagattgatc tcaaattcca gatgcaggaa caagatatgc   4500

ttgcctcctt tggaaatcac ttttggcgta accaccctga gatcgcaccc atcaagggag   4560

cgttggcaac ctggggtctt agtgtcgacg atgtgaccgt ggcttctttc cacggaacct   4620

caactgtcct gaacgagaag aacgagtgct ctattatcca aaaccagctt tctcatctcg   4680

gacgtaccaa aggaagtcgc actctcggtg tattccagaa gagcgtcacc gggcacccga   4740

aaggtcctgc aagttcctgg atgctcaatg gctgcctgca gatcatgagc acggggctcg   4800

tgccaggaaa ccgaaatcta gataatttgg atcccgggtt tgaacagtac gatcatatca   4860

cgttcctgaa ccagaatgtt caaacggctg gcatcaaggc cttctctttg acctcatttg   4920

gcttcggcca gaagggtggt caggtgattg gtgtgcaccc caaatatctg tttgcgacaa   4980

ttccgaagga tgtgttcgac gactacgcga agaggttgaa gaagaggcgg gcgattgcga   5040

ctgtcgcatt ccatgaggca ttgctcgaga ataacatgtt tgtggcgaag gacgacccgc   5100

cgtacgatgt tgtacaggag atgaagacgc tactggatcc aaatgctagg tgggagtag    5159
```

<210> SEQ ID NO 22
<211> LENGTH: 1608
<212> TYPE: PRT
<213> ORGANISM: Lipomyces starkeyi

<400> SEQUENCE: 22

```
Met Thr Ser Val Ser Asp Glu Glu Arg Ala Arg Thr His Thr Leu Val
1               5                   10                  15

Leu Glu Leu Leu Ala His Gln Phe Ala Tyr Pro Val Gln Trp Ile Asp
            20                  25                  30

Thr Gln Asp Ala Leu Leu Gly Glu Glu Lys Ile Glu Arg Phe Val Glu
        35                  40                  45

Ile Gly Pro Ser Asn Thr Leu Thr Gly Ser Ala Lys Gln Thr Ile Gln
    50                  55                  60

Thr Lys Tyr Gln Asp His Asp Thr Ala Ser Ser Ile Gln Arg Gln Leu
65                  70                  75                  80
```

```
Leu Ser Ile Lys Gln Thr Glu Ser Asp Ile Tyr Tyr Ala Thr Gly Glu
                85                  90                  95

Ala Val Glu Val Pro Lys Gln Ala Pro Ala Lys Thr Asp Ala Lys Pro
            100                 105                 110

Thr Ala Pro Ala Pro Ser Pro Glu Pro Ala Ala Thr Ala Pro Ala Pro
        115                 120                 125

Ser Ala Pro Ser Pro Ala Pro Ser Gly Ala Gly Ala Arg Ser Ile Ala
    130                 135                 140

Thr Ala Glu Asp Val Pro Val Lys Ser Glu Asp Ile Val Leu Thr Ile
145                 150                 155                 160

Ile Ala Gln Lys Leu Lys Lys Ser Thr Lys Asp Ile Ser Leu Ser Ser
                165                 170                 175

Asn Ile Lys Ala Leu Val Gly Gly Arg Ser Thr Leu Glu Asn Glu Ile
            180                 185                 190

Val Gly Asp Leu Leu Ser Glu Phe Gly Asn Leu Pro Glu Arg Ser Glu
        195                 200                 205

Glu Leu Ser Leu Thr Glu Ser Gly Glu Thr Leu Asn Ser Ala Asn Ala
    210                 215                 220

Gln Arg Arg Leu Gly Lys Gln Thr Asn Thr Leu Val Gln Arg Leu Ile
225                 230                 235                 240

Ala Ala Ser Met Pro Gly Asp Phe Ser Met Thr Arg Val Arg Lys Tyr
                245                 250                 255

Leu Glu Asp Arg Trp Gly Phe Gln Ala Gly Arg Gln Asp Ser Val Leu
            260                 265                 270

Leu Ser Ala Ile Pro Ser Pro Pro Lys Asn Arg Leu Gly Asp Pro Lys
        275                 280                 285

Glu Val Asn Ala Tyr Ser Asp Ser Leu Val Lys Glu Tyr Ala Gln Ala
    290                 295                 300

Ala Gly Leu Ala Ser Glu Glu Ala Pro Gln Gln Gln Gln Gln Ser Ala
305                 310                 315                 320

Val Gln Val Asn Pro Glu Ala Ile Asn Ala Val Val Arg Arg Gln Glu
                325                 330                 335

Gln Ser Ala Glu Gln Gln Leu Lys Val Tyr Ala Gln Phe Ser Asp Val
            340                 345                 350

Asp Leu His Ala Asp Gly Lys Ser Ala Glu Gln Ser Glu Ser Ala Met
        355                 360                 365

Ser Ala Leu Gln Lys Gln Leu Asp Leu Trp Val Ala Glu His Gly Glu
    370                 375                 380

Ala Tyr Ala Ser Gly Ile Thr Pro Val Phe Asp Ala Lys Lys Leu Arg
385                 390                 395                 400

Glu Tyr Ser Ser Tyr Trp Thr Trp Ala Leu Gln Asp Leu Thr Ala Thr
                405                 410                 415

Phe Tyr Asp Ile Ser Arg Gly Thr Leu Lys Val Asp Pro Glu Val Ile
            420                 425                 430

Asp Asp Ile Ser Tyr Arg Ser Ala Asn Lys Ser Ser Pro Pro Leu Val
        435                 440                 445

Asp Ser Ile Arg Tyr Ser Leu Thr Gln Cys His Asp Glu Lys Ser Lys
    450                 455                 460

Ala Phe Tyr Gln Leu Leu Leu Asn Thr Val Ala Gln Ser Ile Gly Ser
465                 470                 475                 480

Ile Pro Val Phe Lys Thr Ser Thr Asn Phe Leu Gly Pro Arg Thr Thr
                485                 490                 495
```

```
Ile Asp Glu Ser Gly Asn Ile Thr Tyr Ser Glu His Pro Arg Ser Glu
            500                 505                 510

Asp Gly Ser Lys Glu His Leu Gly Glu Pro Thr Arg Leu Pro His Ile
        515                 520                 525

Lys Arg Lys Asn Asp Lys Glu Trp Thr Phe Asp Ser Ala Thr Thr Ala
    530                 535                 540

Leu Tyr Asn Lys Ala Ile Asp Gln Ile Ser Ser Thr Gly Leu Ser Leu
545                 550                 555                 560

Ala Asn Lys Thr Ile Leu Leu Thr Gly Ala Gly Thr Asn Ser Ile Gly
                565                 570                 575

Glu Glu Leu Ser Lys Gly Leu Leu Ala Gly Gly Ala Gln Val Ile Val
            580                 585                 590

Thr Thr Asn Ser Phe Ser Ser Lys Thr Ala Leu Lys Tyr Gln Lys Ile
        595                 600                 605

Tyr Gln Gly His Gly Ser Lys Gly Ser Lys Ser Val Leu Val Pro Phe
    610                 615                 620

Asn Gln Gly Ser Gln Gln Asp Val Glu Ser Ser Val Asp Tyr Ile Tyr
625                 630                 635                 640

Asn Gln Lys Gln Gly Leu Gly Trp Asp Leu Asp Val Val Ile Pro Phe
                645                 650                 655

Ala Ala Ile Ser Val Thr Gly Arg Gln Ile Asp Glu Ile Asp Ser Lys
            660                 665                 670

Ser Glu Ile Ala Gln Arg Ile Met Ser Thr Asn Thr Ile Arg Leu Leu
        675                 680                 685

Gly Ala Ile Lys Arg His Lys Glu Ala Ala Gly Tyr Arg Thr Arg Pro
    690                 695                 700

Thr His Ala Ile Leu Pro Ser Ser Pro Asn His Gly Val Phe Gly Gly
705                 710                 715                 720

Asp Gly Leu Tyr Ser Glu Ser Lys Met Ala Leu Glu Ser Ser Phe Ala
                725                 730                 735

Lys Trp His Ser Glu Gly Trp Ser Asp Tyr Leu Ser Ile Cys Gly Thr
            740                 745                 750

Ser Ile Gly Trp Thr Arg Gly Thr Gly Ser Met His Gln Asn Asp Thr
        755                 760                 765

Val Ala Glu Gly Val Glu Lys Leu Gly Val Arg Thr Phe Ser Arg Pro
    770                 775                 780

Glu Met Ala Leu Cys Ile Leu Ala Leu Leu Ser Arg Pro Leu Val Glu
785                 790                 795                 800

Phe Ser Gln Glu Glu Pro Ser Tyr Ala Asp Phe Ser Gly Gly Met Asp
                805                 810                 815

Lys Val Pro Asp Phe Pro Ser Glu Leu Asn Ala Ile Gln Asp Asn Ile
            820                 825                 830

Lys Ser Ser Ser Glu Ile Arg Arg Ala Val Ala Ala Glu Leu Ala Leu
        835                 840                 845

Asp Asn Gly Ser Asp Leu Lys Ala Thr Lys Ser Ala Lys Asn Glu Gln
    850                 855                 860

Asp Ala Ile Lys Lys Arg Ala Lys Ile Glu Leu Gly Phe Pro Thr Leu
865                 870                 875                 880

Pro Asn Tyr Glu Thr Glu Ile Gln Pro Leu Arg Ser Gln Leu Asp Ser
                885                 890                 895

Met Val Ser Leu Glu His Thr Val Val Ile Val Gly Phe Ser Glu Leu
            900                 905                 910

Gly Pro Cys Gly Asn Ser Arg Thr Arg Trp Glu Met Glu Ala Tyr Asp
```

```
        915                 920                 925

Glu Leu Ser Leu Glu Gly Cys Thr Glu Met Ala Trp Ile Met Gly Leu
    930                 935                 940

Ile Lys Tyr Ser Lys Ala Ser Gly Asn Lys Pro Ala Gly Trp Ile Asp
945                 950                 955                 960

Val Lys Thr Lys Glu Pro Val Glu Glu Phe Asp Val Lys Lys Arg Tyr
                965                 970                 975

Glu Ser Tyr Ile Arg Glu His Thr Gly Ile Arg Leu Ile Glu Pro Thr
            980                 985                 990

Leu Phe Asp Lys Tyr Asn Pro Glu  Lys Lys Gln Met Thr  Gln Glu Ile
        995                 1000                1005

Val Val  Gln Glu Asp Leu Ala  Pro Phe Glu Thr Ser  Lys Asp Ala
    1010                1015                1020

Ala Leu  Ser Phe Lys Arg Glu  His Gly Asp Lys Val  Glu Ile Phe
    1025                1030                1035

Pro Gly  Val Glu Ser Asp Ser  Tyr Ser Val Val Met  Lys Lys Gly
    1040                1045                1050

Ala Val  Ile His Val Pro Lys  Ala Val Lys Phe Arg  Gln Thr Val
    1055                1060                1065

Ala Ala  Gln Ile Pro Thr Gly  Trp Asp Pro Arg Thr  Tyr Gly Ile
    1070                1075                1080

Ser Asp  Asp Ile Ile Asn Gln  Val Asp Pro Val Thr  Leu Tyr Thr
    1085                1090                1095

Leu Val  Thr Thr Val Glu Gly  Leu Leu Ser Ala Gly  Ile Thr Asp
    1100                1105                1110

Pro Tyr  Glu Ile Tyr Lys Tyr  Ile His Val Ser Glu  Leu Gly Asn
    1115                1120                1125

Cys Phe  Gly Ser Gly Leu Gly  Gly Thr Asn Ser Ser  Glu Lys Met
    1130                1135                1140

Tyr Arg  Asp Arg Leu Ala Asp  Lys Pro Val Gln Asn  Asp Ile Leu
    1145                1150                1155

Gln Glu  Thr Phe Leu Asn Thr  Val Gly Ala Trp Val  Asn Met Leu
    1160                1165                1170

Leu Leu  Ser Ser Ser Gly Pro  Asn Lys Thr Ser Val  Gly Ala Cys
    1175                1180                1185

Ala Thr  Ser Val Glu Ser Leu  Asp Thr Ala Tyr Asp  Leu Ile Leu
    1190                1195                1200

Ala Gly  Lys Ala Lys Met Cys  Phe Val Gly Ser Val  Asp Glu Phe
    1205                1210                1215

Ser Glu  Tyr Thr Ser Leu Glu  Phe Ser Asn Met Lys  Ala Thr Ile
    1220                1225                1230

Asn Ala  Glu Thr Glu Arg Glu  Ala Gly Arg Asp Pro  Lys Glu Met
    1235                1240                1245

Ser Arg  Pro Ala Ala Ser Ser  Arg Lys Gly Phe Met  Glu Ser His
    1250                1255                1260

Gly Ala  Gly Leu His Ile Ala  Cys Thr Ala Lys Leu  Ala Ile Glu
    1265                1270                1275

Met Gly  Ser Pro Ile Tyr Gly  Val Ile Ala Phe Thr  Gly Ile Ser
    1280                1285                1290

Ser Asp  Lys Val Gly Arg Ser  Val Pro Ala Pro Gly  Lys Gly Val
    1295                1300                1305

Ser Ser  Asn Ala Arg Glu Ser  Thr Ala Gly Phe Pro  Ser Pro Leu
    1310                1315                1320
```

```
Leu Asp  Ile Glu Tyr Arg Arg  Arg Gln Ile Asp Ile  Arg Arg Gln
    1325                 1330                 1335

Gln Ile  Thr Asn Phe Arg Glu  Val Glu Leu Ser Asn  Leu Glu Asp
    1340                 1345                 1350

Thr Ile  Ser His Leu Met Ala  Asn Asn Asn His Phe  Asn Ala Ser
    1355                 1360                 1365

Glu Tyr  Arg Ala Tyr Met Val  Lys Gln Ile Asp Leu  Lys Phe Gln
    1370                 1375                 1380

Met Gln  Glu Gln Asp Met Leu  Ala Ser Phe Gly Asn  His Phe Trp
    1385                 1390                 1395

Arg Asn  His Pro Glu Ile Ala  Pro Ile Lys Gly Ala  Leu Ala Thr
    1400                 1405                 1410

Trp Gly  Leu Ser Val Asp Asp  Val Thr Val Ala Ser  Phe His Gly
    1415                 1420                 1425

Thr Ser  Thr Val Ser Asn Glu  Lys Asn Glu Cys Ser  Ile Ile Gln
    1430                 1435                 1440

Asn Gln  Leu Ser His Leu Gly  Arg Thr Lys Gly Ser  Arg Thr Leu
    1445                 1450                 1455

Gly Val  Phe Gln Lys Ser Val  Thr Gly His Pro Lys  Gly Pro Ala
    1460                 1465                 1470

Ser Ser  Trp Met Leu Asn Gly  Cys Ser Gln Ile Met  Ser Thr Gly
    1475                 1480                 1485

Leu Val  Pro Gly Asn Arg Asn  Leu Asp Asn Leu Asp  Pro Gly Phe
    1490                 1495                 1500

Glu Gln  Tyr Asp His Ile Thr  Phe Ser Asn Gln Asn  Val Gln Thr
    1505                 1510                 1515

Ala Gly  Ile Lys Ala Phe Ser  Leu Thr Ser Phe Gly  Phe Gly Gln
    1520                 1525                 1530

Lys Gly  Gly Gln Val Ile Gly  Val His Pro Lys Tyr  Ser Phe Ala
    1535                 1540                 1545

Thr Ile  Pro Lys Asp Val Phe  Asp Asp Tyr Ala Lys  Arg Leu Lys
    1550                 1555                 1560

Lys Arg  Arg Ala Ile Ala Thr  Val Ala Phe His Glu  Ala Leu Leu
    1565                 1570                 1575

Glu Asn  Asn Met Phe Val Ala  Lys Asp Asp Pro Pro  Tyr Asp Val
    1580                 1585                 1590

Val Gln  Glu Met Lys Thr Leu  Ser Asp Pro Asn Ala  Arg Trp Glu
    1595                 1600                 1605
```

<210> SEQ ID NO 23
<211> LENGTH: 6132
<212> TYPE: DNA
<213> ORGANISM: Lipomyces starkeyi
<220> FEATURE:
<221> NAME/KEY: Intron
<222> LOCATION: (5030)..(5080)

<400> SEQUENCE: 23

```
atgagggatc gatttttca acatatcggc acgacggcgg ccagtgatga gctgttacct     60

caggagtcac tggtagagct tatcacagac tttctggact tcaaatcaaa gcttttgctt    120

aattggccag gtgccgatag aacatccagg cagaggcttc ttcgagcttt gctcgaccat    180

ctggagagaa atgtccttac agatgacatc cacaccattg cggcgatatc gtccgacgac    240

cccgagcgac ctgctaaaat cattcgatca tactactctg cgtgccatgc atcaggtcgc    300
```

```
cccatagcca agcgccagtc tgcactgctg gattccgttt cgagtggtga ctccaagttg    360
tacgccgtgc tcggtggtca aggaatcact actgcttatc tggatgagct gcgcgaaatc    420
catacaatgt atcacagttt cttggtagat tatatcgaga cattggggga gttcttgaaa    480
tcccttgcat cccagccaga tgtgtctcga tattacccag aaggcctgga tatcatcaac    540
tggctgcgaa acccggaagc aacaccagat gtaagctacc ttgcttcatc ccgagtcagc    600
ttccctatta ttggcatact ccagctcgcg caatatatgg tcagcctgaa ggttttgggt    660
caaaatccct caactttcaa tcccagtctt agcggcatag ctggccactc tcaggggttg    720
gtcattgctg cagtaatcgc tggcgctgtc gactggtcgt ctttcatcga cttgagtcgt    780
acagccgtgg agatactgtt ttcgattgga gttgtcagcc agcagatcta tcctgagaca    840
tcaccagacc caaagatagt ctccgattct atctccaatg atgaaggcac cccttcctct    900
atgctcagca ttcgtggcat ctccgaagct caagtccagg agcacgtgga tgtgtccaac    960
aaatctctac ccgaagatag aaagatttcg attgctctag caaatgggcc acgtaatttc   1020
gtggttgctg gacctgccac atccttgtgt gggctgaacg cacgtttgag gcggtttaaa   1080
gtgtccgcag aagtcgacca gaaccgaatc ccatcaaagg agcgaaaatc gactctcacg   1140
aaccactttc tccctataag tgtgcctttc cacaccaact atctacttcc tgcacttccg   1200
atcttgagaa agcgtctcgg ccatattttc ctacccagta acagtctgca aattccggta   1260
tacgacacaa acactggcga agaccttagc gccttgggta gtgagaatct acttgatagg   1320
ctagtatacc tgatcacagt cgcccctgtt cgctggctca aggcttcaac ctgtgaatcg   1380
gcgtctcata tcgttgactt tggtcctgga ggcagttccg gtattggcgt cgttactagc   1440
cacaacaagc aaggaacggg tgttcgtgtt atgatggctg gcgctttagc tggaaaatcc   1500
tccgaagtcg gttacaaggc cgaacttttc agttggaaca aagcttccat tgtggatagc   1560
aagaattggg caagaagctt tagcccaaga ctgattcggg cgaccgatgg gcaaattcac   1620
ctcgagacca aaatgagcaa gcttttacac atgccaccca tcatggttgc tggcatgacg   1680
ccaactactg tatcctggag atttgtttca gctaccatca atgctggata tcacattgag   1740
ttagctggcg gaggctaccg tgacgaagcc atgttgacaa cagccttgaa caacatcgtg   1800
gctacgattc cacctggacg aggagtttgc atcaacatca tatatgtcga cccccgtgca   1860
gtagcatggc agatcccact tctggagaag ctccatgcgg aaggaatacc aattgatggt   1920
ttgaccattg gcgctggagt gccttcagtc gagatttccc aaagctatat caacgacctt   1980
ggattgaaat atattgcctt caaacctggt tcggtcaatt caatcaagca ggttattagc   2040
attgctaaag ccaattccac cttccccgtc attttgcagt ggactggcgg ccgagccgga   2100
ggccatcact ctttcgaaga cttccacacg ccgattttgg aagtctatgg ccagatccgc   2160
gattgcgaaa atattattct cgtcgctggt agtggctttg gctcagctga ggatgcttat   2220
ccatacttca ctggagcatg gtccaaggct ttcggttatc cccccatgcc ctttgatggt   2280
gtgttgcttg gaagtcgcat gatgacggca aaggaagcct ccaccagtgt ggggtccaag   2340
aagaagatcg ttgagactga cggtcttcct gatggccaat gggagaaaac attcaaaggc   2400
gcagctggag gtgtgattac tgtcatctca gagatgggag agccaatgca cgttctagca   2460
actcgcggta tgagattctg ggctgaaatg gacactatct tcaagatgcc caaggatcag   2520
atggttgcta cgctacagaa gagaagcagc tacatcatca aaaagctcaa cgacgacttc   2580
caaaaagttt ggttcggcaa gaacacggct gaggaagctg tgctactgaa ggagatgact   2640
tatcacgaag tagttgcccg aatggtcgag ctgatgtata tcagtgcaag ggtgtatgg    2700
```

```
atcgataagt cattgaagac ccttacaggt gacttcattc gtcgggttga ggaaagattc   2760
gcaacgagca gcggcagtgg attcgttctt tcggattatg ccgacctcga tgctcctcaa   2820
gtggtgctgg acacccttgt caaaacctac cccgatatca gtgatgatat cattactcct   2880
ttggatgttc agttcttctt gtcgctctgt ctgcgtccag gcaagaaacc agttcctttt   2940
gttccggtcc tcgatgaaaa cttgtcattc tatttcaaga aagattcgct gtggcagtct   3000
gagaaccttt gggcggttgt tggtaatgat gcagatcgta cacagatctt gcacggaccg   3060
gtagcagctc aacattcgaa gacctacgac gaacctgtcc aggacatcct cgacggcatc   3120
aagaatgggc tggtttcttc attgctcaaa gaagcttaca atggagagat caggaatctt   3180
cccgttcaga aggctccatt ggaaataacg ccacaagctc attggtctga ctccgaacgc   3240
aatgtgtcta tcaccgagtc ttcagagtca gtcgtctacg caatctcttc ggcgcgtgat   3300
gatttaccct cgccaagttc gtggtataga atgatcgcag gtgaccaata cacatggcgt   3360
tatgcgctcc tcagttcaga aactgtcatt tccggcaaca agcggttacc aaaccctatt   3420
cgcaaaatct gcacgccttc cagtgacctt cgtgtaactg ttgaaaacca taccgagcca   3480
tcgaaaatgg ttatcaccat ccaagctgca tcagatacgg agaaccccga tactgttgtg   3540
aagataaggt tgcagggatc ctgcatagtt gctgattgca tattgagtcc aacaactact   3600
catgtatcgc caaccttgcg attggcgttc tcataccacc cggatgcggt gtacgcgccg   3660
atacgggaga actcagatgg cttactcgat gaggtttcag aattctacag aaaactttgg   3720
tttggcgatg aacaactcga ctttgatgcg cagcctaccc aagatttctc gggagaaaca   3780
atgaccatta ctcgggaggc aatcagctct tttctccaag ccaccggcag tagttgcgag   3840
acataccgta gccgcgcaaa tcaggaactg cctgcacctt tggactttgg cattgttatt   3900
gcttggaaag ctctcctgaa accaatcttt ttgagaaaga atggtggcaa tattctcaag   3960
cttgtacatc tctccaacaa gttcaagcgt gtggatggag cagcttcttt aagcgctggc   4020
gacaaagtgt cgacttcttc ccgcatcaca gcggttcgca ttcaggatgc aggcaaagtg   4080
gttgaggtac ttgcggtcat taccaaggat ggaagtcctg tgatggaagt tgtctcgcaa   4140
ttcatgtatc gcggaaaata cactgacttc gaaacaactt ttgaacgaaa agttgaagtc   4200
ccgatgcagg tccatttggg ttcacgaaag gacgtcgcaa tcctcaaatc caagccttgg   4260
ttccaattaa ccaaccccga ctccgaattg ttggacagga ccttcatttt ccgtctcgaa   4320
actacgcaag tgaagtctac cgctactgct ggcaccgttt tggtggttgg cactgtttct   4380
gagaagcacg ctacagatgg tgaacgctca gtagcttcaa tcaactatac tactgcgctc   4440
tcctccgtca atcccatttt gcgctatctc aacacgcatg gtagcggagt cgaaggtcct   4500
gttttgctcg aaaatgcaat tccagttcat ggtgccagtg gaattccact caagaggccg   4560
atgtctagcg ctgcttatgc aaaggtctcc ggggattaca atcctatcca cgtgtcgaac   4620
acctttgcat tgctcgccaa cttaccaggc tcgattgttc atggcatgca tacaagctct   4680
gccattggat cattgcttga aacttggact gccaaaggtc gcgtgggcgc agtgcgcagt   4740
tttgaagctt cttttgtcgg tatggttctt ccggatgatc tggtagatgt cgagttttgg   4800
catacggcta tgatgaaagg ccgcaaagtg atcaagatta cagccaagaa gacagacagt   4860
ggtgagatgg tgttgaaggg cgaagccgag gtggaggaac agagatctgc ctacctgttc   4920
accggccagg gttcacagga acccaacatg ggcatggacc tttatgcaag cagcccaatt   4980
gctcgatctg tgtgggatat tgccgacaag ttctacttga agacttatgg ttcgttatcc   5040
```

```
tttcctgtat acgataccca gttattaatt ctttttctag gttttgagat cacaaagatc   5100

gtcagagaga atcccaagga gatgactatt cattttggag gcgtcaatgg cagacgtatt   5160

cgccagaact acctttcatt gactctgcaa actactggtg atgacggtca gccaatcttg   5220

gagaaagtct tcaaggacat caacgaggac tcagagtcct acactttcaa gtcgcccaag   5280

ggtcttctcc atgcaacgca gttcacgcaa gcggctatta ccctggtaga actcgcacgg   5340

tacaaggaca tggaagcccg aggtcttatt tcggagaatt acaactttgc gggccactcc   5400

cttggagagt atccagccct agcatcattc gcacaaataa tgtcgattga gcagttagtc   5460

gcaatttgtt tctaccgtgg tatggcgatg caagttaccg tcaaacgtga cgagcaaggc   5520

gcttcagact actccttgtg tgctgtcaac ccgagtcgag tttcaaagac tttcaacgaa   5580

aagatgttgc gcttcattac caagaccatt tcgcaacaga ctgggtggct tctggagatt   5640

gtgaatttca acatctcaaa cagacaatat gtctgtgcag gagaactcat agcactcgat   5700

tgtcttacga aactacttga ccgcatcgca aagggcctga atgtcgactg gatcaatcga   5760

cctggaagtg gattagatgg taagactgtg ttcttatcaa ctgtccgttc catcatacaa   5820

gaggcacaag caaagaaaac acgcgtcgaa ttgaaacgag gtacgggcat tacacctctg   5880

gaaggcattg acgtgccgtt ccactcgact ctccttcgtc caggtgttgc cacattccgt   5940

gactttttgg catcaaagat tgatccgtca aatatcgatg cgaaaaagct cgttaataaa   6000

tgggtcccta atctcacagg gaagccattt aggaatgacc ggaagtattt tgaatatgtc   6060

tacaatctta cagggtctgt gcctcttcag aagctgttgg gagaatggag ggaaatagat   6120

ttggttatgt ag                                                       6132
```

<210> SEQ ID NO 24
<211> LENGTH: 2026
<212> TYPE: PRT
<213> ORGANISM: Lipomyces starkeyi

<400> SEQUENCE: 24

```
Met Arg Asp Arg Phe Phe Gln His Ile Gly Thr Thr Ala Ala Ser Asp
1               5                   10                  15

Glu Ser Leu Pro Gln Glu Ser Ser Val Glu Leu Ile Thr Asp Phe Ser
            20                  25                  30

Asp Phe Lys Ser Lys Leu Leu Leu Asn Trp Pro Gly Ala Asp Arg Thr
        35                  40                  45

Ser Arg Gln Arg Leu Leu Arg Ala Leu Leu Asp His Ser Glu Arg Asn
    50                  55                  60

Val Leu Thr Asp Asp Ile His Thr Ile Ala Ala Ile Ser Ser Asp Asp
65                  70                  75                  80

Pro Glu Arg Pro Ala Lys Ile Ile Arg Ser Tyr Tyr Ser Ala Cys His
                85                  90                  95

Ala Ser Gly Arg Pro Ile Ala Lys Arg Gln Ser Ala Ser Ser Asp Ser
            100                 105                 110

Val Ser Ser Gly Asp Ser Lys Leu Tyr Ala Val Leu Gly Gly Gln Gly
        115                 120                 125

Ile Thr Thr Ala Tyr Ser Asp Glu Ser Arg Glu Ile His Thr Met Tyr
    130                 135                 140

His Ser Phe Leu Val Asp Tyr Ile Glu Thr Leu Gly Glu Phe Leu Lys
145                 150                 155                 160

Ser Leu Ala Ser Gln Pro Asp Val Ser Arg Tyr Tyr Pro Glu Gly Ser
                165                 170                 175
```

```
Asp Ile Ile Asn Trp Ser Arg Asn Pro Glu Ala Thr Pro Asp Val Ser
            180                 185                 190

Tyr Leu Ala Ser Ser Arg Val Ser Phe Pro Ile Ile Gly Ile Leu Gln
        195                 200                 205

Leu Ala Gln Tyr Met Val Ser Ser Lys Val Leu Gly Gln Asn Pro Ser
    210                 215                 220

Thr Phe Asn Pro Ser Leu Ser Gly Ile Ala Gly His Ser Gln Gly Leu
225                 230                 235                 240

Val Ile Ala Ala Val Ile Ala Gly Ala Val Asp Trp Ser Ser Phe Ile
                245                 250                 255

Asp Leu Ser Arg Thr Ala Val Glu Ile Ser Phe Ser Ile Gly Val Val
            260                 265                 270

Ser Gln Gln Ile Tyr Pro Glu Thr Ser Pro Asp Pro Lys Ile Val Ser
        275                 280                 285

Asp Ser Ile Ser Asn Asp Glu Gly Thr Pro Ser Ser Met Leu Ser Ile
    290                 295                 300

Arg Gly Ile Ser Glu Ala Gln Val Gln Glu His Val Asp Val Ser Asn
305                 310                 315                 320

Lys Ser Leu Pro Glu Asp Arg Lys Ile Ser Ile Ala Leu Ala Asn Gly
                325                 330                 335

Pro Arg Asn Phe Val Val Ala Gly Pro Ala Thr Ser Leu Cys Gly Ser
            340                 345                 350

Asn Ala Arg Leu Arg Arg Phe Lys Val Ser Ala Glu Val Asp Gln Asn
        355                 360                 365

Arg Ile Pro Ser Lys Glu Arg Lys Ser Thr Leu Thr Asn His Phe Leu
    370                 375                 380

Pro Ile Ser Val Pro Phe His Thr Asn Tyr Leu Leu Pro Ala Leu Pro
385                 390                 395                 400

Ile Leu Arg Lys Arg Leu Gly His Ile Phe Leu Pro Ser Asn Ser Ser
                405                 410                 415

Gln Ile Pro Val Tyr Asp Thr Asn Thr Gly Glu Asp Leu Ser Ala Leu
            420                 425                 430

Gly Ser Glu Asn Leu Leu Asp Arg Leu Val Tyr Ser Ile Thr Val Ala
        435                 440                 445

Pro Val Arg Trp Leu Lys Ala Ser Thr Cys Glu Ser Ala Ser His Ile
    450                 455                 460

Val Asp Phe Gly Pro Gly Gly Ser Ser Gly Ile Gly Val Val Thr Ser
465                 470                 475                 480

His Asn Lys Gln Gly Thr Gly Val Arg Val Met Met Ala Gly Ala Leu
                485                 490                 495

Ala Gly Lys Ser Ser Glu Val Gly Tyr Lys Ala Glu Leu Phe Ser Trp
            500                 505                 510

Asn Lys Ala Ser Ile Val Asp Ser Lys Asn Trp Ala Arg Ser Phe Ser
        515                 520                 525

Pro Arg Ser Ile Arg Ala Thr Asp Gly Gln Ile His Leu Glu Thr Lys
    530                 535                 540

Met Ser Lys Leu Leu His Met Pro Pro Ile Met Val Ala Gly Met Thr
545                 550                 555                 560

Pro Thr Thr Val Ser Trp Arg Phe Val Ser Ala Thr Ile Asn Ala Gly
                565                 570                 575

Tyr His Ile Glu Leu Ala Gly Gly Gly Tyr Arg Asp Glu Ala Met Leu
            580                 585                 590

Thr Thr Ala Leu Asn Asn Ile Val Ala Thr Ile Pro Pro Gly Arg Gly
```

```
        595                 600                 605

Val Cys Ile Asn Ile Ile Tyr Val Asp Pro Arg Ala Val Ala Trp Gln
    610                 615                 620

Ile Pro Leu Ser Glu Lys Leu His Ala Glu Gly Ile Pro Ile Asp Gly
625                 630                 635                 640

Leu Thr Ile Gly Ala Gly Val Pro Ser Val Glu Ile Ser Gln Ser Tyr
                645                 650                 655

Ile Asn Asp Leu Gly Leu Lys Tyr Ile Ala Phe Lys Pro Gly Ser Val
            660                 665                 670

Asn Ser Ile Lys Gln Val Ile Ser Ile Ala Lys Ala Asn Ser Thr Phe
        675                 680                 685

Pro Val Ile Leu Gln Trp Thr Gly Gly Arg Ala Gly Gly His His Ser
    690                 695                 700

Phe Glu Asp Phe His Thr Pro Ile Leu Glu Val Tyr Gly Gln Ile Arg
705                 710                 715                 720

Asp Cys Glu Asn Ile Ile Leu Val Ala Gly Ser Gly Phe Gly Ser Ala
                725                 730                 735

Glu Asp Ala Tyr Pro Tyr Phe Thr Gly Ala Trp Ser Lys Ala Phe Gly
            740                 745                 750

Tyr Pro Pro Met Pro Phe Asp Gly Val Leu Leu Gly Ser Arg Met Met
        755                 760                 765

Thr Ala Lys Glu Ala Ser Thr Ser Val Gly Ser Lys Lys Lys Ile Val
    770                 775                 780

Glu Thr Asp Gly Leu Pro Asp Gly Gln Trp Glu Lys Thr Phe Lys Gly
785                 790                 795                 800

Ala Ala Gly Gly Val Ile Thr Val Ile Ser Glu Met Gly Glu Pro Met
                805                 810                 815

His Val Leu Ala Thr Arg Gly Met Arg Phe Trp Ala Glu Met Asp Thr
            820                 825                 830

Ile Phe Lys Met Pro Lys Asp Gln Met Val Ala Thr Leu Gln Lys Arg
        835                 840                 845

Ser Ser Tyr Ile Ile Lys Lys Leu Asn Asp Asp Phe Gln Lys Val Trp
    850                 855                 860

Phe Gly Lys Asn Thr Ala Glu Glu Ala Val Leu Ser Lys Glu Met Thr
865                 870                 875                 880

Tyr His Glu Val Val Ala Arg Met Val Glu Ser Met Tyr Ile Ser Ala
                885                 890                 895

Arg Gly Val Trp Ile Asp Lys Ser Leu Lys Thr Leu Thr Gly Asp Phe
            900                 905                 910

Ile Arg Arg Val Glu Glu Arg Phe Ala Thr Ser Ser Gly Ser Gly Phe
        915                 920                 925

Val Leu Ser Asp Tyr Ala Asp Leu Asp Ala Pro Gln Val Val Ser Asp
    930                 935                 940

Thr Leu Val Lys Thr Tyr Pro Asp Ile Ser Asp Asp Ile Ile Thr Pro
945                 950                 955                 960

Leu Asp Val Gln Phe Phe Leu Ser Leu Cys Ser Arg Pro Gly Lys Lys
                965                 970                 975

Pro Val Pro Phe Val Pro Val Leu Asp Glu Asn Leu Ser Phe Tyr Phe
            980                 985                 990

Lys Lys Asp Ser Ser Trp Gln Ser  Glu Asn Leu Trp Ala  Val Val Gly
        995                 1000                1005

Asn Asp  Ala Asp Arg Thr Gln  Ile Leu His Gly Pro  Val Ala Ala
    1010                1015                1020
```

```
Gln His  Ser Lys Thr Tyr Asp  Glu Pro Val Gln Asp  Ile Leu Asp
    1025                 1030                 1035

Gly Ile  Lys Asn Gly Ser Val  Ser Ser Leu Leu Lys  Glu Ala Tyr
    1040                 1045                 1050

Asn Gly  Glu Ile Arg Asn Leu  Pro Val Gln Lys Ala  Pro Leu Glu
    1055                 1060                 1065

Ile Thr  Pro Gln Ala His Trp  Ser Asp Ser Glu Arg  Asn Val Ser
    1070                 1075                 1080

Ile Thr  Glu Ser Ser Glu Ser  Val Val Tyr Ala Ile  Ser Ser Ala
    1085                 1090                 1095

Arg Asp  Asp Leu Pro Ser Pro  Ser Ser Trp Tyr Arg  Met Ile Ala
    1100                 1105                 1110

Gly Asp  Gln Tyr Thr Trp Arg  Tyr Ala Leu Leu Ser  Ser Glu Thr
    1115                 1120                 1125

Val Ile  Ser Gly Asn Lys Arg  Leu Pro Asn Pro Ile  Arg Lys Ile
    1130                 1135                 1140

Cys Thr  Pro Ser Ser Asp Leu  Arg Val Thr Val Glu  Asn His Thr
    1145                 1150                 1155

Glu Pro  Ser Lys Met Val Ile  Thr Ile Gln Ala Ala  Ser Asp Thr
    1160                 1165                 1170

Glu Asn  Pro Asp Thr Val Val  Lys Ile Arg Leu Gln  Gly Ser Cys
    1175                 1180                 1185

Ile Val  Ala Asp Cys Ile Leu  Ser Pro Thr Thr Thr  His Val Ser
    1190                 1195                 1200

Pro Thr  Leu Arg Leu Ala Phe  Ser Tyr His Pro Asp  Ala Val Tyr
    1205                 1210                 1215

Ala Pro  Ile Arg Glu Asn Ser  Asp Gly Leu Leu Asp  Glu Val Ser
    1220                 1225                 1230

Glu Phe  Tyr Arg Lys Leu Trp  Phe Gly Asp Glu Gln  Leu Asp Phe
    1235                 1240                 1245

Asp Ala  Gln Pro Thr Gln Asp  Phe Ser Gly Glu Thr  Met Thr Ile
    1250                 1255                 1260

Thr Arg  Glu Ala Ile Ser Ser  Phe Leu Gln Ala Thr  Gly Ser Ser
    1265                 1270                 1275

Cys Glu  Thr Tyr Arg Ser Arg  Ala Asn Gln Glu Ser  Pro Ala Pro
    1280                 1285                 1290

Leu Asp  Phe Gly Ile Val Ile  Ala Trp Lys Ala Leu  Ser Lys Pro
    1295                 1300                 1305

Ile Phe  Leu Arg Lys Asn Gly  Gly Asn Ile Leu Lys  Leu Val His
    1310                 1315                 1320

Leu Ser  Asn Lys Phe Lys Arg  Val Asp Gly Ala Ala  Ser Leu Ser
    1325                 1330                 1335

Ala Gly  Asp Lys Val Ser Thr  Ser Ser Arg Ile Thr  Ala Val Arg
    1340                 1345                 1350

Ile Gln  Asp Ala Gly Lys Val  Val Glu Val Leu Ala  Val Ile Thr
    1355                 1360                 1365

Lys Asp  Gly Ser Pro Val Met  Glu Val Val Ser Gln  Phe Met Tyr
    1370                 1375                 1380

Arg Gly  Lys Tyr Thr Asp Phe  Glu Thr Thr Phe Glu  Arg Lys Val
    1385                 1390                 1395

Glu Val  Pro Met Gln Val His  Leu Gly Ser Arg Lys  Asp Val Ala
    1400                 1405                 1410
```

```
Ile Leu  Lys Ser Lys Pro Trp  Phe Gln Leu Thr Asn  Pro Asp Ser
    1415                 1420                 1425

Glu Leu  Leu Asp Arg Thr Phe  Ile Phe Arg Leu Glu  Thr Thr Gln
    1430                 1435                 1440

Val Lys  Ser Thr Ala Thr Ala  Gly Thr Val Leu Val  Val Gly Thr
    1445                 1450                 1455

Val Ser  Glu Lys His Ala Thr  Asp Gly Glu Arg Ser  Val Ala Ser
    1460                 1465                 1470

Ile Asn  Tyr Thr Thr Ala Leu  Ser Ser Val Asn Pro  Ile Leu Arg
    1475                 1480                 1485

Tyr Leu  Asn Thr His Gly Ser  Gly Val Glu Gly Pro  Val Leu Leu
    1490                 1495                 1500

Glu Asn  Ala Ile Pro Val His  Gly Ala Ser Gly Ile  Pro Leu Lys
    1505                 1510                 1515

Arg Pro  Met Ser Ser Ala Ala  Tyr Ala Lys Val Ser  Gly Asp Tyr
    1520                 1525                 1530

Asn Pro  Ile His Val Ser Asn  Thr Phe Ala Leu Leu  Ala Asn Leu
    1535                 1540                 1545

Pro Gly  Ser Ile Val His Gly  Met His Thr Ser Ser  Ala Ile Gly
    1550                 1555                 1560

Ser Leu  Leu Glu Thr Trp Thr  Ala Lys Gly Arg Val  Gly Ala Val
    1565                 1570                 1575

Arg Ser  Phe Glu Ala Ser Phe  Val Gly Met Val Leu  Pro Asp Asp
    1580                 1585                 1590

Ser Val  Asp Val Glu Phe Trp  His Thr Ala Met Met  Lys Gly Arg
    1595                 1600                 1605

Lys Val  Ile Lys Ile Thr Ala  Lys Lys Thr Asp Ser  Gly Glu Met
    1610                 1615                 1620

Val Leu  Lys Gly Glu Ala Glu  Val Glu Glu Gln Arg  Ser Ala Tyr
    1625                 1630                 1635

Ser Phe  Thr Gly Gln Gly Ser  Gln Glu Pro Asn Met  Gly Met Asp
    1640                 1645                 1650

Leu Tyr  Ala Ser Ser Pro Ile  Ala Arg Ser Val Trp  Asp Ile Ala
    1655                 1660                 1665

Asp Lys  Phe Tyr Leu Lys Thr  Tyr Gly Phe Glu Ile  Thr Lys Ile
    1670                 1675                 1680

Val Arg  Glu Asn Pro Lys Glu  Met Thr Ile His Phe  Gly Gly Val
    1685                 1690                 1695

Asn Gly  Arg Arg Ile Arg Gln  Asn Tyr Leu Ser Leu  Thr Ser Gln
    1700                 1705                 1710

Thr Thr  Gly Asp Asp Gly Gln  Pro Ile Leu Glu Lys  Val Phe Lys
    1715                 1720                 1725

Asp Ile  Asn Glu Asp Ser Glu  Ser Tyr Thr Phe Lys  Ser Pro Lys
    1730                 1735                 1740

Gly Leu  Leu His Ala Thr Gln  Phe Thr Gln Ala Ala  Ile Thr Ser
    1745                 1750                 1755

Val Glu  Leu Ala Arg Tyr Lys  Asp Met Glu Ala Arg  Gly Leu Ile
    1760                 1765                 1770

Ser Glu  Asn Tyr Asn Phe Ala  Gly His Ser Leu Gly  Glu Tyr Pro
    1775                 1780                 1785

Ala Leu  Ala Ser Phe Ala Gln  Ile Met Ser Ile Glu  Gln Leu Val
    1790                 1795                 1800

Ala Ile  Cys Phe Tyr Arg Gly  Met Ala Met Gln Val  Thr Val Lys
```

```
    1805                1810                1815

Arg Asp  Glu Gln Gly Ala Ser  Asp Tyr Ser Leu Cys  Ala Val Asn
    1820                1825                1830

Pro Ser  Arg Val Ser Lys Thr  Phe Asn Glu Lys Met  Leu Arg Phe
    1835                1840                1845

Ile Thr  Lys Thr Ile Ser Gln  Gln Thr Gly Trp Leu  Ser Glu Ile
    1850                1855                1860

Val Asn  Phe Asn Ile Ser Asn  Arg Gln Tyr Val Cys  Ala Gly Glu
    1865                1870                1875

Leu Ile  Ala Leu Asp Cys Leu  Thr Lys Leu Leu Asp  Arg Ile Ala
    1880                1885                1890

Lys Gly  Ser Asn Val Asp Trp  Ile Asn Arg Pro Gly  Ser Gly Leu
    1895                1900                1905

Asp Gly  Lys Thr Val Phe Leu  Ser Thr Val Arg Ser  Ile Ile Gln
    1910                1915                1920

Glu Ala  Gln Ala Lys Lys Thr  Arg Val Glu Leu Lys  Arg Gly Thr
    1925                1930                1935

Gly Ile  Thr Pro Ser Glu Gly  Ile Asp Val Pro Phe  His Ser Thr
    1940                1945                1950

Leu Leu  Arg Pro Gly Val Ala  Thr Phe Arg Asp Phe  Leu Ala Ser
    1955                1960                1965

Lys Ile  Asp Pro Ser Asn Ile  Asp Ala Lys Lys Leu  Val Asn Lys
    1970                1975                1980

Trp Val  Pro Asn Leu Thr Gly  Lys Pro Phe Arg Asn  Asp Arg Lys
    1985                1990                1995

Tyr Phe  Glu Tyr Val Tyr Asn  Leu Thr Gly Ser Val  Pro Leu Gln
    2000                2005                2010

Lys Ser  Leu Gly Glu Trp Arg  Glu Ile Asp Leu Val  Met
    2015                2020                2025


<210> SEQ ID NO 25
<211> LENGTH: 1827
<212> TYPE: DNA
<213> ORGANISM: Lipomyces starkeyi
<220> FEATURE:
<221> NAME/KEY: Intron
<222> LOCATION: (51)..(162)
<220> FEATURE:
<221> NAME/KEY: Intron
<222> LOCATION: (241)..(296)
<220> FEATURE:
<221> NAME/KEY: Intron
<222> LOCATION: (436)..(492)

<400> SEQUENCE: 25

atgccaaggg tcttcatcgg tgcactggat gccggcacca cgtctacaag gtgaggactg      60

ggccatttga gccgaggacg tcgtgcacgc tcacgctcac ccggccatat cctctgggaa     120

ctctttgaaa ggttccgtta gtgcatatgc taacaaccgc agattcatta tatttgacga     180

tgctggtagg ccttacgcta cacaccagat tgaattcgag cagcattatc cacatgctgg     240

gtgagttgcg ctgttaaata cgccttctgg aaaacaatac gctgaccgag taatagctgg     300

cacgagcaat acccttacga gattatcaag tgcgcgaatg actgtattga gggcgctgtc     360

aagaagtttg tcgcagatgg atacaatgtc tccgacataa aggcggttgg aattacaaac     420

cagcgtgaat ccactgtaaa tccttgttcc ttcttacaga tattaagaac agtctaacaa     480

aaaataacat aggtcgtctg ggattctgag acggggaagc cactgtataa tgcaattgct     540
```

```
tggcctgaca cgcgtactgc gcgactagta catcacttca agaacaagaa cggcgccgaa    600
gacctagtgc gaatctgcgg tctgccactg tctacctatc cgtccgcgct caagctggtg    660
tggctgttag aaaacgttca cggcgtccag gaggcacgaa agcgtggaac tttgatgttc    720
ggtaccgttg acacctggtt agtgtacaat ctgaccggtg gcggtaagac tggaaccgac    780
accaggtttg tgacagatac caccaatgcc tcgcgaacta tgttcctaaa tattaactct    840
ctcaagtacg atgatttcct ccttgatttc tttggagttt ctcaaggagt gagactccct    900
gacgttgtgt gctccgcaga cgacaaagct tacggtaata tcgcttccgg tgtcctcgct    960
ggtgtaccaa ttgcgtcgtg tctcggtgac cagtcagccg cgttggtcgg acagcgggcg   1020
ttcagtgtgg gcatgggcaa gaacacgtac ggaactggtt tgttcttgct gtacaacact   1080
ggtgaggagc cagtcttctc gaagaacggt ctcttaacca ctgtcggata tcatttcaag   1140
ggaaagaagc ctatatacgc tctggaaggg tccattgctg tcggtggcgc tgcagttaag   1200
ttcttgcgag ataatttacg gttgatttcg ttctccgatg aggtcgggca attggcagcg   1260
aaggtccccg acgctggtgg ggtcattttt gtcacggcct tctcgggact gttcgcgcct   1320
tactggattg acgataccca gggaaccatc tacggtatca cgaactacac aaccaaagaa   1380
cacattgctc gagcaaccat tgaggccacc tgttatcaga ctagagcagt tttggaagct   1440
atggctaagg attctggcta cgagttgaag acgctcaagg tcgacggtgg catgagtaac   1500
tcggatatat gcatgcaaat ccaatccgac attattggca ttgacgtcgt tcggccggag   1560
tatagggaga ctaccgcatt gggggcagcc attgcagcag gttttgcagt tggagtctat   1620
agtagctttg aggagttgaa gcgagtgaac acggatggag agaccacatt caagccttcc   1680
atcactgaga agaagcgcga gaagttgtat aacctctggc agcgtgctgt atcgcgatgt   1740
ggtggttggt tgcgggatga ggatgacgac tctgagattg aggaggagac aagagttggg   1800
gatgggaccc aaaagcagtt tgcatag                                       1827
```

<210> SEQ ID NO 26
<211> LENGTH: 533
<212> TYPE: PRT
<213> ORGANISM: Lipomyces starkeyi

<400> SEQUENCE: 26

```
Met Pro Arg Val Phe Ile Gly Ala Leu Asp Ala Gly Thr Thr Ser Thr
1               5                   10                  15

Arg Phe Ile Ile Phe Asp Asp Ala Gly Arg Pro Tyr Ala Thr His Gln
            20                  25                  30

Ile Glu Phe Glu Gln His Tyr Pro His Ala Gly Trp His Glu Gln Tyr
        35                  40                  45

Pro Tyr Glu Ile Ile Lys Cys Ala Asn Asp Cys Ile Glu Gly Ala Val
    50                  55                  60

Lys Lys Phe Val Ala Asp Gly Tyr Asn Val Ser Asp Ile Lys Ala Val
65                  70                  75                  80

Gly Ile Thr Asn Gln Arg Glu Ser Thr Val Val Trp Asp Ser Glu Thr
                85                  90                  95

Gly Lys Pro Leu Tyr Asn Ala Ile Ala Trp Pro Asp Thr Arg Thr Ala
            100                 105                 110

Arg Leu Val His His Phe Lys Asn Lys Asn Gly Ala Glu Asp Leu Val
        115                 120                 125

Arg Ile Cys Gly Leu Pro Leu Ser Thr Tyr Pro Ser Ala Leu Lys Leu
    130                 135                 140
```

```
Val Trp Leu Leu Glu Asn Val His Gly Val Gln Glu Ala Arg Lys Arg
145                 150                 155                 160

Gly Thr Leu Met Phe Gly Thr Val Asp Thr Trp Leu Val Tyr Asn Leu
                165                 170                 175

Thr Gly Gly Gly Lys Thr Gly Thr Asp Thr Arg Phe Val Thr Asp Thr
            180                 185                 190

Thr Asn Ala Ser Arg Thr Met Phe Leu Asn Ile Asn Ser Leu Lys Tyr
        195                 200                 205

Asp Asp Phe Leu Leu Asp Phe Phe Gly Val Ser Gln Gly Val Arg Leu
    210                 215                 220

Pro Asp Val Val Cys Ser Ala Asp Asp Lys Ala Tyr Gly Asn Ile Ala
225                 230                 235                 240

Ser Gly Val Leu Ala Gly Val Pro Ile Ala Ser Cys Leu Gly Asp Gln
                245                 250                 255

Ser Ala Ala Leu Val Gly Gln Arg Ala Phe Ser Val Gly Met Gly Lys
            260                 265                 270

Asn Thr Tyr Gly Thr Gly Leu Phe Leu Leu Tyr Asn Thr Gly Glu Glu
        275                 280                 285

Pro Val Phe Ser Lys Asn Gly Leu Leu Thr Thr Val Gly Tyr His Phe
    290                 295                 300

Lys Gly Lys Lys Pro Ile Tyr Ala Leu Glu Gly Ser Ile Ala Val Gly
305                 310                 315                 320

Gly Ala Ala Val Lys Phe Leu Arg Asp Asn Leu Arg Leu Ile Ser Phe
                325                 330                 335

Ser Asp Glu Val Gly Gln Leu Ala Ala Lys Val Pro Asp Ala Gly Gly
            340                 345                 350

Val Ile Phe Val Thr Ala Phe Ser Gly Leu Phe Ala Pro Tyr Trp Ile
        355                 360                 365

Asp Asp Thr Gln Gly Thr Ile Tyr Gly Ile Thr Asn Tyr Thr Thr Lys
    370                 375                 380

Glu His Ile Ala Arg Ala Thr Ile Glu Ala Thr Cys Tyr Gln Thr Arg
385                 390                 395                 400

Ala Val Leu Glu Ala Met Ala Lys Asp Ser Gly Tyr Glu Leu Lys Thr
                405                 410                 415

Leu Lys Val Asp Gly Gly Met Ser Asn Ser Asp Ile Cys Met Gln Ile
            420                 425                 430

Gln Ser Asp Ile Ile Gly Ile Asp Val Val Arg Pro Glu Tyr Arg Glu
        435                 440                 445

Thr Thr Ala Leu Gly Ala Ala Ile Ala Ala Gly Phe Ala Val Gly Val
    450                 455                 460

Tyr Ser Ser Phe Glu Glu Leu Lys Arg Val Asn Thr Asp Gly Glu Thr
465                 470                 475                 480

Thr Phe Lys Pro Ser Ile Thr Glu Lys Lys Arg Glu Lys Leu Tyr Asn
                485                 490                 495

Leu Trp Gln Arg Ala Val Ser Arg Cys Gly Gly Trp Leu Arg Asp Glu
            500                 505                 510

Asp Asp Asp Ser Glu Ile Glu Glu Glu Thr Arg Val Gly Asp Gly Thr
        515                 520                 525

Gln Lys Gln Phe Ala
    530
```

<210> SEQ ID NO 27
<211> LENGTH: 1842
<212> TYPE: DNA

<213> ORGANISM: Lipomyces starkeyi
<220> FEATURE:
<221> NAME/KEY: Intron
<222> LOCATION: (66)..(177)
<220> FEATURE:
<221> NAME/KEY: Intron
<222> LOCATION: (256)..(311)
<220> FEATURE:
<221> NAME/KEY: Intron
<222> LOCATION: (451)..(507)

<400> SEQUENCE: 27

```
atgactaccg attccatgcc aagggtcttc atcggtgcac tggatgccgg caccacgtct      60

acaaggtgag gactgggcca tttgagccga ggacgtcgtg cacgctcacg ctcacccggc     120

catatcctct gggaactctt tgaaaggttc cgttagtgca tatgctaaca accgcagatt     180

cattatattt gacgatgctg gtaggcctta cgctacacac cagattgaat tcgagcagca     240

ttatccacat gctgggtgag ttgcgctgtt aaatacgcct tctggaaaac aatacgctga     300

ccgagtaata gctggcacga gcaataccct tacgagatta tcaagtgcgc gaatgactgt     360

attgagggcg ctgtcaagaa gtttgtcgca gatggataca atgtctccga cataaaggcg     420

gttggaatta caaaccagcg tgaatccact gtaaatcctt gttccttctt acagatatta     480

agaacagtct aacaaaaaat aacataggtc gtctgggatt ctgagacggg gaagccactg     540

tataatgcaa ttgcttggcc tgacacgcgt actgcgcgac tagtacatca cttcaagaac     600

aagaacggcg ccgaagacct agtgcgaatc tgcggtctgc cactgtctac ctatccgtcc     660

gcgctcaagc tggtgtggct gttagaaaac gttcacggcg tccaggaggc acgaaagcgt     720

ggaactttga tgttcggtac cgttgacacc tggttagtgt acaatctgac cggtggcggt     780

aagactggaa ccgacaccag gtttgtgaca gataccacca atgcctcgcg aactatgttc     840

ctaaatatta actctctcaa gtacgatgat ttcctccttg atttctttgg agtttctcaa     900

ggagtgagac tccctgacgt tgtgtgctcc gcagacgaca aagcttacgg taatatcgct     960

tccggtgtcc tcgctggtgt accaattgcg tcgtgtctcg gtgaccagtc agccgcgttg    1020

gtcggacagc gggcgttcag tgtgggcatg ggcaagaaca cgtacggaac tggtttgttc    1080

ttgctgtaca acactggtga ggagccagtc ttctcgaaga acggtctctt aaccactgtc    1140

ggatatcatt tcaagggaaa gaagcctata tacgctctgg aagggtccat tgctgtcggt    1200

ggcgctgcag ttaagttctt gcgagataat ttacggttga tttcgttctc cgatgaggtc    1260

gggcaattgg cagcgaaggt ccccgacgct ggtggggtca tttttgtcac ggccttctcg    1320

ggactgttcg cgccttactg gattgacgat acccagggaa ccatctacgg tatcacgaac    1380

tacacaacca aagaacacat tgctcgagca accattgagg ccacctgtta tcagactaga    1440

gcagttttgg aagctatggc taaggattct ggctacgagt tgaagacgct caaggtcgac    1500

ggtggcatga gtaactcgga tatatgcatg caaatccaat ccgacattat tggcattgac    1560

gtcgttcggc cggagtatag ggagactacc gcattggggg cagccattgc agcaggtttt    1620

gcagttggag tctatagtag ctttgaggag ttgaagcgag tgaacacgga tggagagacc    1680

acattcaagc cttccatcac tgagaagaag cgcgagaagt tgtataacct ctggcagcgt    1740

gctgtatcgc gatgtggtgg ttggttgcgg gatgaggatg acgactctga gattgaggag    1800

gagacaagag ttggggatgg gacccaaaag cagtttgcat ag                       1842
```

<210> SEQ ID NO 28
<211> LENGTH: 538
<212> TYPE: PRT

<213> ORGANISM: Lipomyces starkeyi

<400> SEQUENCE: 28

```
Met Thr Thr Asp Ser Met Pro Arg Val Phe Ile Gly Ala Leu Asp Ala
1               5                   10                  15

Gly Thr Thr Ser Thr Arg Phe Ile Ile Phe Asp Asp Ala Gly Arg Pro
            20                  25                  30

Tyr Ala Thr His Gln Ile Glu Phe Glu Gln His Tyr Pro His Ala Gly
        35                  40                  45

Trp His Glu Gln Tyr Pro Tyr Glu Ile Ile Lys Cys Ala Asn Asp Cys
    50                  55                  60

Ile Glu Gly Ala Val Lys Lys Phe Val Ala Asp Gly Tyr Asn Val Ser
65                  70                  75                  80

Asp Ile Lys Ala Val Gly Ile Thr Asn Gln Arg Glu Ser Thr Val Val
                85                  90                  95

Trp Asp Ser Glu Thr Gly Lys Pro Leu Tyr Asn Ala Ile Ala Trp Pro
            100                 105                 110

Asp Thr Arg Thr Ala Arg Leu Val His His Phe Lys Asn Lys Asn Gly
        115                 120                 125

Ala Glu Asp Leu Val Arg Ile Cys Gly Leu Pro Leu Ser Thr Tyr Pro
    130                 135                 140

Ser Ala Leu Lys Leu Val Trp Leu Leu Glu Asn Val His Gly Val Gln
145                 150                 155                 160

Glu Ala Arg Lys Arg Gly Thr Leu Met Phe Gly Thr Val Asp Thr Trp
                165                 170                 175

Leu Val Tyr Asn Leu Thr Gly Gly Gly Lys Thr Gly Thr Asp Thr Arg
            180                 185                 190

Phe Val Thr Asp Thr Thr Asn Ala Ser Arg Thr Met Phe Leu Asn Ile
        195                 200                 205

Asn Ser Leu Lys Tyr Asp Asp Phe Leu Leu Asp Phe Phe Gly Val Ser
    210                 215                 220

Gln Gly Val Arg Leu Pro Asp Val Val Cys Ser Ala Asp Asp Lys Ala
225                 230                 235                 240

Tyr Gly Asn Ile Ala Ser Gly Val Leu Ala Gly Val Pro Ile Ala Ser
                245                 250                 255

Cys Leu Gly Asp Gln Ser Ala Ala Leu Val Gly Gln Arg Ala Phe Ser
            260                 265                 270

Val Gly Met Gly Lys Asn Thr Tyr Gly Thr Gly Leu Phe Leu Leu Tyr
        275                 280                 285

Asn Thr Gly Glu Glu Pro Val Phe Ser Lys Asn Gly Leu Leu Thr Thr
    290                 295                 300

Val Gly Tyr His Phe Lys Gly Lys Lys Pro Ile Tyr Ala Leu Glu Gly
305                 310                 315                 320

Ser Ile Ala Val Gly Gly Ala Ala Val Lys Phe Leu Arg Asp Asn Leu
                325                 330                 335

Arg Leu Ile Ser Phe Ser Asp Glu Val Gly Gln Leu Ala Ala Lys Val
            340                 345                 350

Pro Asp Ala Gly Gly Val Ile Phe Val Thr Ala Phe Ser Gly Leu Phe
        355                 360                 365

Ala Pro Tyr Trp Ile Asp Asp Thr Gln Gly Thr Ile Tyr Gly Ile Thr
    370                 375                 380

Asn Tyr Thr Thr Lys Glu His Ile Ala Arg Ala Thr Ile Glu Ala Thr
385                 390                 395                 400
```

```
Cys Tyr Gln Thr Arg Ala Val Leu Glu Ala Met Ala Lys Asp Ser Gly
                405                 410                 415

Tyr Glu Leu Lys Thr Leu Lys Val Asp Gly Gly Met Ser Asn Ser Asp
            420                 425                 430

Ile Cys Met Gln Ile Gln Ser Asp Ile Ile Gly Ile Asp Val Val Arg
        435                 440                 445

Pro Glu Tyr Arg Glu Thr Thr Ala Leu Gly Ala Ala Ile Ala Ala Gly
    450                 455                 460

Phe Ala Val Gly Val Tyr Ser Ser Phe Glu Glu Leu Lys Arg Val Asn
465                 470                 475                 480

Thr Asp Gly Glu Thr Thr Phe Lys Pro Ser Ile Thr Glu Lys Lys Arg
                485                 490                 495

Glu Lys Leu Tyr Asn Leu Trp Gln Arg Ala Val Ser Arg Cys Gly Gly
            500                 505                 510

Trp Leu Arg Asp Glu Asp Asp Asp Ser Glu Ile Glu Glu Glu Thr Arg
        515                 520                 525

Val Gly Asp Gly Thr Gln Lys Gln Phe Ala
    530                 535
```

```
<210> SEQ ID NO 29
<211> LENGTH: 1831
<212> TYPE: DNA
<213> ORGANISM: Lipomyces starkeyi
<220> FEATURE:
<221> NAME/KEY: Intron
<222> LOCATION: (10)..(234)
<220> FEATURE:
<221> NAME/KEY: Intron
<222> LOCATION: (332)..(393)
<220> FEATURE:
<221> NAME/KEY: Intron
<222> LOCATION: (846)..(901)
<220> FEATURE:
<221> NAME/KEY: Intron
<222> LOCATION: (1168)..(1227)

<400> SEQUENCE: 29

atgggtcagg taagtcaatt ctgctatttt acgtccactc attcgagcag cgccaatttc     60

ttactgtttg cgattggaat tgattatcaa attcctttat gtgtttcagt gatcgaaata    120

tggcgcgctt gcttggtaac cgaagatgat gcgctagtcc caattgggtt agcgtctttt    180

cttaacgggt ctctcttctc cgaccgtggc agcctcgcta acacccaagg acagaacttg    240

atcctcaacg ctgctgacca cggctacaca gtggttgctt tcaatcgtac tgtttccaag    300

gttgatcact tccttgccaa tgaagccaag ggtatgttaa tttgagctaa atttggctca    360

attgagtgtg gaggttgacg ccgattggaa taggcaagag cgttgttggt gctcactcca    420

ttgcggagct ctgcgccaag ttgaagaagc cccgtcgagt tattcttctc gttaaggctg    480

gtaaggctgt tgacgatttc attgacttgc tcttgccaca catggagcct ggtgacatca    540

tcatcgacgg tggtaactct tatttccccg actccaaccg ccgctgcaag gagctggctg    600

ctaagggctt cctctttgtc ggctctggcg tttccggtgg tgaggagggt gcccgctatg    660

gtcccagttt gatgcctggt ggtaacgagg ctgcctggcc gtacatcaag aacatcttcc    720

aggatattgc tgccaagtct gacggtgagc cttgctgcga ctgggtcggt gacgaaggcg    780

ctggtcactt cgtcaagatg gtgcacaatg gtattgagta tggtgatatg cagttgattt    840

gcgaggtatg ttggtagttt agtggtccct ccaattaaac acgcattaac aattcctcta    900

ggcgtacgat attttgaagc gcggtgctgg attcaccgac aaggagattg gcgatgtttt    960
```

```
cactcagtgg aacaagggtg tccttgactc tttcttgatc gagattacgc gtgacatttt   1020

gtacttcaat gacgacgatg gaactcctct cgttgagaag attctcgaca ctgccggtca   1080

gaagggtacc ggcaagtgga ctgccattaa cgctctcgac cttggtatgc ccgttacctt   1140

gatcggcgag gctgtcttcg ctcgaacgta agctgatagg tctcctatat tgaatgcttt   1200

gaggcaaaaa gactaatctc tggtcagttt gtccgctatc aagcccgaac gtgtccgcgc   1260

cagcaagatc ttgaccggcc ctgtccccgc cttcaagggt gacaagaagg aacttgtcga   1320

ccaactcgag caggctctct atgcttccaa gattatctcc tatgcgcagg gtttcatgtt   1380

gatcagagag gctggccgag agtacggctg gacgttgaat aaccccgcca ttgcccttat   1440

gtggagaggt ggttgcatta tccggtctgt cttcttggcg gatatcaccc gtgcctaccg   1500

ccagaaacct gacttggaga accttctatt cgacgaattc ttccacaccg ccattgacaa   1560

ggcacagcca tcgtggcgcc agacggttgc caatgctgct ctctggggta ttcccactcc   1620

cgctttctct accgctcttt ccttctacga cggttacagg agcgagagac ttccggccaa   1680

tcttctccag gcacagcgtg actacttcgg tgctcacacc ttccacatct tgcccgaatt   1740

ctcgagcgag aagtacccta aggatactga cgtccatgtt aactggactg gcagaggtgg   1800

caatgtttct gcctccacct accttgctta a                                  1831
```

<210> SEQ ID NO 30
<211> LENGTH: 475
<212> TYPE: PRT
<213> ORGANISM: Lipomyces starkeyi

<400> SEQUENCE: 30

```
Met Gly Gln Asn Leu Ile Leu Asn Ala Ala Asp His Gly Tyr Thr Val
1               5                   10                  15

Val Ala Phe Asn Arg Thr Val Ser Lys Val Asp His Phe Leu Ala Asn
            20                  25                  30

Glu Ala Lys Gly Lys Ser Val Val Gly Ala His Ser Ile Ala Glu Leu
        35                  40                  45

Cys Ala Lys Leu Lys Lys Pro Arg Arg Val Ile Leu Leu Val Lys Ala
    50                  55                  60

Gly Lys Ala Val Asp Asp Phe Ile Asp Leu Leu Leu Pro His Met Glu
65                  70                  75                  80

Pro Gly Asp Ile Ile Ile Asp Gly Gly Asn Ser Tyr Phe Pro Asp Ser
                85                  90                  95

Asn Arg Arg Cys Lys Glu Leu Ala Ala Lys Gly Phe Leu Phe Val Gly
            100                 105                 110

Ser Gly Val Ser Gly Gly Glu Glu Gly Ala Arg Tyr Gly Pro Ser Leu
        115                 120                 125

Met Pro Gly Gly Asn Glu Ala Ala Trp Pro Tyr Ile Lys Asn Ile Phe
    130                 135                 140

Gln Asp Ile Ala Ala Lys Ser Asp Gly Glu Pro Cys Cys Asp Trp Val
145                 150                 155                 160

Gly Asp Glu Gly Ala Gly His Phe Val Lys Met Val His Asn Gly Ile
                165                 170                 175

Glu Tyr Gly Asp Met Gln Leu Ile Cys Glu Ala Tyr Asp Ile Leu Lys
            180                 185                 190

Arg Gly Ala Gly Phe Thr Asp Lys Glu Ile Gly Asp Val Phe Thr Gln
        195                 200                 205

Trp Asn Lys Gly Val Leu Asp Ser Phe Leu Ile Glu Ile Thr Arg Asp
    210                 215                 220
```

```
Ile Leu Tyr Phe Asn Asp Asp Asp Gly Thr Pro Leu Val Glu Lys Ile
225                 230                 235                 240

Leu Asp Thr Ala Gly Gln Lys Gly Thr Gly Lys Trp Thr Ala Ile Asn
                245                 250                 255

Ala Leu Asp Leu Gly Met Pro Val Thr Leu Ile Gly Glu Ala Val Phe
            260                 265                 270

Ala Arg Thr Leu Ser Ala Ile Lys Pro Glu Arg Val Arg Ala Ser Lys
        275                 280                 285

Ile Leu Thr Gly Pro Val Pro Ala Phe Lys Gly Asp Lys Lys Glu Leu
    290                 295                 300

Val Asp Gln Leu Glu Gln Ala Leu Tyr Ala Ser Lys Ile Ile Ser Tyr
305                 310                 315                 320

Ala Gln Gly Phe Met Leu Ile Arg Glu Ala Gly Arg Glu Tyr Gly Trp
                325                 330                 335

Thr Leu Asn Asn Pro Ala Ile Ala Leu Met Trp Arg Gly Gly Cys Ile
            340                 345                 350

Ile Arg Ser Val Phe Leu Ala Asp Ile Thr Arg Ala Tyr Arg Gln Lys
        355                 360                 365

Pro Asp Leu Glu Asn Leu Leu Phe Asp Glu Phe Phe His Thr Ala Ile
    370                 375                 380

Asp Lys Ala Gln Pro Ser Trp Arg Gln Thr Val Ala Asn Ala Ala Leu
385                 390                 395                 400

Trp Gly Ile Pro Thr Pro Ala Phe Ser Thr Ala Leu Ser Phe Tyr Asp
                405                 410                 415

Gly Tyr Arg Ser Glu Arg Leu Pro Ala Asn Leu Leu Gln Ala Gln Arg
            420                 425                 430

Asp Tyr Phe Gly Ala His Thr Phe His Ile Leu Pro Glu Phe Ser Ser
        435                 440                 445

Glu Lys Tyr Pro Lys Asp Thr Asp Val His Val Asn Trp Thr Gly Arg
    450                 455                 460

Gly Gly Asn Val Ser Ala Ser Thr Tyr Leu Ala
465                 470                 475
```

<210> SEQ ID NO 31
<211> LENGTH: 1121
<212> TYPE: DNA
<213> ORGANISM: Lipomyces starkeyi
<220> FEATURE:
<221> NAME/KEY: Intron
<222> LOCATION: (42)..(94)

<400> SEQUENCE: 31

```
atgcttaacc tcaaagtatc tgttatcggt tctggcaact ggtaggcgcc tcctttttca     60

attcattaaa ttgctttact gactgtctcc ataggggcag cgccattgcg aaaatagtgg    120

ccgagaacgc ggctgagaac agcgacattt tcgagaccga cgttcgcatg tgggttttcg    180

aggagcttgt tgctggccag aagctcaccg aaattatcaa tacccagcac gagaacgtca    240

agtacttgcc aggcatcaaa ctgccgtcca acgtcgtggc tgtgccagac cttttggacg    300

ccgtcaagga tgccaacctc ttagtcttca acgtgcctca tcagtttctt ccacggatat    360

gtagccagct gaaaggcaaa gtgccgtcca ccgtcagagc tgtgtcttgc atcaaaggtg    420

tcgaggtttc tggcgatggc atcaccatca tcgcagacta tatctctcag gaactcggca    480

tttactgcgg tgccttgtct ggcgccaatc ttgctcccga agttgcgcaa gagaaatttt    540

ccgagacgac aatcgcgtac aaagttcccg atccaagcga ctccattgac gcacgcgtcg    600
```

```
taaggacgct cttccacaga ccttacttcc acgtaaacgt cgttggtgat gtcgccggtg    660

tgtctctttg tggtgcttta aaaaacattg tggcattggc atcaggattt gtagacggaa    720

tggcatgggg cgataatgcc aaggctgcca ttattcgaag aggattgtta gagatgacca    780

agtttggccg tgaattcttc ccggaatgca atgccagtac cttcaccgaa gaatcatgtg    840

gtgttgccga tgtcattact tcctgctctg gtgggcgcaa taacaagctt ggtgcggcga    900

tgattaagac caggcgaccc atttttgagc ttgaggaaga gttgctcaag ggtcagaagg    960

ctcaaggagt tacgactgcc caggaggtgc acgaattttt ggagcggcgg ggcaagttgg   1020

aagacttccc tcttttcacc gcagtccacg acattatttt caacggactc gacagctatg   1080

ctctgccgca gattctcgaa gatgtcgagc agaagttcta a                       1121
```

<210> SEQ ID NO 32
<211> LENGTH: 355
<212> TYPE: PRT
<213> ORGANISM: Lipomyces starkeyi

<400> SEQUENCE: 32

```
Met Leu Asn Leu Lys Val Ser Val Ile Gly Ser Gly Asn Trp Gly Ser
1               5                   10                  15

Ala Ile Ala Lys Ile Val Ala Glu Asn Ala Ala Glu Asn Ser Asp Ile
            20                  25                  30

Phe Glu Thr Asp Val Arg Met Trp Val Phe Glu Glu Leu Val Ala Gly
        35                  40                  45

Gln Lys Leu Thr Glu Ile Ile Asn Thr Gln His Glu Asn Val Lys Tyr
    50                  55                  60

Leu Pro Gly Ile Lys Ser Pro Ser Asn Val Val Ala Val Pro Asp Leu
65                  70                  75                  80

Leu Asp Ala Val Lys Asp Ala Asn Leu Leu Val Phe Asn Val Pro His
                85                  90                  95

Gln Phe Leu Pro Arg Ile Cys Ser Gln Ser Lys Gly Lys Val Pro Ser
            100                 105                 110

Thr Val Arg Ala Val Ser Cys Ile Lys Gly Val Glu Val Ser Gly Asp
        115                 120                 125

Gly Ile Thr Ile Ile Ala Asp Tyr Ile Ser Gln Glu Leu Gly Ile Tyr
    130                 135                 140

Cys Gly Ala Leu Ser Gly Ala Asn Leu Ala Pro Glu Val Ala Gln Glu
145                 150                 155                 160

Lys Phe Ser Glu Thr Thr Ile Ala Tyr Lys Val Pro Asp Pro Ser Asp
                165                 170                 175

Ser Ile Asp Ala Arg Val Val Arg Thr Leu Phe His Arg Pro Tyr Phe
            180                 185                 190

His Val Asn Val Val Gly Asp Val Ala Gly Val Ser Leu Cys Gly Ala
        195                 200                 205

Leu Lys Asn Ile Val Ala Leu Ala Ser Gly Phe Val Asp Gly Met Ala
    210                 215                 220

Trp Gly Asp Asn Ala Lys Ala Ala Ile Ile Arg Arg Gly Leu Leu Glu
225                 230                 235                 240

Met Thr Lys Phe Gly Arg Glu Phe Phe Pro Glu Cys Asn Ala Ser Thr
                245                 250                 255

Phe Thr Glu Glu Ser Cys Gly Val Ala Asp Val Ile Thr Ser Cys Ser
            260                 265                 270

Gly Gly Arg Asn Asn Lys Leu Gly Ala Ala Met Ile Lys Thr Arg Arg
```

```
        275                 280                 285

Pro Ile Phe Glu Leu Glu Glu Glu Leu Leu Lys Gly Gln Lys Ala Gln
    290                 295                 300

Gly Val Thr Thr Ala Gln Glu Val His Glu Phe Leu Glu Arg Arg Gly
305                 310                 315                 320

Lys Leu Glu Asp Phe Pro Leu Phe Thr Ala Val His Asp Ile Ile Phe
                325                 330                 335

Asn Gly Leu Asp Ser Tyr Ala Ser Pro Gln Ile Leu Glu Asp Val Glu
            340                 345                 350

Gln Lys Phe
        355


<210> SEQ ID NO 33
<211> LENGTH: 1930
<212> TYPE: DNA
<213> ORGANISM: Lipomyces starkeyi
<220> FEATURE:
<221> NAME/KEY: Intron
<222> LOCATION: (67)..(121)
<220> FEATURE:
<221> NAME/KEY: Intron
<222> LOCATION: (398)..(447)
<220> FEATURE:
<221> NAME/KEY: Intron
<222> LOCATION: (598)..(652)
<220> FEATURE:
<221> NAME/KEY: Intron
<222> LOCATION: (852)..(902)

<400> SEQUENCE: 33

atggctccta aatcgtcgac tcgtgtgcca ttgtcggtta aagggcccat tgattgtcca      60

tatgaggtaa ttccagatca actctgagat gctgtccaac tactaacaaa ccatgattca     120

gggcaaagaa atgctcaacc tgccgcagtt caaccgagga acagctttca cagcagagga     180

acgtgacctg tttaatcttg tggggaatct tcccgctgcc ctgcagactc tgcagaatca     240

agtcgacaga gcgtacgatc agtattcctc gatctcgacg gctttgggga agaatacctt     300

tttgatgagt ttaaaggtgc aaaatgaggt cctgtatttt aagttgttgc aggatcattt     360

gaaggagatg tttagtataa tttacacgcc gactgaggta ggatcaaatt tagttttgtt     420

ggtaagatat tgctgaacga tgagtagagt gaagctattg agcattattc gagactgttt     480

agacgcccgg agggctgctt tctgaacatc aaccaccctg agtatatcga acggtctctg     540

gcggcgtggg gtacagagga ggacattgac tatatcatcg ttagtgacgg cgaggaggta     600

tgacatgatt ttgttctaga gttttcgaaa tgcactcatg ccggttatgc agatcctcgg     660

aattggcgat caaggagtcg gagctatcgg aatctcaagt gcaaaagctg tgcttatgac     720

tctatgcgcc ggcgtccatc catcgagatg cattccagtc gcgcttgatg ttggcacgga     780

taacgagcag ttgctcgagg atgagctata ccttggcaat aggcacaaca gagtccgcgg     840

cgggcgatat ggtgagctga tcgaatattc taagctttcg tgacgtgcta atttatttat     900

agataaattt gtggacgatt ttgtgcaatg tgtcaagaaa ctgtatcctc gtgcggttct     960

ccactttgag gatttcggac tacctaatgc cagaagacta ctcgacacct acagaccacg    1020

actagcgtgc tttaatgacg atgttcaggg tactggcgct gtcactttgg ccgcactctc    1080

atcagccgtc cgggtggccg gaattgactt ccgagacctc agaacggtga tctttggagc    1140

gggaacagca ggaactggca tcgcggatca gctgcgcgac tttctcaaca cacaagggat    1200

ttccaagcaa caagttatcg atcatatttg gcttgttgac aagccaggat tgcttcttaa    1260
```

```
atcaatgcat gataaactta catcagcgca acgtccgtac gctgcgtcgg acgatcgttg   1320

gaaagagatc gacaccaagt cattgtcaga aatcgtgaag aaagtgaagc cgcatgtgtt   1380

gattgggtgc tccacgaagc caaaagcatt caacgaagca gttcttcgtg agatggccaa   1440

acacgttgaa cggccgattg tctttcccct gagcaatccc acgcgactac acgaagcgac   1500

gccggcggag atttttaagt acacggacgg taaggcgctg gtggccaccg gttcgccgtt   1560

tgatcctgtc gatggcaagg aaattgccga gaacaataac tgtttcgtgt accctggtat   1620

tggcatgggg tcgatcttga gcagggccga tagagtcaca gagacgatga ttgcggcagt   1680

cgtgaaggag cttgcgtcgt tggcgccgtc ggagaaagat cctactggcg cactcttgcc   1740

tgatgtggca gatattagag atatttctgc gaagatcgcg actgcagtag tgttgcaagc   1800

gttagaggag ggaactgcga gagtggaaga gattgaaggt atcaaagttc cacgagacag   1860

agatcactgc ctggaatggg tcaaagagca gatgtggaaa cctgagtata gaccattgag   1920

aaaggtgtga                                                          1930
```

<210> SEQ ID NO 34
<211> LENGTH: 572
<212> TYPE: PRT
<213> ORGANISM: Lipomyces starkeyi

<400> SEQUENCE: 34

```
Met Ala Pro Lys Ser Ser Thr Arg Val Pro Leu Ser Val Lys Gly Pro
1               5                   10                  15

Ile Asp Cys Pro Tyr Glu Gly Lys Glu Met Leu Asn Leu Pro Gln Phe
            20                  25                  30

Asn Arg Gly Thr Ala Phe Thr Ala Glu Glu Arg Asp Leu Phe Asn Leu
        35                  40                  45

Val Gly Asn Leu Pro Ala Ala Leu Gln Thr Leu Gln Asn Gln Val Asp
    50                  55                  60

Arg Ala Tyr Asp Gln Tyr Ser Ser Ile Ser Thr Ala Leu Gly Lys Asn
65                  70                  75                  80

Thr Phe Leu Met Ser Leu Lys Val Gln Asn Glu Val Leu Tyr Phe Lys
                85                  90                  95

Leu Leu Gln Asp His Leu Lys Glu Met Phe Ser Ile Ile Tyr Thr Pro
            100                 105                 110

Thr Glu Ser Glu Ala Ile Glu His Tyr Ser Arg Leu Phe Arg Arg Pro
        115                 120                 125

Glu Gly Cys Phe Leu Asn Ile Asn His Pro Glu Tyr Ile Glu Arg Ser
    130                 135                 140

Leu Ala Ala Trp Gly Thr Glu Glu Asp Ile Asp Tyr Ile Ile Val Ser
145                 150                 155                 160

Asp Gly Glu Glu Ile Leu Gly Ile Gly Asp Gln Gly Val Gly Ala Ile
                165                 170                 175

Gly Ile Ser Ser Ala Lys Ala Val Leu Met Thr Leu Cys Ala Gly Val
            180                 185                 190

His Pro Ser Arg Cys Ile Pro Val Ala Leu Asp Val Gly Thr Asp Asn
        195                 200                 205

Glu Gln Leu Leu Glu Asp Glu Leu Tyr Leu Gly Asn Arg His Asn Arg
    210                 215                 220

Val Arg Gly Gly Arg Tyr Asp Lys Phe Val Asp Asp Phe Val Gln Cys
225                 230                 235                 240

Val Lys Lys Leu Tyr Pro Arg Ala Val Leu His Phe Glu Asp Phe Gly
                245                 250                 255
```

```
Leu Pro Asn Ala Arg Arg Leu Leu Asp Thr Tyr Arg Pro Arg Leu Ala
            260                 265                 270

Cys Phe Asn Asp Asp Val Gln Gly Thr Gly Ala Val Thr Leu Ala Ala
        275                 280                 285

Leu Ser Ser Ala Val Arg Val Ala Gly Ile Asp Phe Arg Asp Leu Arg
    290                 295                 300

Thr Val Ile Phe Gly Ala Gly Thr Ala Gly Thr Gly Ile Ala Asp Gln
305                 310                 315                 320

Leu Arg Asp Phe Leu Asn Thr Gln Gly Ile Ser Lys Gln Gln Val Ile
                325                 330                 335

Asp His Ile Trp Leu Val Asp Lys Pro Gly Leu Leu Leu Lys Ser Met
            340                 345                 350

His Asp Lys Leu Thr Ser Ala Gln Arg Pro Tyr Ala Ala Ser Asp Asp
        355                 360                 365

Arg Trp Lys Glu Ile Asp Thr Lys Ser Leu Ser Glu Ile Val Lys Lys
    370                 375                 380

Val Lys Pro His Val Leu Ile Gly Cys Ser Thr Lys Pro Lys Ala Phe
385                 390                 395                 400

Asn Glu Ala Val Leu Arg Glu Met Ala Lys His Val Glu Arg Pro Ile
                405                 410                 415

Val Phe Pro Leu Ser Asn Pro Thr Arg Leu His Glu Ala Thr Pro Ala
            420                 425                 430

Glu Ile Phe Lys Tyr Thr Asp Gly Lys Ala Leu Val Ala Thr Gly Ser
        435                 440                 445

Pro Phe Asp Pro Val Asp Gly Lys Glu Ile Ala Glu Asn Asn Asn Cys
    450                 455                 460

Phe Val Tyr Pro Gly Ile Gly Met Gly Ser Ile Leu Ser Arg Ala Asp
465                 470                 475                 480

Arg Val Thr Glu Thr Met Ile Ala Ala Val Val Lys Glu Leu Ala Ser
                485                 490                 495

Leu Ala Pro Ser Glu Lys Asp Pro Thr Gly Ala Leu Leu Pro Asp Val
            500                 505                 510

Ala Asp Ile Arg Asp Ile Ser Ala Lys Ile Ala Thr Ala Val Val Leu
        515                 520                 525

Gln Ala Leu Glu Glu Gly Thr Ala Arg Val Glu Glu Ile Glu Gly Ile
    530                 535                 540

Lys Val Pro Arg Asp Arg Asp His Cys Leu Glu Trp Val Lys Glu Gln
545                 550                 555                 560

Met Trp Lys Pro Glu Tyr Arg Pro Leu Arg Lys Val
                565                 570
```

<210> SEQ ID NO 35
<211> LENGTH: 1542
<212> TYPE: DNA
<213> ORGANISM: Marinobacter aquaeolei

<400> SEQUENCE: 35

```
atggcaatac agcaggtaca tcacgctgac acttcatcat caaaggtgct cggacagctc      60

cgtggcaagc gggttctgat caccggtacc actggctttc tgggcaaggt ggtcctcgaa     120

aggctgattc gggcggtgcc tgatatcggc gcaatttacc tgctgatccg gggcaataaa     180

cggcatccgg atgctcgttc ccgtttcctg gaagaaattg ccacctcctc ggtgtttgac     240

cgtcttcgcg aggccgattc agagggattt gacgcctttc tggaagagcg cattcactgc     300
```

```
gtgaccggtg aggtgaccga agcgggtttc gggatagggc aggaagacta tcgcaaactc    360

gccaccgaac tggatgcggt gatcaactcc gctgcaagcg tgaatttccg tgaagagctc    420

gacaaggcgc tggccatcaa caccctgtgc cttcggaata ttgccggcat ggtggatttg    480

aatccgaagc ttgcggtcct gcaggtctcc acctgctatg tcaatggcat gaactcgggg    540

caggtaaccg aatcggtgat caagccggca ggcgaggccg tgccgcgttc cccggacggc    600

ttctatgaga tagaagagct tgttcgcctg cttcaggata aaattgaaga cgttcaggcc    660

cgttattccg gcaaagtgct ggagaggaag ctggtggacc tggggattcg ggaagccaac    720

cgctatggct ggagcgatac ctacaccttt accaagtggc tgggcgaaca gttgctgatg    780

aaggcgttaa acgggcgcac gctgaccatt ctgcgtcctt cgattatcga aagtgccctg    840

gaggaaccag cgcccggctg gattgagggg gtgaaggtgg cagatgccat catcctggct    900

tacgcacggg aaaaagtcac cctcttcccg ggcaaacgct ccggtatcat cgatgtgatt    960

ccagtggacc tggtggccaa ctccatcatc ctttccctgg cggaagctct tggagaaccc   1020

ggtcgacgtc gcatctatca atgttgcagc gggggcggca atccaatctc cctgggtgag   1080

ttcatcgatc atctcatggc ggaatcaaaa gccaattacg ctgcctacga tcacctgttc   1140

taccggcagc ccagcaagcc gtttctggcg gttaaccggg cgctgtttga tttggtgatc   1200

agtggtgttc gcttaccgct ctccctgacg gaccgtgtgc tcaaattact gggaaattcc   1260

cgggacctga aaatgctcag gaatctggat accacccagt cgctggcaac catttttggt   1320

ttctacaccg cgccggatta tatcttccgg aacgatgagc tgatggcgct ggcgaaccgg   1380

atgggtgagg tcgataaagg gctgttcccg gtggatgccc gcctgattga ctgggagctc   1440

tacctgcgca agattcacct ggccgggctc aatcgctatg ccctgaaaga acgaaaggtg   1500

tacagtctga aaaccgcgcg ccagcgcaaa aaagctgcct ga                       1542
```

<210> SEQ ID NO 36
<211> LENGTH: 513
<212> TYPE: PRT
<213> ORGANISM: Marinobacter aquaeolei

<400> SEQUENCE: 36

```
Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
        35                  40                  45

Ile Gly Ala Ile Tyr Leu Leu Ile Arg Gly Asn Lys Arg His Pro Asp
    50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140

Ala Ile Asn Thr Leu Cys Leu Arg Asn Ile Ala Gly Met Val Asp Leu
145                 150                 155                 160
```

```
Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
            180                 185                 190

Ala Val Pro Arg Ser Pro Asp Gly Phe Tyr Glu Ile Glu Glu Leu Val
        195                 200                 205

Arg Leu Leu Gln Asp Lys Ile Glu Asp Val Gln Ala Arg Tyr Ser Gly
    210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285

Glu Gly Val Lys Val Ala Asp Ala Ile Ile Leu Ala Tyr Ala Arg Glu
    290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Arg Ile Tyr Gln Cys Cys Ser Gly Gly
            340                 345                 350

Gly Asn Pro Ile Ser Leu Gly Glu Phe Ile Asp His Leu Met Ala Glu
        355                 360                 365

Ser Lys Ala Asn Tyr Ala Ala Tyr Asp His Leu Phe Tyr Arg Gln Pro
    370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
            420                 425                 430

Gln Ser Leu Ala Thr Ile Phe Gly Phe Tyr Thr Ala Pro Asp Tyr Ile
        435                 440                 445

Phe Arg Asn Asp Glu Leu Met Ala Leu Ala Asn Arg Met Gly Glu Val
    450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510

Ala
```

<210> SEQ ID NO 37
<211> LENGTH: 1514
<212> TYPE: DNA
<213> ORGANISM: Lipomyces starkeyi
<220> FEATURE:
<221> NAME/KEY: Intron
<222> LOCATION: (329)..(381)

<400> SEQUENCE: 37

```
atgactgcca gtgctgagac aacgtccgcg cagcctgtcg tcgagtcggc tcgcgcaagg     60

ccacccagat caagctcaac gtcgccttct cgttcggttg gtagtgctgc gtcgactgcg    120

aagcaagcgt ctcctacatt cgtccacatc tccgagcaac cgttcactct ccagaactgg    180

tacaagcaca tcagctggct caatgtcacg ctgatcatct tcatccctgt cattggctgc    240

actaccgcgg ttttcactcc tctgcaatct aagactgcca tccttgcctt tgtctactac    300

gccctgacgg gcctcggtat cactgcgggt atgtattgct attatactgc agtatatgat    360

tagagtgaac taattgatca ggttatcacc gcctctggtc gcaccgtgct tacagtgccc    420

gtcttcctct ccgtattcta ctcgctgctt tcggcggcgg tgctgttgag ggttccattc    480

gctggtggtc cgctggtcac cgtgtccatc acagattcac cgatactgag aaggacccct    540

actctgtccg caagggtctg ctctattctc acatgggctg gatggtgttt ctccacaacc    600

ccaagaagtc cggccgggtc gatatcaccg acttgaacgc tgaccctgtc gtcagatggc    660

agcacaagaa ctacattctc gtccttctct ttatgggttt catcttcccc atggtagttg    720

ccggcctcgg atggggtgac tggaagggtg gtctcatctg ggctggcatt gtccgtttga    780

cagttgtcca ccatgccact tttgtgtca actcgctcgc tcactggctc ggtgaccagc    840

ctttcgacga ccgccgctct ccgcgtgacc acttcttgac tgccatcgtt acgttcggcg    900

agggctatca caacttccac catgagttcc cctctgacta ccgtaacgcc ataagatggt    960

atcagtatga tcccactaag tggctcatct ggttcctcaa gaagatcggc tttgcttatg   1020

accttaagac cttctctcac aatgccatcc agcaaggcct cgtccagcag aggcagaaaa   1080

agctcgacaa gtggcgcgca cgtcttaact ggggtgttcc tctcgagcag ctcccggtca   1140

tggaatttga agagtaccag gagcaggcca agacgcgtgc gctcgtcctc attgctggtg   1200

ttgtccacga tgtcaccaac tttattgagc agcatcctgg tggaaaggct ctgatccagt   1260

caggtattgg caaggatgcc accgctgtct tcaatggcgg tgtctacgac cactccaatg   1320

ctgcccacaa cctgctcggt accatgcgtg ttggtgtcat tcgcggcggc atggaagtcg   1380

aggtctggaa gatggctcag cgagagaata aggagtcaac gatcaagtcc gattcgaata   1440

atgccaatat cgtccgtgca ggttctcagg caacccggat acaagctccc atccagggcg   1500

ctggtgccgc ttag                                                     1514
```

<210> SEQ ID NO 38
<211> LENGTH: 486
<212> TYPE: PRT
<213> ORGANISM: Lipomyces starkeyi

<400> SEQUENCE: 38

```
Met Thr Ala Ser Ala Glu Thr Thr Ser Ala Gln Pro Val Val Glu Ser
1               5                   10                  15

Ala Arg Ala Arg Pro Pro Arg Ser Ser Ser Thr Ser Pro Ser Arg Ser
            20                  25                  30

Val Gly Ser Ala Ala Ser Thr Ala Lys Gln Ala Ser Pro Thr Phe Val
        35                  40                  45

His Ile Ser Glu Gln Pro Phe Thr Leu Gln Asn Trp Tyr Lys His Ile
    50                  55                  60

Ser Trp Leu Asn Val Thr Leu Ile Ile Phe Ile Pro Val Ile Gly Cys
65                  70                  75                  80

Thr Thr Ala Val Phe Thr Pro Leu Gln Ser Lys Thr Ala Ile Leu Ala
                85                  90                  95
```

```
Phe Val Tyr Tyr Ala Leu Thr Gly Leu Gly Ile Thr Ala Gly Tyr His
            100                 105                 110

Arg Leu Trp Ser His Arg Ala Tyr Ser Ala Arg Leu Pro Leu Arg Ile
        115                 120                 125

Leu Leu Ala Ala Phe Gly Gly Gly Ala Val Glu Gly Ser Ile Arg Trp
    130                 135                 140

Trp Ser Ala Gly His Arg Val His His Arg Phe Thr Asp Thr Glu Lys
145                 150                 155                 160

Asp Pro Tyr Ser Val Arg Lys Gly Leu Leu Tyr Ser His Met Gly Trp
                165                 170                 175

Met Val Phe Leu His Asn Pro Lys Lys Ser Gly Arg Val Asp Ile Thr
            180                 185                 190

Asp Leu Asn Ala Asp Pro Val Val Arg Trp Gln His Lys Asn Tyr Ile
        195                 200                 205

Leu Val Leu Leu Phe Met Gly Phe Ile Phe Pro Met Val Val Ala Gly
    210                 215                 220

Leu Gly Trp Gly Asp Trp Lys Gly Gly Leu Ile Trp Ala Gly Ile Val
225                 230                 235                 240

Arg Leu Thr Val Val His His Ala Thr Phe Cys Val Asn Ser Leu Ala
                245                 250                 255

His Trp Leu Gly Asp Gln Pro Phe Asp Asp Arg Arg Ser Pro Arg Asp
            260                 265                 270

His Phe Leu Thr Ala Ile Val Thr Phe Gly Glu Gly Tyr His Asn Phe
        275                 280                 285

His His Glu Phe Pro Ser Asp Tyr Arg Asn Ala Ile Arg Trp Tyr Gln
    290                 295                 300

Tyr Asp Pro Thr Lys Trp Leu Ile Trp Phe Leu Lys Lys Ile Gly Phe
305                 310                 315                 320

Ala Tyr Asp Leu Lys Thr Phe Ser His Asn Ala Ile Gln Gln Gly Leu
                325                 330                 335

Val Gln Gln Arg Gln Lys Lys Leu Asp Lys Trp Arg Ala Arg Leu Asn
            340                 345                 350

Trp Gly Val Pro Leu Glu Gln Leu Pro Val Met Glu Phe Glu Glu Tyr
        355                 360                 365

Gln Glu Gln Ala Lys Thr Arg Ala Leu Val Leu Ile Ala Gly Val Val
    370                 375                 380

His Asp Val Thr Asn Phe Ile Glu Gln His Pro Gly Gly Lys Ala Leu
385                 390                 395                 400

Ile Gln Ser Gly Ile Gly Lys Asp Ala Thr Ala Val Phe Asn Gly Gly
                405                 410                 415

Val Tyr Asp His Ser Asn Ala Ala His Asn Leu Leu Gly Thr Met Arg
            420                 425                 430

Val Gly Val Ile Arg Gly Gly Met Glu Val Glu Val Trp Lys Met Ala
        435                 440                 445

Gln Arg Glu Asn Lys Glu Ser Thr Ile Lys Ser Asp Ser Asn Asn Ala
    450                 455                 460

Asn Ile Val Arg Ala Gly Ser Gln Ala Thr Arg Ile Gln Ala Pro Ile
465                 470                 475                 480

Gln Gly Ala Gly Ala Ala
                485
```

<210> SEQ ID NO 39
<211> LENGTH: 1936
<212> TYPE: DNA

<213> ORGANISM: Lipomyces starkeyi
<220> FEATURE:
<221> NAME/KEY: Intron
<222> LOCATION: (164)..(224)
<220> FEATURE:
<221> NAME/KEY: Intron
<222> LOCATION: (326)..(382)

<400> SEQUENCE: 39

```
atggcttcct cagttcctca agctcccgtc acttccctac tctcggaggc tcgcggtaag     60

accgtacagc gtgataataa tgaattaccc ggtgctcgtt ccattgacac cgaggctacg    120

ttccagcatt ggatctacga catggttatc tggagtttat caggtgtgta caccgtatgc    180

tttaattagc aagccgatac tgccatatta acttgcgcat tcagtcgtgt tcgatctatt    240

tttccgtgaa atccgcccga ggggcgcata ccgaatcccg agacatggtc cgattatctt    300

tgttgccgct ccgcacgcca atcaggtgag tcttggccgc aatgatacca tcatacgacg    360

tatggagcta acacgaagac agtttattga ccccatcatg ctcatgcgtc aaattcgaat    420

tgaagcaggt cgcagaatat cgtttctggc ggccgaaagt tcaatgcacc gcaaattcgt    480

cggcactgtc gctcgatcag tttcttcaat tccggttgct agagctcagg acttggcgtc    540

tcacggaact ggtttgatct atattgaaga taaggagaag ccgttggtta tcaagggcca    600

gggaaccaag tttatgaagg aatgcagtca aggcgggttg ataatgttgg cgaagtcact    660

tggcagcgcc gagattgata gcatcgtgtc tgatgtcgag ttgattttgc gccggccttt    720

caaggaggag aaagccatcg agtatttatt ttccggtccg tccaagttta aaaaagcgcc    780

aaaggtcgac cagtcacaga tgtaccagaa ggtcttcgaa agactgaatg acggtggatg    840

tatcggtatc tttcccgaag gcggttcaca tgaccgacca gacttattac cactaaaagc    900

cggtgtcgcg gttatggctc ttggtgccct agagcagaac ccagagtgcg acatcagaat    960

tgtcccttgc ggtatgaact acttccaccc tcacaaattc cgatcacgag cagttattga   1020

gtttggtcct ccacttaacg ttcccaagga gcttgtcaag acgtacagtg aaggaaataa   1080

gagagattct atacaccagc tcttggaaat gattcatagc gcgttgttgg ctgttactgt   1140

tacctcgccg gattacgaca cattgatggt tattcaagcg gctcgacgac tatacaaacc   1200

cgcacacaag aaaatcccgc tatcgttggt tatcgagatg aatcggcggt tagtcatagg   1260

gtatacacat tacaaggacg atccacggat tattcatctt cgggaagccg ttgcgaacta   1320

taacaagcag ttgagacatt tgggaatcct ggatcatcag gttgagtacg caacattgcc   1380

aataccggag attgtcggaa aattagtcta ccggtcgctg aaactattta ttctggcatt   1440

gggcgctctg cccggagcta ttcttttcgc accggtattc atcgcgacca agatgatttc   1500

caagaagaag gcagccgaag cgttgaaggc gtcgaccgtg aagatcgctg ccagggatgt   1560

tgtcgcgaca tggaagattc tcgtagcgct gggtctcgcg ccgacgctat actggttcta   1620

cgcacttttg gcgacatggg cgacgtggaa gtacgatctt gttcctcaag tgcgaccggt   1680

gtggctcgtg actcttgcgg ctatgattat tttcccggcg atcacgtacg ctgcacttag   1740

aattggagag atcggaatgg atattttcaa gtcattaaag ccgcttgtga catgcttgaa   1800

cccgaataat ttgaacacga ttgcgaagtt gcggattacg agagaggaat tgtcgaagga   1860

agtcaccgag atgattaatt cattaggccc ggatgtcttt ccagagttcg actctcaccg   1920

gttaatgcag agttag                                                   1936
```

<210> SEQ ID NO 40
<211> LENGTH: 605

<212> TYPE: PRT
<213> ORGANISM: Lipomyces starkeyi

<400> SEQUENCE: 40

```
Met Ala Ser Ser Val Pro Gln Ala Pro Val Thr Ser Leu Leu Ser Glu
1               5                   10                  15

Ala Arg Gly Lys Thr Val Gln Arg Asp Asn Asn Glu Leu Pro Gly Ala
            20                  25                  30

Arg Ser Ile Asp Thr Glu Ala Thr Phe Gln His Trp Ile Tyr Asp Met
        35                  40                  45

Val Ile Trp Ser Leu Ser Val Val Phe Asp Leu Phe Phe Arg Glu Ile
    50                  55                  60

Arg Pro Arg Gly Ala Tyr Arg Ile Pro Arg His Gly Pro Ile Ile Phe
65                  70                  75                  80

Val Ala Ala Pro His Ala Asn Gln Phe Ile Asp Pro Ile Met Leu Met
                85                  90                  95

Arg Gln Ile Arg Ile Glu Ala Gly Arg Arg Ile Ser Phe Leu Ala Ala
            100                 105                 110

Glu Ser Ser Met His Arg Lys Phe Val Gly Thr Val Ala Arg Ser Val
        115                 120                 125

Ser Ser Ile Pro Val Ala Arg Ala Gln Asp Leu Ala Ser His Gly Thr
    130                 135                 140

Gly Leu Ile Tyr Ile Glu Asp Lys Glu Lys Pro Leu Val Ile Lys Gly
145                 150                 155                 160

Gln Gly Thr Lys Phe Met Lys Glu Cys Ser Gln Gly Gly Leu Ile Met
                165                 170                 175

Leu Ala Lys Ser Leu Gly Ser Ala Glu Ile Asp Ser Ile Val Ser Asp
            180                 185                 190

Val Glu Leu Ile Leu Arg Arg Pro Phe Lys Glu Glu Lys Ala Ile Glu
        195                 200                 205

Tyr Leu Phe Ser Gly Pro Ser Lys Phe Lys Lys Ala Pro Lys Val Asp
    210                 215                 220

Gln Ser Gln Met Tyr Gln Lys Val Phe Glu Arg Leu Asn Asp Gly Gly
225                 230                 235                 240

Cys Ile Gly Ile Phe Pro Glu Gly Gly Ser His Asp Arg Pro Asp Leu
                245                 250                 255

Leu Pro Leu Lys Ala Gly Val Ala Val Met Ala Leu Gly Ala Leu Glu
            260                 265                 270

Gln Asn Pro Glu Cys Asp Ile Arg Ile Val Pro Cys Gly Met Asn Tyr
        275                 280                 285

Phe His Pro His Lys Phe Arg Ser Arg Ala Val Ile Glu Phe Gly Pro
    290                 295                 300

Pro Leu Asn Val Pro Lys Glu Leu Val Lys Thr Tyr Ser Glu Gly Asn
305                 310                 315                 320

Lys Arg Asp Ser Ile His Gln Leu Leu Glu Met Ile His Ser Ala Leu
                325                 330                 335

Leu Ala Val Thr Val Thr Ser Pro Asp Tyr Asp Thr Leu Met Val Ile
            340                 345                 350

Gln Ala Ala Arg Arg Leu Tyr Lys Pro Ala His Lys Lys Ile Pro Leu
        355                 360                 365

Ser Leu Val Ile Glu Met Asn Arg Arg Leu Val Ile Gly Tyr Thr His
    370                 375                 380

Tyr Lys Asp Asp Pro Arg Ile Ile His Leu Arg Glu Ala Val Ala Asn
385                 390                 395                 400
```

```
Tyr Asn Lys Gln Leu Arg His Leu Gly Ile Leu Asp His Gln Val Glu
                405                 410                 415

Tyr Ala Thr Leu Pro Ile Pro Glu Ile Val Gly Lys Leu Val Tyr Arg
            420                 425                 430

Ser Leu Lys Leu Phe Ile Leu Ala Leu Gly Ala Leu Pro Gly Ala Ile
        435                 440                 445

Leu Phe Ala Pro Val Phe Ile Ala Thr Lys Met Ile Ser Lys Lys Lys
    450                 455                 460

Ala Ala Glu Ala Leu Lys Ala Ser Thr Val Lys Ile Ala Ala Arg Asp
465                 470                 475                 480

Val Val Ala Thr Trp Lys Ile Leu Val Ala Leu Gly Leu Ala Pro Thr
                485                 490                 495

Leu Tyr Trp Phe Tyr Ala Leu Leu Ala Thr Trp Ala Thr Trp Lys Tyr
            500                 505                 510

Asp Leu Val Pro Gln Val Arg Pro Val Trp Leu Val Thr Leu Ala Ala
        515                 520                 525

Met Ile Ile Phe Pro Ala Ile Thr Tyr Ala Ala Leu Arg Ile Gly Glu
    530                 535                 540

Ile Gly Met Asp Ile Phe Lys Ser Leu Lys Pro Leu Val Thr Cys Leu
545                 550                 555                 560

Asn Pro Asn Asn Leu Asn Thr Ile Ala Lys Leu Arg Ile Thr Arg Glu
                565                 570                 575

Glu Leu Ser Lys Glu Val Thr Glu Met Ile Asn Ser Leu Gly Pro Asp
            580                 585                 590

Val Phe Pro Glu Phe Asp Ser His Arg Leu Met Gln Ser
        595                 600                 605
```

<210> SEQ ID NO 41
<211> LENGTH: 1213
<212> TYPE: DNA
<213> ORGANISM: Lipomyces starkeyi
<220> FEATURE:
<221> NAME/KEY: Intron
<222> LOCATION: (355)..(406)
<220> FEATURE:
<221> NAME/KEY: Intron
<222> LOCATION: (477)..(525)
<220> FEATURE:
<221> NAME/KEY: Intron
<222> LOCATION: (642)..(694)

<400> SEQUENCE: 41

```
atggccgcca gtgacgtcgt cctctcaggt ctcggtatcg taatcgcatt cacgatgagt      60

ttgaacatcc tcggtctcat ctacaggcca ctacaattct atggcaagtt cctgctatgc     120

tttctgagca tgtgcacatg tgcctcgtat ggtttccttg cgtccatttt gttgtcgctg     180

attggcaaga aagggttgag tcagtggacg gccggaaggg cgtttagtac gctgacgtgc     240

cctctgattg gcctcaagat cgatatcaag aacgaagaga ttttgagaaa gacgagacca     300

gctattatta ttgcgaatca tcagagtgaa ttggatgttc ttttattagg ccgggtatga     360

tgctagcgaa tatttatttt aacgttcgat gctgacacgt gtttagatat ttccaaaata     420

ctgcagtgtg actgcgaaga gtagtttgaa atatgtccca tttttgggat ggttcagtat     480

gttcttcggc tcgtttgcgt tagccatact aacatgagga tctagtgatg atcagcggca     540

ctgttttcat tgaccgccag aacagaggaa aggctatcaa ggctcttgat ggtgccatta     600

atgccatgaa gaagaataac caatgtgtct ttatcttccc tgtccgttat attccttctt     660
```

```
catttcaatg ttgctcatgc tgacttcatt acaggaaggc acaaggtcat atttcaccga    720

accagacatg ctgaagttca agcgtggagc gttccatctg gctatacagt caggcttccc    780

aattatcccc gtcgtgatct caaactactc gcatgtgttc aacttccgca aacgcattct    840

ccaagctgga acaatcgaca tccaagtcct cgatcctgtc acaactgaag gtatttcaaa    900

cgaagactta gacgacctcg tcgaaactac ccgcataaag atgcttaagg tgcttaagga    960

gatctcaccg aaagccgtaa aagagccgac tggtgatgtc gaagcggatg atactactct   1020

tttgtcagca tctggcaccg ctaatggatc tgacctcgtc ggcactattg acgatgacga   1080

tgtccttgaa ccgcgaataa cacgcgacac cgatgcttca gagatttcgg ccgcgttgtc   1140

cgagtctgcg accgaagaaa ctgatttgac accggatgtt tccaaagtta tcgagcttga   1200

cacccgaaac taa                                                      1213
```

<210> SEQ ID NO 42
<211> LENGTH: 352
<212> TYPE: PRT
<213> ORGANISM: Lipomyces starkeyi

<400> SEQUENCE: 42

```
Met Ala Ala Ser Asp Val Val Leu Ser Gly Leu Gly Ile Val Ile Ala
1               5                   10                  15

Phe Thr Met Ser Leu Asn Ile Leu Gly Leu Ile Tyr Arg Pro Leu Gln
            20                  25                  30

Phe Tyr Gly Lys Phe Ser Leu Cys Phe Ser Ser Met Cys Thr Cys Ala
        35                  40                  45

Ser Tyr Gly Phe Leu Ala Ser Ile Leu Leu Ser Ser Ile Gly Lys Lys
    50                  55                  60

Gly Leu Ser Gln Trp Thr Ala Gly Arg Ala Phe Ser Thr Ser Thr Cys
65                  70                  75                  80

Pro Ser Ile Gly Leu Lys Ile Asp Ile Lys Asn Glu Glu Ile Leu Arg
                85                  90                  95

Lys Thr Arg Pro Ala Ile Ile Ile Ala Asn His Gln Ser Glu Leu Asp
            100                 105                 110

Val Leu Leu Leu Gly Arg Ile Phe Pro Lys Tyr Cys Ser Val Thr Ala
        115                 120                 125

Lys Ser Ser Leu Lys Tyr Val Pro Phe Leu Gly Trp Phe Met Met Ile
    130                 135                 140

Ser Gly Thr Val Phe Ile Asp Arg Gln Asn Arg Gly Lys Ala Ile Lys
145                 150                 155                 160

Ala Leu Asp Gly Ala Ile Asn Ala Met Lys Lys Asn Asn Gln Cys Val
                165                 170                 175

Phe Ile Phe Pro Glu Gly Thr Arg Ser Tyr Phe Thr Glu Pro Asp Met
            180                 185                 190

Ser Lys Phe Lys Arg Gly Ala Phe His Ser Ala Ile Gln Ser Gly Phe
        195                 200                 205

Pro Ile Ile Pro Val Val Ile Ser Asn Tyr Ser His Val Phe Asn Phe
    210                 215                 220

Arg Lys Arg Ile Leu Gln Ala Gly Thr Ile Asp Ile Gln Val Leu Asp
225                 230                 235                 240

Pro Val Thr Thr Glu Gly Ile Ser Asn Glu Asp Leu Asp Asp Leu Val
                245                 250                 255

Glu Thr Thr Arg Ile Lys Met Leu Lys Val Leu Lys Glu Ile Ser Pro
            260                 265                 270
```

```
Lys Ala Val Lys Glu Pro Thr Gly Asp Val Glu Ala Asp Asp Thr Thr
        275                 280                 285

Leu Leu Ser Ala Ser Gly Thr Ala Asn Gly Ser Asp Leu Val Gly Thr
    290                 295                 300

Ile Asp Asp Asp Asp Val Leu Glu Pro Arg Ile Thr Arg Asp Thr Asp
305                 310                 315                 320

Ala Ser Glu Ile Ser Ala Ala Leu Ser Glu Ser Ala Thr Glu Glu Thr
                325                 330                 335

Asp Leu Thr Pro Asp Val Ser Lys Val Ile Glu Leu Asp Thr Arg Asn
            340                 345                 350


<210> SEQ ID NO 43
<211> LENGTH: 1832
<212> TYPE: DNA
<213> ORGANISM: Lipomyces starkeyi
<220> FEATURE:
<221> NAME/KEY: Intron
<222> LOCATION: (45)..(294)
<220> FEATURE:
<221> NAME/KEY: Intron
<222> LOCATION: (368)..(416)

<400> SEQUENCE: 43

atggctgata ctatcatctc ttccacgaag gcctccgaca ctgggtatgt gtgctctctc     60

ctaatcattc gcagccgcgc tctgccggcg cgagcagtcg gacggccttc ctccgtctac    120

tcgataagcc cgagttgtta gctacagcac ctcaattcat tcgttgatga cttctgacta    180

ttcgaggatt atcacgaatg acttacagag cattgcgtgt gaattgattg tgttaatcgc    240

cgatggagat gtgaaggact tatctgtacg atcatttttg ctaacaatgt ctagtgccgt    300

cccactacct ccgaactcga tcattgtggt cctgggagca tctggtgatc ttgcgaaaaa    360

gaagacagta cgttactatt atttggttgc ttatatgccg atagctgatc gaatagtacc    420

cggcgttgtt cggcttatat cgctatggat tgttgccaaa gaatgtcaag atcgtcggtt    480

atgcgcgcac aaagatggac gatgcagact acaagaagcg catatcgtca tatatgaaga    540

ctcctaccga gactatcgag acgcagttga aggagttcct ggcgatgacg tcgtacgtat    600

caggacagta cgaccaagac gaaggcttca ttagcttgac gaagcatata gaggaactcg    660

aaggcgatgt cgaggagcgt taccgtctat tttacatggc gctcccgcct aatgttttca    720

ttcctgtcgc ccagcacctt aagaagaact gctaccccaa gtctggcggt gcgagaatca    780

tcattgaaaa gccattcggt cacgatctgg ccagctcacg agagttgcag acagctcttc    840

agccgatttg gactgaagac gaaattttcc gtatcgacca ctacctcggc aaggagatgg    900

ttaagaacat tttgattctg cggtttggca atgagttctt tggcgctgcc tggaacaaga    960

accatgtgtc gtcagtccag attactttca aggagccctt cggcaccgag ggtcgtggtg   1020

gttacttcga tcagtttggt attattcgag acgttatgca gaaccatttg ctccaggttc   1080

tcacgatgat cgccatggag cggcccgttt cattctctgc cgaggacatc cgtgacgaaa   1140

aagttcgtgt actacgggcc atgccaatca ttgatcccaa gaacgttgtc atcggccagt   1200

acgataagtc cctcgatggt accaagccga gctaccagga cgacgccacc gttcccaagg   1260

gctcgcgctg cccaacattc gctgcaattg tgatgtacat caagaacgac cgatgggacg   1320

gtgtcccgtt tattctcaag gccggcaagg cgctcgatgc cgccaaagtc gaggttcgtg   1380

ttcagttcaa ggacgtcacg tccggcattt tcaaggatat accccgaaac gagcttgtcc   1440

tgcgaattca gcctgacgag gccgtgtacg tcaaaatgaa caccaagctc cctggtttaa   1500
```

```
ccatgaagac ttccgtcacc gagcttgacc tgacctacaa gcgccggttc tcggacctca   1560

agattcctga agcgtacgag gccctcatcc tcgatgcgat caatggtgac cactccaact   1620

ttgttcgaga cgatgagctc gacgcgtcct ggaagatttt cactccattt ctgcactacc   1680

tcgatgagaa caccgatatc gtaccggcca aatatcctta cggttcgcga gggccggctt   1740

tccttgatga ctttcttgcg tcgtacgggt acgcacgcga gcagcatggc atgtaccagt   1800

ggcctacaac caaggtcaat ggcaacttgt aa                                  1832
```

```
<210> SEQ ID NO 44
<211> LENGTH: 510
<212> TYPE: PRT
<213> ORGANISM: Lipomyces starkeyi

<400> SEQUENCE: 44

Met Ala Asp Thr Ile Ile Ser Ser Thr Lys Ala Ser Asp Thr Gly Ala
1               5                   10                  15

Val Pro Leu Pro Pro Asn Ser Ile Ile Val Val Ser Gly Ala Ser Gly
            20                  25                  30

Asp Leu Ala Lys Lys Lys Thr Tyr Pro Ala Leu Phe Gly Leu Tyr Arg
        35                  40                  45

Tyr Gly Leu Leu Pro Lys Asn Val Lys Ile Val Gly Tyr Ala Arg Thr
    50                  55                  60

Lys Met Asp Asp Ala Asp Tyr Lys Lys Arg Ile Ser Ser Tyr Met Lys
65                  70                  75                  80

Thr Pro Thr Glu Thr Ile Glu Thr Gln Leu Lys Glu Phe Ser Ala Met
                85                  90                  95

Thr Ser Tyr Val Ser Gly Gln Tyr Asp Gln Asp Glu Gly Phe Ile Ser
            100                 105                 110

Leu Thr Lys His Ile Glu Glu Leu Glu Gly Asp Val Glu Glu Arg Tyr
        115                 120                 125

Arg Leu Phe Tyr Met Ala Leu Pro Pro Asn Val Phe Ile Pro Val Ala
    130                 135                 140

Gln His Leu Lys Lys Asn Cys Tyr Pro Lys Ser Gly Gly Ala Arg Ile
145                 150                 155                 160

Ile Ile Glu Lys Pro Phe Gly His Asp Ser Ala Ser Ser Arg Glu Leu
                165                 170                 175

Gln Thr Ala Leu Gln Pro Ile Trp Thr Glu Asp Glu Ile Phe Arg Ile
            180                 185                 190

Asp His Tyr Leu Gly Lys Glu Met Val Lys Asn Ile Leu Ile Ser Arg
        195                 200                 205

Phe Gly Asn Glu Phe Phe Gly Ala Ala Trp Asn Lys Asn His Val Ser
    210                 215                 220

Ser Val Gln Ile Thr Phe Lys Glu Pro Phe Gly Thr Glu Gly Arg Gly
225                 230                 235                 240

Gly Tyr Phe Asp Gln Phe Gly Ile Ile Arg Asp Val Met Gln Asn His
                245                 250                 255

Leu Leu Gln Val Leu Thr Met Ile Ala Met Glu Arg Pro Val Ser Phe
            260                 265                 270

Ser Ala Glu Asp Ile Arg Asp Glu Lys Val Arg Val Leu Arg Ala Met
        275                 280                 285

Pro Ile Ile Asp Pro Lys Asn Val Val Ile Gly Gln Tyr Asp Lys Ser
    290                 295                 300

Leu Asp Gly Thr Lys Pro Ser Tyr Gln Asp Asp Ala Thr Val Pro Lys
305                 310                 315                 320
```

```
Gly Ser Arg Cys Pro Thr Phe Ala Ala Ile Val Met Tyr Ile Lys Asn
                325                 330                 335

Asp Arg Trp Asp Gly Val Pro Phe Ile Leu Lys Ala Gly Lys Ala Leu
            340                 345                 350

Asp Ala Ala Lys Val Glu Val Arg Val Gln Phe Lys Asp Val Thr Ser
        355                 360                 365

Gly Ile Phe Lys Asp Ile Pro Arg Asn Glu Leu Val Ser Arg Ile Gln
    370                 375                 380

Pro Asp Glu Ala Val Tyr Val Lys Met Asn Thr Lys Leu Pro Gly Leu
385                 390                 395                 400

Thr Met Lys Thr Ser Val Thr Glu Leu Asp Ser Thr Tyr Lys Arg Arg
                405                 410                 415

Phe Ser Asp Leu Lys Ile Pro Glu Ala Tyr Glu Ala Leu Ile Leu Asp
            420                 425                 430

Ala Ile Asn Gly Asp His Ser Asn Phe Val Arg Asp Asp Glu Leu Asp
        435                 440                 445

Ala Ser Trp Lys Ile Phe Thr Pro Phe Ser His Tyr Leu Asp Glu Asn
    450                 455                 460

Thr Asp Ile Val Pro Ala Lys Tyr Pro Tyr Gly Ser Arg Gly Pro Ala
465                 470                 475                 480

Phe Leu Asp Asp Phe Leu Ala Ser Tyr Gly Tyr Ala Arg Glu Gln His
                485                 490                 495

Gly Met Tyr Gln Trp Pro Thr Thr Lys Val Asn Gly Asn Leu
            500                 505                 510
```

<210> SEQ ID NO 45
<211> LENGTH: 2781
<212> TYPE: DNA
<213> ORGANISM: Lipomyces starkeyi
<220> FEATURE:
<221> NAME/KEY: Intron
<222> LOCATION: (71)..(122)
<220> FEATURE:
<221> NAME/KEY: Intron
<222> LOCATION: (730)..(779)
<220> FEATURE:
<221> NAME/KEY: Intron
<222> LOCATION: (1096)..(1143)
<220> FEATURE:
<221> NAME/KEY: Intron
<222> LOCATION: (1861)..(1912)
<220> FEATURE:
<221> NAME/KEY: Intron
<222> LOCATION: (2147)..(2201)
<220> FEATURE:
<221> NAME/KEY: 3'UTR
<222> LOCATION: (2754)..(2781)

<400> SEQUENCE: 45

```
atggctgacc ttgacatcga atatgtgctt tcgcagctat ctcttgacga gaaagtctcg      60

ctgacaggag gttagtatca atctattcgc cattggcact tcattgacgc gtatggtgac     120

aggtcgagac atgtggcaca caactcctat tccccgtctg ggaataccgt cactgcggct     180

ctcagatggt ccgaacgggg tacgtgggac caagttcttt gacagtactc cagcggcctg     240

ccttccgtgt ggaaccggcc tgggtgcaac gtgggacgta cagttattga gagaagtggg     300

caactttctt ggattggagg caaaagccaa aggcgcgcat gtgcttctag gcccaacagt     360

taacgtgcag cggagcccac tgggtggacg aggatttgag tcgttttccg aagaccccgt     420

actttcagga tttcttgcag cagcatattg taatggcgta caggaccaga acattatacc     480
```

-continued

```
gtcgataaag cactttgtgt gcaacgatca ggaagacaaa cgcatgtcgg tcaatattac    540
agttggcgat agagctctgc gagagatcta tctcctccct ttcatgcttg ccgttcgcga    600
tgcgagtcct ggttcgttta tgacagcgta caacaaatta aatgggacac actgcagcga    660
gaacaaaaaa cttttgcatg atgtccttcg tagcgaatgg ggctggaatg gactgcttgt    720
aagcgattgg taaactctgg ctcatattca ccattgcgtg cagaagctaa atttactagg    780
tatgggactt acagcaccac tgaggcgatt gaagcaggac tggatttgga gatgcctggt    840
ccaacgagat ggagaacaat cactctgtca catgcagtga gctcggggaa ggtggaagag    900
aagctacttg acgtacgggt ccggaatgtt ttgagtgccg tcaaggaggc tcacaaaagt    960
ggcattcccg caggatgcag ggagacgacg cgaaacacac cagaagatag aattttactc   1020
cggcgcgctg ccgcaaattc cattgtattg ctcaagaacg aagaccatgt actgcctttg   1080
aagagcgatc gaacggtaca ttgacaacta ttgagcccta aatgcaaaat actgactcta   1140
cagactgcga tcataggttc aaacgccaaa attgctacat tctgcggagg aggcagcgca   1200
tcacttaatc catactactc cacgtccgtc cttgattccg tacgtgccaa atgcggagat   1260
gtaagcttcg ctgagggtcc tttttctcat ctcgaatttt ccttgctcga tggattgatc   1320
gtagatacaa atggccgtcc tggcttcact tttcggtcat atctcgaacc gccagaagtc   1380
aaagggcgag aatgtataga caagatgttt gtgaagacca ctaagttctt tttgaccgac   1440
tattctcctc cgaacttgaa atcttcactc ttttggactg aaatggaggc atatttgacc   1500
ccggatagga gcggtttgtg ggactttggg ctctgtaccc aaggtactgc aaggctttat   1560
attgatggtg ctgaagttgt tgataacgca acccggcaag agccgggcaa tgcattccta   1620
ggagcaggaa cgaaggaagt tataggaaca atcgatcttg tagcggggag aaagtacaag   1680
cttcttatca gtttcggtag cgcaccaact tcaaagctcg tcaagaaggg cgtagttaca   1740
ttccgcaaag gtggtgtgcg tctccgtggt ggaccaaaaa ttgatgtgga gaaagcaatt   1800
gaagaggcaa ctgaggtagc aaagaagact cagcaagttg tgattgttgt cggtctgaat   1860
gtaaggcaca tagtctgtat tatttttacc aagggcttac tcataatttc agggggactg   1920
ggaggtagag ggtcaagatc gctcagatat gagtcttccg cctcacacag acgaacttat   1980
aactagggtt ttgggagtca ggcccgacgc agtagttgtc aatcaaagtg gtgcgcctgt   2040
tgcaatgcca tgggcagatc aagcgaaggc tatagtgcaa atgtggtacg gaggcaacga   2100
gggaggaaac ggtctcgcag acgtgctctt cggagatgtt aatccggtca gtgctattgc   2160
atgtatgttt cgtttattgc acatgttgat tgatctcaca gggcggcaag ctgccattga   2220
cattcccgaa gcgtatttct gattgtccgg catatctcca ttccaagtcc aacaagggtc   2280
gcatgatata tggcgaaggc atattcgtgg gctatcgcta ctacgagaca attgatttgt   2340
ccgtgcggtt cccattcggg catggacttt catacacaac cttctcgcaa agcgcgcttc   2400
gggttcaaac tgacgacagg aagctcatcg tgcaacttaa gctcgagaat tctggggact   2460
ttgacggctc ggaggtgatc caggtttata tttctcaccc caaatcgtcc gtgtcacgtc   2520
ctgtgaaaga actgaaaggt ttctcaaaag tgatgcttaa atcaaaagag agcattgatg   2580
taaaaattga tattcccatt aagtatgcaa cttccttctg ggacgagagt gagaacgcgt   2640
ggacctcgga agcgggcgtt tacgaagtgt tcgtcggaaa tagtagtcag tcagagcgtt   2700
ttttatgcag cacatttgag acgagcaaga cattttcttg gaatgggctt tgagatatgt   2760
tgtaatagag gaaatcactt a                                             2781
```

<210> SEQ ID NO 46
<211> LENGTH: 831
<212> TYPE: PRT
<213> ORGANISM: Lipomyces starkeyi

<400> SEQUENCE: 46

```
Met Ala Asp Leu Asp Ile Glu Tyr Val Leu Ser Gln Leu Ser Leu Asp
1               5                   10                  15

Glu Lys Val Ser Leu Thr Gly Gly Arg Asp Met Trp His Thr Thr Pro
            20                  25                  30

Ile Pro Arg Leu Gly Ile Pro Ser Leu Arg Leu Ser Asp Gly Pro Asn
        35                  40                  45

Gly Val Arg Gly Thr Lys Phe Phe Asp Ser Thr Pro Ala Ala Cys Leu
    50                  55                  60

Pro Cys Gly Thr Gly Leu Gly Ala Thr Trp Asp Val Gln Leu Leu Arg
65                  70                  75                  80

Glu Val Gly Asn Phe Leu Gly Leu Glu Ala Lys Ala Lys Gly Ala His
                85                  90                  95

Val Leu Leu Gly Pro Thr Val Asn Val Gln Arg Ser Pro Leu Gly Gly
            100                 105                 110

Arg Gly Phe Glu Ser Phe Ser Glu Asp Pro Val Leu Ser Gly Phe Leu
        115                 120                 125

Ala Ala Ala Tyr Cys Asn Gly Val Gln Asp Gln Asn Ile Ile Pro Ser
    130                 135                 140

Ile Lys His Phe Val Cys Asn Asp Gln Glu Asp Lys Arg Met Ser Val
145                 150                 155                 160

Asn Ile Thr Val Gly Asp Arg Ala Leu Arg Glu Ile Tyr Leu Leu Pro
                165                 170                 175

Phe Met Leu Ala Val Arg Asp Ala Ser Pro Gly Ser Phe Met Thr Ala
            180                 185                 190

Tyr Asn Lys Leu Asn Gly Thr His Cys Ser Glu Asn Lys Lys Leu Leu
        195                 200                 205

His Asp Val Leu Arg Ser Glu Trp Gly Trp Asn Gly Leu Leu Val Ser
    210                 215                 220

Asp Trp Tyr Gly Thr Tyr Ser Thr Thr Glu Ala Ile Glu Ala Gly Leu
225                 230                 235                 240

Asp Leu Glu Met Pro Gly Pro Thr Arg Trp Arg Thr Ile Thr Leu Ser
                245                 250                 255

His Ala Val Ser Ser Gly Lys Val Glu Glu Lys Leu Leu Asp Val Arg
            260                 265                 270

Val Arg Asn Val Leu Ser Ala Val Lys Glu Ala His Lys Ser Gly Ile
        275                 280                 285

Pro Ala Gly Cys Arg Glu Thr Thr Arg Asn Thr Pro Glu Asp Arg Ile
    290                 295                 300

Leu Leu Arg Arg Ala Ala Ala Asn Ser Ile Val Leu Leu Lys Asn Glu
305                 310                 315                 320

Asp His Val Leu Pro Leu Lys Ser Asp Arg Thr Thr Ala Ile Ile Gly
                325                 330                 335

Ser Asn Ala Lys Ile Ala Thr Phe Cys Gly Gly Gly Ser Ala Ser Leu
            340                 345                 350

Asn Pro Tyr Tyr Ser Thr Ser Val Leu Asp Ser Val Arg Ala Lys Cys
        355                 360                 365

Gly Asp Val Ser Phe Ala Glu Gly Pro Phe Ser His Leu Glu Phe Ser
    370                 375                 380
```

```
Leu Leu Asp Gly Leu Ile Val Asp Thr Asn Gly Arg Pro Gly Phe Thr
385                 390                 395                 400

Phe Arg Ser Tyr Leu Glu Pro Pro Glu Val Lys Gly Arg Glu Cys Ile
                405                 410                 415

Asp Lys Met Phe Val Lys Thr Thr Lys Phe Phe Leu Thr Asp Tyr Ser
            420                 425                 430

Pro Pro Asn Leu Lys Ser Ser Leu Phe Trp Thr Glu Met Glu Ala Tyr
        435                 440                 445

Leu Thr Pro Asp Arg Ser Gly Leu Trp Asp Phe Gly Leu Cys Thr Gln
    450                 455                 460

Gly Thr Ala Arg Leu Tyr Ile Asp Gly Ala Glu Val Val Asp Asn Ala
465                 470                 475                 480

Thr Arg Gln Glu Pro Gly Asn Ala Phe Leu Gly Ala Gly Thr Lys Glu
                485                 490                 495

Val Ile Gly Thr Ile Asp Leu Val Ala Gly Arg Lys Tyr Lys Leu Leu
            500                 505                 510

Ile Ser Phe Gly Ser Ala Pro Thr Ser Lys Leu Val Lys Lys Gly Val
        515                 520                 525

Val Thr Phe Arg Lys Gly Gly Val Arg Leu Arg Gly Gly Pro Lys Ile
    530                 535                 540

Asp Val Glu Lys Ala Ile Glu Glu Ala Thr Glu Val Ala Lys Lys Thr
545                 550                 555                 560

Gln Gln Val Val Ile Val Val Gly Leu Asn Gly Asp Trp Glu Val Glu
                565                 570                 575

Gly Gln Asp Arg Ser Asp Met Ser Leu Pro Pro His Thr Asp Glu Leu
            580                 585                 590

Ile Thr Arg Val Leu Gly Val Arg Pro Asp Ala Val Val Val Asn Gln
        595                 600                 605

Ser Gly Ala Pro Val Ala Met Pro Trp Ala Asp Gln Ala Lys Ala Ile
    610                 615                 620

Val Gln Met Trp Tyr Gly Gly Asn Glu Gly Gly Asn Gly Leu Ala Asp
625                 630                 635                 640

Val Leu Phe Gly Asp Val Asn Pro Gly Gly Lys Leu Pro Leu Thr Phe
                645                 650                 655

Pro Lys Arg Ile Ser Asp Cys Pro Ala Tyr Leu His Ser Lys Ser Asn
            660                 665                 670

Lys Gly Arg Met Ile Tyr Gly Glu Gly Ile Phe Val Gly Tyr Arg Tyr
        675                 680                 685

Tyr Glu Thr Ile Asp Leu Ser Val Arg Phe Pro Phe Gly His Gly Leu
    690                 695                 700

Ser Tyr Thr Thr Phe Ser Gln Ser Ala Leu Arg Val Gln Thr Asp Asp
705                 710                 715                 720

Arg Lys Leu Ile Val Gln Leu Lys Leu Glu Asn Ser Gly Asp Phe Asp
                725                 730                 735

Gly Ser Glu Val Ile Gln Val Tyr Ile Ser His Pro Lys Ser Ser Val
            740                 745                 750

Ser Arg Pro Val Lys Glu Leu Lys Gly Phe Ser Lys Val Met Leu Lys
        755                 760                 765

Ser Lys Glu Ser Ile Asp Val Lys Ile Asp Ile Pro Ile Lys Tyr Ala
    770                 775                 780

Thr Ser Phe Trp Asp Glu Ser Glu Asn Ala Trp Thr Ser Glu Ala Gly
785                 790                 795                 800

Val Tyr Glu Val Phe Val Gly Asn Ser Ser Gln Ser Glu Arg Phe Leu
```

```
                805                 810                 815

Cys Ser Thr Phe Glu Thr Ser Lys Thr Phe Ser Trp Asn Gly Leu
            820                 825                 830


<210> SEQ ID NO 47
<211> LENGTH: 2237
<212> TYPE: DNA
<213> ORGANISM: Lipomyces starkeyi
<220> FEATURE:
<221> NAME/KEY: 5'UTR
<222> LOCATION: (1)..(253)
<220> FEATURE:
<221> NAME/KEY: Intron
<222> LOCATION: (320)..(377)
<220> FEATURE:
<221> NAME/KEY: Intron
<222> LOCATION: (484)..(540)
<220> FEATURE:
<221> NAME/KEY: Intron
<222> LOCATION: (903)..(956)
<220> FEATURE:
<221> NAME/KEY: Intron
<222> LOCATION: (1103)..(1153)
<220> FEATURE:
<221> NAME/KEY: 3'UTR
<222> LOCATION: (2064)..(2237)

<400> SEQUENCE: 47

tttgaccccg catccttaga atttattgct ttttcttcac ttagtaaaag atatgggccc     60

gtgacgagcg acatgctgtc acttctaact tatatcttct tggccatagg ccttgttagt    120

ctaccagtgc cccacaatat ctgagcacca tataagttcc ccatctcctc tctttagaat    180

cccacattca ggcaaagttc tttatttaag acatataact gaatagaaat ttaccgctta    240

attcattgtc atcatgggaa tactgaagac gtcaaacgaa gggagcgcgg aggcagctct    300

tggaaaggaa atcctagaag tgggtacatc ttcaaccatc tctttcacga ggatccaact    360

aacagagtat actcaaggtg ttgccgatac atcatcagcc ttggtacaag acaaagcatc    420

tcgtgcatct caacttgatc ctcctggtcc ctctattctc ctccgctacg attggctttg    480

atggtaggca aatcagtttt tactcttcaa aaatattctc atagcataac cataatccag    540

gcggaatgat gaacggtctt cagaccctca ctcagtggag aacatatttc tctcatccca    600

atagctccac tctgggagcg atcaatgccc tttatcccat cgggaagctg cttggtcttt    660

ttccgtccac ctggctctct gatcggttcg gtcgaaagag gcccatgctt gttggcttta    720

ttttattgtt catcgggacg gttcttcaag gtgcttctca ggacatagct atgttgatcg    780

tctctcgttt tgtgatgggg ttcggaacgg ctttccttgc tcagccgtca cctatcttga    840

tcacagaact tgcttacccg acacagcgtg gtaaaatcac aagcttatat aacaccttct    900

acgtatgcac atattgcatt gcttcaatcg tttatatatg cttacctatt tgatagtatg    960

taggtgctgt tctagcggct tggtcgacct atggcacctt ccggttagcc tctaactgga   1020

gctggaggat cccttcaatc atgcagggcg catttcctct catacaattt tgctttttct   1080

tcttaattcc agaatctcca aggtattcac tttgtgtttt attctcctaa ttcactactg   1140

accgagcaac cagatggctt gtggcccagg gtcgagttga agacgcacgg aaagtcctcg   1200

tcaaatatca cgctggaggt gatgaagcct caccactagt cgactacgaa atccgtgaaa   1260

tggaagagag tattcagctc gagaagctta ttaactctca atcctcctac atagacctaa   1320

ttcgcactcc cgcgaatcgc aagcgtacat tcatcgccgc catcttaggc ttcttcaccc   1380

aatggagcgg caactcagtt atctcctact atctgactct cgtacttgat acaattggta   1440
```

```
tcacttccgt ttcctcgcaa gcactcatca acggcctcct tcagaccttc aactggttcg   1500

cagctgttct agcgggtgca ttgatggtgg accgtatcgg gcgccgcaaa ctcttcctca   1560

tctccactgg cggaatgctt gcgtcatata ttatctggac cgtcttaagc agtgttttca   1620

caacgacgct aaatcagaaa gtaggtaata ccgtagtggc ctttatcttt atctattact   1680

tcttctacga cattgccttc acacctctga tgcccgctta tgttgttgaa atataccaat   1740

acacactgcg cggtcgtgga gtcactgcag catatacggt cgactattgt ggacttatcc   1800

ttggtaactt tgtcaatccg gtggcgatga aaaagattgg ctggcactac tatattttat   1860

tttgtgttct ccttacattc tcgtttactc ttatctggtt cttctttccc gaaaccaaag   1920

gacacaccct cgaggagata gcagaagtct ttgatgggcc ccgaggaaat ggtcaggacg   1980

ttgaagttaa cgacgatcac gagaaaatcg agagcaacaa aaccagtcat atcgaggtcc   2040

ctcgtatggc agaggtcgca taaggttgga agtaatctgc aggaaagggt tcaaaaggtc   2100

actgttcaag attcaaatac taccatatgt gttgtttagc agttagttgt agcagtagct   2160

ctgtggcatc gtcgagatgt tggcgttcat catcatctcg ccagggtatt tgagccacat   2220

gatatggaat tttattc                                                  2237
```

<210> SEQ ID NO 48
<211> LENGTH: 529
<212> TYPE: PRT
<213> ORGANISM: Lipomyces starkeyi

<400> SEQUENCE: 48

```
Met Gly Ile Ser Lys Thr Ser Asn Glu Gly Ser Ala Glu Ala Ala Leu
1               5                   10                  15

Gly Lys Glu Ile Leu Glu Val Leu Pro Ile His His Gln Pro Trp Tyr
            20                  25                  30

Lys Thr Lys His Leu Val His Leu Asn Leu Ile Leu Ser Val Pro Leu
        35                  40                  45

Phe Ser Ser Ala Thr Ile Gly Phe Asp Gly Gly Met Met Asn Gly Leu
    50                  55                  60

Gln Thr Leu Thr Gln Trp Arg Thr Tyr Phe Ser His Pro Asn Ser Ser
65                  70                  75                  80

Thr Ser Gly Ala Ile Asn Ala Leu Tyr Pro Ile Gly Lys Ser Leu Gly
                85                  90                  95

Leu Phe Pro Ser Thr Trp Leu Ser Asp Arg Phe Gly Arg Lys Arg Pro
            100                 105                 110

Met Leu Val Gly Phe Ile Leu Leu Phe Ile Gly Thr Val Leu Gln Gly
        115                 120                 125

Ala Ser Gln Asp Ile Ala Met Leu Ile Val Ser Arg Phe Val Met Gly
    130                 135                 140

Phe Gly Thr Ala Phe Leu Ala Gln Pro Ser Pro Ile Leu Ile Thr Glu
145                 150                 155                 160

Leu Ala Tyr Pro Thr Gln Arg Gly Lys Ile Thr Ser Leu Tyr Asn Thr
                165                 170                 175

Phe Tyr Tyr Val Gly Ala Val Leu Ala Ala Trp Ser Thr Tyr Gly Thr
            180                 185                 190

Phe Arg Leu Ala Ser Asn Trp Ser Trp Arg Ile Pro Ser Ile Met Gln
        195                 200                 205

Gly Ala Phe Pro Leu Ile Gln Phe Cys Phe Phe Phe Leu Ile Pro Glu
    210                 215                 220

Ser Pro Arg Trp Leu Val Ala Gln Gly Arg Val Glu Asp Ala Arg Lys
```

-continued

```
225                 230                 235                 240

Val Leu Val Lys Tyr His Ala Gly Gly Asp Glu Ala Ser Pro Leu Val
                245                 250                 255

Asp Tyr Glu Ile Arg Glu Met Glu Glu Ser Ile Gln Leu Glu Lys Leu
            260                 265                 270

Ile Asn Ser Gln Ser Ser Tyr Ile Asp Leu Ile Arg Thr Pro Ala Asn
        275                 280                 285

Arg Lys Arg Thr Phe Ile Ala Ala Ile Leu Gly Phe Phe Thr Gln Trp
    290                 295                 300

Ser Gly Asn Ser Val Ile Ser Tyr Tyr Ser Thr Leu Val Leu Asp Thr
305                 310                 315                 320

Ile Gly Ile Thr Ser Val Ser Ser Gln Ala Leu Ile Asn Gly Leu Leu
                325                 330                 335

Gln Thr Phe Asn Trp Phe Ala Ala Val Leu Ala Gly Ala Leu Met Val
            340                 345                 350

Asp Arg Ile Gly Arg Arg Lys Leu Phe Leu Ile Ser Thr Gly Gly Met
        355                 360                 365

Leu Ala Ser Tyr Ile Ile Trp Thr Val Leu Ser Ser Val Phe Thr Thr
    370                 375                 380

Thr Leu Asn Gln Lys Val Gly Asn Thr Val Val Ala Phe Ile Phe Ile
385                 390                 395                 400

Tyr Tyr Phe Phe Tyr Asp Ile Ala Phe Thr Pro Ser Met Pro Ala Tyr
                405                 410                 415

Val Val Glu Ile Tyr Gln Tyr Thr Ser Arg Gly Arg Gly Val Thr Ala
            420                 425                 430

Ala Tyr Thr Val Asp Tyr Cys Gly Leu Ile Leu Gly Asn Phe Val Asn
        435                 440                 445

Pro Val Ala Met Lys Lys Ile Gly Trp His Tyr Tyr Ile Leu Phe Cys
    450                 455                 460

Val Leu Leu Thr Phe Ser Phe Thr Leu Ile Trp Phe Phe Phe Pro Glu
465                 470                 475                 480

Thr Lys Gly His Thr Leu Glu Glu Ile Ala Glu Val Phe Asp Gly Pro
                485                 490                 495

Arg Gly Asn Gly Gln Asp Val Glu Val Asn Asp Asp His Glu Lys Ile
            500                 505                 510

Glu Ser Asn Lys Thr Ser His Ile Glu Val Pro Arg Met Ala Glu Val
        515                 520                 525

Ala


<210> SEQ ID NO 49
<211> LENGTH: 2136
<212> TYPE: DNA
<213> ORGANISM: Lipomyces starkeyi
<220> FEATURE:
<221> NAME/KEY: 5'UTR
<222> LOCATION: (1)..(40)
<220> FEATURE:
<221> NAME/KEY: Intron
<222> LOCATION: (119)..(171)
<220> FEATURE:
<221> NAME/KEY: Intron
<222> LOCATION: (461)..(509)
<220> FEATURE:
<221> NAME/KEY: Intron
<222> LOCATION: (1015)..(1073)
<220> FEATURE:
<221> NAME/KEY: 3'UTR
<222> LOCATION: (1736)..(2136)
```

<400> SEQUENCE: 49

```
tggcagcatt gcaatttcgc tactccacac gcgactaaag atggctaccg gcattctacg     60
cgtcgcagat ggagccaaaa tcgttgatgc caatggcgat caagtggtcc ttcgcggggt    120
cagtcactga cggtgcagtt tacaactgtg tttactaaca atgtcactgt agacagcttt    180
aggtggccat atgatgatgg agaacttcat gaatggcttt ccgggcagag aaatgcaggt    240
gcgcaaggcg atcggaaagg ttcttggccc cgaaaagagt gacttctttt ttgacaagtt    300
cctcgagtac ttctttatgg acgaggatgc tgcattcttg aaatctcttg gcctaaactc    360
tctccgcgtg ccttttaact accaccacct cgaagacgac atgaatcccg gcgtaatcgt    420
tcaggacggc ttcaaacata ttgaccgcgt tgttgaaata gtgagtctct tagctgccag    480
tggtattgga ttagcaactg ataatttagt gcgcccgcca tggcatctac accattctgg    540
accttcattc ggcgccgggc ggacagtctc aagattggca ctgcgataat ccgactggat    600
atgcggcgtt ctgggaccag aaatcctttc aagatcgagt cgttaaccta tggaaaacca    660
tcgcagccag gtacaggggg aatccctgga ttgcaggata caaccctctg aacgagcctg    720
ccgacgagga gtggacccgc cttttggcgt tttacgaccg catcgagaag actattcgcg    780
aggttgaccc tgaccatatt ctctggctcg atgggaatac attcgcaatg gatttctctg    840
gattcacgaa agtttttcca aacactgtct atgccataca cgactactgc ggatatggat    900
ttccaaatcg aattggaagg taccagtgca aacccgagca ggacaaatac attcgtgcga    960
tgtacgacag aaaggtcgag tttatgaaga cgcacaatgt gccaatctgg aatggtagtc   1020
aagttttaca tgctacgatt gcgagcccgg cacggtcact aacatatgaa caggtgagtt   1080
tggaccgatc tacgagcgcg aggaatacaa cccggattac aaagtgcaga acgaggagcg   1140
ttacaacatg ctggagaagc agctttcaat ctattccgct gagggcatcc attggtccat   1200
ctgggcgtac aaggatatca atgttatggg aatgcgctac gttgactctg attcggcctg   1260
gatcaaactc cttggtcctt tcatccacaa gaaacgcgaa cttgcggtcg attcatgggc   1320
ctacgacgac gcgcatcttc aggaaggatt gtttggtccc ttgcacaggt ggattgaaga   1380
gaacgtcccg gagaagtaca gcaaaaagta tccgtggcag tggcgcatgc atatgcacgt   1440
cttcagaggg atccgcggca ttactctggc tgagtatctc atcccagagt ttgccgacta   1500
ctttagcggc aagacgtttg aggagctaga tgagctcgca agcagctggt cttttgcgaa   1560
aactgttggc cgggatgaat taaatcgact gttgaaactt catgcgacga tgcagcctga   1620
cgatcctcac cttgtcaacg tcatcccgcc tgcaaacaag cggcagacta acggtccag    1680
aggcgtattt gagctgtcgc ctttggagct gtcaatgcag aaggcacgtg attaagttac   1740
gatgaagtgc tcagcataat agccaatgtt attgcgggaa tagtaaccca attgtatttt   1800
gtgtttatga acagcaaata atattcatag taaccttgac aagatcaata actgcagcta   1860
atagcttcaa tgaacttgca aagacaagtt atccagaact attcgttgac aaacttcgcg   1920
ctttgaatgg cctgtattgt cgtgctcgtt actgcatgtg gctgaggacg cacctaccgc   1980
acttaacgct gaattgtatc cttgaatgct tttcatagca atgtggaata tgaaatgtga   2040
aataagggac tgcgggaata ttaagcatac taatatgtct atacggccgt gtccaagaac   2100
acaagaagaa tttagaaaac aataaagact attttg                             2136
```

<210> SEQ ID NO 50
<211> LENGTH: 510
<212> TYPE: PRT
<213> ORGANISM: Lipomyces starkeyi

<400> SEQUENCE: 50

```
Met Ala Thr Gly Ile Leu Arg Val Ala Asp Gly Ala Lys Ile Val Asp
1               5                   10                  15

Ala Asn Gly Asp Gln Val Val Leu Arg Gly Thr Ala Leu Gly Gly His
            20                  25                  30

Met Met Met Glu Asn Phe Met Asn Gly Phe Pro Gly Arg Glu Met Gln
        35                  40                  45

Val Arg Lys Ala Ile Gly Lys Val Leu Gly Pro Glu Lys Ser Asp Phe
    50                  55                  60

Phe Phe Asp Lys Phe Leu Glu Tyr Phe Phe Met Asp Glu Asp Ala Ala
65                  70                  75                  80

Phe Leu Lys Ser Leu Gly Leu Asn Ser Leu Arg Val Pro Phe Asn Tyr
                85                  90                  95

His His Leu Glu Asp Asp Met Asn Pro Gly Val Ile Val Gln Asp Gly
            100                 105                 110

Phe Lys His Ile Asp Arg Val Val Glu Ile Cys Ala Arg His Gly Ile
        115                 120                 125

Tyr Thr Ile Ser Asp Leu His Ser Ala Pro Gly Gly Gln Ser Gln Asp
    130                 135                 140

Trp His Cys Asp Asn Pro Thr Gly Tyr Ala Ala Phe Trp Asp Gln Lys
145                 150                 155                 160

Ser Phe Gln Asp Arg Val Val Asn Leu Trp Lys Thr Ile Ala Ala Arg
                165                 170                 175

Tyr Arg Gly Asn Pro Trp Ile Ala Gly Tyr Asn Pro Ser Asn Glu Pro
            180                 185                 190

Ala Asp Glu Glu Trp Thr Arg Leu Leu Ala Phe Tyr Asp Arg Ile Glu
        195                 200                 205

Lys Thr Ile Arg Glu Val Asp Pro Asp His Ile Leu Trp Leu Asp Gly
    210                 215                 220

Asn Thr Phe Ala Met Asp Phe Ser Gly Phe Thr Lys Val Phe Pro Asn
225                 230                 235                 240

Thr Val Tyr Ala Ile His Asp Tyr Cys Gly Tyr Gly Phe Pro Asn Arg
                245                 250                 255

Ile Gly Arg Tyr Gln Cys Lys Pro Glu Gln Asp Lys Tyr Ile Arg Ala
            260                 265                 270

Met Tyr Asp Arg Lys Val Glu Phe Met Lys Thr His Asn Val Pro Ile
        275                 280                 285

Trp Asn Gly Glu Phe Gly Pro Ile Tyr Glu Arg Glu Glu Tyr Asn Pro
    290                 295                 300

Asp Tyr Lys Val Gln Asn Glu Glu Arg Tyr Asn Met Ser Glu Lys Gln
305                 310                 315                 320

Leu Ser Ile Tyr Ser Ala Glu Gly Ile His Trp Ser Ile Trp Ala Tyr
                325                 330                 335

Lys Asp Ile Asn Val Met Gly Met Arg Tyr Val Asp Ser Asp Ser Ala
            340                 345                 350

Trp Ile Lys Leu Leu Gly Pro Phe Ile His Lys Lys Arg Glu Leu Ala
        355                 360                 365

Val Asp Ser Trp Ala Tyr Asp Asp Ala His Leu Gln Glu Gly Leu Phe
    370                 375                 380

Gly Pro Leu His Arg Trp Ile Glu Glu Asn Val Pro Glu Lys Tyr Ser
385                 390                 395                 400

Lys Lys Tyr Pro Trp Gln Trp Arg Met His Met His Val Phe Arg Gly
```

```
                405                 410                 415

Ile Arg Gly Ile Thr Ser Ala Glu Tyr Leu Ile Pro Glu Phe Ala Asp
            420                 425                 430

Tyr Phe Ser Gly Lys Thr Phe Glu Glu Leu Asp Glu Leu Ala Ser Ser
        435                 440                 445

Trp Ser Phe Ala Lys Thr Val Gly Arg Asp Glu Leu Asn Arg Ser Leu
    450                 455                 460

Lys Leu His Ala Thr Met Gln Pro Asp Asp Pro His Leu Val Asn Val
465                 470                 475                 480

Ile Pro Pro Ala Asn Lys Arg Gln Thr Asn Gly Ser Arg Gly Val Phe
                485                 490                 495

Glu Ser Ser Pro Leu Glu Ser Ser Met Gln Lys Ala Arg Asp
            500                 505                 510


<210> SEQ ID NO 51
<211> LENGTH: 2288
<212> TYPE: DNA
<213> ORGANISM: Lipomyces starkeyi
<220> FEATURE:
<221> NAME/KEY: Intron
<222> LOCATION: (285)..(348)
<220> FEATURE:
<221> NAME/KEY: Intron
<222> LOCATION: (449)..(503)

<400> SEQUENCE: 51

atggcgttca aagtggagat tgactcgttc ggaaatttcc gcgataacga gaaccgagtc     60

attactctac gcggtatcaa tctcgccgcc gactctaagc tgccggctag tccgccaata    120

ccatcgcatg tttcggagaa ctttttcgat ggcgataatg tatcgtttgt tggacgtccg    180

tttcctttga acgagggtga tgtacatctt gcaaggataa agagctgggg gtttaacgtt    240

attcgctatg tttatacttg ggaggcacta gagcatgcgg gaccgtaagc tgtgttgtgg    300

acttctcgaa cttaggacgt atattaactc ctcgttctca ttatttagtg gaaaatatga    360

tgatgtgttt attcagaaca caattgcatt tttgagaaaa ataaaggact atggatttta    420

cgtgtttatg gatccccatc aggacgtggt atgctttgcc tgttacctaa acagtcatag    480

atagagacgc taactcggtt cagtggagcc gtttttctgg agggtccggt gcgcctatgt    540

ggactttgta tgctgcggga ttggatccaa aagcattcgc aaagaccgag gcggctgtcg    600

tccaaaatac ttggccagat cccgcaactt ttccacgaat gacctgggca actaattacg    660

acagacttgc gtgccttacg atttttacaa tgttttgggc cggaaaggat tttgctccga    720

aatgtataat tgacggacaa aatattcagg attatttgca gggtcacttc attgacgcta    780

ttaagcactt tgcacaacag gtgtatgaag atggtgattt gggcgacgac ttcattcttg    840

ggtgggagtc aatcaacgag cctttccgtg gttttctcgg caacagaaat ctcacagttt    900

atcccgagta ccagaaactt cagaagtaca cctcccctac gccattccaa gccattttgt    960

taggcgccgg tcgaacgctt gatatcgcag tttacgattt cgggttactt ggagcttata   1020

aagttggcac tcaggtcgtt aatgctgacg gatattcagc atggcttccc aaagattatg   1080

acgattcacg gtacggatgg aagcgcaatc ctgagtggaa gcttggcgag tgcgtctggg   1140

cgcagcacgg cgtgtgggat ccggagacgg ataatatctt acgtcctgat tactttctag   1200

atgctccaga cggcacgcga cttgacggcg aatcgtgggc agagacgtac ttcattgacc   1260

actggaataa atttgccgac actatccgat cgatccgttc ggagacaatg ttgttttgcc   1320

agactccggt tttggctgtg ccgccgaatt ttgtggaact tggtgccttg agatctcgca   1380
```

```
tggtgtttac gcctcatttt tacgacgggc tgacgcttat ccgcaagcac tggagtagat   1440

tctggaacgt tgatgtcatc ggcgtgttga gaggtaaata ctggagcccc gtgtttgcgc   1500

tcagatttgg cgagacctct atcaggaact gtcttcgtga ccagttgaaa actttgaaat   1560

atgaaggggt cgaaagtttc ggtattggtg tcccctgcct gatgagcgag atcggcattc   1620

cttacgacat gaatgaaaag acagcctatg tcgacggtga ttacacggcc caaattcgag   1680

cactagatgc aaatatatat gctttggaag gcgcgaaact gcatcatact tactgggtgt   1740

acgcctcctg caactctcac aaatggggcg accattggaa cggtgaggat ctcagcctct   1800

ggagtccatc tgatgttaag cacaggatca gtggctcaca atattcgtac tcgctcgccc   1860

cgtccgattc tagtttaatg gcgggaaagc agtattcttt tacagacgaa tcgcagatca   1920

cagatacagt gggatcgcga gcgatagagg catttagccg tccgttcccg cttgttacgg   1980

tcggtgttcc tcaggaatac ggatttgata ttaataatgc catgttctct atggaactct   2040

atgcggatga ggaagtcgcg tccaaacttg taccctcgga gattcatgtt ccggattttc   2100

attacccgaa tggagacctt caagtcgaag tctcgtcggg acgttgggag ctcgatagac   2160

ccaaccaaat tctccgatgg tggcatgatg gtggtaagca gacaatcaaa ataattggga   2220

ttagaggagg tcagacaatg aagccgggga agaattctta tgctgaattc tgtgccgtct   2280

gttcgtag                                                            2288
```

```
<210> SEQ ID NO 52
<211> LENGTH: 722
<212> TYPE: PRT
<213> ORGANISM: Lipomyces starkeyi

<400> SEQUENCE: 52

Met Ala Phe Lys Val Glu Ile Asp Ser Phe Gly Asn Phe Arg Asp Asn
1               5                   10                  15

Glu Asn Arg Val Ile Thr Leu Arg Gly Ile Asn Leu Ala Ala Asp Ser
            20                  25                  30

Lys Leu Pro Ala Ser Pro Pro Ile Pro Ser His Val Ser Glu Asn Phe
        35                  40                  45

Phe Asp Gly Asp Asn Val Ser Phe Val Gly Arg Pro Phe Pro Leu Asn
    50                  55                  60

Glu Gly Asp Val His Leu Ala Arg Ile Lys Ser Trp Gly Phe Asn Val
65                  70                  75                  80

Ile Arg Tyr Val Tyr Thr Trp Glu Ala Leu Glu His Ala Gly Pro Gly
                85                  90                  95

Lys Tyr Asp Asp Val Phe Ile Gln Asn Thr Ile Ala Phe Leu Arg Lys
            100                 105                 110

Ile Lys Asp Tyr Gly Phe Tyr Val Phe Met Asp Pro His Gln Asp Val
        115                 120                 125

Trp Ser Arg Phe Ser Gly Gly Ser Gly Ala Pro Met Trp Thr Leu Tyr
    130                 135                 140

Ala Ala Gly Leu Asp Pro Lys Ala Phe Ala Lys Thr Glu Ala Ala Val
145                 150                 155                 160

Val Gln Asn Thr Trp Pro Asp Pro Ala Thr Phe Pro Arg Met Thr Trp
                165                 170                 175

Ala Thr Asn Tyr Asp Arg Leu Ala Cys Leu Thr Ile Phe Thr Met Phe
            180                 185                 190

Trp Ala Gly Lys Asp Phe Ala Pro Lys Cys Ile Ile Asp Gly Gln Asn
        195                 200                 205
```

```
Ile Gln Asp Tyr Leu Gln Gly His Phe Ile Asp Ala Ile Lys His Phe
    210                 215                 220

Ala Gln Gln Val Tyr Glu Asp Gly Asp Leu Gly Asp Asp Phe Ile Leu
225                 230                 235                 240

Gly Trp Glu Ser Ile Asn Glu Pro Phe Arg Gly Phe Leu Gly Asn Arg
                245                 250                 255

Asn Leu Thr Val Tyr Pro Glu Tyr Gln Lys Leu Gln Lys Tyr Thr Ser
            260                 265                 270

Pro Thr Pro Phe Gln Ala Ile Leu Leu Gly Ala Gly Arg Thr Leu Asp
        275                 280                 285

Ile Ala Val Tyr Asp Phe Gly Leu Leu Gly Ala Tyr Lys Val Gly Thr
    290                 295                 300

Gln Val Val Asn Ala Asp Gly Tyr Ser Ala Trp Leu Pro Lys Asp Tyr
305                 310                 315                 320

Asp Asp Ser Arg Tyr Gly Trp Lys Arg Asn Pro Glu Trp Lys Leu Gly
                325                 330                 335

Glu Cys Val Trp Ala Gln His Gly Val Trp Asp Pro Glu Thr Asp Asn
            340                 345                 350

Ile Leu Arg Pro Asp Tyr Phe Leu Asp Ala Pro Asp Gly Thr Arg Leu
        355                 360                 365

Asp Gly Glu Ser Trp Ala Glu Thr Tyr Phe Ile Asp His Trp Asn Lys
    370                 375                 380

Phe Ala Asp Thr Ile Arg Ser Ile Arg Ser Glu Thr Met Leu Phe Cys
385                 390                 395                 400

Gln Thr Pro Val Leu Ala Val Pro Pro Asn Phe Val Glu Leu Gly Ala
                405                 410                 415

Leu Arg Ser Arg Met Val Phe Thr Pro His Phe Tyr Asp Gly Leu Thr
            420                 425                 430

Leu Ile Arg Lys His Trp Ser Arg Phe Trp Asn Val Asp Val Ile Gly
        435                 440                 445

Val Leu Arg Gly Lys Tyr Trp Ser Pro Val Phe Ala Leu Arg Phe Gly
    450                 455                 460

Glu Thr Ser Ile Arg Asn Cys Leu Arg Asp Gln Leu Lys Thr Leu Lys
465                 470                 475                 480

Tyr Glu Gly Val Glu Ser Phe Gly Ile Gly Val Pro Cys Leu Met Ser
                485                 490                 495

Glu Ile Gly Ile Pro Tyr Asp Met Asn Glu Lys Thr Ala Tyr Val Asp
            500                 505                 510

Gly Asp Tyr Thr Ala Gln Ile Arg Ala Leu Asp Ala Asn Ile Tyr Ala
        515                 520                 525

Leu Glu Gly Ala Lys Leu His His Thr Tyr Trp Val Tyr Ala Ser Cys
    530                 535                 540

Asn Ser His Lys Trp Gly Asp His Trp Asn Gly Glu Asp Leu Ser Leu
545                 550                 555                 560

Trp Ser Pro Ser Asp Val Lys His Arg Ile Ser Gly Ser Gln Tyr Ser
                565                 570                 575

Tyr Ser Leu Ala Pro Ser Asp Ser Ser Leu Met Ala Gly Lys Gln Tyr
            580                 585                 590

Ser Phe Thr Asp Glu Ser Gln Ile Thr Asp Thr Val Gly Ser Arg Ala
        595                 600                 605

Ile Glu Ala Phe Ser Arg Pro Phe Pro Leu Val Thr Val Gly Val Pro
    610                 615                 620
```

```
Gln Glu Tyr Gly Phe Asp Ile Asn Asn Ala Met Phe Ser Met Glu Leu
625                 630                 635                 640

Tyr Ala Asp Glu Glu Val Ala Ser Lys Leu Val Pro Ser Glu Ile His
                645                 650                 655

Val Pro Asp Phe His Tyr Pro Asn Gly Asp Leu Gln Val Glu Val Ser
            660                 665                 670

Ser Gly Arg Trp Glu Leu Asp Arg Pro Asn Gln Ile Leu Arg Trp Trp
        675                 680                 685

His Asp Gly Gly Lys Gln Thr Ile Lys Ile Ile Gly Ile Arg Gly Gly
    690                 695                 700

Gln Thr Met Lys Pro Gly Lys Asn Ser Tyr Ala Glu Phe Cys Ala Val
705                 710                 715                 720

Cys Ser


<210> SEQ ID NO 53
<211> LENGTH: 1263
<212> TYPE: DNA
<213> ORGANISM: Lipomyces starkeyi

<400> SEQUENCE: 53

atgacaacac tactcccatt catgctggtg ctcagcttac tcgtcacctc ggcggcagct      60

catggctata tcacaaactt ctggaatccg acgaagcaga cgtacggtaa gtgcatccgg     120

ccgtatgtgc tctaccatga gaagaaccca atcacggacc ggtactcgga cgaaatgacg     180

tgcggccatc tgccaggcgg ggcaacgttc ccgagcagga cgtgcagcgt agcgaaagcg     240

ggtgacaagg tcgcgttgca gtggtccgtc atggatagga gtcatatcgg gccagtgttg     300

gtgtatatcg cgtcggcaga gagcaagggg gaaggcgaag cgtggtggaa gatctactac     360

gaaggatacg acgcagagac ggactattgg gcgacttcaa agctctggga caacggcggc     420

acgctctgga tctcgctgcc agactatctt ccggttggcg agtacatcat ccgcggcgaa     480

atcatcgcca tccataatgc gtcatatatt gatggcgctc aaatctatgt caattgcatt     540

cacatcaaca tcgaggccgc ggcggaatct aacacaatcg acattaacac tattccgaaa     600

gtcgcgtttc ccggctacta cacctatgac acgccgggtc tgcatctcaa tgtctggtgg     660

ccgcctccta tcggctatcc ggaggtcggt ccgccaatat tcacgccgtc cactgcctca     720

ctagctgcca ctaacaccat cgcgtctttc gctgaccaaa cgggcgactc ctcagacggc     780

aatctcgtcg ttcagccatg cagcacgtca ataactatcg cgtatcaggc gacgagctcg     840

agggtgttct acgagcctgt gacggctaag gcccagctag tttcggttat cccgacgccg     900

tcgtccaagt tgcaatcgcg actcgggact gtcgccgctg tgttccccga cttgacctgc     960

tcatcaacat cgacgccgcc gacagcgaca atgccttctc tcatctccac cacttcgact    1020

gcatcatctg ccagacgtac cgcagtcttt ccagatctca cctgctcatc gtcgtccacg    1080

ttgtctttag ctgcaaccac attcctgact gcagtcacca tagagactgc gtcccagcat    1140

atacgtacac taacagtcac gctcgaccca gtgaccgtcc acgctatcgt caccgtctcc    1200

gtctacaaga ctgagtacgt gaccgacaca gtcactgtcg gggacatgaa tattgcttac    1260

tag                                                                  1263


<210> SEQ ID NO 54
<211> LENGTH: 420
<212> TYPE: PRT
<213> ORGANISM: Lipomyces starkeyi

<400> SEQUENCE: 54
```

```
Met Thr Thr Leu Leu Pro Phe Met Leu Val Leu Ser Leu Leu Val Thr
1               5                   10                  15

Ser Ala Ala Ala His Gly Tyr Ile Thr Asn Phe Trp Asn Pro Thr Lys
            20                  25                  30

Gln Thr Tyr Gly Lys Cys Ile Arg Pro Tyr Val Leu Tyr His Glu Lys
        35                  40                  45

Asn Pro Ile Thr Asp Arg Tyr Ser Asp Glu Met Thr Cys Gly His Leu
    50                  55                  60

Pro Gly Gly Ala Thr Phe Pro Ser Arg Thr Cys Ser Val Ala Lys Ala
65                  70                  75                  80

Gly Asp Lys Val Ala Leu Gln Trp Ser Val Met Asp Arg Ser His Ile
                85                  90                  95

Gly Pro Val Leu Val Tyr Ile Ala Ser Ala Glu Ser Lys Gly Glu Gly
            100                 105                 110

Glu Ala Trp Trp Lys Ile Tyr Tyr Glu Gly Tyr Asp Ala Glu Thr Asp
        115                 120                 125

Tyr Trp Ala Thr Ser Lys Leu Trp Asp Asn Gly Gly Thr Leu Trp Ile
    130                 135                 140

Ser Leu Pro Asp Tyr Leu Pro Val Gly Glu Tyr Ile Ile Arg Gly Glu
145                 150                 155                 160

Ile Ile Ala Ile His Asn Ala Ser Tyr Ile Asp Gly Ala Gln Ile Tyr
                165                 170                 175

Val Asn Cys Ile His Ile Asn Ile Glu Ala Ala Ala Glu Ser Asn Thr
            180                 185                 190

Ile Asp Ile Asn Thr Ile Pro Lys Val Ala Phe Pro Gly Tyr Tyr Thr
        195                 200                 205

Tyr Asp Thr Pro Gly Leu His Leu Asn Val Trp Trp Pro Pro Pro Ile
    210                 215                 220

Gly Tyr Pro Glu Val Gly Pro Pro Ile Phe Thr Pro Ser Thr Ala Ser
225                 230                 235                 240

Leu Ala Ala Thr Asn Thr Ile Ala Ser Phe Ala Asp Gln Thr Gly Asp
                245                 250                 255

Ser Ser Asp Gly Asn Leu Val Val Gln Pro Cys Ser Thr Ser Ile Thr
            260                 265                 270

Ile Ala Tyr Gln Ala Thr Ser Ser Arg Val Phe Tyr Glu Pro Val Thr
        275                 280                 285

Ala Lys Ala Gln Leu Val Ser Val Ile Pro Thr Pro Ser Ser Lys Leu
    290                 295                 300

Gln Ser Arg Leu Gly Thr Val Ala Ala Val Phe Pro Asp Leu Thr Cys
305                 310                 315                 320

Ser Ser Thr Ser Thr Pro Pro Thr Ala Thr Met Pro Ser Leu Ile Ser
                325                 330                 335

Thr Thr Ser Thr Ala Ser Ser Ala Arg Arg Thr Ala Val Phe Pro Asp
            340                 345                 350

Leu Thr Cys Ser Ser Ser Ser Thr Leu Ser Leu Ala Ala Thr Thr Phe
        355                 360                 365

Leu Thr Ala Val Thr Ile Glu Thr Ala Ser Gln His Ile Arg Thr Leu
    370                 375                 380

Thr Val Thr Leu Asp Pro Val Thr Val His Ala Ile Val Thr Val Ser
385                 390                 395                 400

Val Tyr Lys Thr Glu Tyr Val Thr Asp Thr Val Thr Val Gly Asp Met
                405                 410                 415
```

```
Asn Ile Ala Tyr
            420


<210> SEQ ID NO 55
<211> LENGTH: 2057
<212> TYPE: DNA
<213> ORGANISM: Lipomyces starkeyi
<220> FEATURE:
<221> NAME/KEY: Intron
<222> LOCATION: (409)..(462)
<220> FEATURE:
<221> NAME/KEY: Intron
<222> LOCATION: (579)..(637)
<220> FEATURE:
<221> NAME/KEY: Intron
<222> LOCATION: (981)..(1028)

<400> SEQUENCE: 55

atgtcatttc gccaggcatt gttctcagct acccggactc atcgtgtgct gcttcgctcc     60

gttgccgcgg gcgggatcct gagcaccaca gcgttcttcc tctcgaacac agactcgttc    120

ggctcaatac accaccaggc tgagcaggac gtgccattga actatcctgt cccggccccc    180

tttgccttgc cccgtcccg agaagaacag atcaagaagt tggaaaccga acagttcgac    240

ttgctgatca taggcggtgg agctaccggt gccggctgcg cattggatgc cgtcagcaga    300

ggattaaagg tcgcgttggt tgagcgtgat gactttgcat gtggtacaag tagtaggagt    360

acgaagcttg tacacggtgg tgtgagatac ttggagaaag cattctgggt aggtgacaat    420

cacagctatg gcatgacatg aacgctaaca gcgtgatttc agaacctcga ctatgagcag    480

tacaaattgg tcaaggaggc acttgctgag cgtgctactt tcttgaaaat tgcgcctcat    540

ttgagtttcc cgctcccaat catggtccct gtctacaagt atgtctatag gccattttga    600

tctataagct taatcaatct aataatgcat tgcgtaggtg gtggcaagtc ccatattact    660

gggctggaac caagatgtac gatcttattg ctggaaagga gaacatggaa tcaagttact    720

tcatgggccg tggtaagacc ctcgagaact tcccaatgct taagcctcag aacttgaagg    780

gtgccattgt ctactacgac ggtagtcaca atgactcgcg aatgaacact gctatcgctc    840

tcactgctgc tcagaaaggt gccgttatcc tgaaccacat ggaggttaca gagttgtcca    900

aggacgcgtc tggtcgcgtc aatggtgctg ttgtccgcga caatgacggt actgctggga    960

agatccaggt tgatgctaag gtatgttgtg gagatacaat ttatatagtg cttgctgacc   1020

tgtttcaggg tgttattaac gcgaccggtc cgttcgcgga ccggatccgt cagctcgata   1080

ctcctgttgc gatcgacatc gtcgctccat catccggtgt gcatgtgatt cttcctgact   1140

actactgctc tcccagcatg ggtttgatcg acccagctac ttctgatgga cgagtagttt   1200

tctttcttcc atggcaaggc catactcttg ccggtacaac cgactctcct accacagtca   1260

cgaaggatcc tattccttcc gaggacgaga taagctggat cttgaacgaa attcaacact   1320

acgttgccga tgatattacc gttcgccggg aagatgttct tgccgcttgg agcggtatcc   1380

gtccattagt ccgcgaccca cgtgctaaga acacagagtc gctggtccgc aaccatttga   1440

tcaccctttc cgacagtggt ctcttgactg tcgctggcgg caagtggact acctatcgag   1500

aaatggcaga agacactgtc aacacctctg tcaaagagtt cggtcttgag ccgaccgccc   1560

catgtggaac caaggatatc aagcttgtcg gggctgaggg atacagaaaa ctcatgttca   1620

ttcacttgat ccagacattt ggcattgaga ctggcatagc caagcatctt gctgacaact   1680

atggagatcg tgcgtacgac gtcgtcaggc tttcagccac tacgggcgag agatggccca   1740

caagaggtgt caagctgtcg ccagcttatc cgtacattga tggcgagatc cgttacgcag   1800
```

```
ttcagcacga gtatgctcga acggctgtcg acgtgctgtc gcgacgcatc cgtctcgcgt   1860

tcttgaactc caaggctgcg ttggagagct tgcccaaggt catcgatatc atggccgaag   1920

agttgaagtg ggacaaggcg cgtcaggaca aggagtggga tgacaccatc aggttcttgt   1980

acagcatggg tctccagaac gggaagtact tctcgagagc ggacgttgag agcggaaaaa   2040

caaaaatgtt gggttaa                                                  2057


<210> SEQ ID NO 56
<211> LENGTH: 631
<212> TYPE: PRT
<213> ORGANISM: Lipomyces starkeyi

<400> SEQUENCE: 56

Met Ser Phe Arg Gln Ala Leu Phe Ser Ala Thr Arg Thr His Arg Val
1               5                   10                  15

Leu Leu Arg Ser Val Ala Ala Gly Gly Ile Leu Ser Thr Thr Ala Phe
            20                  25                  30

Phe Leu Ser Asn Thr Asp Ser Phe Gly Ser Ile His His Gln Ala Glu
        35                  40                  45

Gln Asp Val Pro Leu Asn Tyr Pro Val Pro Ala Pro Phe Ala Leu Pro
    50                  55                  60

Pro Ser Arg Glu Glu Gln Ile Lys Lys Leu Glu Thr Glu Gln Phe Asp
65                  70                  75                  80

Leu Leu Ile Ile Gly Gly Gly Ala Thr Gly Ala Gly Cys Ala Leu Asp
                85                  90                  95

Ala Val Ser Arg Gly Leu Lys Val Ala Leu Val Glu Arg Asp Asp Phe
            100                 105                 110

Ala Cys Gly Thr Ser Ser Arg Ser Thr Lys Leu Val His Gly Gly Val
        115                 120                 125

Arg Tyr Leu Glu Lys Ala Phe Trp Asn Leu Asp Tyr Glu Gln Tyr Lys
    130                 135                 140

Leu Val Lys Glu Ala Leu Ala Glu Arg Ala Thr Phe Leu Lys Ile Ala
145                 150                 155                 160

Pro His Leu Ser Phe Pro Leu Pro Ile Met Val Pro Val Tyr Lys Trp
                165                 170                 175

Trp Gln Val Pro Tyr Tyr Trp Ala Gly Thr Lys Met Tyr Asp Leu Ile
            180                 185                 190

Ala Gly Lys Glu Asn Met Glu Ser Ser Tyr Phe Met Gly Arg Gly Lys
        195                 200                 205

Thr Leu Glu Asn Phe Pro Met Leu Lys Pro Gln Asn Leu Lys Gly Ala
    210                 215                 220

Ile Val Tyr Tyr Asp Gly Ser His Asn Asp Ser Arg Met Asn Thr Ala
225                 230                 235                 240

Ile Ala Leu Thr Ala Ala Gln Lys Gly Ala Val Ile Leu Asn His Met
                245                 250                 255

Glu Val Thr Glu Leu Ser Lys Asp Ala Ser Gly Arg Val Asn Gly Ala
            260                 265                 270

Val Val Arg Asp Asn Asp Gly Thr Ala Gly Lys Ile Gln Val Asp Ala
        275                 280                 285

Lys Gly Val Ile Asn Ala Thr Gly Pro Phe Ala Asp Arg Ile Arg Gln
    290                 295                 300

Leu Asp Thr Pro Val Ala Ile Asp Ile Val Ala Pro Ser Ser Gly Val
305                 310                 315                 320
```

```
His Val Ile Leu Pro Asp Tyr Tyr Cys Ser Pro Ser Met Gly Leu Ile
                325                 330                 335

Asp Pro Ala Thr Ser Asp Gly Arg Val Val Phe Phe Leu Pro Trp Gln
            340                 345                 350

Gly His Thr Leu Ala Gly Thr Thr Asp Ser Pro Thr Thr Val Thr Lys
        355                 360                 365

Asp Pro Ile Pro Ser Glu Asp Glu Ile Ser Trp Ile Leu Asn Glu Ile
    370                 375                 380

Gln His Tyr Val Ala Asp Asp Ile Thr Val Arg Arg Glu Asp Val Leu
385                 390                 395                 400

Ala Ala Trp Ser Gly Ile Arg Pro Leu Val Arg Asp Pro Arg Ala Lys
                405                 410                 415

Asn Thr Glu Ser Leu Val Arg Asn His Leu Ile Thr Leu Ser Asp Ser
            420                 425                 430

Gly Leu Leu Thr Val Ala Gly Gly Lys Trp Thr Thr Tyr Arg Glu Met
        435                 440                 445

Ala Glu Asp Thr Val Asn Thr Ser Val Lys Glu Phe Gly Leu Glu Pro
    450                 455                 460

Thr Ala Pro Cys Gly Thr Lys Asp Ile Lys Leu Val Gly Ala Glu Gly
465                 470                 475                 480

Tyr Arg Lys Leu Met Phe Ile His Leu Ile Gln Thr Phe Gly Ile Glu
                485                 490                 495

Thr Gly Ile Ala Lys His Leu Ala Asp Asn Tyr Gly Asp Arg Ala Tyr
            500                 505                 510

Asp Val Val Arg Leu Ser Ala Thr Thr Gly Glu Arg Trp Pro Thr Arg
        515                 520                 525

Gly Val Lys Leu Ser Pro Ala Tyr Pro Tyr Ile Asp Gly Glu Ile Arg
    530                 535                 540

Tyr Ala Val Gln His Glu Tyr Ala Arg Thr Ala Val Asp Val Leu Ser
545                 550                 555                 560

Arg Arg Ile Arg Leu Ala Phe Leu Asn Ser Lys Ala Ala Leu Glu Ser
                565                 570                 575

Leu Pro Lys Val Ile Asp Ile Met Ala Glu Glu Leu Lys Trp Asp Lys
            580                 585                 590

Ala Arg Gln Asp Lys Glu Trp Asp Asp Thr Ile Arg Phe Leu Tyr Ser
        595                 600                 605

Met Gly Leu Gln Asn Gly Lys Tyr Phe Ser Arg Ala Asp Val Glu Ser
    610                 615                 620

Gly Lys Thr Lys Met Leu Gly
625                 630
```

<210> SEQ ID NO 57
<211> LENGTH: 1879
<212> TYPE: DNA
<213> ORGANISM: Lipomyces starkeyi
<220> FEATURE:
<221> NAME/KEY: Intron
<222> LOCATION: (439)..(493)
<220> FEATURE:
<221> NAME/KEY: Intron
<222> LOCATION: (861)..(911)
<220> FEATURE:
<221> NAME/KEY: Intron
<222> LOCATION: (1301)..(1349)
<220> FEATURE:
<221> NAME/KEY: Intron
<222> LOCATION: (1625)..(1675)

<400> SEQUENCE: 57

```
atgtcgaccg ctgcacaatc tgatacagac aacgaggata tatcgactgt cgatttggtt     60
gactctcgtg cagatactca cacatcttca aatgttatgt tgcaacagca aaaatcgcgt    120
cggagactaa tcgggaaaga cgccgagcca agaacacagc atccgtctgg aggcaaatcg    180
gagaaggagg agttgacgaa gccggatgac tcaaagggac ccataaaatt aagtcacata    240
tacccgatac atgccgttag ccgaggcagt attctgtcac gagagtcgac aactcctaca    300
ccgagttttg ttgggtttcg aaacttagcc atgatagtgc tagggaagtt acagtattca    360
ttattctttt ggtgcgatcg ggctaacatt ccgacagccg tcagcaatct tcgattggtg    420
attgaaaatt actcaaaggt atgcctgctc gacagaaata attgtggctg tatgacgagc    480
tgactttgaa cagtacggcg ttctgatccg attcgcccga ctcggtattt cacaaaagga    540
cattctgtat tgcatattct tgaccgctac catcccgctg cacctattta ttgctattgt    600
cattgaaaga ctagttgcga ttccgacggt aaactacgtc gcttcgctca gcgagagcga    660
ggataaaaaa cgctccaacc ccaaaatggg acggaagggg ggcagtatat cgattttgcg    720
tcctaagcca aaatatatgt ggcgcctgat cgtcctattg cattcaataa acgcaatggc    780
ttgcttgtgg gttacgactg ttgttgttta caattctatt tatcatcccc ttattgggac    840
agcttgtgaa tttcatgcag gtgagctata ctctaatttg tggtacgcat tgtaccgcta    900
acaagttgac agtgattgtg tgtcttaagg tcgcatcgtt tgcgcttacc aatcgcgatc    960
ttcgggagtc gatgctgaac tctcaacctg tgccagccat atacaacttg gccccttatc   1020
caaaaaactt aaccctcaag aacttgtcat acttttggtg ggcgccgact cttgtttatc   1080
aacctgtcta tccgcgatcg ccttcattcc ggcctttgtt ttttgtcaag cggattctgg   1140
agatggtggg cctatcattt ttaatatggt tcttgtcagc tcaatatgct gtgccgacgc   1200
tagaaaatag tttggtgcat tttcacagtt tgcaattcat gggaattatg gagcgactca   1260
tgaagcttgc tagcattagc atggctattt ggcttgctgg gtatgttcgg atagcaactt   1320
tggtctcgtg atgataaact aatttcgtta gttttttctg catttttcag tctggactca   1380
atgcgcttgc ggaggtaatg cggtttggtg acagagcctt ttacgacgac tggtggaaca   1440
gcaaatctgt gggagagtat tggcgtctgt ggaataagcc ggttacgaat tacttccggc   1500
gtcatattta cgtaccgctt gtgcgccgcg ggtggaattc tgcgacagcc agtgtcatgg   1560
tatttttcgt cagcgcggtg ttgcatgagc tagttgttgg agttccgacg cataacgtaa   1620
ttgggtacga ttgcctttat atagtatgaa aattgctgtt aactgagtta ataacagagt   1680
tgcattctcg tcgatgattc tacaaatccc actcatacaa gtaaccgcgc ctctggagaa   1740
gatgcatgga cctacatctg gaataatagg gaactgtatc ttttggttta gcttcttcat   1800
cggtcagcct ctgggcgtgc tactttacta ttttgcgtgg aacgttagta tgagcaaagt   1860
aaagatggtc gagagctag                                                1879
```

```
<210> SEQ ID NO 58
<211> LENGTH: 555
<212> TYPE: PRT
<213> ORGANISM: Lipomyces starkeyi

<400> SEQUENCE: 58

Met Ser Thr Ala Ala Gln Ser Asp Thr Asp Asn Glu Asp Ile Ser Thr
1               5                   10                  15

Val Asp Leu Val Asp Ser Arg Ala Asp Thr His Thr Ser Ser Asn Val
            20                  25                  30
```

```
Met Leu Gln Gln Gln Lys Ser Arg Arg Arg Leu Ile Gly Lys Asp Ala
        35                  40                  45

Glu Pro Arg Thr Gln His Pro Ser Gly Gly Lys Ser Glu Lys Glu Glu
    50                  55                  60

Leu Thr Lys Pro Asp Asp Ser Lys Gly Pro Ile Lys Leu Ser His Ile
65                  70                  75                  80

Tyr Pro Ile His Ala Val Ser Arg Gly Ser Ile Leu Ser Arg Glu Ser
                85                  90                  95

Thr Thr Pro Thr Pro Ser Phe Val Gly Phe Arg Asn Leu Ala Met Ile
            100                 105                 110

Val Leu Gly Lys Leu Gln Tyr Ser Leu Phe Phe Trp Cys Asp Arg Ala
        115                 120                 125

Asn Ile Pro Thr Ala Val Ser Asn Leu Arg Leu Val Ile Glu Asn Tyr
    130                 135                 140

Ser Lys Tyr Gly Val Leu Ile Arg Phe Ala Arg Leu Gly Ile Ser Gln
145                 150                 155                 160

Lys Asp Ile Leu Tyr Cys Ile Phe Leu Thr Ala Thr Ile Pro Leu His
                165                 170                 175

Leu Phe Ile Ala Ile Val Ile Glu Arg Leu Val Ala Ile Pro Thr Val
            180                 185                 190

Asn Tyr Val Ala Ser Leu Ser Glu Ser Glu Asp Lys Lys Arg Ser Asn
        195                 200                 205

Pro Lys Met Gly Arg Lys Gly Gly Ser Ile Ser Ile Leu Arg Pro Lys
    210                 215                 220

Pro Lys Tyr Met Trp Arg Leu Ile Val Leu Leu His Ser Ile Asn Ala
225                 230                 235                 240

Met Ala Cys Leu Trp Val Thr Thr Val Val Val Tyr Asn Ser Ile Tyr
                245                 250                 255

His Pro Leu Ile Gly Thr Ala Cys Glu Phe His Ala Val Ile Val Cys
            260                 265                 270

Leu Lys Val Ala Ser Phe Ala Leu Thr Asn Arg Asp Leu Arg Glu Ser
        275                 280                 285

Met Leu Asn Ser Gln Pro Val Pro Ala Ile Tyr Asn Leu Ala Pro Tyr
    290                 295                 300

Pro Lys Asn Leu Thr Leu Lys Asn Leu Ser Tyr Phe Trp Trp Ala Pro
305                 310                 315                 320

Thr Leu Val Tyr Gln Pro Val Tyr Pro Arg Ser Pro Ser Phe Arg Pro
                325                 330                 335

Leu Phe Phe Val Lys Arg Ile Leu Glu Met Val Gly Leu Ser Phe Leu
            340                 345                 350

Ile Trp Phe Leu Ser Ala Gln Tyr Ala Val Pro Thr Leu Glu Asn Ser
        355                 360                 365

Leu Val His Phe His Ser Leu Gln Phe Met Gly Ile Met Glu Arg Leu
    370                 375                 380

Met Lys Leu Ala Ser Ile Ser Met Ala Ile Trp Leu Ala Gly Phe Phe
385                 390                 395                 400

Cys Ile Phe Gln Ser Gly Leu Asn Ala Leu Ala Glu Val Met Arg Phe
                405                 410                 415

Gly Asp Arg Ala Phe Tyr Asp Asp Trp Trp Asn Ser Lys Ser Val Gly
            420                 425                 430

Glu Tyr Trp Arg Leu Trp Asn Lys Pro Val Thr Asn Tyr Phe Arg Arg
        435                 440                 445

His Ile Tyr Val Pro Leu Val Arg Arg Gly Trp Asn Ser Ala Thr Ala
```

```
    450                 455                 460

Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                485                 490                 495

Leu Gln Ile Pro Leu Ile Gln Val Thr Ala Pro Leu Glu Lys Met His
            500                 505                 510

Gly Pro Thr Ser Gly Ile Ile Gly Asn Cys Ile Phe Trp Phe Ser Phe
        515                 520                 525

Phe Ile Gly Gln Pro Leu Gly Val Leu Leu Tyr Tyr Phe Ala Trp Asn
    530                 535                 540

Val Ser Met Ser Lys Val Lys Met Val Glu Ser
545                 550                 555


<210> SEQ ID NO 59
<211> LENGTH: 2382
<212> TYPE: DNA
<213> ORGANISM: Lipomyces starkeyi
<220> FEATURE:
<221> NAME/KEY: Intron
<222> LOCATION: (166)..(295)
<220> FEATURE:
<221> NAME/KEY: Intron
<222> LOCATION: (366)..(420)

<400> SEQUENCE: 59

atggcaagta aatcagtatc agccgcagct ggatcgcggc agtcatctgt ttcatcgacc      60

ggatccattg atccattctc tgtcgcccag gtctactatg gccctgagac tgatttcact     120

acccacaaga tgagcaatct tattcgcacg aggactctgt cgacggtatg ttgtatattg     180

cttactttaa taatgcatgg atcgggaaga aatccactgg cgttccacag atcctattca     240

aagcgtggcg acctatagtg aaacgatttt cagacgctaa ttgtgtgtcg attaggtaca     300

aacgcgaagc agtaacaata cgcctgacta tctgaaatca gttcctcgca gaagagcatc     360

tcaaggtttg tcatgcggtg gaaattgtcg caaggttgcc gcaactgatt tgtggttata     420

gacgctgagt ccctgacgcc gcgcaagttc ctcgtcgacg tgaacttgac tcttcaggcg     480

ctgcttgaaa gcgaagacac tgacggaaac atgcaaataa cgattgagga tctgggtccg     540

aaagtattgc agctcggtac cgcgaactcg aacgggttca acaagttcga cattcgcggc     600

acttacatgt tgtcgaacct tttgcaagag ctcactcttg ccaaggagta cggccgaaag     660

tcgattatcc tggacgaaca gcgtctgaac gagaatccag tcagcaggtt gtcccgattg     720

atccgtacac agttctggga ctcgctaacc cgtcggatcg acgcttctct gttggaaatt     780

atcgctgtcg atcccaagaa ccgttcaaag gatcagagcc ctcgaatcta cgttccgcca     840

acggagaagg agcaatatga atactatgtc aaggaagctt ctaaacgccc tcatctgaat     900

ctccaggtgg agtatcttcc tgccactatc acggcggaat gggtcaagtc agtcaatgag     960

aaagcgggat tacttgcact ggcgatggac catgtggtcg atgaattcac tggacaatcg    1020

acattgcgag ggaaaccttt tgttgtgcct ggtggacgat tcaacgagct ctatgggtgg    1080

gactcgtata tgattgcctt aggtctattg gtggatggaa gagtcgatct tgctaagggt    1140

atcctcgaaa acttcatctt cgaaatcaac aattacggga agatcttgaa tgccaatcgt    1200

tcttactatc tttgcaggtc gcagccacca tttttgacag acttggcttt gaaggtgtat    1260

gaaaaaacga tattcgaacc aggagcattg gagttactga aagaatcgtt caaggctgca    1320

atcgtggagt ataagcaagt ttggacgtcc cctccacgat tggatcaaga gtcgggattg    1380
```

```
tcgtgctacc atccggatgg cattggtata ccgcctgaga ctgaggctag tcattttgag   1440
cacctcttga tgccttatgc ggaaaagcat aagctctcct tggaggattt ccagagacaa   1500
tacaatgatg gaatagtcaa ggagcctgct ctcgacgagt atttcgttca cgatcgagct   1560
gtccgagaat ctggtcatga cactacttac cgactcgaga aacgttgtgc caatctggca   1620
acaatcgatt tgaacagctt gttgtacaag tacgaagtcg atatcgctca tactatccga   1680
acaatgtttg gtgataagct ggtgctccat gacggaagtg tagaaaccag tgcgtcttgg   1740
gatcgtcgtg cacgacgacg aaagaatttg attgatcaat atttgtggga tgaggaaaag   1800
ggcatgtatt ttgattacga cattgtgcag aaaaagaagt ctgattatga gtctgctacg   1860
acattctggg cgatgtgggc tggttgcgcg tctcccaagc aagccgccag actagtttcg   1920
gacgcgctac caaagttcga agagtttggc ggtctggttt ctgggactga gaggtctcgc   1980
ggggtcatag gacttgatcg accgaacaga cagtgggact acccttacgg atgggcgccg   2040
caacagattc ttgcctgggt tggcttgatc agatatggat atgaagaaga tgctgagcga   2100
ctagtctatc gatggctgta catgattacc aaagcctttg tggattataa cggtattgtt   2160
gtcgagaaat atgatgtcac gcgaccagtg gatccacacc gcgtcgacgc cgagtatggt   2220
aaccaggggt cagatttcaa gggagttgcc aaggaaggat ttggctgggt aaatgcgtcc   2280
tatacttttg ggctgacgtt gattaccagt cacgcgcgac gtgctctcgg ggcatgcact   2340
ccaccaggtc ttttctatgc gagccagtac tcttacgttt aa                      2382
```

```
<210> SEQ ID NO 60
<211> LENGTH: 731
<212> TYPE: PRT
<213> ORGANISM: Lipomyces starkeyi

<400> SEQUENCE: 60

Met Ala Ser Lys Ser Val Ser Ala Ala Ala Gly Ser Arg Gln Ser Ser
1               5                   10                  15

Val Ser Ser Thr Gly Ser Ile Asp Pro Phe Ser Val Ala Gln Val Tyr
            20                  25                  30

Tyr Gly Pro Glu Thr Asp Phe Thr Thr His Lys Met Ser Asn Leu Ile
        35                  40                  45

Arg Thr Arg Thr Leu Ser Thr Val Gln Thr Arg Ser Ser Asn Asn Thr
    50                  55                  60

Pro Asp Tyr Leu Lys Ser Val Pro Arg Arg Arg Ala Ser Gln Asp Ala
65                  70                  75                  80

Glu Ser Leu Thr Pro Arg Lys Phe Leu Val Asp Val Asn Leu Thr Leu
                85                  90                  95

Gln Ala Leu Leu Glu Ser Glu Asp Thr Asp Gly Asn Met Gln Ile Thr
            100                 105                 110

Ile Glu Asp Leu Gly Pro Lys Val Leu Gln Leu Gly Thr Ala Asn Ser
        115                 120                 125

Asn Gly Phe Asn Lys Phe Asp Ile Arg Gly Thr Tyr Met Leu Ser Asn
    130                 135                 140

Leu Leu Gln Glu Leu Thr Leu Ala Lys Glu Tyr Gly Arg Lys Ser Ile
145                 150                 155                 160

Ile Leu Asp Glu Gln Arg Leu Asn Glu Asn Pro Val Ser Arg Leu Ser
                165                 170                 175

Arg Leu Ile Arg Thr Gln Phe Trp Asp Ser Leu Thr Arg Arg Ile Asp
            180                 185                 190
```

```
Ala Ser Leu Leu Glu Ile Ile Ala Val Asp Pro Lys Asn Arg Ser Lys
        195                 200                 205

Asp Gln Ser Pro Arg Ile Tyr Val Pro Pro Thr Glu Lys Glu Gln Tyr
    210                 215                 220

Glu Tyr Tyr Val Lys Glu Ala Ser Lys Arg Pro His Leu Asn Leu Gln
225                 230                 235                 240

Val Glu Tyr Leu Pro Ala Thr Ile Thr Ala Glu Trp Val Lys Ser Val
                245                 250                 255

Asn Glu Lys Ala Gly Leu Leu Ala Leu Ala Met Asp His Val Val Asp
            260                 265                 270

Glu Phe Thr Gly Gln Ser Thr Leu Arg Gly Lys Pro Phe Val Val Pro
        275                 280                 285

Gly Gly Arg Phe Asn Glu Leu Tyr Gly Trp Asp Ser Tyr Met Ile Ala
    290                 295                 300

Leu Gly Leu Leu Val Asp Gly Arg Val Asp Leu Ala Lys Gly Ile Leu
305                 310                 315                 320

Glu Asn Phe Ile Phe Glu Ile Asn Asn Tyr Gly Lys Ile Leu Asn Ala
                325                 330                 335

Asn Arg Ser Tyr Tyr Leu Cys Arg Ser Gln Pro Pro Phe Leu Thr Asp
            340                 345                 350

Leu Ala Leu Lys Val Tyr Glu Lys Thr Ile Phe Glu Pro Gly Ala Leu
        355                 360                 365

Glu Leu Leu Lys Glu Ser Phe Lys Ala Ala Ile Val Glu Tyr Lys Gln
    370                 375                 380

Val Trp Thr Ser Pro Pro Arg Leu Asp Gln Glu Ser Gly Leu Ser Cys
385                 390                 395                 400

Tyr His Pro Asp Gly Ile Gly Ile Pro Pro Glu Thr Glu Ala Ser His
                405                 410                 415

Phe Glu His Leu Leu Met Pro Tyr Ala Glu Lys His Lys Leu Ser Leu
            420                 425                 430

Glu Asp Phe Gln Arg Gln Tyr Asn Asp Gly Ile Val Lys Glu Pro Ala
        435                 440                 445

Leu Asp Glu Tyr Phe Val His Asp Arg Ala Val Arg Glu Ser Gly His
    450                 455                 460

Asp Thr Thr Tyr Arg Leu Glu Lys Arg Cys Ala Asn Leu Ala Thr Ile
465                 470                 475                 480

Asp Leu Asn Ser Leu Leu Tyr Lys Tyr Glu Val Asp Ile Ala His Thr
                485                 490                 495

Ile Arg Thr Met Phe Gly Asp Lys Leu Val Leu His Asp Gly Ser Val
            500                 505                 510

Glu Thr Ser Ala Ser Trp Asp Arg Arg Ala Arg Arg Arg Lys Asn Leu
        515                 520                 525

Ile Asp Gln Tyr Leu Trp Asp Glu Glu Lys Gly Met Tyr Phe Asp Tyr
    530                 535                 540

Asp Ile Val Gln Lys Lys Lys Ser Asp Tyr Glu Ser Ala Thr Thr Phe
545                 550                 555                 560

Trp Ala Met Trp Ala Gly Cys Ala Ser Pro Lys Gln Ala Ala Arg Leu
                565                 570                 575

Val Ser Asp Ala Leu Pro Lys Phe Glu Glu Phe Gly Gly Leu Val Ser
            580                 585                 590

Gly Thr Glu Arg Ser Arg Gly Val Ile Gly Leu Asp Arg Pro Asn Arg
        595                 600                 605

Gln Trp Asp Tyr Pro Tyr Gly Trp Ala Pro Gln Gln Ile Leu Ala Trp
```

```
    610                 615                 620

Val Gly Leu Ile Arg Tyr Gly Tyr Glu Glu Asp Ala Glu Arg Leu Val
625                 630                 635                 640

Tyr Arg Trp Leu Tyr Met Ile Thr Lys Ala Phe Val Asp Tyr Asn Gly
                645                 650                 655

Ile Val Val Glu Lys Tyr Asp Val Thr Arg Pro Val Asp Pro His Arg
            660                 665                 670

Val Asp Ala Glu Tyr Gly Asn Gln Gly Ser Asp Phe Lys Gly Val Ala
        675                 680                 685

Lys Glu Gly Phe Gly Trp Val Asn Ala Ser Tyr Thr Phe Gly Leu Thr
    690                 695                 700

Leu Ile Thr Ser His Ala Arg Arg Ala Leu Gly Ala Cys Thr Pro Pro
705                 710                 715                 720

Gly Leu Phe Tyr Ala Ser Gln Tyr Ser Tyr Val
                725                 730


<210> SEQ ID NO 61
<211> LENGTH: 3176
<212> TYPE: DNA
<213> ORGANISM: Lipomyces starkeyi
<220> FEATURE:
<221> NAME/KEY: Intron
<222> LOCATION: (1276)..(1328)
<220> FEATURE:
<221> NAME/KEY: Intron
<222> LOCATION: (2040)..(2090)

<400> SEQUENCE: 61

atgagattaa atgttttact ttctggctgt gttgctctat cgcatctcgc gctcgccagt      60

gtttcactta agttaaggca gcagctgtcc aaagaggctg tcacgaacga tccgattctt     120

gacggcgtcg agtacaatga tggcacctgg acgttaacaa accgtctgct cactacgaac     180

aggttccaac ttcagccata tgtttctaac ggatatattg gtgcccgtct gccgttggaa     240

ggtaccggct acgtccaaga cacttttgag agcgaggacg gcggcagtgt caatggcgcc     300

gagccgacga atggttggcc cctgttttcg cctcggttca cgggagcgta catcgcgggc     360

ttttgggact tgcagccaaa caccacagcc acaaatttcc cagagttatt gacgagaggc     420

ggcgagagtg taatttcgac cgtgcccgta tggtctacac tgttagtcac tgctcacgga     480

gataccttca acgtcaattg tcctctagga aatgtgcaca actatacgca gtcgctttcc     540

atgaaggacg gtatcgtcag gaccaaacta gaatggtacc cgaatgggaa tgcgtcgcag     600

gcgatttctc tcgcgtacga ggtcttggcc cacagagtga ttccgacgct ggcaatggtt     660

aagctggaag tactggccgc cgaagatacc aatatcaagc tctccgacat tctcgacggc     720

gcgggttcgt tccggacgat atttttggag aagaactact catcgcatga cgctaccggc     780

atgtggactg gcgttcgtcc ttatggtttg accagtgttc aggcttacga atactcgcac     840

ctcgagtttt cggattcggc tgtggtcaac ataagcagtc ggcaaaagtc tcctattgcg     900

aacaagagcc cggcaacgat atcgcaagag tttgaagtgt cactcgaagc tggcaagccg     960

ttcttggtct acaagttcgt cggtatcgcc tcgtcggatg cgtataagga cccgaagcgc    1020

gtagctgcat acacggcgcg tattgctgcg tcaattggat ataggctggc aaaggcggat    1080

cacaagcttg cgtggcataa gctttgggaa tctggcgaca ttgtctttcc tggggacaag    1140

gagcttcaga tttctatccg agcttcgctc ttccacttgt tgagtgctct ccggtcgggg    1200

gacgagcctt ctggtcgagg tgacaattcg atcgcagttt ctggactcag ttcggactcc    1260
```

```
tatggaggcc tggtggtaag tattgaaatt gcggaacggg ctgcatgaga gttgctgatc   1320
aatataagtt ctgggacgcc gacacgtgga tgtatcctgc gatgtctgtg cttcatccca   1380
agtatgcggc gaatgtcaac aacttccggc aacgaattca taaccagtcg attgagaacg   1440
cgcggtcata taacctcagt ggtgccatct actcgtggac gtctggtcgt ttcggcaact   1500
gcactggcac cggtccttgc gttgactacg agtatcatat caacgtcgat attgcccaag   1560
ctcactggaa tcaatttctg ttgtcgaatg atacggactg gttggaggcg aaaggatggc   1620
cgatcattcg tgatgcggcg gagatgtttt cgtcgtatgt cgtgaagaac gcgtcgacgg   1680
gaccatacta ctacacgtac aatatgaccg accctgacga gtatgccaat tttgtcgaca   1740
acggcgcgtt cacgaacgca ggcatttcca agcttatggg atgggcgcga cgagccgctg   1800
agattgttgg acaggactca aatccggagt gggcagatat tgaggagaat atttacattc   1860
cggtcaactc ggacgtgaat ctggtgttgg aattctcgaa tatgaatggg tcagtagaga   1920
tcaagcaggc ggacgtggtt ttgcttgact atcctctcga atatcaccgt tcgtggcagc   1980
agagtttgaa caatctggat tttacgcca tggctcagag tgcagatggt ccagctatgg   2040
tacgcggtga ttgttatgca attgagagtc gttttaaccg aaacttttag acatgggcga   2100
ttttcgcaat cagctctgcg gaactgagtc ctgtcggctg cgcatcgtac acgtacctcc   2160
tgtacgcgtc gcagccgtac ctgcgggcgc cgttttacca gttttcggag cagatggacg   2220
acaacgcgac gacgaacggc ggtacgaggc ccgcgttccc gttcttgacg ggccacggcg   2280
ggtttctgca ggttctgacg cacggattca cgggcttccg acctcgcgag gacgtgtttt   2340
acctcgatcc ttcgctgccg ccgcagattg agcgcgggta cacggttaac gggatgaaat   2400
ggcgggacag cgttttcgac gtgacgatta agcttgacga gacagttata caccgtcgta   2460
ccaaagcgac gtcgagatcg cggactggga atgcggatct ggtggagtat ctttcggcgc   2520
actacgacaa gcggcggcac gacgacgagg gctcgagtat tcaaaagggc ggcacgccag   2580
ttaccgtccg tatcggcgcc ggcgacggaa aaggcgatta cacgctgtac gaaggtggtc   2640
ggctcgttgt gcctacccgc cggctgatc tcaatggcac gttagtggcg ggcaatgtcg   2700
cgcaatgcca gcccgccatc tcgaacgtga cctgggcgag cggacatttc ccgatctcgg   2760
ccgtcgacgg gtcgaattcg acgtcctggc agccatctac gcgcgaccca tccgcgctgc   2820
tggtcgattt ggggaaagcc acgactgtcg ctggcgtgag cctaaactgg gggcgcacgc   2880
ctccgctggc attttcggtc gggtacgcag ccacggtcgt cgacgatggt ccgacgttcg   2940
gcagcgtgga tttcgcgtgg cctatcgtgc ggcagaacgt gtcgatttct gacgaataca   3000
acgccgcgac ggcgctcgag gtcaggttgt cggtcggcaa cgtcacgacc gcaggcctgg   3060
ccgaaaccgt gcgtacgcgg tggataatgt tggtcgtgga agggtcgtac gacacggggt   3120
tgcggtacgg cgacgtcggt gccactgttg ccgagtttgc ggtcattgag ggtgga       3176
```

<210> SEQ ID NO 62
<211> LENGTH: 1023
<212> TYPE: PRT
<213> ORGANISM: Lipomyces starkeyi

<400> SEQUENCE: 62

```
Met Arg Leu Asn Val Leu Leu Ser Gly Cys Val Ala Leu Ser His Leu
1               5                   10                  15

Ala Leu Ala Ser Val Ser Leu Lys Leu Arg Gln Gln Leu Ser Lys Glu
            20                  25                  30

Ala Val Thr Asn Asp Pro Ile Leu Asp Gly Val Glu Tyr Asn Asp Gly
```

```
        35                  40                  45

Thr Trp Thr Leu Thr Asn Arg Leu Leu Thr Thr Asn Arg Phe Gln Leu
    50                  55                  60

Gln Pro Tyr Val Ser Asn Gly Tyr Ile Gly Ala Arg Leu Pro Leu Glu
65                  70                  75                  80

Gly Thr Gly Tyr Val Gln Asp Thr Phe Glu Ser Glu Asp Gly Gly Ser
                85                  90                  95

Val Asn Gly Ala Glu Pro Thr Asn Gly Trp Pro Leu Phe Ser Pro Arg
            100                 105                 110

Phe Thr Gly Ala Tyr Ile Ala Gly Phe Trp Asp Leu Gln Pro Asn Thr
        115                 120                 125

Thr Ala Thr Asn Phe Pro Glu Leu Leu Thr Arg Gly Gly Glu Ser Val
    130                 135                 140

Ile Ser Thr Val Pro Val Trp Ser Thr Leu Leu Val Thr Ala His Gly
145                 150                 155                 160

Asp Thr Phe Asn Val Asn Cys Pro Leu Gly Asn Val His Asn Tyr Thr
                165                 170                 175

Gln Ser Leu Ser Met Lys Asp Gly Ile Val Arg Thr Lys Leu Glu Trp
            180                 185                 190

Tyr Pro Asn Gly Asn Ala Ser Gln Ala Ile Ser Leu Ala Tyr Glu Val
        195                 200                 205

Leu Ala His Arg Val Ile Pro Thr Leu Ala Met Val Lys Leu Glu Val
    210                 215                 220

Leu Ala Ala Glu Asp Thr Asn Ile Lys Leu Ser Asp Ile Leu Asp Gly
225                 230                 235                 240

Ala Gly Ser Phe Arg Thr Ile Phe Leu Glu Lys Asn Tyr Ser Ser His
                245                 250                 255

Asp Ala Thr Gly Met Trp Thr Gly Val Arg Pro Tyr Gly Leu Thr Ser
            260                 265                 270

Val Gln Ala Tyr Glu Tyr Ser His Leu Glu Phe Ser Asp Ser Ala Val
        275                 280                 285

Val Asn Ile Ser Ser Arg Gln Lys Ser Pro Ile Ala Asn Lys Ser Pro
    290                 295                 300

Ala Thr Ile Ser Gln Glu Phe Glu Val Ser Leu Glu Ala Gly Lys Pro
305                 310                 315                 320

Phe Leu Val Tyr Lys Phe Val Gly Ile Ala Ser Ser Asp Ala Tyr Lys
                325                 330                 335

Asp Pro Lys Arg Val Ala Ala Tyr Thr Ala Arg Ile Ala Ala Ser Ile
            340                 345                 350

Gly Tyr Arg Leu Ala Lys Ala Asp His Lys Leu Ala Trp His Lys Leu
        355                 360                 365

Trp Glu Ser Gly Asp Ile Val Phe Pro Gly Asp Lys Glu Leu Gln Ile
    370                 375                 380

Ser Ile Arg Ala Ser Leu Phe His Leu Leu Ser Ala Leu Arg Ser Gly
385                 390                 395                 400

Asp Glu Pro Ser Gly Arg Gly Asp Asn Ser Ile Ala Val Ser Gly Leu
                405                 410                 415

Ser Ser Asp Ser Tyr Gly Gly Leu Val Phe Trp Asp Ala Asp Thr Trp
            420                 425                 430

Met Tyr Pro Ala Met Ser Val Leu His Pro Lys Tyr Ala Ala Asn Val
        435                 440                 445

Asn Asn Phe Arg Gln Arg Ile His Asn Gln Ser Ile Glu Asn Ala Arg
    450                 455                 460
```

```
Ser Tyr Asn Leu Ser Gly Ala Ile Tyr Ser Trp Thr Ser Gly Arg Phe
465                 470                 475                 480

Gly Asn Cys Thr Gly Thr Gly Pro Cys Val Asp Tyr Glu Tyr His Ile
                485                 490                 495

Asn Val Asp Ile Ala Gln Ala His Trp Asn Gln Phe Leu Leu Ser Asn
            500                 505                 510

Asp Thr Asp Trp Leu Glu Ala Lys Gly Trp Pro Ile Ile Arg Asp Ala
        515                 520                 525

Ala Glu Met Phe Ser Ser Tyr Val Val Lys Asn Ala Ser Thr Gly Pro
    530                 535                 540

Tyr Tyr Tyr Thr Tyr Asn Met Thr Asp Pro Asp Glu Tyr Ala Asn Phe
545                 550                 555                 560

Val Asp Asn Gly Ala Phe Thr Asn Ala Gly Ile Ser Lys Leu Met Gly
                565                 570                 575

Trp Ala Arg Arg Ala Ala Glu Ile Val Gly Gln Asp Ser Asn Pro Glu
            580                 585                 590

Trp Ala Asp Ile Glu Glu Asn Ile Tyr Ile Pro Val Asn Ser Asp Val
        595                 600                 605

Asn Leu Val Leu Glu Phe Ser Asn Met Asn Gly Ser Val Glu Ile Lys
    610                 615                 620

Gln Ala Asp Val Val Leu Leu Asp Tyr Pro Leu Glu Tyr His Arg Ser
625                 630                 635                 640

Trp Gln Gln Ser Leu Asn Asn Leu Asp Phe Tyr Ala Met Ala Gln Ser
                645                 650                 655

Ala Asp Gly Pro Ala Met Thr Trp Ala Ile Phe Ala Ile Ser Ser Ala
            660                 665                 670

Glu Leu Ser Pro Val Gly Cys Ala Ser Tyr Thr Tyr Leu Leu Tyr Ala
        675                 680                 685

Ser Gln Pro Tyr Leu Arg Ala Pro Phe Tyr Gln Phe Ser Glu Gln Met
    690                 695                 700

Asp Asp Asn Ala Thr Thr Asn Gly Gly Thr Arg Pro Ala Phe Pro Phe
705                 710                 715                 720

Leu Thr Gly His Gly Gly Phe Leu Gln Val Leu Thr His Gly Phe Thr
                725                 730                 735

Gly Phe Arg Pro Arg Glu Asp Val Phe Tyr Leu Asp Pro Ser Leu Pro
            740                 745                 750

Pro Gln Ile Glu Arg Gly Tyr Thr Val Asn Gly Met Lys Trp Arg Asp
        755                 760                 765

Ser Val Phe Asp Val Thr Ile Lys Leu Asp Glu Thr Val Ile His Arg
    770                 775                 780

Arg Thr Lys Ala Thr Ser Arg Ser Arg Thr Gly Asn Ala Asp Leu Val
785                 790                 795                 800

Glu Tyr Leu Ser Ala His Tyr Asp Lys Arg Arg His Asp Asp Glu Gly
                805                 810                 815

Ser Ser Ile Gln Lys Gly Gly Thr Pro Val Thr Val Arg Ile Gly Ala
            820                 825                 830

Gly Asp Gly Lys Gly Asp Tyr Thr Leu Tyr Glu Gly Gly Arg Leu Val
        835                 840                 845

Val Pro Thr Arg Arg Ala Asp Leu Asn Gly Thr Leu Val Ala Gly Asn
    850                 855                 860

Val Ala Gln Cys Gln Pro Ala Ile Ser Asn Val Thr Trp Ala Ser Gly
865                 870                 875                 880
```

```
His Phe Pro Ile Ser Ala Val Asp Gly Ser Asn Ser Thr Ser Trp Gln
                885                 890                 895

Pro Ser Thr Arg Asp Pro Ser Ala Leu Leu Val Asp Leu Gly Lys Ala
            900                 905                 910

Thr Thr Val Ala Gly Val Ser Leu Asn Trp Gly Arg Thr Pro Pro Leu
        915                 920                 925

Ala Phe Ser Val Gly Tyr Ala Ala Thr Val Val Asp Asp Gly Pro Thr
    930                 935                 940

Phe Gly Ser Val Asp Phe Ala Trp Pro Ile Val Arg Gln Asn Val Ser
945                 950                 955                 960

Ile Ser Asp Glu Tyr Asn Ala Ala Thr Ala Leu Glu Val Arg Leu Ser
                965                 970                 975

Val Gly Asn Val Thr Thr Ala Gly Leu Ala Glu Thr Val Arg Thr Arg
            980                 985                 990

Trp Ile Met Leu Val Val Glu Gly  Ser Tyr Asp Thr Gly  Leu Arg Tyr
        995                 1000                1005

Gly Asp  Val Gly Ala Thr Val  Ala Glu Phe Ala Val  Ile Glu Gly
    1010                 1015                1020
```

<210> SEQ ID NO 63
<211> LENGTH: 1385
<212> TYPE: DNA
<213> ORGANISM: Lipomyces starkeyi
<220> FEATURE:
<221> NAME/KEY: Intron
<222> LOCATION: (204)..(254)

<400> SEQUENCE: 63

```
atgaccatcg gcactgccat tcagtgctcc tcgttctcac ttgctcagtt catcatcggc     60

cgcattgtca ctggctgcgg aaacggattt attacagcga cggtgccgat gtggcagtct    120

gagtgtgcta aagcggaggc acgtggccag ttagttatga ttcagggtgc gctgattact    180

ggcggtattg ccttatctta ctggtaattc tgctttgact caattggctt aatatttgat    240

aatgacatgg ttttaggatt gactttgcat tctacttcgt ccccggccaa gctgattggc    300

gtttccctat cgctttccaa gccgtgtttg caatcatcct catgtgcaca gtcctggaac    360

tccctgagtc ccctcgatgg ctcttaaaaa agggtcacga gaaagaagca gcccttgtct    420

ttgcctcgct tgctgatttg cctgaggaca gcccagttat cgccgaacaa gtcgaagagg    480

tcaagtcgac cctcacctct gagccccgct cgtcgttccg agaaatattc acctttacac    540

atgagaaaca ctttcatcgg actatgctcg ctttttggaa ccaggtcatg cagcaaattt    600

ctggtatcaa ccttatcaca tactacgccg gaaccatcta cgagaattcc ataggtctca    660

caccgatgaa agcaaagatc cttgccgctt gcaacggtac cgagtacttc atggcggcgt    720

gggtcgcgtt ctacacgatc gagcgtctcg gccgccgcaa gttgatgctc ataggtgctg    780

ttggccaagc gatcaccatg gcgattctca ccggcaccgc gcacgcggct gacaatgcaa    840

acagcaaagg gggtatcgca gccgccgtct tcctcttcgt ctttaacacg ttcttcggga    900

ttggctggct tggtatgact tggttgtatc ctgctgagat cgtgtcgctc caagtccgcg    960

cgcctgcaaa tggtctttcg accgccggca actggatcgc caatttctta gtcgtcatga   1020

ttacccccat cgcctttaat aatattggcg cctacactta cctcgtcttc gcagtcatca   1080

atgcagtgat ggtgcccacc gtctacttct tctacccgga gacatcgggt cgctcgctcg   1140

aggaaatcga cgatatcttc gcacagagca actcatggac cccgtgggat gtcgttggaa   1200

tcgcgaaccg catgccaaag catcacaccg atgttaacga aatcggagtt gaggagaacg   1260
```

gcaaggcata tttaaagcat aggacgagca gccagggcga cgaacacgac gagaaggtgg 1320
gtcgtttcga gactggaagt ggtagcgaga gttcaccagg cgtcgcagga gaaatcaatg 1380
attag 1385

<210> SEQ ID NO 64
<211> LENGTH: 443
<212> TYPE: PRT
<213> ORGANISM: Lipomyces starkeyi

<400> SEQUENCE: 64

Met Thr Ile Gly Thr Ala Ile Gln Cys Ser Ser Phe Ser Leu Ala Gln
1 5 10 15

Phe Ile Ile Gly Arg Ile Val Thr Gly Cys Gly Asn Gly Phe Ile Thr
20 25 30

Ala Thr Val Pro Met Trp Gln Ser Glu Cys Ala Lys Ala Glu Ala Arg
35 40 45

Gly Gln Leu Val Met Ile Gln Gly Ala Leu Ile Thr Gly Gly Ile Ala
50 55 60

Leu Ser Tyr Arg Ile Asp Phe Ala Phe Tyr Phe Val Pro Gly Gln Ala
65 70 75 80

Asp Trp Arg Phe Pro Ile Ala Phe Gln Ala Val Phe Ala Ile Ile Leu
85 90 95

Met Cys Thr Val Leu Glu Leu Pro Glu Ser Pro Arg Trp Leu Leu Lys
100 105 110

Lys Gly His Glu Lys Glu Ala Ala Leu Val Phe Ala Ser Leu Ala Asp
115 120 125

Leu Pro Glu Asp Ser Pro Val Ile Ala Glu Gln Val Glu Glu Val Lys
130 135 140

Ser Thr Leu Thr Ser Glu Pro Arg Ser Ser Phe Arg Glu Ile Phe Thr
145 150 155 160

Phe Thr His Glu Lys His Phe His Arg Thr Met Leu Ala Phe Trp Asn
165 170 175

Gln Val Met Gln Gln Ile Ser Gly Ile Asn Leu Ile Thr Tyr Tyr Ala
180 185 190

Gly Thr Ile Tyr Glu Asn Ser Ile Gly Leu Thr Pro Met Lys Ala Lys
195 200 205

Ile Leu Ala Ala Cys Asn Gly Thr Glu Tyr Phe Met Ala Ala Trp Val
210 215 220

Ala Phe Tyr Thr Ile Glu Arg Leu Gly Arg Arg Lys Leu Met Leu Ile
225 230 235 240

Gly Ala Val Gly Gln Ala Ile Thr Met Ala Ile Leu Thr Gly Thr Ala
245 250 255

His Ala Ala Asp Asn Ala Asn Ser Lys Gly Gly Ile Ala Ala Ala Val
260 265 270

Phe Leu Phe Val Phe Asn Thr Phe Phe Gly Ile Gly Trp Leu Gly Met
275 280 285

Thr Trp Leu Tyr Pro Ala Glu Ile Val Ser Leu Gln Val Arg Ala Pro
290 295 300

Ala Asn Gly Leu Ser Thr Ala Gly Asn Trp Ile Ala Asn Phe Leu Val
305 310 315 320

Val Met Ile Thr Pro Ile Ala Phe Asn Asn Ile Gly Ala Tyr Thr Tyr
325 330 335

Leu Val Phe Ala Val Ile Asn Ala Val Met Val Pro Thr Val Tyr Phe

```
            340                 345                 350

Phe Tyr Pro Glu Thr Ser Gly Arg Ser Leu Glu Glu Ile Asp Asp Ile
        355                 360                 365

Phe Ala Gln Ser Asn Ser Trp Thr Pro Trp Asp Val Val Gly Ile Ala
    370                 375                 380

Asn Arg Met Pro Lys His His Thr Asp Val Asn Glu Ile Gly Val Glu
385                 390                 395                 400

Glu Asn Gly Lys Ala Tyr Leu Lys His Arg Thr Ser Ser Gln Gly Asp
                405                 410                 415

Glu His Asp Glu Lys Val Gly Arg Phe Glu Thr Gly Ser Gly Ser Glu
            420                 425                 430

Ser Ser Pro Gly Val Ala Gly Glu Ile Asn Asp
        435                 440


<210> SEQ ID NO 65
<211> LENGTH: 1712
<212> TYPE: DNA
<213> ORGANISM: Lipomyces starkeyi
<220> FEATURE:
<221> NAME/KEY: Intron
<222> LOCATION: (86)..(136)
<220> FEATURE:
<221> NAME/KEY: Intron
<222> LOCATION: (576)..(626)

<400> SEQUENCE: 65

atgtcaaagc gataccacgg actacggggc catatgctca acaaagccat cgccaccatt     60

gctggtatcg gtttcctact gtttggttac tatccccgtt tgatccctag atatgcattg    120

cagctaacaa tttccaggat acgatcaggg cgtaatgggg agcttgctca cgctcaagac    180

attcaccggg accttcccgt ccttggatac cagtaatggt ctttcggcat cggttcgttc    240

gcacaattcc actattcagg gaactgcagt cgctctctac gaaatcggat gcatgatggg    300

cgcattgaca accatgtggc ttggcgacaa gcttggtaga cggaagatta tctttatcgg    360

cgcctttgtt atgattgtgg gaactgcgat tcagtgttcc tcctttaccc tggcgcagtt    420

tattgtcggg agaattatta ctggatacgg taatggctac atcactgcca ctgttccaat    480

gtggcagtcc gagtgcgcaa aagcagaatc ccgaggaaaa ttggtcatgg tccagggtgc    540

attgattacc ggtggtatcg ccatttccta ctggtctgtc cccgttttcc ccctcgatat    600

gcattatagc taacaatttt tgtaggattg actttggctt ctactttgtt gataacgaag    660

tcaattggcg attcccaatc gcgtttcaag ctatttttgc gatcattcta ctatgcactg    720

tccttcaatt gccggaatct ccgcgatggt tgattcgtca cggtaatgag caggaggcaa    780

aatatgtctt ttctgccctc gcggatgttg acatcaccca tcctcttatc gatgagcaag    840

taaacgagat taaggcgacc atcacagcgg agcaccaggg cagaatccgg gaaatattca    900

cgttcactaa gaagaagcac ttccatcgca ctatgcttgc tttttggaat caggccatgc    960

agcaagtgac tggtattaat ctcattacat actacgccgc gacgatttac gagaactcaa   1020

ttgggttgtc accactgaat tcgaaaatct tagctgcagc aaatggaaca gagtatttca   1080

ttgtatcatg gatcgcgttc ttcactatcg aacgaattgg ccgtcgcaaa ctgatgttgt   1140

tcggcgcaat gggacaagct gctactatgg ctatgcttac cggcactgcg catgcagctg   1200

acagaggaaa cagccaagcc ggtattgctg ctgctgcctt tctcttcgtg tttaatacgt   1260

tcttcgcaat cggatggctg ggaatgacat ggctttatcc cgctgaaatc gtatcgctgc   1320

aggtccgtgc accggcgaac ggcctttcga ccgcagcgaa ttggatttc aactttatgg    1380
```

```
ttgtcatgat cacaccggtc gcgttcaaca gcattggagc gtacacgtac ttggtattcg   1440

ctgtcatcaa tgcgataatg gtaccctgtg tctacctatt ctatccggag accgccggcc   1500

gttcgctcga agagattgac gagatcttcg agaaaagcaa tccctggacg ccctgggacg   1560

tcgtcggcat cgcaagtaaa ttaccacgcc atcatattga tgttcttgaa atcgtagatg   1620

agcaacacga tatagaggcc ggcgtcaaga gaagacatcc acacggtgca gcagatcaag   1680

agaagccggt tgtattgcat tctgaagtat aa                                 1712
```

<210> SEQ ID NO 66
<211> LENGTH: 535
<212> TYPE: PRT
<213> ORGANISM: Lipomyces starkeyi

<400> SEQUENCE: 66

```
Met Ser Lys Arg Tyr His Gly Leu Arg Gly His Met Leu Asn Lys Ala
1               5                   10                  15

Ile Ala Thr Ile Ala Gly Ile Gly Phe Leu Leu Phe Gly Tyr Asp Gln
            20                  25                  30

Gly Val Met Gly Ser Leu Leu Thr Leu Lys Thr Phe Thr Gly Thr Phe
        35                  40                  45

Pro Ser Leu Asp Thr Ser Asn Gly Leu Ser Ala Ser Val Arg Ser His
    50                  55                  60

Asn Ser Thr Ile Gln Gly Thr Ala Val Ala Leu Tyr Glu Ile Gly Cys
65                  70                  75                  80

Met Met Gly Ala Leu Thr Thr Met Trp Leu Gly Asp Lys Leu Gly Arg
                85                  90                  95

Arg Lys Ile Ile Phe Ile Gly Ala Phe Val Met Ile Val Gly Thr Ala
            100                 105                 110

Ile Gln Cys Ser Ser Phe Thr Leu Ala Gln Phe Ile Val Gly Arg Ile
        115                 120                 125

Ile Thr Gly Tyr Gly Asn Gly Tyr Ile Thr Ala Thr Val Pro Met Trp
    130                 135                 140

Gln Ser Glu Cys Ala Lys Ala Glu Ser Arg Gly Lys Leu Val Met Val
145                 150                 155                 160

Gln Gly Ala Leu Ile Thr Gly Gly Ile Ala Ile Ser Tyr Trp Ile Asp
                165                 170                 175

Phe Gly Phe Tyr Phe Val Asp Asn Glu Val Asn Trp Arg Phe Pro Ile
            180                 185                 190

Ala Phe Gln Ala Ile Phe Ala Ile Ile Leu Leu Cys Thr Val Leu Gln
        195                 200                 205

Leu Pro Glu Ser Pro Arg Trp Leu Ile Arg His Gly Asn Glu Gln Glu
    210                 215                 220

Ala Lys Tyr Val Phe Ser Ala Leu Ala Asp Val Asp Ile Thr His Pro
225                 230                 235                 240

Leu Ile Asp Glu Gln Val Asn Glu Ile Lys Ala Thr Ile Thr Ala Glu
                245                 250                 255

His Gln Gly Arg Ile Arg Glu Ile Phe Thr Phe Thr Lys Lys Lys His
            260                 265                 270

Phe His Arg Thr Met Leu Ala Phe Trp Asn Gln Ala Met Gln Gln Val
        275                 280                 285

Thr Gly Ile Asn Leu Ile Thr Tyr Tyr Ala Ala Thr Ile Tyr Glu Asn
    290                 295                 300

Ser Ile Gly Leu Ser Pro Leu Asn Ser Lys Ile Leu Ala Ala Ala Asn
```

```
305                 310                 315                 320

Gly Thr Glu Tyr Phe Ile Val Ser Trp Ile Ala Phe Phe Thr Ile Glu
                325                 330                 335

Arg Ile Gly Arg Arg Lys Leu Met Leu Phe Gly Ala Met Gly Gln Ala
            340                 345                 350

Ala Thr Met Ala Met Leu Thr Gly Thr Ala His Ala Ala Asp Arg Gly
        355                 360                 365

Asn Ser Gln Ala Gly Ile Ala Ala Ala Ala Phe Leu Phe Val Phe Asn
    370                 375                 380

Thr Phe Phe Ala Ile Gly Trp Leu Gly Met Thr Trp Leu Tyr Pro Ala
385                 390                 395                 400

Glu Ile Val Ser Leu Gln Val Arg Ala Pro Ala Asn Gly Leu Ser Thr
                405                 410                 415

Ala Ala Asn Trp Ile Phe Asn Phe Met Val Val Met Ile Thr Pro Val
            420                 425                 430

Ala Phe Asn Ser Ile Gly Ala Tyr Thr Tyr Leu Val Phe Ala Val Ile
        435                 440                 445

Asn Ala Ile Met Val Pro Cys Val Tyr Leu Phe Tyr Pro Glu Thr Ala
    450                 455                 460

Gly Arg Ser Leu Glu Glu Ile Asp Glu Ile Phe Glu Lys Ser Asn Pro
465                 470                 475                 480

Trp Thr Pro Trp Asp Val Val Gly Ile Ala Ser Lys Leu Pro Arg His
                485                 490                 495

His Ile Asp Val Leu Glu Ile Val Asp Glu Gln His Asp Ile Glu Ala
            500                 505                 510

Gly Val Lys Arg Arg His Pro His Gly Ala Ala Asp Gln Glu Lys Pro
        515                 520                 525

Val Val Leu His Ser Glu Val
    530                 535


<210> SEQ ID NO 67
<211> LENGTH: 1134
<212> TYPE: DNA
<213> ORGANISM: Lipomyces starkeyi

<400> SEQUENCE: 67

atggaaaagg cgagtgctag ccatggactt gcgagaacgg gcatgtctag taccgaagac      60

agtaactgct cgtctactcc agcatctgac ttctcctcga aggggccgta taagcatgat     120

caatcacctg ctcgcatggt ggaccatgaa gacttcctta ctcgtcctga tattcgcggc     180

gatgacgagg aagaaataga agctgaggag agacgccgcc gcgtcaaggt gtcactgtac     240

aagcagtttc gtcgagatat tcgagagccg ctttctgaga tgcttggtag tgctcttctt     300

atcattatcg gagatggtgc tgtggctcag gcattgttgt cgaattatca gatgggtaac     360

gaggtcacta tcaacctgtg cttcggcttt ggtcttacta tgggctatct tacagcaatc     420

actggcggag cagcaggaca tctgaaccca gctattacac tgacgaactg tattttccga     480

ggatttccgt ggtggaaact gccaatttat gttttggcgc aggtagtggg atgtggcgtc     540

ggcgctgctt gtgtcttcgg catttatagg aatgcgatta ctgcctacga tggaggccaa     600

cgacaggtga ctggtccttt gaggacagct ggtatttact gcacatatcc ggttagcttt     660

cttgacttgc ccggtcgtgc aatgcaggag ttcttcgcga ctattgtttt ggtgttcttc     720

gtaaatgcta tcgcatgcca gtcctccccg catttgcctt acaagcttcc tgtggaatgg     780

aatctggtcc gtgcgctggt gcttggactt tcattgtatg gtatcggagc ctcccttggt     840
```

```
tggcagactg gatatgctat caatcctgct cgtgattttg gacctcgatt agtttcatac     900

atggctggat atggacgcga agttttcaca acagctggtc attacttctg gattcctata     960

gtgatgccct gtgtgggtgc cattacggga caattacttt tcgatttcat ggtgtatgaa    1020

ggcgaacacg ataatttcgt cacgaatccc gaggtggcag tcaaaagatt aaaggagaat    1080

gtggtaggaa gtaagaaaag gtcggaggcc gatattgaga tgaggggata ttga          1134


<210> SEQ ID NO 68
<211> LENGTH: 377
<212> TYPE: PRT
<213> ORGANISM: Lipomyces starkeyi

<400> SEQUENCE: 68

Met Glu Lys Ala Ser Ala Ser His Gly Leu Ala Arg Thr Gly Met Ser
1               5                   10                  15

Ser Thr Glu Asp Ser Asn Cys Ser Ser Thr Pro Ala Ser Asp Phe Ser
            20                  25                  30

Ser Lys Gly Pro Tyr Lys His Asp Gln Ser Pro Ala Arg Met Val Asp
        35                  40                  45

His Glu Asp Phe Leu Thr Arg Pro Asp Ile Arg Gly Asp Asp Glu Glu
    50                  55                  60

Glu Ile Glu Ala Glu Glu Arg Arg Arg Arg Val Lys Val Ser Leu Tyr
65                  70                  75                  80

Lys Gln Phe Arg Arg Asp Ile Arg Glu Pro Leu Ser Glu Met Leu Gly
                85                  90                  95

Ser Ala Leu Leu Ile Ile Ile Gly Asp Gly Ala Val Ala Gln Ala Leu
            100                 105                 110

Leu Ser Asn Tyr Gln Met Gly Asn Glu Val Thr Ile Asn Leu Cys Phe
        115                 120                 125

Gly Phe Gly Leu Thr Met Gly Tyr Leu Thr Ala Ile Thr Gly Gly Ala
    130                 135                 140

Ala Gly His Leu Asn Pro Ala Ile Thr Leu Thr Asn Cys Ile Phe Arg
145                 150                 155                 160

Gly Phe Pro Trp Trp Lys Leu Pro Ile Tyr Val Leu Ala Gln Val Val
                165                 170                 175

Gly Cys Gly Val Gly Ala Ala Cys Val Phe Gly Ile Tyr Arg Asn Ala
            180                 185                 190

Ile Thr Ala Tyr Asp Gly Gly Gln Arg Gln Val Thr Gly Pro Leu Arg
        195                 200                 205

Thr Ala Gly Ile Tyr Cys Thr Tyr Pro Val Ser Phe Leu Asp Leu Pro
    210                 215                 220

Gly Arg Ala Met Gln Glu Phe Phe Ala Thr Ile Val Leu Val Phe Phe
225                 230                 235                 240

Val Asn Ala Ile Ala Cys Gln Ser Ser Pro His Leu Pro Tyr Lys Leu
                245                 250                 255

Pro Val Glu Trp Asn Leu Val Arg Ala Leu Val Leu Gly Leu Ser Leu
            260                 265                 270

Tyr Gly Ile Gly Ala Ser Leu Gly Trp Gln Thr Gly Tyr Ala Ile Asn
        275                 280                 285

Pro Ala Arg Asp Phe Gly Pro Arg Leu Val Ser Tyr Met Ala Gly Tyr
    290                 295                 300

Gly Arg Glu Val Phe Thr Thr Ala Gly His Tyr Phe Trp Ile Pro Ile
305                 310                 315                 320
```

```
Val Met Pro Cys Val Gly Ala Ile Thr Gly Gln Leu Leu Phe Asp Phe
                325                 330                 335

Met Val Tyr Glu Gly Glu His Asp Asn Phe Val Thr Asn Pro Glu Val
            340                 345                 350

Ala Val Lys Arg Leu Lys Glu Asn Val Val Gly Ser Lys Lys Arg Ser
        355                 360                 365

Glu Ala Asp Ile Glu Met Arg Gly Tyr
    370                 375


<210> SEQ ID NO 69
<211> LENGTH: 2199
<212> TYPE: DNA
<213> ORGANISM: Lipomyces starkeyi
<220> FEATURE:
<221> NAME/KEY: Intron
<222> LOCATION: (408)..(459)

<400> SEQUENCE: 69

tggactcgaa agtgtccgcg cgcgcggcag cacttgccgg ccatctctcc atgagaaatt     60

cgtcggccga gagcaaggat acgtctatcc ttggacttgg aaatccaatg gcatctatgg    120

ccgtggaacg cacaaaggcg tcattcccga ttcgtgagct cacctatttt ctcgatggcg    180

gcaaggagat gaccgcagta aaggagcgaa tgatgactga gctggaacgt gatccggtct    240

tccaaaacgt ggacttttat gatcttacaa aggaacaatt acgcgagcgt actatgtcta    300

aaattgccag gttgatccat tatatcacgt ctgagcggga ggaaatttca cacttgcggt    360

tttcgctcgt tggcctcatc gatatgggtt tgctcaccag aacagggtaa gtaagtatct    420

ccttattatt gcattgacgg gtgctaatga aggtgtagtg tccactacgc tttgttcttc    480

ggctctctgc gaggctcggc atcgccgaaa cagttttcgt actggatctc acaaggagcc    540

gccgagatga agggcatggt tggctgcttt tgcatgaccg agctggcgca cggcagcaac    600

gtcgccggtc tcgagactac cgccacattt gacgagcgaa cggacgagtt tatcatccat    660

actccacata tcggcgcaac caagtggtgg ataggtggtg ccgctcatac agcaacacac    720

acggtctgct ttgctagatt gatagtgaag ggtaaagatt acggagtcaa gtcatttgtc    780

gttccactcc gtgatccgaa gacatacgac cttaaaccag gcgtcagcat cggcgacatc    840

ggcaagaaga tgggtcgtga cggcattgat aatggctggg ttcagttctc gtatgtgcga    900

attccacgac agttcatgtt gatgaaacac agcaaagttg accgtcacgg aaatgtcact    960

cagcccccac ttgagcagct tgcgtatggt gcgttggttg ttggccgcgt ctcaatggtc   1020

gccgactcgg ctcagatgag caagcgtttt gtgacgattg ctcttagata cgctgccgtc   1080

agacggcaat ttacgtcgaa gaagggtgaa gttgagacga agattttgga ttacgcatta   1140

catcagcggc gactgctacc gctacttgct cagactttcg cgatgcagtt cagttcggat   1200

gaaatgtcgg ccatgcaccg ggcattgatg cggaagattg attcaactga tcctagtgac   1260

ctgaaggcta tggcggttgt gattgaagag ttgaaggaag tattcaccac tagtgccggt   1320

ttgaaggctt tcactacctg ggcttgtgct gagacgattg atcagacgcg tcaggcatgc   1380

ggtgggcatg gatactctgc atatagtggt ttcggacaag catacaatga ctgggttgtg   1440

caatgtacct gggagggaga caataacatt ctcgcgcttt ctgccggccg cggtcttgtt   1500

cagcgctatc tggacgtcca gagaggttcc aaagcccctc cacaaacgga atatctcaac   1560

aagctcgcca gactcaagtt cgcacaggca gggtcgcgcc agattgactc tgccgcggtt   1620

ctttccgaag cttgggaggc tgttgcggct gctgttgtat cgaaggctgg cgaatcattc   1680
```

```
atcgcgctaa gaaagaaagg tctttctgcc gacgaggcat ttgaggagac atcacagcag   1740

cgcttccttg ctgctagaat ccataccaaa tgctttttgg tcttgaagtt ttttgaccgc   1800

atttcctcct ccggaccgga gatcaaaccg gttttgactg atctctctta tctgtatgcg   1860

atgtggtcca tcgagaatga cgccggacta tttctccaag ccgaattctt cacatccgag   1920

caaattgacg acattcgtga actgtgcaac ttatactgcc gcaaagtccg cgagcaggct   1980

gtcccaatta ctgatgcgtt caacttgagt gatttcttca tcaactctgc tatcggcaga   2040

tatgatggca atgtctacga gaattatttt acgcaggtta agaggcagaa tccatcaaag   2100

ccacaagctc catatttcga gaaagtgata aagccgtttg tgcacagggt tgctgaagta   2160

gaagttgatg ctgaggagtt agatgaggat gaggcgtag                          2199
```

<210> SEQ ID NO 70
<211> LENGTH: 715
<212> TYPE: PRT
<213> ORGANISM: Lipomyces starkeyi

<400> SEQUENCE: 70

```
Met Asp Ser Lys Val Ser Ala Arg Ala Ala Ala Leu Ala Gly His Leu
1               5                   10                  15

Ser Met Arg Asn Ser Ser Ala Glu Ser Lys Asp Thr Ser Ile Leu Gly
            20                  25                  30

Leu Gly Asn Pro Met Ala Ser Met Ala Val Glu Arg Thr Lys Ala Ser
        35                  40                  45

Phe Pro Ile Arg Glu Leu Thr Tyr Phe Leu Asp Gly Gly Lys Glu Met
    50                  55                  60

Thr Ala Val Lys Glu Arg Met Met Thr Glu Leu Glu Arg Asp Pro Val
65                  70                  75                  80

Phe Gln Asn Val Asp Phe Tyr Asp Leu Thr Lys Glu Gln Leu Arg Glu
                85                  90                  95

Arg Thr Met Ser Lys Ile Ala Arg Leu Ile His Tyr Ile Thr Ser Glu
            100                 105                 110

Arg Glu Glu Ile Ser His Leu Arg Phe Ser Leu Val Gly Leu Ile Asp
        115                 120                 125

Met Gly Leu Leu Thr Arg Thr Gly Val His Tyr Ala Leu Phe Phe Gly
    130                 135                 140

Ser Leu Arg Gly Ser Ala Ser Pro Lys Gln Phe Ser Tyr Trp Ile Ser
145                 150                 155                 160

Gln Gly Ala Ala Glu Met Lys Gly Met Val Gly Cys Phe Cys Met Thr
                165                 170                 175

Glu Leu Ala His Gly Ser Asn Val Ala Gly Leu Glu Thr Thr Ala Thr
            180                 185                 190

Phe Asp Glu Arg Thr Asp Glu Phe Ile Ile His Thr Pro His Ile Gly
        195                 200                 205

Ala Thr Lys Trp Trp Ile Gly Gly Ala Ala His Thr Ala Thr His Thr
    210                 215                 220

Val Cys Phe Ala Arg Leu Ile Val Lys Gly Lys Asp Tyr Gly Val Lys
225                 230                 235                 240

Ser Phe Val Val Pro Leu Arg Asp Pro Lys Thr Tyr Asp Leu Lys Pro
                245                 250                 255

Gly Val Ser Ile Gly Asp Ile Gly Lys Lys Met Gly Arg Asp Gly Ile
            260                 265                 270

Asp Asn Gly Trp Val Gln Phe Ser Tyr Val Arg Ile Pro Arg Gln Phe
        275                 280                 285
```

```
Met Leu Met Lys His Ser Lys Val Asp Arg His Gly Asn Val Thr Gln
    290                 295                 300

Pro Pro Leu Glu Gln Leu Ala Tyr Gly Ala Leu Val Val Gly Arg Val
305                 310                 315                 320

Ser Met Val Ala Asp Ser Ala Gln Met Ser Lys Arg Phe Val Thr Ile
                325                 330                 335

Ala Leu Arg Tyr Ala Ala Val Arg Arg Gln Phe Thr Ser Lys Lys Gly
            340                 345                 350

Glu Val Glu Thr Lys Ile Leu Asp Tyr Ala Leu His Gln Arg Arg Leu
        355                 360                 365

Leu Pro Leu Leu Ala Gln Thr Phe Ala Met Gln Phe Ser Ser Asp Glu
    370                 375                 380

Met Ser Ala Met His Arg Ala Leu Met Arg Lys Ile Asp Ser Thr Asp
385                 390                 395                 400

Pro Ser Asp Leu Lys Ala Met Ala Val Val Ile Glu Glu Leu Lys Glu
                405                 410                 415

Val Phe Thr Thr Ser Ala Gly Leu Lys Ala Phe Thr Thr Trp Ala Cys
            420                 425                 430

Ala Glu Thr Ile Asp Gln Thr Arg Gln Ala Cys Gly Gly His Gly Tyr
        435                 440                 445

Ser Ala Tyr Ser Gly Phe Gly Gln Ala Tyr Asn Asp Trp Val Val Gln
    450                 455                 460

Cys Thr Trp Glu Gly Asp Asn Asn Ile Leu Ala Leu Ser Ala Gly Arg
465                 470                 475                 480

Gly Leu Val Gln Arg Tyr Leu Asp Val Gln Arg Gly Ser Lys Ala Pro
                485                 490                 495

Pro Gln Thr Glu Tyr Leu Asn Lys Leu Ala Arg Leu Lys Phe Ala Gln
            500                 505                 510

Ala Gly Ser Arg Gln Ile Asp Ser Ala Ala Val Leu Ser Glu Ala Trp
        515                 520                 525

Glu Ala Val Ala Ala Ala Val Val Ser Lys Ala Gly Glu Ser Phe Ile
    530                 535                 540

Ala Leu Arg Lys Lys Gly Leu Ser Ala Asp Glu Ala Phe Glu Glu Thr
545                 550                 555                 560

Ser Gln Gln Arg Phe Leu Ala Ala Arg Ile His Thr Lys Cys Phe Leu
                565                 570                 575

Val Leu Lys Phe Phe Asp Arg Ile Ser Ser Ser Gly Pro Glu Ile Lys
            580                 585                 590

Pro Val Leu Thr Asp Leu Ser Tyr Leu Tyr Ala Met Trp Ser Ile Glu
        595                 600                 605

Asn Asp Ala Gly Leu Phe Leu Gln Ala Glu Phe Phe Thr Ser Glu Gln
    610                 615                 620

Ile Asp Asp Ile Arg Glu Leu Cys Asn Leu Tyr Cys Arg Lys Val Arg
625                 630                 635                 640

Glu Gln Ala Val Pro Ile Thr Asp Ala Phe Asn Leu Ser Asp Phe Phe
                645                 650                 655

Ile Asn Ser Ala Ile Gly Arg Tyr Asp Gly Asn Val Tyr Glu Asn Tyr
            660                 665                 670

Phe Thr Gln Val Lys Arg Gln Asn Pro Ser Lys Pro Gln Ala Pro Tyr
        675                 680                 685

Phe Glu Lys Val Ile Lys Pro Phe Val His Arg Val Ala Glu Val Glu
    690                 695                 700
```

```
Val Asp Ala Glu Glu Leu Asp Glu Asp Glu Ala
705                 710                 715


<210> SEQ ID NO 71
<211> LENGTH: 2787
<212> TYPE: DNA
<213> ORGANISM: Lipomyces starkeyi
<220> FEATURE:
<221> NAME/KEY: Intron
<222> LOCATION: (182)..(228)
<220> FEATURE:
<221> NAME/KEY: Intron
<222> LOCATION: (2091)..(2142)

<400> SEQUENCE: 71

atgccgcacg aactacgatt tgacggtcaa accgttgtca ttacaggtgc cggcggcggt     60

ctagggaggg catacgcttt atttttcgga tcccgcggcg ctaatgttgt cgttaacgat    120

ttgggctcta gttccaaggg cgaaggccac tcgacaaagg cagctgacgt tgtagtggaa    180

ggtgagcttg cattactgtc aatgttgtgt ggaacaattc taatgtagaa atagaaatta    240

agaaggctgg aggaaacgct gttccgaatt acgattcggt cgaattcggt gacagaattg    300

ttgagaccgc gattaaagca ttcggcagcg tgcatgtgct aatcaacaat gccggcatac    360

tgcgtgatat ctcgttcaag aacatgaaag acgcagattg ggacttgatc caacttgtac    420

atctcaaggg cgcgtacaaa accacgaaag ccgcctggcc agtattccgc aaacaaaagt    480

tcggccgaat tatcaacact gcttctgcgg cgggcttgta cggaagtttc gggcaggcca    540

attattcggc tgcgaaactc ggattggttg gattcacaga gactttggcc aaggaagggg    600

ccaaatacgg catttttgct aacgtgatag cgcctatggc ggccagcaga atgacacaga    660

cggtcatgcc cgaggatctg ttgagcatgc tgaagcccga atgggttgtt cctctcgttt    720

cgtaccttac acacaaggac acggacgata ccggcggaat ctacgaggtt ggcgcagggt    780

tcgtttcaaa gcttcgctgg gagcgatcaa atggcgctct tttcaagact gatgacagtt    840

tcacacccgc atcgatcctt gcgcgatggt ctgagattca ggacttcgag tccaaaacac    900

cacagtaccc gactggccca aatgacttca tgacgcttct cgagtcggca cgtgaactgc    960

catccaacaa acaaggcgac gtccccgttg acgtgaagga caaagtcgtc attgtcaccg   1020

gctccggcgg cggtcttggt cgcgcatacg ctcttttatt cgctaagctc ggtgctaagc   1080

ttgttatcaa cgatgtcggc gacccaaatg gtacggttaa tgaaattaac aagctctatg   1140

gcgaaggcac tgcaatatct gatcgtcatt ccgtcgagga aggagacgca gtcgtcaaga   1200

cagcagttga ccactttgga accgtgcatg tagtcgtcaa caatgccgga atcttgcgtg   1260

acaagtcctt cgctagtatg actgacgacc tgtgggatca agtcatagcc gtccacttgc   1320

gcggtacata taagattacc aaggcagctt ggccatactt cttgaagcaa aaattcggac   1380

gaatcgtcaa cactacttcg acgtctggta tatacggcaa ttttggtcag gctaactacg   1440

ctactgccaa atgcgcaata attggcttca caaaaacaat tgcattggaa ggaaagaaat   1500

acaacatttt cgcgaatgcg attgccccca atgctggtac caatatgact cgtactattt   1560

tgcctgagga gattgtgcag gctttcaagc cggactatgt agcgcctctt gccgtcctct   1620

tgtcctctga cagggcccct gttactggcg aaatctttga gaccggctct ggttggatcg   1680

gaaatacaag atggcagcgg accggcggcg ttggattccc tgtcgacaag ccgcttacac   1740

ctgaggccat ccaggagaat tgggcgaaga tcactgactt tagtgacggc cgtgcgactt   1800

acccgaagac cacacaagag agcatgggtg cgattctcga gaatatgtcg aacaaaacct   1860
```

```
cagtatcatc gtcatcggct tcggagcaga caggccccga ttttcatttc agttatgaaa   1920

ctagagatct aatcctatat aacctcggag ttggtgcgaa ggcgtccgaa ttgaagtacg   1980

tgtttgaagg tgcggatgat ttcacagtct tgcctaccta cggtgttgtt ccatactttg   2040

gcgcatctgg ttcattagac ttcagcgagc ttgttcccaa ctttaacccg gtatggtttt   2100

acccattctc ttcacgacga ttttgatact aactttacta agatgatgct tctccatggc   2160

gagcaatatc tggaaatcaa atcctggcca cttcccacgt cgggtgggag gctcgtttcc   2220

aaagcccgtc taattgaagt tcttgacaag ggcaaggctg cctgcgttat cactggtact   2280

gagacaaatg acgccgagac aggaaagcca gttttctaca atgagtcgac catcgtcctt   2340

cgcggttccg gtggttttgg cggacctagc aagggcaagg accgaggtgc tgctacagct   2400

gccaacactc cgcccaagcg tgcgcccgat ttcgttgctg tagtcaagac tactgaagac   2460

caagcagcca tctatcgatt gtccggcgat tataacccac ttcacattga ccctgagttc   2520

gcggcagtcg gtaagttccc gaaaccaatc ctacacggtc tttgcacgtt tggtattgct   2580

ggaaaacaga tatatgacaa gttcggaatg ttcaagaaca ttaaggttcg tttcgctggt   2640

cacgttttcc cgggcgagac attaaaggtt gagatgtgga agcttggcgg tggcaagatt   2700

attttccaga caactgttat tgaacgaaat acagttgcta tatcgtcggc tgctgtggag   2760

ttaataactg atacatcgaa gttgtag                                       2787
```

<210> SEQ ID NO 72
<211> LENGTH: 870
<212> TYPE: PRT
<213> ORGANISM: Lipomyces starkeyi

<400> SEQUENCE: 72

```
Met Pro His Glu Leu Arg Phe Asp Gly Gln Thr Val Val Ile Thr Gly
1               5                   10                  15

Ala Gly Gly Gly Leu Gly Arg Ala Tyr Ala Leu Phe Phe Gly Ser Arg
            20                  25                  30

Gly Ala Asn Val Val Val Asn Asp Leu Gly Ser Ser Ser Lys Gly Glu
        35                  40                  45

Gly His Ser Thr Lys Ala Ala Asp Val Val Val Glu Glu Ile Glu Ile
    50                  55                  60

Lys Lys Ala Gly Gly Asn Ala Val Pro Asn Tyr Asp Ser Val Glu Phe
65                  70                  75                  80

Gly Asp Arg Ile Val Glu Thr Ala Ile Lys Ala Phe Gly Ser Val His
                85                  90                  95

Val Leu Ile Asn Asn Ala Gly Ile Ser Arg Asp Ile Ser Phe Lys Asn
            100                 105                 110

Met Lys Asp Ala Asp Trp Asp Leu Ile Gln Leu Val His Leu Lys Gly
        115                 120                 125

Ala Tyr Lys Thr Thr Lys Ala Ala Trp Pro Val Phe Arg Lys Gln Lys
    130                 135                 140

Phe Gly Arg Ile Ile Asn Thr Ala Ser Ala Ala Gly Leu Tyr Gly Ser
145                 150                 155                 160

Phe Gly Gln Ala Asn Tyr Ser Ala Ala Lys Leu Gly Leu Val Gly Phe
                165                 170                 175

Thr Glu Thr Leu Ala Lys Glu Gly Ala Lys Tyr Gly Ile Phe Ala Asn
            180                 185                 190

Val Ile Ala Pro Met Ala Ala Ser Arg Met Thr Gln Thr Val Met Pro
        195                 200                 205
```

```
Glu Asp Ser Leu Ser Met Ser Lys Pro Glu Trp Val Val Pro Leu Val
    210                 215                 220

Ser Tyr Leu Thr His Lys Asp Thr Asp Asp Thr Gly Gly Ile Tyr Glu
225                 230                 235                 240

Val Gly Ala Gly Phe Val Ser Lys Leu Arg Trp Glu Arg Ser Asn Gly
                245                 250                 255

Ala Leu Phe Lys Thr Asp Asp Ser Phe Thr Pro Ala Ser Ile Leu Ala
            260                 265                 270

Arg Trp Ser Glu Ile Gln Asp Phe Glu Ser Lys Thr Pro Gln Tyr Pro
        275                 280                 285

Thr Gly Pro Asn Asp Phe Met Thr Leu Leu Glu Ser Ala Arg Glu Ser
    290                 295                 300

Pro Ser Asn Lys Gln Gly Asp Val Pro Val Asp Val Lys Asp Lys Val
305                 310                 315                 320

Val Ile Val Thr Gly Ser Gly Gly Gly Leu Gly Arg Ala Tyr Ala Leu
                325                 330                 335

Leu Phe Ala Lys Leu Gly Ala Lys Leu Val Ile Asn Asp Val Gly Asp
            340                 345                 350

Pro Asn Gly Thr Val Asn Glu Ile Asn Lys Leu Tyr Gly Glu Gly Thr
        355                 360                 365

Ala Ile Ser Asp Arg His Ser Val Glu Glu Gly Asp Ala Val Val Lys
    370                 375                 380

Thr Ala Val Asp His Phe Gly Thr Val His Val Val Val Asn Asn Ala
385                 390                 395                 400

Gly Ile Leu Arg Asp Lys Ser Phe Ala Ser Met Thr Asp Asp Ser Trp
                405                 410                 415

Asp Gln Val Ile Ala Val His Leu Arg Gly Thr Tyr Lys Ile Thr Lys
            420                 425                 430

Ala Ala Trp Pro Tyr Phe Leu Lys Gln Lys Phe Gly Arg Ile Val Asn
        435                 440                 445

Thr Thr Ser Thr Ser Gly Ile Tyr Gly Asn Phe Gly Gln Ala Asn Tyr
    450                 455                 460

Ala Thr Ala Lys Cys Ala Ile Ile Gly Phe Thr Lys Thr Ile Ala Leu
465                 470                 475                 480

Glu Gly Lys Lys Tyr Asn Ile Phe Ala Asn Ala Ile Ala Pro Asn Ala
                485                 490                 495

Gly Thr Asn Met Thr Arg Thr Ile Leu Pro Glu Glu Ile Val Gln Ala
            500                 505                 510

Phe Lys Pro Asp Tyr Val Ala Pro Leu Ala Val Leu Leu Ser Ser Asp
        515                 520                 525

Arg Ala Pro Val Thr Gly Glu Ile Phe Glu Thr Gly Ser Gly Trp Ile
    530                 535                 540

Gly Asn Thr Arg Trp Gln Arg Thr Gly Gly Val Gly Phe Pro Val Asp
545                 550                 555                 560

Lys Pro Leu Thr Pro Glu Ala Ile Gln Glu Asn Trp Ala Lys Ile Thr
                565                 570                 575

Asp Phe Ser Asp Gly Arg Ala Thr Tyr Pro Lys Thr Thr Gln Glu Ser
            580                 585                 590

Met Gly Ala Ile Leu Glu Asn Met Ser Asn Lys Thr Ser Val Ser Ser
        595                 600                 605

Ser Ser Ala Ser Glu Gln Thr Gly Pro Asp Phe His Phe Ser Tyr Glu
    610                 615                 620

Thr Arg Asp Leu Ile Leu Tyr Asn Leu Gly Val Gly Ala Lys Ala Ser
```

```
625                 630                 635                 640

Glu Leu Lys Tyr Val Phe Glu Gly Ala Asp Asp Phe Thr Val Leu Pro
                645                 650                 655

Thr Tyr Gly Val Val Pro Tyr Phe Gly Ala Ser Gly Ser Leu Asp Phe
            660                 665                 670

Ser Glu Leu Val Pro Asn Phe Asn Pro Met Met Leu Leu His Gly Glu
        675                 680                 685

Gln Tyr Ser Glu Ile Lys Ser Trp Pro Leu Pro Thr Ser Gly Gly Arg
    690                 695                 700

Leu Val Ser Lys Ala Arg Leu Ile Glu Val Leu Asp Lys Gly Lys Ala
705                 710                 715                 720

Ala Cys Val Ile Thr Gly Thr Glu Thr Asn Asp Ala Glu Thr Gly Lys
                725                 730                 735

Pro Val Phe Tyr Asn Glu Ser Thr Ile Val Leu Arg Gly Ser Gly Gly
            740                 745                 750

Phe Gly Gly Pro Ser Lys Gly Lys Asp Arg Gly Ala Ala Thr Ala Ala
        755                 760                 765

Asn Thr Pro Pro Lys Arg Ala Pro Asp Phe Val Ala Val Val Lys Thr
    770                 775                 780

Thr Glu Asp Gln Ala Ala Ile Tyr Arg Leu Ser Gly Asp Tyr Asn Pro
785                 790                 795                 800

Leu His Ile Asp Pro Glu Phe Ala Ala Val Gly Lys Phe Pro Lys Pro
                805                 810                 815

Ile Leu His Gly Leu Cys Thr Phe Gly Ile Ala Gly Lys Gln Ile Tyr
            820                 825                 830

Asp Lys Phe Gly Met Phe Lys Asn Ile Lys Val Arg Phe Ala Gly His
        835                 840                 845

Val Phe Pro Gly Glu Thr Leu Lys Val Glu Met Trp Lys Leu Gly Gly
    850                 855                 860

Gly Lys Ile Ile Phe Gln
865                 870
```

<210> SEQ ID NO 73
<211> LENGTH: 3759
<212> TYPE: DNA
<213> ORGANISM: Lipomyces starkeyi

<400> SEQUENCE: 73

```
atggatgact cgatggatga ctcgattgaa caagatccat gggtcgagga cgagacattg     60

ttatctcgac cacagaatac cgggccatcg ccgccatttc acacaattat aactggtctt    120

attaatccgg tattgaaggc gtcaaataag aagactggat ttcacggagg acctgcgacg    180

aatgtgcgca taacaagatt caaggttcta agtaattata ttcaaagatg gaagcaggaa    240

gttgggaacg atatctaccc gtgctttcgg ctaagtgagt tgctatcaac tctcgttctt    300

gtggggttaa ttgctaattg tattttagtt ctgccatatg tgagtattcg aagatcattg    360

caatggactt gctactaatt ctgagatcaa atcagaaaga caaagagcga caaatgcatg    420

tgatttagct taatctgaag gtctcgccca atattaacga tagataggta cggcttaaaa    480

gaaaaagcaa ttgcgcggtt acttattaag gttattctcg actttacttc tgctagtgtc    540

gggactggat atgttgacct gtcatagatc ctcggcatct cacctgaatc agaagatgcg    600

aactcaatgg tcaactacaa gcttccaggt caatatagag gtgccggcga ctttgcagag    660

cgatgctacg aggtcatcaa gcaacgtcag attagaacag agtatggatc aatgaccatc    720
```

```
gaagacgtca acggtctatt ggacgaactc agtaagcaca gcaaatcgta tgcctgtagt    780
tgttctgata gcaactatat gtgatgctga tgacgagata gtgatgacca acttccaata    840
ctatctaagt tttatcactt gatgaatgcc gaggagatga agtggttaat ccgagttatt    900
ttacgacgtg agtttgacaa ttaaggaacc ttggctgaat ctaacttgca cagaaatgca    960
cataggtgtt tctgaacgga cattattctc agcatggcat ccaaatgcaa acgaactcta   1020
taatatttcc agcagtctta aacgcgtatg ctgggaactg ttcgatagca attacagact   1080
gtcggacgat gtaagatatc aagcttctga ttacctctac gacgctaata tcaataggcg   1140
aaagatgtga atctgatgag ttgtttccaa ccacagctag cagcttttcc caaagcctcg   1200
tacgatcaag tcataaggag catgaacaaa gagacattct tcatcgaaga gaaactagat   1260
ggagagagaa tccaagtgca catgtctgac tacggaaaag tgttcaagtt ttacagccgt   1320
cgagcaaaag attatacata tctctatggc agctctctag acgataagaa cggtgctctg   1380
acgaagcatc ttcgaggggt gtttgaagaa accgtggaaa agtatgtaaa tggttgagta   1440
ttgaacgggc tttactgacg ttgtatagct gcatattgga tggagaaatg gtgtcctggg   1500
atcccgttga tgaaaagatt gaaccctttg gctacttaaa aactgccgcg aatgccgaga   1560
aagaagacgc gggcgagtca tatccattat gtgagtatcc ggccttaatc attatcagca   1620
tttactaact gattctaaga ccgcgtattt gacatattgt atgccaacaa caaatcggta   1680
gtgaactact ctttggtaca acgacagttg ctgttacaac gagttgttaa ccccgctcct   1740
acacatttcg aaattcatcc gcatgaagaa gggtcaacga aggaagatat tgaacgacgc   1800
ctgcggcaag tcatagcaga gtcgtacgtg atcatgagta cgcatggtat ttcaaacgct   1860
tatttcatgc aggtctgagg gactggtcat caaattgcct accgcgccat atgttgtgaa   1920
tggcagggag gattcatgga ttaaggtcaa acccgagtac atgctagaat ttggcgaaaa   1980
tttggattgt ctcgttattg gtacgagctt cattgcacat ctgaacccat cgaagactaa   2040
cgcttagtag ggggatatta cgggcaaggc aaacgaggtg agatcctcgc cagtttcctc   2100
tgcggtcttc gagtagaaga cgagcaagat cccgatgcac cacccaaatt ctggtctttc   2160
tgccgagtag gaggtggttt cacagctgca gaatatggaa caattcggca tttaactgac   2220
ggacagtggc aaaaatggga ttcccggcga ccgccactgc agtacatgga gctcgcaggt   2280
gacaagaacg agaaggaaat gccggacgtg tggattctgc ccgagaaatc cgttgtgctg   2340
gagattaagg ctgcgagtgt cgtacccgag tctgaacagt accggacgaa tgttacgctg   2400
aggtttccgc ggttcagacg aatacgacaa gataagaatt atcttactgc gttgtcgttg   2460
aaggaattta tgactttgaa ggagcaagct gagactgagt ctcaagagcg gcaattgtat   2520
attctgttga tatgcactat ttggaccggt actgataata tcctagggaa ttggaggagc   2580
acagacgaac ttccaaacgg cccaagaagg tagactatta tatatatcta tatggagcaa   2640
ctagaattga ctgagagcag caactaagaa ttttaggagg caacgagacg gtggttctgg   2700
aaggcgctcc tacgagtcaa atttttgatg gccatatctt ctgtacgtat aacaatgtgc   2760
taatgatcga catttgccaa tctgggatgt ataggtgtgt ttgttgattc taaacgaaaa   2820
accgagctgc agaagatcat catcagtcac ggcgggacca caattcaaga tgtacccgcc   2880
ggacctcaga atatgacaca cgttatagcc gacaaagatc ttgtcaaaat cgcgagtctt   2940
aagaggcagg ggaagtggaa tattatcaga ccgacgtgga ttcaggactg tgttttcaat   3000
cagaggattg ttccatacga gccgaggtca gctttaggtt ttcatgaata ggttgctagg   3060
tgtgcttgtg ctgacgagat ggtaggcatg tatattttgc cacggaaggt ttgcttgaag   3120
```

```
cagttcgacg acacgtggat ccgtacggag atagttacac tcggtcaatg gaagatatca   3180

aagaattgcg agatatgctc aaccttatgc ccgatccaag tatcgacgct atcgcaaaag   3240

aatatgacat tttactcagc gaatctgact cgtcgtttta taacattccg agcttgatat   3300

tctacaatac tgtgatgtat ctcgacgagc cagatcttcc atcgagcgag aatctaccgc   3360

ggcattcgca cgattcatct gcaactttca ggtatttctc ttcacaccaa tacaaaaaaa   3420

attatgtaaa tgctgatatc tctcaaagac tgcaaattgc ggcaaactac gcaaccttcg   3480

gcggcgcaag actatcggac gacatcaaca gccgagaaat aacacacatt gtcaccatgt   3540

gtgacgcgcc caagaatcga atcacggcta tccgaagtga aatttctttg tgcgtatatt   3600

tttgctgaca gtgggggttg tggaaagagc ctaattgata tttttagtcg cctgagagtg   3660

cctcgcgtgg tatctgtcga atggattgag cagtcttgga aagaaactac aaggttgagc   3720

gaagaaggta tgaatataat ctcaaccgta cgtgcctaa                          3759
```

<210> SEQ ID NO 74
<211> LENGTH: 956
<212> TYPE: PRT
<213> ORGANISM: Lipomyces starkeyi

<400> SEQUENCE: 74

```
Met Asp Asp Ser Met Asp Asp Ser Ile Glu Gln Asp Pro Trp Val Glu
1               5                   10                  15

Asp Glu Thr Leu Leu Ser Arg Pro Gln Asn Thr Gly Pro Ser Pro Pro
            20                  25                  30

Phe His Thr Ile Ile Thr Gly Leu Ile Asn Pro Val Leu Lys Ala Ser
        35                  40                  45

Asn Lys Lys Thr Gly Phe His Gly Gly Pro Ala Thr Asn Val Arg Ile
    50                  55                  60

Thr Arg Phe Lys Val Leu Ser Asn Tyr Ile Gln Arg Trp Lys Gln Glu
65                  70                  75                  80

Val Gly Asn Asp Ile Tyr Pro Cys Phe Arg Leu Ile Leu Pro Tyr Thr
                85                  90                  95

Lys Ser Asp Lys Cys Met Tyr Gly Leu Lys Glu Lys Ala Ile Ala Arg
            100                 105                 110

Leu Leu Ile Lys Ile Leu Gly Ile Ser Pro Glu Ser Glu Asp Ala Asn
        115                 120                 125

Ser Met Val Asn Tyr Lys Leu Pro Gly Gln Tyr Arg Gly Ala Gly Asp
    130                 135                 140

Phe Ala Glu Arg Cys Tyr Glu Val Ile Lys Gln Arg Gln Ile Arg Thr
145                 150                 155                 160

Glu Tyr Gly Ser Met Thr Ile Glu Asp Val Asn Gly Leu Leu Asp Glu
                165                 170                 175

Leu Ser Lys His Ser Lys Ser Asp Asp Gln Leu Pro Ile Leu Ser Lys
            180                 185                 190

Phe Tyr His Leu Met Asn Ala Glu Glu Met Lys Trp Leu Ile Arg Val
        195                 200                 205

Ile Leu Arg Gln Met His Ile Gly Val Ser Glu Arg Thr Leu Phe Ser
    210                 215                 220

Ala Trp His Pro Asn Ala Asn Glu Leu Tyr Asn Ile Ser Ser Ser Leu
225                 230                 235                 240

Lys Arg Val Cys Trp Glu Leu Phe Asp Ser Asn Tyr Arg Leu Ser Asp
                245                 250                 255
```

```
Asp Ala Lys Asp Val Asn Leu Met Ser Cys Phe Gln Pro Gln Leu Ala
            260                 265                 270

Ala Phe Pro Lys Ala Ser Tyr Asp Gln Val Ile Arg Ser Met Asn Lys
        275                 280                 285

Glu Thr Phe Phe Ile Glu Glu Lys Leu Asp Gly Glu Arg Ile Gln Val
    290                 295                 300

His Met Ser Asp Tyr Gly Lys Val Phe Lys Phe Tyr Ser Arg Arg Ala
305                 310                 315                 320

Lys Asp Tyr Thr Tyr Leu Tyr Gly Ser Ser Leu Asp Asp Lys Asn Gly
                325                 330                 335

Ala Leu Thr Lys His Leu Arg Gly Val Phe Glu Glu Thr Val Glu Asn
            340                 345                 350

Cys Ile Leu Asp Gly Glu Met Val Ser Trp Asp Pro Val Asp Glu Lys
        355                 360                 365

Ile Glu Pro Phe Gly Tyr Leu Lys Thr Ala Ala Asn Ala Glu Lys Glu
    370                 375                 380

Asp Ala Gly Glu Ser Tyr Pro Leu Tyr Arg Val Phe Asp Ile Leu Tyr
385                 390                 395                 400

Ala Asn Asn Lys Ser Val Val Asn Tyr Ser Leu Val Gln Arg Gln Leu
                405                 410                 415

Leu Leu Gln Arg Val Val Asn Pro Ala Pro Thr His Phe Glu Ile His
            420                 425                 430

Pro His Glu Glu Gly Ser Thr Lys Glu Asp Ile Glu Arg Arg Leu Arg
        435                 440                 445

Gln Val Ile Ala Glu Ser Ser Glu Gly Leu Val Ile Lys Leu Pro Thr
    450                 455                 460

Ala Pro Tyr Val Val Asn Gly Arg Glu Asp Ser Trp Ile Lys Val Lys
465                 470                 475                 480

Pro Glu Tyr Met Leu Glu Phe Gly Glu Asn Leu Asp Cys Leu Val Ile
                485                 490                 495

Gly Gly Tyr Tyr Gly Gln Gly Lys Arg Gly Glu Ile Leu Ala Ser Phe
            500                 505                 510

Leu Cys Gly Leu Arg Val Glu Asp Glu Gln Asp Pro Asp Ala Pro Pro
        515                 520                 525

Lys Phe Trp Ser Phe Cys Arg Val Gly Gly Gly Phe Thr Ala Ala Glu
    530                 535                 540

Tyr Gly Thr Ile Arg His Leu Thr Asp Gly Gln Trp Gln Lys Trp Asp
545                 550                 555                 560

Ser Arg Arg Pro Pro Leu Gln Tyr Met Glu Leu Ala Gly Asp Lys Asn
                565                 570                 575

Glu Lys Glu Met Pro Asp Val Trp Ile Leu Pro Glu Lys Ser Val Val
            580                 585                 590

Leu Glu Ile Lys Ala Ala Ser Val Val Pro Glu Ser Glu Gln Tyr Arg
        595                 600                 605

Thr Asn Val Thr Leu Arg Phe Pro Arg Phe Arg Arg Ile Arg Gln Asp
    610                 615                 620

Lys Asn Tyr Leu Thr Ala Leu Ser Leu Lys Glu Phe Met Thr Leu Lys
625                 630                 635                 640

Glu Gln Ala Glu Thr Glu Ser Gln Glu Arg Gln Leu Glu Leu Glu Glu
                645                 650                 655

His Arg Arg Thr Ser Lys Arg Pro Lys Lys Gln Leu Arg Ile Leu Gly
            660                 665                 670

Gly Asn Glu Thr Val Val Leu Glu Gly Ala Pro Thr Ser Gln Ile Phe
```

-continued

```
        675                 680                 685

Asp Gly His Ile Phe Cys Val Phe Val Asp Ser Lys Arg Lys Thr Glu
    690                 695                 700

Leu Gln Lys Ile Ile Ile Ser His Gly Gly Thr Thr Ile Gln Asp Val
705                 710                 715                 720

Pro Ala Gly Pro Gln Asn Met Thr His Val Ile Ala Asp Lys Asp Leu
                725                 730                 735

Val Lys Ile Ala Ser Leu Lys Arg Gln Gly Lys Trp Asn Ile Ile Arg
            740                 745                 750

Pro Thr Trp Ile Gln Asp Cys Val Phe Asn Gln Arg Ile Val Pro Tyr
        755                 760                 765

Glu Pro Arg His Val Tyr Phe Ala Thr Glu Gly Leu Leu Glu Ala Val
    770                 775                 780

Arg Arg His Val Asp Pro Tyr Gly Asp Ser Tyr Thr Arg Ser Met Glu
785                 790                 795                 800

Asp Ile Lys Glu Leu Arg Asp Met Leu Asn Leu Met Pro Asp Pro Ser
                805                 810                 815

Ile Asp Ala Ile Ala Lys Glu Tyr Asp Ile Leu Leu Ser Glu Ser Asp
            820                 825                 830

Ser Ser Phe Tyr Asn Ile Pro Ser Leu Ile Phe Tyr Asn Thr Val Met
        835                 840                 845

Tyr Leu Asp Glu Pro Asp Leu Pro Ser Ser Glu Asn Leu Pro Arg His
    850                 855                 860

Ser His Asp Ser Ser Ala Thr Phe Arg Leu Gln Ile Ala Ala Asn Tyr
865                 870                 875                 880

Ala Thr Phe Gly Gly Ala Arg Leu Ser Asp Asp Ile Asn Ser Arg Glu
                885                 890                 895

Ile Thr His Ile Val Thr Met Cys Asp Ala Pro Lys Asn Arg Ile Thr
            900                 905                 910

Ala Ile Arg Ser Glu Ile Ser Phe Arg Leu Arg Val Pro Arg Val Val
        915                 920                 925

Ser Val Glu Trp Ile Glu Gln Ser Trp Lys Glu Thr Thr Arg Leu Ser
    930                 935                 940

Glu Glu Gly Met Asn Ile Ile Ser Thr Val Arg Ala
945                 950                 955
```

<210> SEQ ID NO 75
<211> LENGTH: 1000
<212> TYPE: DNA
<213> ORGANISM: Lipomyces starkeyi

<400> SEQUENCE: 75

```
tcaaaaccta gacagcggct ctacggtcaa atcaaaacac atcactctgt agtgtccaac     60

gtcagtcgga taactaggca gctgagcaag tgaatgggct gtatgtctct gagataatgt    120

cggccagctt agctagcagt agcagccagt agagtgtttg tgcgttgcat ggaggcaaat    180

ctcgcaccag actaggacta cagagctgag aaggatgaag tcggcaatca gaggattagc    240

tctatcgcat ctcaatcaaa tgcaacagca gacggacgcc acacggggcc aagaccgcaa    300

aggctaggaa actgtcgaaa attgtgcccg cgaaggcttc tgccggggta gccgagagcg    360

tatgtaatat gatactactg agaggaagtt ccagtcgctc caaatgggtt gggtcggtgc    420

ggcggtcggc gaaagcggca atcgccaccg gttgctctag acggcaacaa agatgccagt    480

ctgagcgacc gtgccgagag tttcttccgc agtgatagtc ggcgcgtaga cgtgggcacg    540
```

```
cgctatcgcc cgcattttcg tgtgcttgcc ctataacgcc tgccgccacg caaaaaaaca    600

agccgcggta cccggccgtt gtttgtttat gtgctggcca ggaccgggtt aggtcgctcc    660

cccgggccgc ccaatcgcag cgaacagcag tcggcgccga ctcgttcccc tccagtagca    720

ccgtagcaga ctctgtcccc ggctcggccg cgccgccaac gctcgtatat attcccgcga    780

ctcgcccggc ccactcttgt ttctttcttc tcttactctc cctccgtccc ttcccgtccg    840

tcggttttgt tcatttcgtt cgcgcttgcc attccgcgat cgtttccctt tcgtttttg     900

tttgtctgtg atttttccgt agctacgcgc gcaggagggt gccgtgtttg cttcctaata    960

ccgcaacaat agtcttaatc tgttaattac caccacaaca                         1000
```

<210> SEQ ID NO 76
<211> LENGTH: 1000
<212> TYPE: DNA
<213> ORGANISM: Lipomyces starkeyi

<400> SEQUENCE: 76

```
cacacttcag tgggcagacg acatggctag tacggctcgg cgccggacac ggaagagcag     60

gccgaaacgc gtgacctggg aaagtcggcg cccacggatg gtgctgctgc gactccggcg    120

gaatcgttcg tgtcgcgctg aatcaagctc agcacagaca cggggtgctg gcagtctggg    180

taagaagaat atttctcttt tgagtctccc ttaacagcag cgcacacaat acaaaaacag    240

tcgacatcta acgccgcggc ccttaaagcg gtgcctctct cgagactgtg tcgagcttat    300

gtcgaccatg tccgtgttgc gatcacgacc agtaggtacc gcaggcagcg tatcgaccaa    360

gttctgtctg gccacgagga atcccgtctc gcatgctacg cgctgtctgt cgagcgtgtc    420

gtaatattac tgtcccgtgt gttgtgcggg gggtgggga ggaactttcc tgtcgtttgt     480

gtgcacgaca cagagtgcct ttacagatct gtgggtattg gcgtgtcggc atcgcttccg    540

gacttctcat tggatccccc aacggttctg ccttacccgg ccggctcaat ccgacactca    600

gcaaataaga gccgtcctct ctttgcttct tcatttccgc tgctcctcgt tgcgtcttct    660

cgtcttccta cacatatccc tctccccatc ctcttttcgt cgtactacct cgtctacaaa    720

tatgcctgct ccttcgcgaa ttgctacgtc tttcgtccgc gcctcccagc gccctttggc    780

tgcgtcctat ctcagggccg cgcgcctcta ctccacggcg aaggaacctg tacgttgctc    840

tcactataaa ttttattcta gacaattgat ccacgccgct tctgtgtttg gcatcatgca    900

tgctcttctc gtcacagcaa tccgtcgaga tcaaattgct cttgttttgc ctccatttcg    960

gccgattacc acttctgtac taacacatca ctcgttctag                         1000
```

<210> SEQ ID NO 77
<211> LENGTH: 678
<212> TYPE: DNA
<213> ORGANISM: Lipomyces starkeyi

<400> SEQUENCE: 77

```
atttatgtta ccggtggttt tttatttaaa ttttgtgtag tattaataac ggttggcaca     60

ataagcttgt gccactatta taattattat tgttaaattg ttattgttat taaattgtta    120

ttattattac atcatggacg gagttaaaag atattctgct cagtgggctc ggaggaacgg    180

ggggtcggtt gccctccagg cggacctaac cagtcatgag ccaactaact tccttgttag    240

aaggccatta gcggagccgc agtgtcggca atggctatat ttttgggcaa cggcactaga    300

cggtaggcta gagctgttga gcacgtgaat gaatggtcga gggcagggtg gatccggcaa    360

ttgtccagca agccatgttt ccgatgaggc tcttgcccgg ggaattcgga ttacttaaat    420
```

```
tgtatttcaa ggaacttatg gggtgtggcc ttcccatgtc actctaattt ttttgtgcga    480

cctaaaggtt gctggggttc gaagctcccg cttgtcgccg caaaccttaa acgcacttcc    540

gcttcgctca tacatacaaa tacaatagag tggcccctcc tccctcggcc acgttcccat    600

cttgctgatt ttatctcgct gcctcattga tcccatccac tctattttca cggttttcgt    660

cgtctcacta cattgatc                                                  678
```

<210> SEQ ID NO 78
<211> LENGTH: 1000
<212> TYPE: DNA
<213> ORGANISM: Lipomyces starkeyi

<400> SEQUENCE: 78

```
catcaagaat atgcgtaatt tgcaagtcct gtgcacaaag gaagagtagg agcgggctaa     60

tcgaaggtgc gaaacgttat cagcggtgac gaatagctgt tatcggtcga tagagcgcat    120

gccggggtcc tcgctcggtc tggcctctct tttcactatt atattagctc tccactagtg    180

cggagtactg acggttgaca gcttctggtg tcttccatcg tatagacttg aacttgcggg    240

ctctgtctgc taaatctgtt cttcacattg tatgtcaact acacatactc tttcgataac    300

ggcttcattc ccgccgacac aagtgtggct ctgcgtgtaa tatacggcga atccgtcgtg    360

ctccactggc tctgcgcact gacacaagac gagcccttcg tcggtgttgc ggccacgccg    420

ctgacgcgta tacgccagaa cccgcacaac gtcgattcgt gtacccccga agttaaggtt    480

tcagtggcgt cgcagacccg aacgaccaga cccgaaataa tgtctgttgc gcagttgtgc    540

cgtaagtcgc ctcaaactag ttgcgcctcg ccattgatta tctgctcccg atcagcgagg    600

acggtagttt ctcgaaattg cactgcaacg gagactcagt ctgactccgt atcacgaccg    660

ccgcaggggc gaaagtttcc ttaccttgtc ctgttctaat atgttcaaag cacagtactg    720

acaacacgac cttgacactg ttccggacgt cgggtcagcc acagaacgcc actagcgtcg    780

aggttagccc caatatggtc tagcgccatt cactctgctg ggtctccttg cgctccgtga    840

ctccctgatt ccgggtcagc tttcagacac ttccgacccg gctaccagta ccgcctactt    900

tctcaccggt gcctccttct gctacttaat ctctttctcg cccgtcgacg tttttctcct    960

ctccacagac tacctacgca acctatccac atctttcaca                         1000
```

<210> SEQ ID NO 79
<211> LENGTH: 998
<212> TYPE: DNA
<213> ORGANISM: Lipomyces starkeyi

<400> SEQUENCE: 79

```
ttaatttgct gaagcggttt gcctctggta cgtaagatta cggagctgtc cctttccgcg     60

ctatcagcca ataccacaca accagcctga atttgtactg catccagcat ttatctcgcg    120

tgttagtgtg ctatgcccga gaactggcag acagatttca ccacgtaaaa tgtgcagata    180

ggtgaaaggt ccaaatcaac cgtctgaccg gtagatccgg ctcggtcggg aacgaacgat    240

gatgacgata gtgttgcgga tgctgaataa ttattgtctg cggcatatgt ggccactggc    300

aaaaccgccg ccccatcatg agtcttgcac ctgcggaatg ctcatcattt taatccgcgg    360

agcaaatttt tctctggtgg tcaggctgcg tagtaattag ctggggtgct ctgtgcgtca    420

tagcaaggct ggctgcgggc caatcatatt cccgtatgct ggggcgcgcc agacgaacgt    480

cacccgtggc tggcggtgtg gcgctggcgg cgcatagacg tggcggtgcg tagtttatca    540
```

```
ccttgctggg taccgtcagc ttgtctacct gctggacctc gggtaatcat ggcctgaaga    600

tagggcaaca gtatagtcgg acggaagcta ctgcgtgcgt gcatcacgac tagaaacaga    660

attaaagaaa atggtgacgt ctgggaatag ctgctattgg gaagtgaacg gcggaggctt    720

gtttgggcaa tgatgctatg tacgcagtac gctggaagcg gtgagaataa taatggcttg    780

gtctgtggtt ctcgatgctg ccatccgtac cacacagtac actccagcac gccctcccta    840

cccaccaact cacttctcct ccgtcgctct gcagcttata ataatccgaa ctgccgcccc    900

gaccctttct cttttctccc ttcgcctcag gcattttaat tccatactcc gcccttccca    960

gataaaagtt atctatctta ctctaatcca cattcgca                            998


<210> SEQ ID NO 80
<211> LENGTH: 584
<212> TYPE: DNA
<213> ORGANISM: Lipomyces starkeyi

<400> SEQUENCE: 80

tacatagatg tacaatagat tgtaaataga cgatattcgt agtgagtacg cgacacatct     60

gtttgtaaac aaaccctctc gcaaccgcta ttgttgtcct attattgggc gtgcgatcgt    120

tgggatagtg gctaacgggg ctgtcagctg gtcgcccatt ggcgggacca cttattctgg    180

agagtctgcc ggataatcga tggacatttg ggcgaatcgc gactcaacag ttactgcaca    240

ttgcagactg gccgcacatg tgagcacggc accagtgctg ctcagttgca tggtataata    300

gtcgacagca attggattga catatacaaa aaattacatg accttttttac attgagtttg   360

aaatggaaag catatcaaat aaaagtctag gaaaatgttg agctgccgcg tgttctgccc    420

gtgatgcctg tgcacacgcg gctaacaccg attgcagcgt atgtgtcgtt gcttcggcgt    480

ggtagcaata aatcttgcgc tcgcctctga gtgcctttct attctctcca tctctctact    540

ctcccctcct tcaaccactc tgcgtccgta tcactacagc caac                     584


<210> SEQ ID NO 81
<211> LENGTH: 1000
<212> TYPE: DNA
<213> ORGANISM: Lipomyces starkeyi

<400> SEQUENCE: 81

accattaaga ttcactgtcc ttgatcaccg gcgagatatc gggccatcag ggatgagtgg     60

atataatata ttaatagtgt gaattaggaa tagagcagag gagatgttgt tctcacagca    120

tcactaatgc atagcacaag aatgcggaga aatcgcctgt ccgcctgggg caaggggaag    180

cctccgatag tatcattgac cagctgagcc gaccctgagt cgatagagtt ttggcgtgtg    240

gtcaatattc aggtggggcc gagcccttcg ctaagcctca tctattaact ttccttattc    300

ggtcagggct tgagcactgc cagctaaacc ctacatatta catcctaacc ctgggcaata    360

aacagtcaca gcccatatgt gtggctgtgc gagtgcggaa cgtgtcagct cgtgaagcac    420

atggagtgcg aacaggagtt agacgacacc gcacatggaa attagggctg tatcgacact    480

ttattgccac cgccacgacg gcaaattgtg gtcgctgtat ccgcaaaggg gaggccggcc    540

ttgtcagtgg tcagcaatgt agaatagacg tagctggtgg tggacaggct aaccatgggg    600

acagtcgatc tgcattagtg gtccactgag gcaccgggaa gacaaagaca aaaaaatgcg    660

gacgaaaaac attgacgtca gccaaatccg agcgatgttt acgacttccc ttgtcgggca    720

ccggctagtt aatgcaaagt gctggcataa gtgcgcaaac gcaagcgcgg tacgtgcgct    780

gagcgtagag taaaaaaaat tttcttagcc gcgagcctag caacggcgcc aggccgtatc    840
```

```
tttctataaa gctctgcttc acccgccaca atttccattc cttttcttct ttttttcttt    900

gtctactcac acccgaaatc atagcatttc catctgagta tctttaatct taatcacatc    960

catccactta tcttttatac atcctcttta atctttcaaa                          1000
```

<210> SEQ ID NO 82
<211> LENGTH: 672
<212> TYPE: DNA
<213> ORGANISM: Lipomyces starkeyi

<400> SEQUENCE: 82

```
cgcgcataga tcatgactga tgcggggtac cagatcgtgc gttggtccga gctacggacg     60

caaagagaaa caccggtgca tatgcaaatt catgttatag atcatatgtt ggctttggga    120

ttatgaagtg tatcatgtca attgggaact aaggagattg ggtcgcatta tcttttaatt    180

ggtgtatcaa tctaatattt agagagatta tttgagtaca agcatttctt ccgacgctgg    240

ctcatactgg ccgaaggccc gactgagaca tgcattgggg attatcgtct ccagaccact    300

ctcgaggttg actcagaaga agcttccttg gtgtggtgga actcactcgg aaggtgtcgc    360

gctgggtcga gacagtggat atgttgccgg gtggtcgata gcagcgtgtc aaattgtatc    420

cgctgattta ggcaatattc tcgtattgct aataatcgag cttaagtctc cactttcctc    480

aacaaacagc tcagctttta tatggggtta gggtagtatc ccacggccat ccggccgcac    540

tgacggatgc ctgttccttt ccgtgtgccg catacccccc gatttttttc gttcccaatt    600

ggattcacac tattgcagac gaatacattc gtacactttc ttctaaattt gcatatatta    660

taactattta at                                                        672
```

<210> SEQ ID NO 83
<211> LENGTH: 399
<212> TYPE: DNA
<213> ORGANISM: Lipomyces starkeyi

<400> SEQUENCE: 83

```
tgtattcgtt gatagatggg cgttgagtgc acgagaagaa tcgcgagtga acttgttagg     60

cctactctcg aggcggagtg gcgctatgct gaccggcgcc gcatgtgggt gacagcaagg    120

gcatgctgag acgtacgtac ttcgttctca caattactta tagacccaac ggaatgcgcc    180

ttctgcgtca ctgttttctt tcggctgtcc aaccaccacg cagcagagca gccgacgccc    240

cgtgcccaca tctgccgtca tcaggcaacg tttttcatat ttttaagtcg atccctgctc    300

ttccttcgtc ttccgttccg ccctcgtctc tagagagaat aaattctata taaacacctt    360

tacgttctgt cgcctcgatt ctcgtcttcg tctagtaca                           399
```

<210> SEQ ID NO 84
<211> LENGTH: 878
<212> TYPE: DNA
<213> ORGANISM: Lipomyces starkeyi

<400> SEQUENCE: 84

```
gaggtcagat gggacgagat gagattgtac aataggttaa tattgccgta gctcatggtg     60

attgcatagg ttggttgggt ttgtgctggg ttgacaagtg tattatggaa ttaaatgtat    120

atgatggttt tgtttcgaat tccaaggcgg ctgtgtcact cggggacgat ctcgtcacta    180

aggagaacat ggacacgtta cgaggtctga taatttcagg agacgcggga tggcaaccgg    240

tctgataatt atcagattgt ctcgaacaaa gagacagacg catttggtca tcgtatatgg    300
```

-continued

```
ccgatacagt cggcagcgca gttgtcttgt agatctgtcc agactcagga actcgctttt    360

cgctgagttc gatgaattgt gtacgatcgt aatgttaatt tattatgatt tgatatgata    420

gagtgatatg tgacatctca ttcgcgggag caattgccag gcttcaaaat actgggtcgg    480

ctagagtagt ataatcaaaa tcagataaga aagtgtcact ggggagccct ggcttagttt    540

acactttgca caattagcta ctctgtggtt ggccggttaa cttgcttata ataattgctc    600

ttaatatgat tggctggaat tttttcaaca gcgcttcagc caatggatgt gctggcaata    660

gtaagcattt taccgtcagc caccgccgca agggcgagca ctatcaggcg atctctcggc    720

gccgcatgac tcacgggtag gtagactctc tataaagcag tctgttcctc gatcttcagc    780

tagtcatacc aaaaatccta tcatttaata tctcgacttg gctcttaccc tacacaatat    840

actacaacct tcgcttcatt gcttctacta taattaca                            878
```

<210> SEQ ID NO 85
<211> LENGTH: 750
<212> TYPE: DNA
<213> ORGANISM: Lipomyces starkeyi

<400> SEQUENCE: 85

```
acgttttttt gtgttattgc gcgcttgttt tggaacggca tttgtatgtg acatagtggg     60

ttcattctag cagaaaagct gttttgaaag attatagagg gtgttgacac tttggcggct    120

ggaggaatta tgcgagatag agatgatttc gaatgggagt aatttgggaa aagagttata    180

gtttgatttt cgctttttat ccatataccg gacggacgga attggaaagt attatatgag    240

tatgatacat gtgttaatta ataagtaata tataccgttg tgtttattta tatgtacttg    300

tcgtttttcc ggttactctt tcgtcgcgtc atctctttat ctcgtacatt cttatgctac    360

ttctcttttg ctacatttac tcgttgtttc gtttattatc cgtcgctcat ttggacattt    420

ctcttgttct cgacttgttt tccgatggaa tgttatcgca ttacgtcccg tgcaagagtc    480

attgattgtt gtactttatc cacacatttt gttacattac acgatctttt cttttcagtt    540

tttgtgtttt ttacataatg taatagactt ttctttgcca tcatgatatc taaaagttac    600

agttatgttg actgaatttt gcccttgagt gcgtgagttt tgtcagtcgt tttaagacat    660

gccattaatg gcggatttac ccagtcgggg gagcctcaca tggccaagag aggaagaaac    720

ctttccacca atgcgggcaa tgtgattggt                                     750
```

<210> SEQ ID NO 86
<211> LENGTH: 300
<212> TYPE: DNA
<213> ORGANISM: Lipomyces starkeyi

<400> SEQUENCE: 86

```
tggaatccat ctaaaatcgt gggaaccgcc agagagaaca gtttctttgt tcgttcaact     60

gcatgtttat gcattttaat caacttcagt tactaagaat aattttgtgt gttttccttc    120

gctcgttcgt tgctcattac gtgcggtcgg tcgtaatatc gtgtatgtca cttggtccaa    180

atgatccaaa aagattacga attatcgtat aaaacagata gatacatctt taatactaca    240

ccctttgcag ccaattagcg aaaactcgtc aggtccggcg cacgatgacg tcttgccttc    300
```

<210> SEQ ID NO 87
<211> LENGTH: 205
<212> TYPE: DNA
<213> ORGANISM: Lipomyces starkeyi

<400> SEQUENCE: 87

```
atttcttcat ttcttgtatg tgatattagg tgaatgcgtt ggttaagttt ttggtaatgt     60

cacttttgac gtgtttctat aatacataat gttgcgcttg tctttatttc gtgcctagat    120

tgtgagtgct tcatagttgt tcagctccat tgcgttgaga cgtttagtgc ctacttttga    180

gcagattttt taagtgtgcg tgtgt                                          205
```

<210> SEQ ID NO 88
<211> LENGTH: 512
<212> TYPE: DNA
<213> ORGANISM: Lipomyces starkeyi

<400> SEQUENCE: 88

```
gtgtgcggtt gatggtcttc tatcttccca catttcctca caacatgtat agccgtattc     60

tataataccg aattagacaa aagaatgaat ttgtcttata ttataaacaa agaaattaag    120

tttatgttta tgtcgctagt tatttgggat gttacttgcg gattcagctt gctttgatag    180

tattgcctgg gacgcagatc taatgaaaat tttgtaacac agtataacta ggtgtaatca    240

caaattgccg tttaccgcaa tatatttaaa ttatgactcc aattcatgag gattatggcc    300

cgaatttagt tggtcctagt tatttggtta tcgtaatttt attgaataat gttgaaaacc    360

tggctcgagt gctcgaagtt agttcttcag acaggggctt gggtgtcggg tccgacgcgt    420

cgccggtgga ctagccaccc gccgccgcat cgcgcatcac tacatatcga gatcttaaaa    480

acaactttgt tccaccatca ccacccgcta ca                                  512
```

<210> SEQ ID NO 89
<211> LENGTH: 1500
<212> TYPE: DNA
<213> ORGANISM: Lipomyces starkeyi

<400> SEQUENCE: 89

```
acggtcaatg cggtgcaaga tagctctgca attgggtcca gtcggtaaat catatatagt     60

gtcgatcgcg aggatggccg gttgtgcccg attgttgatg tgtttatgtg cttatagact    120

ttgttgttgt ttatgatatg tgtacagcga tttcttatcg cgtgacgttt gtattcgcag    180

gattttgtgc ccttgcttgg atattgcgtg aatcgagcta tgcacggcac tactggtagt    240

gcgaggtgtt tcatggacga tttaaacata caattatttc tcgttgagcc ttgtagatgc    300

aaactaagat tactcacaac gctacgtgcc gggcgacctt atttcctcca tactcttgta    360

agtagtagta ttttggaaga tgtcgctgac ggtaatcgaa tggagttcga ccccaatgac    420

ctgcgttagg ctttcgcaaa gatgctaact tatacaaaaa tatgacaccg agcagcccat    480

gacggtctat ttcacaacta aagaagagtt ggaggcatgg atccaggagc accgtctgta    540

ttgtaagctg cgctagattt attgcgagac agttcttcta ttcaaatgga actttattgg    600

cagcacaatc gacatgaacc agaattaccc agctgtcaaa aaaatggact gatgccaggg    660

tttctcaata ctataacacg cattcctcta aggagctttt gaggttgcgt gaatcagacc    720

ggcaacggta tgcggcggtt aaagttactc tcatatgatg atgattaacg agatggtcta    780

gatgcaggat aaggatagcg atgtgatctt tgcttccctg cgcgttactt ttgtctggag    840

tccatttcat agtaaatcag aatccctgat tataatgggt agctgtgcca aagttgtgca    900

tgaaaacgtt gccatgacag gtgtttttgg gcttttgccg atttcattcg cgactgtcat    960

ttggcttaca atcgctgtac catcacaccg aatttgctca ggtgccccat ctttacgtcg   1020

ctgcataaca gggtgttaac aacatcaccg agtagcaaag cataacaggt tcaccccgcc   1080
```

aggttgctat cgcttagcaa gctcaacaaa catttcagtg acttcaagga ttcaaaatat 1140
tgaatcaagc tcttaatatc tagtaggcta gttgaagata ctttcagcct tggcagaatt 1200
gtgcggaacg ctgttagttt ctatattggg tacacgtttg cagaagtctg caccaatatt 1260
tgccagaaaa ttagagaggt ttcgcaacca tttttacgcc gcaaatttac aggaaataac 1320
ccttacccac ggttttcaag taaatttggt ctcgtaaatt tacacgattt cgtccatcat 1380
gcgtaaaacc ttaatgccaa atttacgcca attttaaggt tagcgttagc ctgaagaggc 1440
aagcgctaaa ccttcttcta aatatcgagc acattagaat ttacgcgtct tcccctaggt 1500

<210> SEQ ID NO 90
<211> LENGTH: 300
<212> TYPE: DNA
<213> ORGANISM: Lipomyces starkeyi

<400> SEQUENCE: 90
aggggcgggt cgattttgtg aaccactgtt ttggacaatg acgagttctc tagagtagtc 60 ccttttttgtt aatatagtgt aaagtgtgca tgtttgccag tgcgctattg ccagcaccaa 120
ttgtataacc actccttccg tttcactata tacaacaaag gcaataaatc gatgcaagtt 180
cactagatat aaatacaggt gtatatatta cacgatcaag acgtcgatga taaagtgtaa 240
tatgcccccc ccctcttcct ctatggctta atttccactg agaccatatt ttcggcattc 300

<210> SEQ ID NO 91
<211> LENGTH: 4869
<212> TYPE: DNA
<213> ORGANISM: Artificial Sequence
<220> FEATURE:
<223> OTHER INFORMATION: pXC301 Base Vector
<220> FEATURE:
<221> NAME/KEY: Kanamycin-r (rev)
<222> LOCATION: (1)..(810)
<220> FEATURE:
<221> NAME/KEY: KanR Primer II
<222> LOCATION: (237)..(257)
<220> FEATURE:
<221> NAME/KEY: KanR Primer I (rev)
<222> LOCATION: (722)..(743)
<220> FEATURE:
<221> NAME/KEY: P_Amp (rev)
<222> LOCATION: (821)..(938)
<220> FEATURE:
<221> NAME/KEY: Vector Sequencing Primer Reverse
<222> LOCATION: (1064)..(1080)
<220> FEATURE:
<221> NAME/KEY: loxRE
<222> LOCATION: (1215)..(1248)
<220> FEATURE:
<221> NAME/KEY: Forward Primer to Clone Ls TDH3 Pro Term
<222> LOCATION: (1235)..(1274)
<220> FEATURE:
<221> NAME/KEY: LsTDH3 Promoter Primer
<222> LOCATION: (1255)..(1275)
<220> FEATURE:
<221> NAME/KEY: LsTDH3 Promoter
<222> LOCATION: (1255)..(2252)
<220> FEATURE:
<221> NAME/KEY: NAT1 ORF
<222> LOCATION: (2253)..(2822)
<220> FEATURE:
<221> NAME/KEY: NAT1 PCR Primer Forward
<222> LOCATION: (2260)..(2289)
<220> FEATURE:
<221> NAME/KEY: NAT1 Sequencing Primer 5' Reverse (rev)
<222> LOCATION: (2260)..(2289)
<220> FEATURE:
<221> NAME/KEY: NAT1 PCR Primer Reverse (rev)
<222> LOCATION: (2736)..(2765)
<220> FEATURE:

```
<221> NAME/KEY: NAT1 Primer Reverse  (rev)
<222> LOCATION: (2802)..(2822)
<220> FEATURE:
<221> NAME/KEY: LsTDH3 Terminator
<222> LOCATION: (2823)..(3335)
<220> FEATURE:
<221> NAME/KEY: Reverse Primer to Clone Ls TDH3 Pro Term (rev)
<222> LOCATION: (3316)..(3355)
<220> FEATURE:
<221> NAME/KEY: loxLE
<222> LOCATION: (3349)..(3382)
<220> FEATURE:
<221> NAME/KEY: Term_bla (rev)
<222> LOCATION: (3435)..(3735)
<220> FEATURE:
<221> NAME/KEY: Vector Sequencing Primer Forward (rev)
<222> LOCATION: (3526)..(3551)
<220> FEATURE:
<221> NAME/KEY: Term_rpoC (rev)
<222> LOCATION: (3736)..(3855)
<220> FEATURE:
<221> NAME/KEY: Ori_pUC (rev)
<222> LOCATION: (4100)..(4772)

<400> SEQUENCE: 91

ttagaaaaac tcatcgagca tcaaatgaaa ctgcaattta ttcatatcag gattatcaat     60

accatatttt tgaaaaagcc gtttctgtaa tgaaggagaa aactcaccga ggcagttcca    120

taggatggca agatcctggt atcggtctgc gattccgact cgtccaacat caatacaacc    180

tattaatttc ccctcgtcaa aaataaggtt atcaagtgag aaatcaccat gagtgacgac    240

tgaatccggt gagaatggca aaagtttatg catttctttc cagacttgtt caacaggcca    300

gccattacgc tcgtcatcaa aatcactcgc atcaaccaaa ccgttattca ttcgtgattg    360

cgcctgagcg aggcgaaata cgcgatcgct gttaaaagga caattacaaa caggaatcga    420

gtgcaaccgg cgcaggaaca ctgccagcgc atcaacaata ttttcacctg aatcaggata    480

ttcttctaat acctggaacg ctgtttttcc ggggatcgca gtggtgagta accatgcatc    540

atcaggagta cggataaaat gcttgatggt cggaagtggc ataaattccg tcagccagtt    600

tagtctgacc atctcatctg taacatcatt ggcaacgcta cctttgccat gtttcagaaa    660

caactctggc gcatcgggct tcccatacaa gcgatagatt gtcgcacctg attgcccgac    720

attatcgcga gcccatttat acccatataa atcagcatcc atgttggaat ttaatcgcgg    780

cctcgacgtt tcccgttgaa tatggctcat attcttcctt tttcaatatt attgaagcat    840

ttatcagggt tattgtctca tgagcggata catatttgaa tgtatttaga aaaataaaca    900

aataggggtc agtgttacaa ccaattaacc aattctgaac attatcgcga gcccatttat    960

acctgaatat ggctcataac accccttgtt tgcctggcgg cagtagcgcg gtggtcccac   1020

ctgaccccat gccgaactca gaagtgaaac gccgtagcgc cgatggtagt gtggggactc   1080

cccatgcgag agtagggaac tgccaggcat caaataaaac gaaaggctca gtcgaaagac   1140

tgggcctttc gcccgggcta attagggggt gtcgcccttc gctgaagcga tcgcggcgcg   1200

cctgcaggcc ggcctaccgt tcgtataatg tatgctatac gaagttatgg atccttaatt   1260

tgctgaagcg gtttgcctct ggtacgtaag attacggagc tgtccctttc cgcgctatca   1320

gccaatacca cacaaccagc ctgaatttgt actgcatcca gcatttatct cgcgtgttag   1380

tgtgctatgc ccgagaactg gcagacagat ttcaccacgt aaaatgtgca gataggtgaa   1440

aggtccaaat caaccgtctg accggtagat ccggctcggt cgggaacgaa cgatgatgac   1500

gatagtgttg cggatgctga ataattattg tctgcggcat atgtggccac tggcaaaacc   1560

gccgccccat catgagtctt gcacctgcgg aatgctcatc attttaatcc gcggagcaaa   1620
```

```
tttttctctg gtggtcaggc tgcgtagtaa ttagctgggg tgctctgtgc gtcatagcaa   1680
ggctggctgc gggccaatca tattcccgta tgctggggcg cgccagacga acgtcacccg   1740
tggctggcgg tgtggcgctg gcggcgcata gacgtggcgg tgcgtagttt atcaccttgc   1800
tgggtaccgt cagcttgtct acctgctgga cctcgggtaa tcatggcctg aagatagggc   1860
aacagtatag tcggacggaa gctactgcgt gcgtgcatca cgactagaaa cagaattaaa   1920
gaaaatggtg acgtctggga atagctgcta ttgggaagtg aacggcggag gcttgtttgg   1980
gcaatgatgc tatgtacgca gtacgctgga agcggtgaga ataataatgg cttggtctgt   2040
ggttctcgat gctgccatcc gtaccacaca gtacactcca gcacgccctc cctacccacc   2100
aactcacttc tcctccgtcg ctctgcagct tataataatc cgaactgccg ccccgaccct   2160
ttctcttttc tcccttcgcc tcaggcattt taattccata ctccgccctt cccagataaa   2220
agttatctat cttactctaa tccacattcg caatgactac tttggatgac actgcataca   2280
gatataggac ttctgtccct ggtgacgctg aagctataga ggcattagat ggctcattca   2340
caacagatac agtttttcgt gtaactgcta ctggtgacgg attcacattg agagaagtcc   2400
cagtcgatcc tccattgacc aaagtgttcc cagatgacga atcagacgat gaatctgatg   2460
ctggtgagga tggagatcca gactcaagaa cattcgttgc atacggagat gatggagatt   2520
tagctggatt tgtcgttgtc agttacagtg gttggaacag gcgtttaacc gtggaagata   2580
ttgaagttgc acccgaacat aggggacacg gtgttggtcg tgccttaatg ggcttagcca   2640
ccgaatttgc aagagaaagg ggagctggtc atttgtggtt agaagttact aatgttaatg   2700
cccctgcaat tcatgcctac aggaggatgg gattcacatt atgcggcttg gatactgcct   2760
tgtatgacgg tacagcttcc gacggcgagc aagctttata catgtccatg ccatgtccat   2820
aagtgtgcgg ttgatggtct tctatcttcc cacatttcct cacaacatgt atagccgtat   2880
tctataatac cgaattagac aaaagaatga atttgtctta tattataaac aaagaaatta   2940
agtttatgtt tatgtcgcta gttatttggg atgttacttg cggattcagc ttgctttgat   3000
agtattgcct gggacgcaga tctaatgaaa attttgtaac acagtataac taggtgtaat   3060
cacaaattgc cgtttaccgc aatatattta aattatgact ccaattcatg aggattatgg   3120
cccgaattta gttggtccta gttatttggt tatcgtaatt ttattgaata atgttgaaaa   3180
cctggctcga gtgctcgaag ttagttcttc agacaggggc ttgggtgtcg ggtccgacgc   3240
gtcgccggtg gactagccac ccgccgccgc atcgcgcatc actacatatc gagatcttaa   3300
aaacaacttt gttccaccat caccacccgc tacatgtcga caccggtgat aacttcgtat   3360
aatgtatgct atacgaacgg tacggaccgc ggcggccgcc taggcgatcg ccgtcaaaag   3420
ggcgacacaa aatttattct aaatgcataa taaatactga taacatctta tagtttgtat   3480
tatattttgt attatcgttg acatgtataa ttttgatatc aaaaactgat tttcccttta   3540
ttattttcga gatttatttt cttaattctc tttaacaaac tagaaatatt gtatatacaa   3600
aaaatcataa ataatagatg aatagtttaa ttataggtgt tcatcaatcg aaaaagcaac   3660
gtatcttatt taaagtgcgt tgcttttttc tcatttataa ggttaaataa ttctcatata   3720
tcaagcaaag tgacaggcgc ccttaaatat tctgacaaat gctctttccc taaactcccc   3780
ccataaaaaa acccgccgaa gcgggttttt acgttatttg cggattaacg attactcgtt   3840
atcagaaccg cccagggggc ccgagcttaa gactggccgt cgttttacaa cacagaaaga   3900
gtttgtagaa acgcaaaaag gccatccgtc aggggccttc tgcttagttt gatgcctggc   3960
```

-continued

```
agttccctac tctcgccttc cgcttcctcg ctcactgact cgctgcgctc ggtcgttcgg   4020

ctgcggcgag cggtatcagc tcactcaaag gcggtaatac ggttatccac agaatcaggg   4080

gataacgcag gaaagaacat gtgagcaaaa ggccagcaaa aggccaggaa ccgtaaaaag   4140

gccgcgttgc tggcgttttt ccataggctc cgcccccctg acgagcatca caaaaatcga   4200

cgctcaagtc agaggtggcg aaacccgaca ggactataaa gataccaggc gtttccccct   4260

ggaagctccc tcgtgcgctc tcctgttccg accctgccgc ttaccggata cctgtccgcc   4320

tttctccctt cgggaagcgt ggcgctttct catagctcac gctgtaggta tctcagttcg   4380

gtgtaggtcg ttcgctccaa gctgggctgt gtgcacgaac cccccgttca gcccgaccgc   4440

tgcgccttat ccggtaacta tcgtcttgag tccaacccgg taagacacga cttatcgcca   4500

ctggcagcag ccactggtaa caggattagc agagcgaggt atgtaggcgg tgctacagag   4560

ttcttgaagt ggtggcctaa ctacggctac actagaagaa cagtatttgg tatctgcgct   4620

ctgctgaagc cagttacctt cggaaaaaga gttggtagct cttgatccgg caaacaaacc   4680

accgctggta gcggtggttt ttttgtttgc aagcagcaga ttacgcgcag aaaaaaagga   4740

tctcaagaag atcctttgat cttttctacg gggtctgacg ctcagtggaa cgacgcgcgc   4800

gtaactcacg ttaagggatt ttggtcatga gcttgcgccg tcccgtcaag tcagcgtaat   4860

gctctgctt                                                           4869
```